US010631482B2

(12) United States Patent
Bolduan et al.

(10) Patent No.: US 10,631,482 B2
(45) Date of Patent: Apr. 28, 2020

(54) HAPLOID INDUCERS

(71) Applicant: KWS SAAT SE & CO. KGAA, Einbeck (DE)

(72) Inventors: Christof Bolduan, Einbeck (DE); Monika Kloiber-Maitz, Einbeck (DE); Markus Niessen, Hannover (DE); Milena Ouzunova, Göttingen (DE); Fridtjof Weltmeier, Einbeck (DE)

(73) Assignee: KWS SAAT SE & CO. KGAA, Einbeck (DE)

( * ) Notice: Subject to any disclaimer, the term of this patent is extended or adjusted under 35 U.S.C. 154(b) by 0 days.

(21) Appl. No.: 15/526,552

(22) PCT Filed: Nov. 12, 2015

(86) PCT No.: PCT/EP2015/076469

§ 371 (c)(1),
(2) Date: May 12, 2017

(87) PCT Pub. No.: WO2016/075255

PCT Pub. Date: May 19, 2016

(65) Prior Publication Data

US 2017/0327832 A1 Nov. 16, 2017

(30) Foreign Application Priority Data

Nov. 12, 2014 (DE) ........................ 10 2014 016 667

(51) Int. Cl.

| | |
|---|---|
| ***A01H 1/08*** | (2006.01) |
| ***A01H 1/06*** | (2006.01) |
| ***C12N 9/20*** | (2006.01) |
| ***A01H 6/46*** | (2018.01) |
| ***C12Q 1/68*** | (2018.01) |
| ***C07K 14/415*** | (2006.01) |
| *C12Q 1/6895* | (2018.01) |

(52) U.S. Cl.

CPC ................. *A01H 1/08* (2013.01); *A01H 1/06* (2013.01); *A01H 6/4684* (2018.05); *C07K 14/415* (2013.01); *C12N 9/20* (2013.01); *C12Q 1/6895* (2013.01); *C12Q 2600/13* (2013.01)

(58) Field of Classification Search

None
See application file for complete search history.

(56) References Cited

U.S. PATENT DOCUMENTS

| | | | |
|---|---|---|---|
| 8,420,782 | B2 | 4/2013 | Bonas et al. |
| 8,440,431 | B2 | 5/2013 | Voytas et al. |
| 8,440,432 | B2 | 5/2013 | Voytas et al. |
| 8,450,471 | B2 | 5/2013 | Voytas et al. |
| 8,586,363 | B2 | 11/2013 | Voytas et al. |
| 8,697,853 | B2 | 4/2014 | Voytas et al. |
| 9,353,378 | B2 | 5/2016 | Bonas et al. |
| 9,677,082 | B2 * | 6/2017 | Chintamanani .... C12N 15/8218 |
| 2011/0145940 | A1 | 6/2011 | Voytas et al. |
| 2012/0122205 | A1 | 1/2012 | Bonas et al. |
| 2012/0064620 | A1 | 3/2012 | Bonas et al. |
| 2012/0178131 | A1 | 7/2012 | Voytas et al. |
| 2012/0178169 | A1 | 7/2012 | Voytas et al. |
| 2012/0214228 | A1 | 8/2012 | Voytas et al. |
| 2013/0122581 | A1 | 1/2013 | Voytas et al. |
| 2014/0335618 | A1 | 4/2014 | Voytas et al. |
| 2014/0298532 | A1 | 10/2014 | Dhawan et al. |
| 2014/0335592 | A1 | 11/2014 | Voytas et al. |
| 2017/0022574 | A1 | 1/2017 | Dhawan et al. |

FOREIGN PATENT DOCUMENTS

| | | | | |
|---|---|---|---|---|
| WO | 2010/079430 | A1 | 7/2010 | |
| WO | 2010083178 | A1 | 7/2010 | |
| WO | 2011044132 | A1 | 4/2011 | |
| WO | 2011/072246 | A1 | 6/2011 | |
| WO | 2012/030893 | A1 | 3/2012 | |
| WO | 2013072832 | A1 | 5/2013 | |
| WO | 2014110274 | A2 | 7/2014 | |
| WO | 2014151749 | A1 | 9/2014 | |
| WO | WO-2014151749 | A1 * | 9/2014 | ......... C12N 15/8218 |
| WO | 2016177887 | A1 | 11/2016 | |

OTHER PUBLICATIONS

Ayele et al. SEQ ID No. 3454 from US Patent Application Publication No. 2016/0017349 (Jan. 21, 2016).*
Singh et al. PLoS ONE 7(2): 1-15 (Feb. 2012).*
Scherer et al. Trends in Plant Science 15(12): 693-700 (Dec. 2010).*
Rietz et al. Planta 219: 743-753 (2004).*
Qiao et al. Theoretical and Applied Genetics 122: 1439-1449 (2011).*
Holk et al. Plant Physiology 130: 90-101 (2002).*
Ow et al. Proc. Natl. Acad. Sci. USA 84: 4870-4874 (1987).*
Barret, P. et al., "A major locus expressed in the male gametophyte with incomplete penetrance is responsible for in situ gynogenesis in maize", Theoretical and Applied Genetics (2008), vol. 117(4), pp. 581-594.
Bordes, J., et al., "Haplodiploidization of maize (*Zea mays* L) through induced gynogenesis assisted by glossy markers and its use in breeding", Agronomie (1997), vol. 17(5), pp. 291-297.
Chen, Ling et al., "Isolation and heterologous transformation analysis of a pollen-specific promoter from wheat (*Triticum aestivum* L.)", Molecular Biology Reports (2010), vol. 37(2), pp. 737-744.
Chevalier, Brett S., et al., "Design, activity, and structure of a highly specific artificial endonuclease", Molecular Cell (2002), vol. 10(4), pp. 895-905.

(Continued)

*Primary Examiner* — David T Fox
(74) *Attorney, Agent, or Firm* — Troutman Sanders LLP

(57) ABSTRACT

The present invention relates to the provision of technical means such as nucleic acids which, after transcription or after expression in a plant, are suitable for mediating the property of a haploid inductor or for increasing the induction capability of a haploid inductor, as well as methods and uses for the production and identification of non-transgenic and transgenic plant haploid inductors, as well as the improvement of existing plant haploid inductors.

16 Claims, 3 Drawing Sheets

Specification includes a Sequence Listing.

(56) References Cited

OTHER PUBLICATIONS

Coe, E. H., "A line of maize with high haploid frequency", American Naturalist (1959), pp. 381-382.
Das, Lekha et al., "Site-selected transposon mutagenesis at the hcf106 locus in maize", The Plant Cell Online (1995), vol. 7(3), pp. 287-294.
Deimling, S. et al., Methodik und Genetik der in-vivo—Haploideninduktion bei Mais. [Methods and genetics of in vivo haploid induction in maize], Presentation Pflanzenzüchtung (1997), vol. 38: pp. 203-224.
Depicker, A., et al., "Nopaline synthase: transcript mapping and DNA sequence", Journal of Molecular and Applied Genetics (1981), vol. 1(6), pp. 561-573.
Dong, X., et al., "Marker-assisted selection and evaluation of high oil in vivo haploid inducers in maize", Molecular Breeding (2014), pp. 1-12.
Dong, X., et al., "Fine mapping of qhir1 influencing in vivo haploid induction in maize", Theoretical and Applied Genetics (2013), vol. 126(7), pp. 1713-1720.
Fire, Andrew, et al., "Potent and specific genetic interference by double-stranded RNA in Caenorhabditis elegans", Nature (1998), vol. 391(6669), pp. 806-811.
Gaj, Thomas, et al., "ZFN, TALEN, and CRISPR/Cas-based methods for genome engineering", Trends in Biotechnology (2013), vol. 31(7), pp. 397-405.
Gurr, Sarah J., et al., "Engineering plants with increased disease resistance: what are we going to express?", Trends in Biotechnology (2005), vol. 23(6), pp. 275-282.
Kato, Naohiro et al., "A systems model of vesicle trafficking in *Arabidopsis* pollen tubes [W][OA]", Plant Physiology (2010), vol. 152(2), pp. 590-601.
Kim, Hae Jin, et al., "Endoplasmic reticulum- and golgi-localized phospholipase A2 plays critical roles in *Arabidopsis* pollen development and germination", The Plant Cell (2011), vol. 23(1), pp. 94-110.
Lloyd, Alan, et al., "Targeted mutagenesis using zinc-finger nucleases in *Arabidopsis*", Proceedings of the National Academy of Sciences of the United States of America (2005), vol. 102(6), pp. 2232-2237.
McCarty, Donald, et al., "Steady-state transposon mutagenesis in inbred maize", The Plant Journal (2005), vol. 44(1), pp. 52-61.
Odell, Joan et al., "Identification of DNA sequences required for activity of the cauliflower mosaic virus 35S promoter", Nature (1985), vol. 313, pp. 810-812.
Prigge, Vanessa et al., "New insights into the genetics of in vivo induction of maternal haploids, the backbone of doubled haploid technology in maize", Genetics (2012), vol. 190(2), pp. 781-793.
Ravi, Maruthachalam et al., "Haploid plants produced by centromere-mediated genome elimination", Nature (2010), vol. 464(7288), pp. 615-618.
Röber, F. K. et al., "In vivo haploid induction in maize-performance of new inducers and significance of doubled haploid lines in hybrid breeding", Maydica (2005), vol. 50, pp. 275-283.
Shibuya, Kenichi et al., "RNA-directed DNA methylation induces transcriptional activation in plants", Proceedings of the National Academy of Sciences (2009), vol. 106(5), pp. 1660-1665.
Silva, George et al., "Meganucleases and other tools for targeted genome engineering: perspectives and challenges for gene therapy", Current Gene Therapy (2011), vol. 11(1), pp. 11-27.
Sylvester, Anne W. et al., "Division and differentiation during normal and liguleless-1 maize leaf development", Development (1990), vol. 110(3), pp. 985-1000.
Till, Bradley J. et al., "Discovery of induced point mutations in maize genes by TILLING", BMC Plant Biology (2004), vol. 4(1), 12, pp. 1-8.
Twell, David et al., "Promoter analysis of genes that are coordinately expressed during pollen development reveals pollen-specific enhancer sequences and shared regulatory elements", Genes & Development (1991), vol. 5(3), pp. 496-507.
Venter, Mauritz "Synthetic promoters: genetic control through cis engineering", Trends in Plant Science (2007), vol. 12(3), pp. 118-124.
Wang, Yuan et al., "Inositol polyphosphate 5-phosphatase-controlled Ins (1, 4, 5) P3/Ca2+ is crucial for maintaining pollen dormancy and regulating early germination of pollen", Development (2012), vol. 139(12), pp. 2221-2233.
Zhao, Yan et al., "Characterization and functional analysis of a pollen-specific gene st901 in Solanum tuberosum", Planta (2006), vol. 224(2), pp. 405-412.
Ayele et al. SEQ ID No. 2123 from International Patent Publication WO 2014/151749 (Sep. 25, 2014).
Van Camp et al. SEQ ID No. 496 from International Patent Publication WO 2013/072832 (May 23, 2013).

* cited by examiner

SEQUENCE LISTING

<160> NUMBER OF SEQ ID NOS: 65

<210> SEQ ID NO 1
<211> LENGTH: 47944
<212> TYPE: DNA
<213> ORGANISM: Zea mays
<220> FEATURE:
<221> NAME/KEY: misc_feature
<222> LOCATION: (12578)..(12677)
<223> OTHER INFORMATION: n is a, c, g, or t
<220> FEATURE:
<221> NAME/KEY: misc_feature
<222> LOCATION: (22322)..(22421)
<223> OTHER INFORMATION: n is a, c, g, or t
<220> FEATURE:
<221> NAME/KEY: misc_feature
<222> LOCATION: (42238)..(42337)
<223> OTHER INFORMATION: n is a, c, g, or t

<400> SEQUENCE: 1
atggggagca gtgaggagca tgttttttta gatcccacca gaatatgtgc atccgtgtca 60
cttcttgctc atgatctcat tggccgaatg cttaatcgag aggtctcttc aaggcccaat 120
gccaaagaag ttctccgtaa gttcaagcac ccttgtaact tgtgctttat atatatgatt 180
ctcaatttat cattgacttt tcctaatggc tttcaacaca gggcaccatg ggtcttattc 240
tacactgatt gcccgcagaa agctgaattc tctaacatat gggatactaa caaaactgca 300
gctcccatga ttcatcggga gatagtcagg tttggttact gtgagtcttc atcttcaaaa 360
tcctcaagtg acaactctga agagcgagat gaatgcggta tagttgatgc actggtgaca 420
acaataacac aggtgaggat ctcagagccc aagaggagtc ggctgttcag cctacccaac 480
gggttgttgc cgccaagcag gaacagtctc cgaacatgaa gatgatgaat ccgtgtgtgg 540
ctttctaact tgacctacct agctcccatc cccatgcatg tataaacgac atttggggaa 600
tgggtagaaa agcagagatt agggattttc gtttccgtcg gtgcagtttt ggtgttccaa 660
tggagttgcg agatgtttat gtgccttagt cttcaatttg ggggttgggg gaaaagtaat 720
tttatgtttt tgttttgtgt ctgcagattc ggaagatgga cttggaggca aggagcctac 780
agcctagcat taaggctggt ttgcttgcaa agctgaggga gtataaatct gacctcaaca 840
acgtcaagag tgagctcaag aggatatttg cgcccaatgc caggcaggct acccgggagg 900
agctcctaga gtttggaatg gctgatactc tcgctgtgag ctaatgctag gacttgactg 960
tgtctacgag actgctccta acaataaact gaagaaagca aaagaaatca ttcaacgtat 1020
tcgccgaaga gaactctaca aggtagtatg atgctttaat tgctcatata caagtgtcat 1080
tttgtcatgt cattacacat ggttaggata catacttaag tttctaacgt aggcgtccac 1140
acaacggatt ggtgcacggt tctgccgatg tatcccacgc acgtgcatgg aaggaggcag 1200
gcacccttcc ccgccgcccc ggatctcgcg ccagcccccg ccctaccccg cctgcccttc 1260
cactcttccc ccgccgcccc cggtcaacgt cacgaacccg ggcctcgtgc cgctcgtcgt 1320
ggccacactg ttcgacgagc gagtcataga gctgctgagc gtgctcgctg atgcggcggt 1380
ggggcgacca ggcaggtggt ccatcggcga agcgccatgg tcgtcgtcgg ggggcacgaa 1440
ccaggcggtg tacgcgcgcc gcgcgcccgg ctcttcatcg cctccacccg ctccagcgtc 1500
tccaccactt ccttcatcga gggccgactg cttggctcgc tggccaggca gccgagcatt 1560
agttgcgccg cttggaacgc ctgcttttgt tgatcgtttg ttttggtctg atttcagtgg 1620

```
gtctatccgc agagaggaag aagcagaagc tctccgagat ccaatccggc gttgaggaag   1680
ctgaatcgct ggtaaataga tgtcgcgacg cgttctgttt tggggatccc cttggctaac   1740
gggacatacg acatttgggg aatgggtaga aaagcagaga ttagggattt ttcgtttccg   1800
tcggtgcagt tttggtgttc caacagagtt gcgagatgtt tatgtgcctt agtcttcaat   1860
ttgggggttg ggggaaaagt aattttatgt ttttgttttg tgtctgcaga ttcagaaaat   1920
ggacctggag gcaaggagcc tacagcctag cattaaggct ggtttgcttg caaagccgag   1980
ggattataaa tctgacctca acaacgtcaa gagtgagctc aagaggatat ctgcgcccaa   2040
tgccaggtag gctacccggg aggagctcgt ggagtctaga atggctgata ctctcgcagt   2100
gagctaatgc taggacttga ctgtgtctac gagactgctc ctaataataa actgaagaaa   2160
gcaaaagaaa tcattcaacg tattcgccga agagaactct acaaggtagt atgatgcttt   2220
aattgctcat atacaagtgt cattttgtca tgtcattaca catggttagg atacatactt   2280
aagtttctaa cgtaggcatc cacacaatgg attggtgcac ggttctgccg atgtatccca   2340
cgcacgcgca tggaaggagg caggcaccct tccctgccgc cccggatctc gcgccagcca   2400
tcgccctacc ccgcctgccc ttccactctt ccccctgaaa gtcgcataga gggggggtga   2460
atagggcgaa tctgaaattt acaaacttaa gcacaactac aagccgggtt aacgttagaa   2520
atataaacga gtccgagaga gagggcgcaa aacaaatcat gagcaaataa agagtgagac   2580
acgatgattt gttttaccga ggttcggttc ttgcaaacct actccccgtt gaggtggtca   2640
caaagaccgg gtctctttca accctttccc tctctcaaac ggtcacttag accgagtgag   2700
cttctcttct caatcaaacg gaacacaaag ttcccgcaag gaccaccaca caattggtgt   2760
ctcttgcctt ggttacaatt gagtttgatc acaagaagaa tgagaaagaa aagaagcgat   2820
ccaagcgcaa gagctcaaat gaacacaaat gtcgctctct ctagtcacta tttgatttgg   2880
agtgattccg gacttgggag aggatttgat cttttggagt gtctagaatt gaatgctata   2940
gctcttgtaa tatgttgaag gtgggaaact tggatgccat tgaatgtggg gtggttgggg   3000
tatttatagc cccaaaacac caaaaaaggc cgttggaagg ctgctctcgc atggcgcacc   3060
ggacagtccg gtgcgccagc cacgtcagca gaccgttggg gttcgaccgt tggagctctg   3120
acttgtgggg cctctgggct gtccggtggt gcaccagaca ggtcctgtag gatgtctggt   3180
gcgccaactg cacgtgctct gtcctctgcg cgcgcaggcg cgcattaaat gcgttgtagt   3240
caaccgttgc gcgcgaagta gccattgctc tgctggcaca ccggacagtc cggtgaatta   3300
tagcggagcg ccctctgatt ttcccgaagg tagcgagttc agcttcgagt gccctggtgc   3360
accggacact gtccggtgcg ccaaaccagg gtgccttccg ggatgtcttt tgctctcttt   3420
gtttgaaccc tttcttggtc tttttattgg cttattgtga acctttgaca cctgtaaaac   3480
ttatagacta gagcaaacta gttagtccaa ttatttgtgt tggacaattc aaccaccaaa   3540
atcaattagg aaataggtgt gagcctaatt ccctttcaat ctcccccttt ttggtgattg   3600
atgccaacac aaaccaaagc aagtatagaa gtgcataatt gaactagttt gcataatgta   3660
agtgcaaagg ttacttagaa ttgaaccaat aaatattttc ataagttatg catggattgt   3720
ttctttattt tcatcatttt ggaccacgct tgcaccacat gttttgtttt tgcaaatcct   3780
tttgtaaata gtcaaaggta aatgaataag attttgagaa gcattttcaa aatttgaaat   3840
tttctccccc tgtttcaaat gcttttcctt tgacttaaac aaaactcccc cctcaaaaat   3900
cctactcata gtgttcaaga gggttttaag atatcaattt tgaaaatgct actttctccc   3960
ccttttgaat ataataagat atcaattgaa aaattcatca ttttaaaacc ttttgaaaat   4020
```

```
gggtggtggt gcggtccttt tgctttgggc taatactttc tccccctttg gcatgaatcg   4080
ccaaaaacga atacttgagt gaaatataag ccccttttaac tactttctcc tgctttggcg   4140
aacataatat gagtgaagat tataccaaag ttggagagtt gcttgaagcg atggtgaagg   4200
atgagttatg gagtggaggt taagcctttg tcttcgccga agattccaat tccctttcaa   4260
tacacctatg acttggttga aaatatactt gaaaacacat tagtcatagc acatgaaaga   4320
gatatgatca aaggtatatt aatgagctat gtatgcaaga catcaaaaga aattcctaga   4380
atcaagaata tttagctcgt gtctaagttt gttcatctag tggcttggta aagatatcag   4440
ctaattgttc cttagtgtta atataggcaa tctcgatatc tcccttttttt tggtgatccc   4500
ttaggaaatg ataccgaatg gctatgtgtt tagtgcggct atgctcaacg ggattatccg   4560
ccatgcggat tgcactctca ttatcacata gaagaggaac tttggttaat ttttaaccat   4620
agtccctaag ggtttgcctc atccaaagta attgtgcgca acaatggcct gcggcaatat   4680
actcggcttc ggcggtagaa agagctacgg aattttgctt ctttgaagcc caagacacca   4740
gggaccttcc caagaactgg caagtcctcg atgtactctt tctattaatt ttacaccccg   4800
cccaatcggc atccgaataa ccaatcaaaa tcaaaatgtg gatcccgtag gataccaaag   4860
cccaaactta ggagtatgaa ctaaatatct caagattcgt tttacggccg taaggtgagc   4920
ttccttaggg tcggcttgga atcttgcaca catgcatacg gaaaagcata atatccggtc   4980
gagatgcaca taaatagagt aaagagccta tcatcgaccg gtatacccttt ttgatcgacg   5040
gatttacctc ccgtgtcgag gtcgagatgc ccattggttc ccatgggtgt cttgatgggt   5100
ttggcatcct tcatcccata cttgtttaga atgtcttgaa tgtacttcgt ttggctaatg   5160
aaggtgccct cttagcgttg cttcacttga aatcacaaga agtacttcaa ctcccccatc   5220
atagacatct cgaatttctg tgtcatgatc ctactaaatt cctcacatgt agattcatta   5280
gtagacccaa atataatatc atcaacataa atttggcata caaacaaatc attgtcaaga   5340
gttttagtaa ataaagtagg atcggccttt ccgactttga aaccattagt gataaggaaa   5400
tctctaaggc attcatacca tgctcttggg gcttgcttga gcccataaag cgccttagag   5460
agtttatata cgtgattagg gtactcacta tcttcaaagc cgggaggttg ctcaacatag   5520
acctcttcct tgattggtcc gttgaggaag gcacttttca cgtccatttg ataaagcttg   5580
aagccatggt aagtagcata ggcaagtaat atgcgaattg actcaagcct agctacgggt   5640
gcataggttt caccaaaatc caaaccttcg acttgtgaat aacccttggc cacaagtcgg   5700
gctttgttcc ttgtcaccac accatgctca tcttgtttgt tgcggaagac ccacttggtt   5760
cctacaacat tttggttagg acgtggaact aaatgtcata cctcattcct agtgaagttg   5820
ttgagctcct cttgcatcgc caccacccaa tccgaatctt gaagtgcttc ctctaaccta   5880
tgtggctcaa tagaggaaac aaaagagtaa tgttcacaaa aatgagcaac ccgagatcta   5940
gtagttaccc ccttatgaat gtcgccgagg atggtgtcga cggggtggtc tcgttggatt   6000
gcttggtgga ctcttgggtg tggcgggcgt tgctcgtcct ccttgtcttg atcatttgca   6060
tctccccctt gatctatgcc gtcatctaga ggtggctcat ttgattgatc ttcttcttca   6120
tcaacttgag cttcatcctc attttgagtc ggtggagatg cttgcatgga ggaggacggt   6180
tgatcttgtg tatttggagg ctcttcggat tccttaggac acacatcccc aatggacatg   6240
ttccttagcg cgatgcatgg agcctcttca tcacctatct catcaagatc aacttgctct   6300
acttgagagc cgttagtttc atcaaacaca acgtcacatg aggcttcaac tagtccagtg   6360
```

```
gacttgttaa agaccctata tgcccttgtg tttgagtcat aaccaagtaa aaagccttct   6420
acagtcttag gagcaaattt agattttcta cctcttttaa caagaataaa gcatttgcta   6480
ccaaaaactc taaaatatga aatattgggc tttttaccgg tgaggagttc gtatgatgtc   6540
ttcttgagga ttcggtgtag atataaccgg ttgatggcgt agcaagcggt gttgactgcc   6600
tcggcccaaa accgatccga agttttgtac tcatcaagca tggttcttgc catgtccaat   6660
agagttcgat tcttcctctc cactacacca ttttgttgtg gcgtgtaggg tgaagagaac   6720
tcatgcttga tgccctcctc ctcaagaaag ccttcgattt gagagttctt gaactccgtc   6780
ccgttgtcgc ttctaatttt cttgatcctt aagccgaact cattttgagc ccgtcttaag   6840
aatcccttta aggtctcttg ggtttgagat ttttcctgta aaaagaatac ccaagtgaag   6900
cgagaataat catccacaat aactagacag tacttactcc cgccgatgct tatgtaagcg   6960
atcgggccga atagatccat gtgtaggagc tccagtggcc tgtcggtcgt cattatgttc   7020
ttatgcggat gatgagagcc aacttgcttc cctgcttggc atgcgctaca aatcctgtct   7080
ttctcaaaat aaacatttgt caatcctaaa atgtgttctc cctttagaag cttgtgaaga   7140
ttcttcatcc caacatgtgc aagtcggcga tgccagagcc aacccatgtt agtcttagca   7200
attaagcaag tgtcgagttc agctctatcg aaatctacca agtatagctg accctctaac   7260
actcccttaa atgctattga atcatcactt cttctaaaga cagtgacacc aacatcagta   7320
aaaagacagt tgtagcccat ttgacacaat tgggatacag aaagcaaatt gtaatctaaa   7380
gaatctacaa gaaaaacatt ggaaatagaa tggtcaggag atatagcaat tttacccaat   7440
cctttgacca aaccttgatt tccatcccca aatgtgatcg ctctttgggg atcttggttt   7500
ttctcatatg aggagaacat ctttttctcc ccagtcatgt ggtttgtgca cccgctgtcg   7560
agtatccagc ttgagccccc ggatgcataa acctacaaaa taattttagt tcttgatttt   7620
aggtacccaa atggttttgg gtcctttggc attagacaca agaactttgg gtacccaaac   7680
acaagtcttg gagcccttgt gcttgccccc aacatatttg gcaactacct tgccggattt   7740
gttagtcaac acataagatg catcaaaagt tttgaatgaa atgtcatgat catttgatgc   7800
actaggagtt ttctttctag gcaacttggc acgggttggt tgcctagagc tagatgtctc   7860
acccttatac ataaaagcat aattaggacc agagtgagac ttcctagaat gaattctcct   7920
aattttgttc tcgggataac cggcagggta taaaatgtaa ccctcgttat cctgaggcat   7980
gggagccttg cccttaacaa agttggacaa tcttttagga ggggcactaa ttttgacatt   8040
gtttcccctt tggaagccaa tgccatcttt aatgcccggg cgtctcccat tataaagcat   8100
gccacgagca aatttaaatt tctcattttc taagttgtgc tcggcaattt tagcatctag   8160
ttttgctata tgatcatttt gttgtttaat taaggtcata tgatcatgaa tagcattaac   8220
atcaacatct ctacatctag tacaaataga tacatgctca acagtagatg tagagggttt   8280
gcaagaatta agttcaacaa tcttagcatg aagaatatca tttttatccc taagatcgga   8340
aattgtagtt ttgcaaacat caaaatcttt agccttagca attaaatttt catttttctg   8400
ttctaaggct agcaagagaa atgtttaatt cttcaatcct agcaagcaaa tcatcattat   8460
tatctttagg attgggaatt gaaacattac aaacatgtga atcaacctta gcatttaaac   8520
tagtattttc atgtctaagg ttgtcaatca tctcatggca agtgcttagc tcactagata   8580
gtttttgaca tttttctact tctagggcgt aagcattttt aaccttaaca tgtttcttgt   8640
tttccttaat aagacaatcc tcttgggaat ccaaaaggtc atctttttca tgaatagcac   8700
taattaattc atttaatttt tccttttgtt ccatgttaag attagcaaaa agggtacgca   8760
```

```
agttatcctc ctcatcacta gcattttcat cactagaggt ttcatattta gtggaggatc   8820
ttgattttac cttcttcctt ttgccgtcct ttgccatgag gcacttgtgg ccgacgttgg   8880
ggaagaggag tcccttggtg acggcgatgt tggcggcgtc ctcgtcgtcg gaggagtcgc   8940
ttgagctttc gtcggaatcc cactcccgac aaacatgggc atcgccgccc ttcttcttgt   9000
agtacttctt cttctccttt cttctcccct tcttgtcgtc gccacggtca ctgtcactag   9060
atatgggaca tttagcaata aaatgaccgg gcttaccaca tttgtagcaa accttcttgg   9120
agcgggactt gtagtctttc cccctccttt gtttgaggat ttggcggaag ctcttgatga   9180
cgagcgccat ttcctcattg tcgagcttgg aggcgtctat tggttgtcga cttggtgtag   9240
cctcctcctt cttttcttcc gttgccttga atgcgacggg ttgagcttcg gatgtggtgg   9300
gttcgtcaag ctcattgatc tttctcgagc cttcgatcat gcactcaaaa cttacaaaat   9360
gcccgataac ttcctcgggg gtcattttag tatatctagg attaccacga attaattgaa   9420
cttgagtagg gttaaggaaa ataagtgatc ttagaataac cttaaccacc tcgtggtcgt   9480
cccactttat gctcccgagg ttgcgcactt ggttcaccaa ggtcttgagc cggttgtaca   9540
tgtgttgtgg ctcctcccct ttgcgaagcc gaaaccgacc gagctccccc tcgatcgttt   9600
cccgcttggt gatctttgtg agctcgtctc cctcgtgcgc ggttttgagc acatcccaaa   9660
cctccttggc gctcttcaac ccttgaactt tgttatactc ctctctactt aaagaggcga   9720
ggagtattgt tgttgcttga gagttgaagt gctcgatttg ggccacctca tcctcatcat   9780
aatccttatc ccctacggat ggtacctgtg caccaaactc aacaacatcc catatacttt   9840
tgtggagtga ggttagatga aatcgcatta aatcactcca cctagcataa tcttcaccat   9900
caaaagttgg tggtttgcct aacgggacgg aaagtaaagg tgcatgttta gaaatgcgag   9960
ggtagtgtag gggaatctta ctaaacttct tacgctcttg gcgtttagaa gttacggagg  10020
gcgcgtcgga gccggaggtt gatgttgatg aagtgtcggt ctcgtagtag accactttcc  10080
tcatcctctt ttgtttgtcc ccactccgat gaggcttgtg ggaagaagat ttttccttct  10140
tctctttgtg gtgagaagaa gatttcttct ccttcccttt gttggaggag ctcttcttct  10200
tctccctccg tttggtgcgg gactcttcca atgaagtgct ctcgttgctt gtagtgggct  10260
tttcgccggt ctccatctcc ttcttggcgt gatctcccga catcacttcg agcggttagg  10320
ctctaacgaa gcaccgggct ctgataccaa ttgatagtcg cctagagggg gggtgaatag  10380
ggcgaaactg aaatttacaa atataaacac aactacaagc cgggttagcg ttagtaatga  10440
agaaacgagt ccgcgagaga gggcgcaaaa caaatcgcaa gcaaatgaag agtgtgacac  10500
gtggatttgt tttaccgagg ttcggttctc gcaaacctac tccccgttga ggaggccaca  10560
aaggcccggg tctctttcaa cccttccctc tctcaaacgg tccctcggac cgagtgagct  10620
tctcttctct aatcaaagtt gggaacaaaa cttcccaaca agggccacca cacaattggt  10680
gcctcttgcc ttgattacaa tgggtttttg atcacaagaa caagtgcgaa agaaaagaag  10740
caatccaagc gcaagagctc aaaaagaaca cggcaaatct ctctctctaa tcactaaagc  10800
cttttgtgga attggagagg atttgatctc ttttggtgtg tctagaattg aatgctagag  10860
ctcttgtagt agttgagaag tggaaaactt ggatgcaatg aatggtgggg tggttggggt  10920
atttatagcc ccaaccacca aacttgaccg ttggctgggt tgtctgttcg atggcgcacc  10980
ggacagtccg gtgcacaccg gacagtccgg tgcccctgcc acgtcatcac tgccgttgga  11040
ttctagccgt tgaagcttct gacttgtggg cccgcctggg tgtccggtgc acaccggaca  11100
```

-continued

```
tctactgttc cttgtccggt gtgccggagt gggcgcgcct gacatctgcg cgcgcagagc  11160
gcgcattaaa tgcgcggcag agagccgttg gcgcggaaat agccgttgct ctcgagtcgc  11220
accggacagt ccggtgcaca ccggacagtc cggtgaatta tagtggacgg gccgatggct  11280
tttcccgaag ctggcgagtt cctgaggccg acctcccttg gcgcaccgga cactgtccgg  11340
tgtacaccgg acagtccggt gaattatagc ggagtcgcct ctggcaattc tcgaaggggg  11400
cgagttggag cttgagtcct ctggtgcacc ggacgctgtc cggtgtacac cggacagtcc  11460
ggtgctctca gaccagaggg ccttcggttc ccactatgct cctttgttga atccaaaaac  11520
ttggtccttt tattggctga gtgtgaacct tttacacctg tgtaatctat aaacttgtgc  11580
aaacttagtt agtccaattg tttgtgttgg gcaattcaac caccaaaatt aattagggac  11640
taggtgtaag cctaattccc tttcagtttt cccgggcggt catccataga acaggtcctt  11700
acggagaggc actcgagaaa ccgctcgagc cccccttgaag accacaagca caacatcata  11760
ataagagaag ggaaaacagc gtatcataga taatctcatc atgttcattg attagagtta  11820
agcaatagca taaagctaaa cagtaatat ccaacccaaa taggtgaaca aggacatgga  11880
taacaaaagc tagtcaatcc ttaggcataa atgtgtaaag cgggaggtga attaaataat  11940
gaataggaca tagataggtc aagggacact tgcctccacc aaccgactgc tgctcagggg  12000
cttctcctgc gggttcctcg ggctcttcaa ccggatcgtt ctctatgcga gcgcaaacat  12060
acacacatcc acatatttaa taccaaagaa cagtacacca tacaatagaa tgcaataagt  12120
aaacagacgt tccacgcggg ctcgcgagta cggttaagag agaaagagga aaagacagtc  12180
gagaaacgat cacgttgcat gattataaat tagccactag cttaatggaa ggaaatttaa  12240
tgtagacact atgtttagcg taaagtaaag tcatgtttca tgtctaatta ttataagcag  12300
gtggagacaa ataaaaggat agccgcgcgg cgagacgcgc gacaaagctc tctaaaacaa  12360
attaagaagt taacgactcg tcgcgcgact gagcacgcag cgagacactt cgccttagtt  12420
aagaggagac gttaagcgtc gcgcgacgaa gcgcacgacg gcatacgtcg actaaactga  12480
gtccaaagtg gaacgtcgcg tcaattccca cgcggcgtta caccttaaac aacctgaaac  12540
aaaatgaacg aatcaagcct gatcatccgc ccccccnnn nnnnnnnnnn nnnnnnnnnn  12600
nnnnnnnnnn nnnnnnnnnn nnnnnnnnnn nnnnnnnnnn nnnnnnnnnn nnnnnnnnnn  12660
nnnnnnnnnn nnnnnnnacc gttcaacaaa caccgcccgg ggttccaacc gaccaggctc  12720
cagatcgccc gaccgatccc ccgtcccggc ctcgcccccc cccttcttcg ctcgcccgcg  12780
ctcgcggtga ttgctcgtta agaagcgtgt tgcgtcgcgc gcttcgccgc gcgacggatt  12840
tatctaaaat tcagattcta tcctgtgttg cgtcgtgcgt ttcgtcgcgc gacgatccat  12900
tttgtttcag gttgtttaag gtgtaacgcc gcgtgtgtat tcacgcgacg ttccactttg  12960
gactcagttt agtcgacgta tgccgtcgtg cgcttcgtcg cgcgacgctt aacgtctcct  13020
cttaactaag gcgaagtgtc tcgctgcgtg ctcagtcgcg cgacgagtcg ttaacttctt  13080
aatttgtttt agagagcttt gtcgcgcgtc tcgccgcgcg gctatccttt tatttgtctc  13140
cacctgctta taataattag atatgaaaca tgactttact ttacgctaaa catagtgtct  13200
acattaaatt tccttccatt aagctagtgg ctaatttata atcatgcaac gtgatcgttt  13260
ctcgactgtc ttttcctctt tctctcttaa ccgtactcgc gagcccgcgt ggaacgtctg  13320
tttacttatt gcattctatt gtatggtgta ctgttctttg gtattaaata tgtggatgtg  13380
tgtatgtttg cgctcgcata gagaacgatc cggttgaaga gcccgaggaa cccgcaggag  13440
aagcccctga gcagcagtcg gttggtggag gcaagtgtcc cttgacctat ctatgtccta  13500
```

```
ttcattattt aattcacctc ccgctttaca catttatgcc taaggattga ctagcttttg  13560
ttatccatgt ccttgttcac ctatttgggt tggattatta ctgtttagct ttatgctatt  13620
gcttaactct aatcaatgaa catgatgaga ttatctatga tacgctgttt tcccttctct  13680
tattatgatg ttgtgcttgt ggtcttcaag gggctcgag cggtttctcg agtgcctctc  13740
cgtaaggacc tgttctatgg atgaccgccc gggaaaacag tgcaaccatg agggtggaat  13800
ggggtgccct tagctgaata attagaggat ccggggtgta gttcacttag ccgtcgtgcc  13860
gtcaatgggg ctcggtgtat gcggctcgct ctgccaagtt tgggttcgcc ccttggggag  13920
gagtgcggtg catttaggaa acctaacggg tggctacagt cccggggaat ctttgtaaag  13980
gctatgtagt gatgccctgc tgggtcacct tggtagtgat caatggagag tcatgatctc  14040
cgggtagaat gggaatcacg gcttgtgggt aaagtgcaca acctctgcag agtgtttgaa  14100
aactgatata tcagccgtgc tcacggttat gagcggccaa gggagctcca gtgattagtg  14160
gtacttgatc agagatactt tggtacaggt ggttatgaga tcgatgattc tggttatgac  14220
tatgatgctg gtaagtggta ctctttccgt ttggaaagga gtacgtttgg gttaataact  14280
tgggttaatg ctaaaacttg gctttctatt agtaaataat aatctgacca actaaaagca  14340
actgcttgac ttatccccac ataaagctag tccactacag ccaaacagga tacttgctga  14400
gtatgttgat gtgtactcac ccttgctcta cacaccaaac cccccccca tccccaggtt  14460
gtcagcattg caaccactgc tcagtcgaag atgaagctgt ggaaggagac ttccaggagt  14520
tccaagatta cgatgagttc taggtgtggg ttagcggcaa cccccagtcg gctgcctgtg  14580
aaggccgcgg ttatctacgt ttcttttccg cactttgatt tattgtaaga actatatgga  14640
cgtctcagac gtatgatgta atcgactatt tcccttagta atactatttt gagcactgtg  14700
tgatgatgtc catgttatgt aactgctgtg tacgtgaata actgatcctg gcacgtacat  14760
ggttcgcatt cggtttgcct tctaaaaccg ggtgtgacat aagtggtatc aaagccgtgc  14820
tgactgtagg accgctaacc tagaatagaa tggtcgctct aaggactata gacctctgtc  14880
tctgccttga ctttgatatc ccttcaaaag ttggtcatac cgaccaaacc tatgttctac  14940
tatatattat accttgctga aaatcatgtt ttattccagt ccttcattta cttatgattc  15000
attatttgct ggtcatatta attctgttct cacctttttg cttgcgatgt cttttgtaga  15060
tggctcgact tagacacact gcacgaaagt cagtcatccc cttcttaccc tcccgccttg  15120
ctgagcgtcc gcttcgccgt cccgtggccg gacagtccag ccacttggag agactacacc  15180
accgcctgcg tgaggagcag gagcgtcgac gacaggagca gcagagctct tccttctcgc  15240
tccaccagga gatagagtct gtgaggagct gctcccctgt gcttcctctg gagccgcccc  15300
ctccaccacc actgggcgcc ccagcttctg gagtagctgc tggaggagac ccagacgatg  15360
gagatggcga cgacagctcg agccacgaca ccgacttctc tgctaacctt gagccggaag  15420
gatgggttac tcgacccatc actcgcgacg ctgctcgcgg gtgtcacttc cacgatgcgc  15480
tcgacaccct gctacgtcgg gcatttaacc agcatacttg gtctgtcgag tatcgctgtg  15540
tggtctacca gcacagtcgc ggggtctacc cggaccgctg ggaggcaacc tgcttggtgc  15600
gctgcccgga gaacagtctc cagggtgcgg aggcctgctc agagcactat tctatctctg  15660
agcgggactc agctgaggca gccatgcaag atgctgcacg gcgtgcgctt tcgcactact  15720
gctcggtttt cggtggggca gctgacggtc ttgacctgaa gtattacccc cgccgtccat  15780
ctggcagcac aggaggcgtg attgtctcac ctgtcggtga gggcaatcct aggttgagca  15840
```

```
gcacagtcaa cctagccgcc gtgctaaaca cggagctgga ccatgcatta gacgagctga  15900
gtagggctcg tgctgagatc gccctgctgc gggctgagcg cgcggaacgt cgtcacctgg  15960
atggtggttc ccccgctccc gtcgggactc agcacccgta ccgctcacct cagcgtggac  16020
accagtctta tggcaatccc gcctgcaaga ccaagataac tctagaacca tatatcgtta  16080
gagttggatc ttgtaattaa tacgaaatat atacatagaa gcttcagtct tagcgttagt  16140
ctcggtctta gttagtctta gttaaacagg gtagtttgct atatcctgtg catttatgtt  16200
tgtcatgatg aactatgttt ggtttggatc tttgtaatga ttgtcaccag agtgtgggta  16260
ccccctgcat tttggtttac ctattatgtt aatagagtta gttatatagt tgggaaacct  16320
tttattccac tctcctcttt atctgagaaa ctgtgtggtc tgtgttggag atcagtgaag  16380
atgctcatct gttcagtgct gttgaagaat tctattctct tttcttatgc tgcaagattt  16440
gccagatcag tcctgatgtg tggttgcatt ctgcagatgt cagagaacag gcgcagagga  16500
ggaaggcgtg ctcagcagga gcgagccgct caacaggagg aggtgcccca gcagcagcac  16560
ctgccgcccc cgcccccgat gtccatcgag cagatgtttc tgatgcagac tcaggcagtt  16620
caagccatcg gtcagactct ggccgccatt cagcagcagc agcagcagca ggccccacct  16680
caacctcaga tgcctcagat gcccagagac aagcgtgctg aattcatgag aggtcatcca  16740
ccaacgttcg ctcattcttc tgaccctatg gatgctgaag attggctgcg cactgtggag  16800
cgggagttgc ataccgctca gtgcgatgac agggagaaag tcctgtatgg tccccgtctg  16860
ttgagaggag cagcccagtc atggtgggag tcttacctcg ccacccatgc ccatcctgac  16920
gccatcacct gggaagagtt cagaggtagc tttcgtcagt accatgttcc tgcaggtctg  16980
atgacagtga agaaggagga gttcctggcc ctcaaggaag ggccattgtc tgtcagtgag  17040
taccgagaca ggtttctgca attgtctcgc tatgctcctg aagatgtcaa caccgacgcc  17100
aagcgacagt accgtttcct gagaggcttg gttgaccctc tgcagtacca actgatgaat  17160
cacaccttcc cgacattcca gcacctgatt gacagagcaa tcatgacaga aggaagcgta  17220
aggagatgga agatcgtaag cgcaagatca gtggacccca gcctggaagc agcaatcgtc  17280
ctcgtttctc aggcaatcaa cctcagcagt tcaggcagaa ccagcgtcca cctcagcagc  17340
agcagcaatt ccaaaggcag tatcctcagc accagtacca gaaccgtcag agcaatcagt  17400
caggaggtca gtttcagagg cagaatcagc aagcacctcg tcttcctgcc ccagcaaatc  17460
agcagaacag tcaggcagca ccagctcagg ttggaaacag agcatgtttc cactgtggag  17520
agcaaggcca ctgggtgatg caatgtccga agaaggcagc ccagcagcag tcaggcccca  17580
atgccccagc gaagcagaat gtgcctcagc ctggagcagg caatcgctct cagccgcgct  17640
ataatcatgg aaggctgaac cacttggagg ctgaagcagt gcaggagacc cccggcatga  17700
tagtaggtat gttcccagtc gactcccata ttgcagaagt gttatttgat actggagcaa  17760
cgcattcttt cattactgca tcatgggtag aagcacataa ccttccaatt actaccatgt  17820
caacccccat tcaaattgac tcagccggtg gtagaattcg agccgatagc atttgtttga  17880
atataagtgt ggaaataagg gggatagcgt ttcccgccaa ccttatagta atgggtactc  17940
aggcaataga tgtcatccta gggatgaatt ggctagataa gtatcaggca gttatcagtt  18000
gtgataaaag gaccatcaag ttggtgtccc cactaggaga ggaagtggtg accgagttag  18060
tcccgcctga gccaaagaaa ggaagttgtt atcagatagc tgttgatagc agtgaagcag  18120
acccaatcga gaggatcaag gttgtgtccg agttcccaga tgtgtttcca aaggacttac  18180
cgggtatgcc accagagcgg aaagttgagt ttgctataga gcttcttccc ggaaccgccc  18240
```

```
ctatctttaa gagagcttac agaatatctg gaccagagtt ggttgagctt aagaagcaga  18300
ttgatgagct gtcagagaaa ggttacattc ggccaagcac ctcgccttgg gccgcccctg  18360
tcctatttgt ggagaagaaa gatggcacca agaggatgtg tatcgattat cgagctttga  18420
atgaagtcac gatcaagaac aagtatccct tgcccagaat agaagatttg ttcgaccagt  18480
tgagaggagc cagtgtgttc tccaagattg atctgaggtc aggttatcat cagctcagga  18540
tccgaccttc ggacattccg aagacggcat tcatttccaa gtatggtttg tatgagttca  18600
cagtgatgtc ttttggtttg accaatgcgc cagcgttctt catgaacttg atgaacagtg  18660
tattcatgga ttatctcgat aagtttgtgg tggtattcat tgatgacatt ctggtttatt  18720
ctcaaagcga agaagagcac gcagatcatt tgaggttggt attgcagaga ttgcgagagc  18780
atcagttgta tgcaaagttg agcaagtgtg agttctggat cagtgaggtc ctgttcttgg  18840
gtcacataat caacaaagaa ggattggttg tggatccgaa gaaagtggca gacattttga  18900
actggaaagc gccaacagat gctagaggaa tcaagagttt cattggaatg gccggatact  18960
atcggcgatt cattgaaggg ttttcgaaga tcgcaaaacc aatgacagcg ttgctaggca  19020
acaaagttga gttcaagtgg acccagaaat gtcaagaggc ctttgaagcg ctgaaagaga  19080
agttgactac agcgcctgtc ctagtcttgc ctgatgtgca caagcccttc tcagtgtatt  19140
gtgatgcttg ttacacaggt ttgggatgtg tgttgatgca agagggaaga gttgtggctt  19200
actcgtcccg acaactgaag gttcatgaga agaattaccc aatccatgat ctagagttgg  19260
cagcagtggt tcacgcactg aagtcatgga ggcactatct gtatggacag aaatgcgatg  19320
tttacacaga tcacaagagt ctgaagtaca tattcactca gtcagagttg aacatgaggc  19380
aacgaagatg gttagagttg atcaaagatt atgagttgga gattcattac catccaggca  19440
aagcaaacgt agtggcagat gctttgagca gaaagagtca agtcaatctg atggtcgctc  19500
gtccgatgcc ttatgagttg gccaaagagt ttgacaagtt gagtctcggt tttctgaata  19560
attcgcgagg agtcaaagtt gagttggaac ctaccttgga gcgcgaaatc aaagaagcgc  19620
agaagaatga tgagaaaatc agcgagatcc ggcgactgat tctagatggc aaaggcaaag  19680
aatttcgaga agatgcagaa ggcgtgatat ggttcaaaga ccgcttgtgt gttcctaatg  19740
tccagtctat tcgggagttg attctcaagg aagctcatga gacgtcctat tcgattcacc  19800
ctggcagtga gaagatgtat caggatctga aaaagaaatt ctggtggtac ggaatgaaga  19860
gggagatcgc agagcatgtg gctaggtgcg atagttgccg aagaattaag gcagagcacc  19920
agagacctgc tggattgttg caaccattgc agatccctca gtggaaatgg gacgaaatcg  19980
gtatggattt catagtcgga ttgcctcgca ctcgagccgg ctacgattcc atctgggtag  20040
tagtggaccg cttgaccaag tcagcccact tcatacctgt caagaccaac tacagcagtg  20100
cagtattggc agaattgtat atgtctcgga tcatttgtct tcatggtgtg ccaaagaaga  20160
tagtgtcaga cagaggaacg cagttcacct ctcatttctg gcagcagttg catgaagctt  20220
tgggcacgca tctgaatttc agttcagctt atcatccaca gacagatggc cagaccgaaa  20280
ggaccaacca aattcttgaa gatatgttga gagcctgtgc gttgcaagat cagtccggat  20340
gggataagag attgccttat gcagagtttt cctgtaacaa cagttaccag gccagcttga  20400
agatgtcacc atttcaggcg ctctatggaa ggagttgtag aactccgttg caatgggatc  20460
agcctggaga aaagcaagtg tttgggccag acattttgct tgaagccgaa gagaacatca  20520
agatggtccg agagaatctg aagatagcgc aatcgaggca gcgaagctat gcagacacaa  20580
```

```
gaagaagaga gctgagtttc gaagtcggag actttgtcta tctgaaagtg tcaccaatca  20640
gaggagtcag aaggttcgga gtgaaaggca agctagcacc ccgctacatt ggtccgtatc  20700
agattcttgc aagacgtgga gaagtggcct atcagctcag tttgccagag aatttgtctg  20760
ctgtgcatga tgtctttcat gtgtctcagt tgaagaagtg cttgcgtgtg ccagaagagc  20820
agttgccagt agaaggtctt gaagtccagg aggacttgac ctacgttgag aagccagtgc  20880
aaatccttga ggttgcagac cgagtcacct ggaggaagac catcagaatg tgcaaagtca  20940
gatgggatca tcactctgag gaagaagcaa cctgggagcg tgaagatgat ctgatggcca  21000
agtaccctga gctctttgct agccaaccct gaatctcgag ggcgagattc ttttaagggg  21060
gataggtttg taacgccctg aatttggggg tagaattttt cttcttttct ctcaccaaat  21120
tcgggcgtta ctctcttttc tctttccccg tttgctcctt cttcccaatt tcaaaccagt  21180
atagcggcag gtgtccgtgt catgtataaa ccaaaaccta agtgtcatgg gtgttgcatc  21240
atgccgaagc acatttcttt gtctgatgtt gagtgttcgt ctcgttccgt tccggatttc  21300
ggttcgcgat ttaattccgt ttagtggtcc gcgctcgtcg cgggttttcg atccgcgaag  21360
tggcccgacc catcccaacc tagtccagcc cagcccagcc ggcccggccc gccccggcct  21420
gcgcgcccct ggcgcccaaa ccccccatg cgcccccct cctctctctc tctcatttgg  21480
atctcccgcg caacaacctc tcctctccct cttccacctc tctctccccg tggtgcccta  21540
ggatttggag acggcgatca ccggattttg gaccccgagg tgagctcccc tcccctcccc  21600
ttctcttctc tctctctctc cctcctcttc ttctccccac gcgcgccccc cttctccccc  21660
tgctcacgcg cgcccctgcc cgcccccgct caccggcggc gcggcgcccc ccgcccctgc  21720
ccggccccgc gcggcggcgc ccgccctccc ccggccgcgg cggcgctcgt ccgccctcac  21780
ccccggccgc ggcgcccgcc cctccccctc gcgcgcggag gcggcgcccg ccctcaccac  21840
gacccgcagc gaccccgccc cgtccccgcc tctcccccg cgcgcggcgg cgcccgcccc  21900
ccgcccctcc ccgcggcggc gctcgcccgc ccgcccctgc ccctccccgc ggcggcgccc  21960
gcccgcccct gctcgcgcgc agcgcggccc cggcgcgccc ccggcatggc ccggcgcggc  22020
cccggtggcc cctgctcgcc ggcgcgaccc cggcgtggcc cccagccccc ggcgcgtccc  22080
cggcgcggcc ccggccggct cggccgcccc tggccggttc aaccgccccc cctggccggt  22140
tcaaccgccc tggccccagc tcgcccgccc gttcccccgt cccggcctcg cccgaccgta  22200
tcttcgctcg cccgcgctcg cggtgattgc tcgttaatta gcgtgttgcg tcgcacgcta  22260
cgccgcgcga cggatttatc taaaattcag attctatcct gtgatacgta gtacaactga  22320
cnnnnnnnnn nnnnnnnnnn nnnnnnnnnn nnnnnnnnnn nnnnnnnnnn nnnnnnnnnn  22380
nnnnnnnnnn nnnnnnnnnn nnnnnnnnnn nnnnnnnnnn ntgggtcggc gctgagatca  22440
gcttgattcg tttttggtta tacatgacac ggacacctgc cgctatactg gtttgaaatt  22500
gggaagaagg agcaaacggg gaaagagaaa agagagtaac gcccgaattt ggtgagagaa  22560
aagaagaaaa aattctaccc ccaaattcag ggcgttacat caggctacaa aggatgccaa  22620
tggtattgct gctctctata ttgttcttgt tctaatgtaa aaactacaac acaactcttt  22680
acttgatccc agaaattcct tctgcctcaa atggagacaa tgacgagtgg tcataagtac  22740
agagattgca gacaaggtaa attttgcaat agaaataact aaccaaccat tagtgcttga  22800
aaaaaactgg actggtgact ggggcacgtg gtttcatcaa catttggacc tcaacggtct  22860
aatcagtata acttagaagt tggctagctc ttgaaaaaca ctgcatgaca ctaagcattt  22920
gtttatttc agctgcttac acccctatga tttcaagtaa ctacttgtct acttgtgata  22980
```

```
atcacctgaa tatgattatt tgaaatgctt atcatgtctc gtcaattgca tttcttttat  23040
gtgtacctga agtctgctct tgcttcctaa tagagttcgt tttttaatac agaaaccact  23100
ctgagatagc cacaatatag taaaagtggc agctaaggta ctaaaaacac ccatgcaaat  23160
aagaaaaaaa tgaatcttgt attttaattt tgttaaatac ctctatagtt tggcgatata  23220
ttatgttacc atcctgctta tagcctgtag gtcattttat atgagccatc aaattgcgat  23280
gacagttgcc acaaatccag tttcatatga aggtattagc tgtgtaacaa gctaattgtt  23340
gctctctgcc caataagtta ttcaattgga ttagtaggtt gcatccaagg ttattcaatt  23400
ggatcagtag gttgcatcca aggtatactg ctgctctctg cccaataagt tattcaattc  23460
gatcagtagg ttgcatgttc ccttcatttt attaaaaaat acataataat ataataagta  23520
cttgtttgtt ctaaaaataa tacttctgta aatgaggata ttaattttcc ttttggtaat  23580
aatgcaggtt gatgatactg aagtcatcag ttttttgctg caaactgaaa taattcctct  23640
gtgcttgcga accatggaga tgggtagtga gctatccaaa attgtatgta gctagccaaa  23700
tattctcatt caaatatcat aatttatctc ttctgcttaa tactggcaaa ggtgtaatag  23760
tttttttagt attgatttgt cacctgaagt ttatcttgtg cactactact ttgccatcat  23820
cagttatctc tagaatactc ttgtcctgta ccattttctc tctgataagc ctaaatttgt  23880
acaattcata agcctaaaag gtgacttata taatatatac aaggaccctc aagagttgtt  23940
tggcaattca gtgactgtcc tgggtcctgt tttggggagc ttctggtagc ttttgcttct  24000
ccaaaagaaa agctagaagc tccccccaaa cagagcagct tcttcaagcc ggtaaaagct  24060
tcaaaagctg taattatact aaaaacagtg aagctccctc agagcagctt cccagctctc  24120
taggagatgc ttttggagaa gctacagttt ccccaaacag ggccctgctc tgttgaaccc  24180
ccccccttcct gatacatatt tgaatatgag tttatagtgt gtgtgggggt gtaagtaggg  24240
gggtaatggg ttctaaattt tatactataa aaattaagga tcggattaga attgagctct  24300
atttctattc atttttgaac taaaattaat taagggctca aatgaattat gaagaagcat  24360
taggatcatg atccattacc acccctacgt gtaagatgtt ttttggtggt tgtggttgat  24420
tttgaatttt aaggccgcat atgtctcatg gaccacacaa gctcatattc atctacattt  24480
gtagccgtca ctaacttagc caaatatgca tatgtggcgg ctagcaacag gtccttggtt  24540
tcttgggtta tttattctct ttttatcgtg tttgaatgtt ttcgtgttca tttgcataac  24600
atcttaggtc tacattagta tatgaattga gatcaaatgt gaattggacc acacaagctc  24660
atattcatct acatttgtag tcgtcactaa cttagccaaa tatgcatatg tccgcttctg  24720
atttcattgt gtcttttctt caggagtttg gggatcaagg agaggactcc attatcttgt  24780
caccgcgact gaaggagatt agtactcctg accgccccac tgccctccgt ttcctaggta  24840
cacgcataac agccattggt atgaatacat gttttatacg tgaatggagt tccagtttaa  24900
tttaaagatt caagttcact acaacaagat tttacagtac tgagcccatt tgactttcct  24960
tgagaaatag tgaaagggaa ttaggcttac acctagttcc taaataattt tggtggttga  25020
attgcccaac acaaataatt ggactaacta gtttgctcta gtgtacaagt tatacaggtg  25080
ccaaggttca caacaagcca attaaaaaga ccaaagttgg gttcaaaata gagagccaaa  25140
ggcatcccga aaggctccct ggtttggcgc accggactgt ccggtggcgc accggacagt  25200
gtccggtgca ccaggggacc tcgcgcagaa ctcctcagcc tcgggaattt ttcggagccg  25260
ccgcgctata attcaccgga ctgtccggtg tacaccggac agtgtccggt gctccaagaa  25320
```

```
aacgcggctc cggaacttgg cagcctcagg aaatcagaac ggctgctccg ctataattca  25380
ccagacatgt ccggtgtaca ccggactgtc cggtgcaact gcggagcaac ggctacttcg  25440
cgccaacggt cacctgcagg cgcattcaat gcgcgccaga agcgcgcaga agtcaggcac  25500
acccatgctg gcgcaccgga cactctacag tacatgtccg gtgcgccacc ggacatcaag  25560
gcgggcccag aagacagaac tccaacggtc aaattccaac gactttggtg acgtggctgg  25620
cgcaccggac tgtccggtgc accatatgac agacagcctc caccaacggt catgtttggt  25680
ggttggggct ataaataccc caaccacccc accattcatt gcatccaagt tttccagctt  25740
ccaaccacta tataagagct agcattcatt gcaaagcaca ccaaaagaga tcaagtcctc  25800
tcccaactcc acacaaagcc ttagtgatta gagagagtga tttgtagtgt tcatttgagc  25860
tcttgcgctt ggatcgcttc ttttctttgg cattctttct tgtgatcaaa cactcacttg  25920
taattgaggc aagagacacc aattgtgtgg tggtccttgc gggaagtttg attcccaagt  25980
gatttgagaa gagaagctca ctcggtccaa gggaccgttt gagagaggga agggttgaaa  26040
gagacccggc ctttgtggcc tcctcaacgg ggagtaggtt tgagagaacc gaacctcggt  26100
aaaacaaatc cacgcgtctc acttcattat tcgcttgcga tttgttttca cgccctctct  26160
cggactcgtt cttatttcta acgctaaccc ggcttgtagt tgtgtttata tttgtaaatt  26220
tcagtttcgc cctattcacc ccccctctag gcgactatca attggtatca gagcccggtg  26280
cttcattaga gcctaaccgc tcgaagtgat gtcgggagat cacgccaaga aggagatgga  26340
gaccggcgaa aagcccacta caagccacgg gagcacttca tcggaagagt cccgcaccaa  26400
gaggaaggag aagaaagact cctccaaagg gaaggagaag aagaaggact cctccaaagg  26460
aaaggagaag aaatcttctt cacacaaaga aaagaaggag aagtcttcct cccacgagcc  26520
gcaacggagt ggggacaaga aaaagaggat gaggaaagtg gtctactacg agaccgattc  26580
ttcatcgaca tccacctctg gctccgacgc ggcgtccgtc acttctaaac gccaagagcg  26640
taagaagtat agtaagattc ccctacgcta ccctcgcatt tctaaacata cacctttact  26700
ttccgtccca ttaggcaaac caccaacttt tgatggtgaa gattatgcta ggtggagtga  26760
tttaatgcga tttcatctaa cctcactcca caaaagtata tgggatgttg ttgagtttgg  26820
tgcacatgta ccatccgtag gggatgaaga ctatgatgag gatgaggtga cccaaatcga  26880
gcacttcaac tcccaagcca caaccatact cctcgcctct ctaagtagag aggaatacaa  26940
caaggtgcaa gggttgaaga atgcgaaaga aatttgggat ctactcaaga ccgcgcacga  27000
gggtgatgaa ctcaccaaga ttaccaagca ggaaacgatc gagggggagc tcagtcgctt  27060
ccgtcttcgc caaggggagg agccacaaga tatgtacaac cggctcaaaa ccttggtgaa  27120
ccaagtgcgc aacctcggga gcaagaaatg ggatgaccac gaggtggtta aggttattct  27180
tagatcactc atcttcctta accccactca agttcaatta attcgtggta atcctagata  27240
tacactaatg acccccgagg aagttattgg gaattttgtg agctttgaat gtatgatcaa  27300
gggctcaaag aagatcaacg agcttgatga tccctccacg tccgaagcac aaccggtggc  27360
tttcaaggcg acggaggaga agaaggagga gtctacacca agtagacaac caattgacgc  27420
ttcaaagctc gacaacgagg agatggcttt aatcatcaaa agctttcgcc aaatcctcaa  27480
gcaacggaag gggaaggatt acaaatcccg ttcaaagaaa gtttgctaca agtgtggtaa  27540
gcccggtcac tttattgcta aatgtccatt atcaagtgac agtgacaggg ataatgacaa  27600
gaagggcaag aggagagaaa agaagaggta ccacaagaag aggggcggtg atgcccacgt  27660
atgccgcgag tgggactcca acgagagctc caccgactcc tccgacgacg aggacgtcgc  27720
```

```
caacatcgcc gacaccaagg gactcctctt ccccaacgtc ggccacaagt gcctcatggc  27780
aaaggacggc aaaaacaaga aggataaatc taaatcctcc actagatatg aatcctctag  27840
tgatgaaaat gttagtgatg aggaagataa cttgcgatct ctttttgcca acctcaacat  27900
gcaacaaaaa gagaaactta atgaattgat tagtgtcatt catgaaaagg atgatctctt  27960
ggacacccaa gaggacttcc ttattaaaga aaataagaag catgttaagg ttaaaaatgc  28020
ttatgctcta aaagtagaaa aatgtgaaaa attgtctagt gagctaagca cttgccatga  28080
gactataaac aaccttagaa atgagaatgc taatttgtta gctaaggttg attctcatat  28140
ttgtaatgtt tcaagttcca atcctagaga taataatgat gatttatttg ctaggattaa  28200
agatttgaac atttcacttg ctagccttag aaatgaaaat gaaaaattgc ttgctaaggc  28260
taaagatttt gatgtttgca atgttactat ttctaacctt agaagtgaaa acgacatatt  28320
acatgctaag gttgtagaat taaaatcttg caaacctcct acatctatag ttgagcatgt  28380
atctatttgt actagatgta gagatattga tgttgatgct attcatgatc acatgacttt  28440
aattaaacaa caaaatgatc atatagcaaa actagatgct aaaattgccg agcataactt  28500
agaaaatgaa aaatttaaat ttgctagaag tatgctctat agtgggagac gccctggcat  28560
caaggatggc attggcttcc aaaggggaga caatgtcaaa cttaatgccc ctcctaaaag  28620
attatctaat tttgtaaagg gcaaggctcc catgcctcag gataacgagg gttacatttt  28680
gtaccctgcc ggttatcccg agagcaaaat taggaggatt cactctagga agtctcactc  28740
tggccctaac catgctttca tgtacaaggg tgagacatct agctctaggc aaccaaccca  28800
tgttaagttg cctaagaaga aaactcctag tgcatcaaat gaacatagca tttcatttaa  28860
gacttttgat gcatcttatg ttttgactaa caaatccggc aaagtagttg ccaagtttgt  28920
tgggggcaaa cacaagggct ccaagacttg tgtttgggta cccaaagttc ttgtttctaa  28980
tgccaaagga cccaaaaccg tttgggtacc taaagtcaag aactaaaatt gttttgtagg  29040
tttatgcatc cggaggctca agttggatac tcgacagcgg gtgcacaaac catatgacag  29100
gggagaagaa gatgttctcc tcctacgaga aaaaccagga tccccaacga gctatcacat  29160
tcggggatgg aaatcaaggt ttggtcaaag gtcttggtaa aatagctata tctcctgacc  29220
attctatttc caatgttttt cttgtagatt cattagatta caatttgctt tctgtatctc  29280
aattatgcaa aatgggctac aactgtcttt tcactgatat aggtgtcact gtctttagaa  29340
gaagtgatga ttcaatagca tttaagggag tgttggaggg tcagctatac ttagtagatt  29400
ttgatagagc tgaactcgac acttgcttaa ttgctaagac taacatgggc tggctctggc  29460
atcgccgact agcacatgtt gggatgaaga atcttcataa gcttctaaag ggagagcaca  29520
ttttaggatt aaccaatgtt cattttgaga atgacagggt ttgtagcgca tgccaggcag  29580
gaaagcaagt tggagcccat catccacaca agaacatcat gacgaccgac aggccgcttg  29640
agctactcca catggatcta ttcggcccga ttgcttacct aagcatcggc gggagtaagt  29700
attgtcttgt gatagtggat gattattctc gcttcacttg ggtgttcttt ttgcaggaaa  29760
aatctcaaac ccaagagacc ttaaaaggat tcttgagacg ggctcaaaat gagttcgcct  29820
taaggatcaa gaaaataaga agcgacaacg gaacggagtt caagaactct caaattgaag  29880
gcttccttga ggaggagggc atcaagcatg agttctcttc tccctacacg tcacaacaaa  29940
atggtgtagt agagaggaag aatcgaactc tattggacat ggcaagaacc atgcttgatg  30000
agtacaagac tttggatcgg ttttgggctg aggcggtcaa caccgcctgc tacgccatca  30060
```

-continued

```
accggttata tctacaccga atcctcaaga agacatctta tgaactccta accggtaaaa  30120
agcccaatat ttcatatttt agagtctttg gtagcaaatg ttttattctt gttaaaagag  30180
gtagaaaatc taaatttgct cctaagactg tagaaggctt tttactagga tatgattcaa  30240
acacaagggc atatagagtc tttaacaagt ccactggaca agttgaagtt tcttgtgacg  30300
ttgtgtttga tgagactaac ggctctcaag tagagcaagt tgatcttgat gaaataggta  30360
atgaagaggc tccatgcatc gcgctaagga acatgtccat tggggatgtg tgtcctaagg  30420
aatccgaaga gcctccaaat gcacaagatc aactatcctc ctccacgcaa gcatctccac  30480
cgactcaaaa tgaggatgaa gctcaagttg atgaagtaga agatcaagca aatgagacac  30540
ctcaagatga cgacaatgat caagggggag atgcaaatga tcaagacaag gaggatgaag  30600
agcataggcc gccacaccca agagtccacc aagcaatcca acgagatcac cccgtcgaca  30660
ccatcctcgg cgacattcat aagggggtaa ctactagatc tcgtattgca catttttgtg  30720
agcattactc ttttgtttcc tctattgagc cacacagggt agaggaagca ctccaagatt  30780
cggattgggt ggtggcgatg caagaggagc tcaacaactt cactaggaat gaggtatggc  30840
atttagttcc acgtcctaat caaaatgttg taggaaccaa atgggtcttc cgcaacaagc  30900
aagatgagca tggtgtggtg acaaggaaca aagctcgact tgtggccaaa ggatactccc  30960
aagtcgaagg tttggatttc ggtgaaacct atgcacccgt agctaggctt gagtcaattc  31020
gtatattatt ggcctatgat acttaccatg gctttaagct ttatcaaatg gacgtgaaaa  31080
gtgccttcct caatggacca atcaaggaag aggtctatgt tgagcaacct cccggctttg  31140
aagacagtga gtaccctaac catgtctata agctctctaa ggcgctttat gggctcaagc  31200
aagccccaag agcatggtat gaatgcctta gagatttcct tattgctaat ggcttcaaag  31260
tcggaaaagc cgatcctaca ctctttacta aaactcttga aaatgacttg tttatatgcc  31320
aaatttatgt tgatgatatt atatttggat ctactaacga gtccacttgt gaagagttta  31380
gtaggatcat gacacagaaa ttcgagatgt ctatgatggg ggagttgaag tattttctag  31440
gattccaagt caagcaactc caagagggca ccttcattag ccaaacaaaa tacactcaag  31500
atattctaag caagtttgga atgaaggatg ccaagcccat caagacaccc atgggaacta  31560
atgggcatct cgacctcgac acgggaggta agtccgtgga tcaaaagcta taccggtcga  31620
tgataggttc tttactctat ttatgtgcat ctcgaccgga cattatgctt tccgtatgca  31680
tgtgtgcaag attccaagcc gaccctaagg aagcccacct tacggccgta aaacgaatct  31740
tgagatatct ggcttatact cctaagtttg ggctttggta tcctagggga tccacatttg  31800
atttgattgg ttattcggat gccgattggg cagggtgcaa aatcaatagg aagagcacat  31860
ccgggacttg ccagttcttg ggaagatcct tgggtgtctt gggcttcaaa gaagcaaaat  31920
tcggtcgctc tttccaccgc cgaagccgag tatattgccc gcaggccact gttgcgcgca  31980
actgctttgg atgaggcaaa ccctgcggga ctatggttac aaactaacca aggtcccttt  32040
gctatgtgat aatgagagtg caatcaaaat ggtcgacaat cccgtcgagc atagccgcac  32100
taagcacata gccattcggt atcactttt gagggatcac caacaaaagg gagatatcga  32160
gatttcatac attaatacta acgatcaatt agctgatatc tttaccaagc ctcttgatga  32220
acaatctttt aacaaactta ggcatgagct caatattctt gattctagga acttcttttg  32280
ttaaattgca cacattgttc ttttatatac ctttgatcat atctctttta tatgctatga  32340
ctaatgtgtt ttcaagtcta tttcaaacca agtcataggt atattgaaag ggaattggag  32400
tcttcggcga agacaaaggc ttccactccg tacctcatcc ttcgccatca cttcaagcaa  32460
```

```
ctctccgttc tcgggggaga taagcatgag catcaaagaa aaggactttg ggggagaaat  32520
gagcccaaag ccaaaggacc ggacttcgtc tttggtataa tcttaactca tttatttatg  32580
accaaaaggg aaaatagcac ttcgagggct ctaatgattc cgtttttggc gattcatgcc  32640
aaaaaggggg agaaatgagc ccaaagcaaa aggaccgcac caccaccaat ttcaaaaact  32700
tagtgttgaa tatttttcaa tttgtatctt attttcaatt ggtatcttat tgtgttcaaa  32760
agggggagaa agtagtattt taaaatgata tatcaaaaac cctcttgaat actaagagga  32820
ggatctcttt tagggggagt tttgtttaag tcaaaggaaa agcatttgaa acagggggag  32880
aaaatttcaa atcttgagaa tgctttgcaa aaatcctatt catttacctt tgactatttg  32940
caaaagaact ttgaaaagga tttacaaaat aatttgcaaa aacaaaactc gtggtgcaag  33000
cgtggtccaa aatgttatat aaagaaagaa acaatccatg catatcttgt aagtattcat  33060
attggctcaa ttccaagcaa cctttacact tacattatgc aaactagttc aattatacac  33120
ttctatattt gctttggttt gtgttggcat caatcaccaa aaagggggag attgaaaggg  33180
aattaggctt acacctagtc cctaattaat tttggtggtt gaattgccca acacaaacaa  33240
ttggactaac taagtttgca caagtttata gattacacag gtgtaaaagg ttcacactca  33300
gccaataaaa ggaccaagtt tttggattca acaaaggagc atagtgggaa ccgaaggccc  33360
tctggtctga gagcaccgga ctgtccggtg tacaccggac agtgtccggt gcaccagagg  33420
actcaagctc caactcgccc ccttcgggaa ttgccagagg cgactccgct ataattcacc  33480
ggactgtccg gtgtacaccg gacagtgtcc ggtgcgccaa gggaggtcgg cctcaggaac  33540
tcgccagctt cgggaaaagc catcggcccg tccactataa ttcaccggac tgtctggtgt  33600
gcaccggact gtccggtgcg actcgagagc aacggctatt tccgcgccaa cggctctctg  33660
ccgcgcattt aatgcgcgct ctgcgcgcgc agatgtcagg cgcgcccact ccggcacacc  33720
ggacaaggaa cagtagatgt ccggtgtgca ccggacaccc aggcgggccc acaagtcaga  33780
agcttcaacg gctagaatcc aacggcagtg atgacgtggc aggggcaccg gactgtccgg  33840
tgtgcaccgg actgtccggt gcgtcatcga acagacaacc cagccaacgg tcaagtttgg  33900
tggttggggc tataaatacc cccaaccacc ccaccattca ttgcatccaa gttttccact  33960
tctcaactac tacaagagct ctagcattca attctagaca caccaaaaga gatcaaatcc  34020
tctccaattc cacaaaaggc tttagtgatt agagagagag atttgccgtg ttctttttga  34080
gctcttgcgc ttggattgct tcttttcttt cgcacttgtt cttgtgatca aaaacccatt  34140
gtaatcaagg caagaggcac caattgtgtg gtggcccttg ttgggaagtt ttgttcccaa  34200
ctttgattag agaagagaag ctcactcggt ccgagggacc gtttgagaga gggaagggtt  34260
gaaagagacc cggcctttgt ggcctcctca acggggagta ggtttgcgag aaccgaacct  34320
cggtaaaaca aatccacgtg tcacactctt catttgcttg cgatttgttt tgcgccctct  34380
ctcgcggact cgtttcttca ttactaacgc taacccggct tgtagttgtg tttatatttg  34440
taaatttcag tttcgcccta ttcacccccc ctctaggcga ctatcaaaaa cagtgcaacc  34500
atgagggtgg aatggggtgc ccttagctga ataattagag gatccggggt gtagttcact  34560
tagccatcgt gccgtcaatg gggctcggtg tatgcggctc gctctgccaa gtttgggttc  34620
gccccttggg gaggagtgcg gtgcatttag gaaacctaac gggtggctac agtcccgggg  34680
aatctttgta aaggctacgt agtgatgccc tgctgggtca ccttggtagt gatcaatgga  34740
gagtcatgat ctccgggcag aatgggaatc acggcttgtg ggtaaagtgc acaacctctg  34800
```

-continued

```
cagagtgttt gaaaactgat atatcagccg tgctcacggt tatgagcagc caagggagct  34860
ccagtgatta gtggtacttg atcagagata ctttggtaca ggtggttatg agatcgatga  34920
ttctggttat gactatgatg ctggtaagtg gtactctttc cgtttggaaa ggagtacgtt  34980
tgggttaata acttgggtta atgctaaaac ttggctttct attagtaaat aataatctga  35040
ccaactaaaa gcaactgctt gacttatccc cacataaagc tagtccacta cagccaaaca  35100
ggatacttgc tgagtatgtt gatgtgtact cacccttgct ctacacacca aacccccccc  35160
ccatccccag gttgtcagca ttgcaaccac tgctcagtcg aagatgaagc tgtggaagga  35220
gacttccagg agttccaaga ttacgacgag ttctaggtgt gggttagcgg caacccccag  35280
tcggctgcct gtgaaggccg cggttatcta cgtttctttt ccgcactttg atttattgta  35340
agaactatat ggacgtctca gacgtatgat gtaatcgact atttccctta gtaatactat  35400
tttgagcact gtgtgatgat gtccatgtta tgtaactgct gtgtacgtga ataactgatc  35460
ctggcacgta catggttcgc attcggtttg ccttctaaaa ccgggtgtga cacctgatta  35520
ctctcaagca aagcctatag gtagtttaag aggttgagta caatgagaaa catttcaatc  35580
attatttgca aaagaaacat tttgatcata ttaaggaaaa tcataggagt gaaagaaaaa  35640
caatgtgtgc aaataactga acctcctgca gctccatcat gctggccaaa gtatgcttcg  35700
acgaattcaa aatatcatca tatgcttgct ctatctgctt atcatgattg caaccttgtt  35760
cggatgggtt cctggcttcc tgcaacagca cagtagaaaa caaactggag tttagaattc  35820
aacttgagac ttcagagttg aaacaaaacc tgtattcaca tatgtagcac cgatgcatat  35880
acaaatacct ttatcagaaa catgaagata tgtgaataca ttattttctc aataaaagtc  35940
atgatagaat tcatgcaaat ttttttagaa ataaataaat gatgaggcat actacaattc  36000
taaaagcagt agcagtgcaa cacgaacgaa cattcaaatt gccccacatt cttgaaactg  36060
tgctgctttg ctctcgttcc aaaaaaaactc cgctaaagta aaacttggaa aggtctggtt  36120
ttgcgtgagc caccaacacc aaccaaactt tacgtcacta tgacagtttc agcctttcgg  36180
tcccggcgac agccatggcg gacgcggggg tgacaggggg tgctggccaa gctgggtgag  36240
ctgacggagg aggaggcgac gacgctgctg cgcgtggacg ccgagatacg ggcattgtgg  36300
cagaagctgg cctacctgca ggcgctcgta cgcggggccg gccgccagcg ccgcgaccgc  36360
gcaagcgagc tgctcctgct ctggctacgc gagaccagag aggttgcttt cgcgggtggt  36420
tctgccatac atagcggcga tggctcttcc tcccaggact accatatcta cacataacaa  36480
tcatgctctc atgaagttgt gatgtaatag gtcacacgat tttaatgtat aagattgtga  36540
agagtaaatt aattcaaatg aattcatgga catgggacaa ctatgtgtta aaaacagaat  36600
ctcctatgta tcctaaccat gtgtaatgac atgacaaaat gacacttgta tatgagcaat  36660
taaagcatca tactaccttg tagagttctc ttcggcgaat acgttgaatg atttcttttg  36720
ctttcttcag tttattgtta ggagcagtct cgtagacaca gtcaagtcct agcattagct  36780
cactgcgaga gtatcagcca ttccagactc caggagctcc tcccgggtag cctgcctggc  36840
aatgggcgca gatatcctct tgagctcact cttaatgcta ggttgtaggc tccttgcttc  36900
caggtccatc ttccgaatct gcagacacaa aacaaaaaca taaaattact tttcccccaa  36960
cccccaaatt gaagactaag gcacataaac atctcgcaac tccgttggaa caccaaaact  37020
gcaccgacgg aaacgaaaaa tccctaatct ctgcttttct acccattccc caaatgtcgt  37080
atgtcccgtt agccaagggg atccccaaaa cagaacgtgt cacgacatct atttaccagc  37140
gattcagctt cctcaacgcc ggattggatc tcagagagct tctgcttctt cctctctgcg  37200
```

```
gacagaccca ccgaaatcag accaaaacaa acggtcaaca aaagaaggct ttccaagcgg  37260
cgctactgac gctcggctgc ctggccggcg agcctcgcag tcggccctcg atgaaggagg  37320
tggtggagac gctggagcgg gtggaggcga tgaagagccg ggcacgcggc gcgcgtacac  37380
cgcccggttc ctgccccccc ccccccccga cgacgaccat ggcgcttcgc cgatggccca  37440
cttgcctggt cgccccgccg tcgcgtcagc gagcgcgctc agcagctccg tgacccgctc  37500
gtcgaaccgc gtggccacgg cgagcggcac gaggcctggg ttcgtgacgt tgaccggggg  37560
gcggcggggg tgaaagggaa ttaggctcac acctatttcc taattgattt tggtggttga  37620
attgtctaac acaaataatt ggactaacta gtttgctcta gtctataagt tttacaggtg  37680
ccaaaggttc ataataagcc aataaaaaga ccaagaaagg gttcaaacaa aaagagcaaa  37740
agacatcccg gaaggcaccc tggtctggcg caccggactg tccggtgtgc caccggacag  37800
tgtccggtgc accagggcac tcgaagctga actcgctacc ttcgggaaaa tcagagggcg  37860
ctccgctata attcaccaga ctgtccggtg aagcaccgga ctgtccggtg tgccagcgga  37920
gcaacggcta cttcgcgcgc aacggtcgac tgcaacgcat tcaatgcgcg cctgcgcgcg  37980
cagagggcag agcactcaca gttggcgcac cggacagtct acaggacctg tccggtgcac  38040
caccggacag cccagaggcc ccacaagtca gagctccaac gatcgaaccc caacgatctg  38100
ctgacgtggc tggcgcaccg gactgtccgg tgcgccatgc gaccgcagcc ttccaacggc  38160
catttttggt ggtttagggc tataaatacc ccaaccaccc cacattcaat ggcatccaag  38220
tttcccacct tcaacacatt acaagagcta taacattcaa ttctagacac tccaaaagat  38280
caaatcctct cccaagtccg gaatcactcc aaatcaaata gtgactagag agagcgacat  38340
ttgtgttcat ttgagctctt gcgcttggat cgcttctttt ctttctcatt cttcttgtga  38400
tcaaactcaa ttgtaaccaa ggcaagagac accaattgtg tggtggtcct tgcaggaact  38460
ttgtgttccg tttgattgag aagagaagct cactcggtct aagtgaccgt ttgagagagg  38520
gaaagggttg aaagagaccc ggtctttgtg accacctcaa tggggagtag gtttgcaaga  38580
accgaacctc ggtaaaacaa atcatcgtgt ctcgctcttt atatttctaa cgttaacccg  38640
gcttgtagtt gtgcttaagt ttgtaaattt cagattcgcc ctattcaccc cccctctagg  38700
cgactttcaa ttggtatcgg agccggtgct tcattagagc ctaactgctc gaagtgatgt  38760
cgggagcatc cgccatgagg gatctcggga ccggcgacaa gaccgcatgc tcgggaagaa  38820
ctcactcaag ggagtccgcc cacaagcata aggaggaatc gtcttcctcc atcaagtccc  38880
atcggatggg tgacaaaaag aagaagatga ggaaggtggt ctactacgag accgactctt  38940
cgtcaccctc cacctccggc tcggaatcgg cctccaccac ttcaaagcgc catgagcgca  39000
agaagtatag taagatgccc cttcgctatc ctcgcatttc tagacgcact ccatcactct  39060
tcgttccatt aggcaaacca cctatatttg aaggtgaaga ttattctatg tggagtgata  39120
aaatgaggca tcacctaacc tcactccaca aaagcatatg ggatattgtt gagtatggag  39180
tgcaggtacc aaagaaggga gataaagatt acgactcgga ggaggttgaa caaatccaac  39240
atttcaaatc caagtcgaga ggagtataat aaggtgcaag ggttgaagag tgcaaaggat  39300
atctgggacg tgctaaagac cgcgcacgaa ggagacgagg taaccaagat caccaagcgg  39360
gagacgatcg agggggagct cggtcgcttc cggcttcgcc aaggggagga gccacaagat  39420
atgtacaacc ggctcaagac cttggtgaac caagtgcgca acctcgggag caaaaaatgg  39480
gatgaccatg aaatggttaa ggttattctt agatcacttg tgttccttaa ccctacgcaa  39540
```

```
gttcaattaa ttcgtggtaa tcctagatat acactaatga ctcccgagga agtaatagga  39600
aactttgtga gctttgagtt gatgatcaaa ggctcaaaga aaattatcga gcacgacggt  39660
ccctccacgc ccgaagcaca accggtcgca ttcaaggcga cagaggagaa gaaagaggag  39720
tctacatcaa gtagacaacc catcgacgcc tctaagctcg acaacgagaa aatggcgctc  39780
atcatcaaga gcttccacca aatcctcaaa caaaggaagg ggaaagatta caagccttgt  39840
tccaaaaggg tgtgctacaa gtgtggtaag cccggtcatt tcattgttaa atgtccttta  39900
tctagtgata gtgacagggg cgacgacaag aagggcaaga ggagagaaaa gaggaggtat  39960
tacaagaaga agggcggcga tgcccatgtg tgccgcgagt gggactccga cgagagttcc  40020
tccgactcct catccgacga ggacgccgcc aacatcgccg tcaccaaagg gctcctcttc  40080
cccaacgtcg gccacaagtg cctcatggca aaggacggca aaaagaagaa ggtaaaatca  40140
aaatcctcca ctaaatatgc atcctctagt gatgaagata atgctagtga tgaggaggat  40200
aatttgcgta cccttttttgt caacctaaac atgcaactac aggaaaaact aaatgaatta  40260
attagtgcta ttcatgagaa agatgatctc ttggactttc aagaggactt cctaattaag  40320
gaaaataaga agcatgttaa ggttaaaaat gcttatgctc tagaagtaga aaaatgtgaa  40380
aaattatcta gtgagctaag cacttgccat gatactatta ccatccttag aaataaaaat  40440
actaaactaa ttgctaaggt tgattctaat atttgtgatg tttcaattcc caatcttaga  40500
gatgataatg ttaatttgct tgctaagatt gaagaattga atgtctctct tgctagcctt  40560
agggttgaaa atgaaaaatt gattgctaag gctaaagaat tagatgtttg caatgcttcc  40620
atttctgatc ttagaaataa caatgatatt ttacgtgcta agattgttga acttaattct  40680
tgcaaaccct ctacatctgc cattgagcat gtcattattt gcactagatg tagagatatt  40740
aacattgatg ctattcatga tcatatggct ttaattaaac aacaaaataa tcatatagca  40800
aaattagatg ctaaaattgc cgagcatgac ttaaaaaatg aaaaatttaa atttgctaga  40860
agcatgctct atagtgggag acgccctggc atcaaggatg gcattggctt ccaaaaggga  40920
aacaatgtca aacttaatgc ctctcctaaa agattgtcaa actttgttaa gggcaaggct  40980
cccatgcctc aggataatga gggttacatt ttgtaccctg ccggttatcc cgagagcaaa  41040
attaggagaa ttcattctag gaagtctcac tctggccata atcatgcttt tatgtataag  41100
ggtgagacat ctagctctag gcaatcaacc cgtgcaaaat tgcctaagaa gaaaactcct  41160
gctgcatcaa atgatcataa catttcattc aaaacttttg atgcatctta tgttttaact  41220
aacaaatccg acaagatagt tgccaagtat gttgggggca aacacaaggg atcaaagact  41280
tgtgtttggg tacccaaagt tcttgtatct aatgtcaaag gacccaaaac catttgggta  41340
cctaaaatca agaactaaac ttgttttgta ggtttatgca tccgggggcc caagttggat  41400
catcgatagc gggtgcacaa accatatgac aggggagaag aaaatgttct cctcctatga  41460
gaaaaaccaa gatccccaaa gagcgatcac attcggggat ggaaaccaag gtttggtcaa  41520
aggattgggt aaaattgcta tatctcctga ccattccatt tccaatgtgt ttcttgtaga  41580
ttctttagat tacaacttgc tttcagtttc gcaattatgt aaaatgggct acaactgtct  41640
ttttacagat ataggtgtta ctgtctttag aagaagtgat gattcagtag catttaaggg  41700
agtgttagag ggtcagctat acttggtaga ttttgataga gctgaactcg acacttgctt  41760
aattgctaag actaacatgg gctggctctg gcatcaccga ctagcacatg ttggaatgaa  41820
gaatcttcac aagcttctaa agggagaaca cattttggga ctaacaaatg ttcactttga  41880
gaaagatagg atttgtagcg catgtcagac agggaagcaa gttggtactc atcatccaca  41940
```

```
caagaacatc atgatgactg acaggccact cgagctccta catatggacc tattcggccc  42000
gatagcttac ataagcatcg gcgggagtaa gtactatcta gttattgtgg atgattatac  42060
tcgcttcact tgggtattct tttgcagga aaaatctcat acccaagaga ccttaaaggg  42120
attcttggga cgggctcaaa atgagttcgg cttaagaatc aaatttgttt taagcgacaa  42180
cgggacggag tcaagaatct caaatcgaag gcacgatctc ctagatccgg cccaaaannn  42240
nnnnnnnnnn nnnnnnnnnn nnnnnnnnnn nnnnnnnnnn nnnnnnnnnn nnnnnnnnnn  42300
nnnnnnnnnn nnnnnnnnnn nnnnnnnnnn nnnnnnncgc tgatgaatca gcttgattcg  42360
tgacacggga ggtaagtccg tggatcaaaa ggtataccgg taagataata ggctctttac  42420
tctatttatg tgcatctcga ccggatatta tgctttccgt atgcatgtgt gcaagattcc  42480
aagctgaccc taaggaagct caccttacgg ccgtaaaacg aatcttgaga tatttggctt  42540
atactcctaa gtttgggctt tggtatccta ggggatccac atttgatttg attggttatt  42600
cggatgctga ttgggcgggg tgtaaaatca atagaaagag cacatcaggg acttgccagt  42660
tcttgggaag atccttggtg tcttgggctt caaagaagca aaattcggtc gctctttcca  42720
ccgccgaagc cgagtacatt gccgcaggcc attgttgcgc gcaattgctt tggatgaggc  42780
aaaccctgcg ggactatggt tacaaattaa cctaagtccc tttgctatgt gataatgaga  42840
gtgcaatcaa gatggcggat aatcccgtcg aacatagccg cactaaacac atagccattc  42900
ggtatcattt tcttagggat caccaacaaa agggagatat cgagatttct tacattaaca  42960
ctaaagatca attagccgat atctttacca agcctcttga tgaacaaacc tttaacaaac  43020
ttaggcatga gctcaatatt cttgattcgc gcaatttctt ttgctaaatt gcacacatag  43080
ctcatttata tacctttgat catatctctt tcatatgcta tgactaatat gttcttcaag  43140
tctatttcaa accaagtcat aggtgtattg aaagggaatt ggagtcttcg gcaaagacaa  43200
aggcttccac tccgtaactc atccttcgtc gtcgctctgg gccactctcc atctttgggg  43260
gagagagcaa aagacttcgt ctttggtaca atcttaactc atttatttat gaccaaaggg  43320
gaagaaagta cttcgagggc tctaatgatt ccgtttttgg cgattcatgc caaaggggga  43380
gagagtatga gcccaaagca aacggaccgc accaccacca atttcaaaaa cttagttttt  43440
caaagagtat tttcaattgg tatcctattg tgttcaaaag gggagaaag tagtattttc  43500
aaaaatgata tatcaaaacc ctcttgaaca ctaagaggtg gatctcattt agggggagtt  43560
ttgtttagtc aaaggaaaag catttgaaac agggggagaa aatttcaaat cttgaaaatg  43620
cttcataaaa tcgtattcat ttacctttga ctttttgcaa aagaactttg aaaaggattt  43680
acaaaatagt ttgcaaaaac aaaacatgtg gtgcaagtgt ggtccaaaat gataaaaaca  43740
aaggaacgat ccatgcatat cttgtaagta tttatattgg ctcaaatcca agcaaccttt  43800
gcacttacat tatgcaaact agttcaatta tgcattttat acttgctttg gtttgtgttg  43860
gcatcaatca ccaaaaaggg ggagattgaa agggaattag gcttacacct agttcctaaa  43920
taattttggt ggttgaattg cccaacacaa ataattggac taactagttt gctctagtgt  43980
acaagttata caggtgccaa ggttcacaac aagccaatta aaaagaccaa agttgggttc  44040
aaaatagaga gccaaaggca tcccgaaagg ctccctggtt tggcgcaccg gactgtccgg  44100
tggcgcaccg gacagtgtcc ggtgcaccag gggacctcgc gcagaactcc tcagcctcgg  44160
gaatttttcg gagccgccgc gctataattc accggactgt ccggtgtaca ccggacagtg  44220
tccggtgctc caagaaaaca cggctccaga acttggcagc ctcgggaaat cagaacggct  44280
```

```
gctccgctat aattcaccgg acatgtccgg tgtacaccgg actgtccggt gcaactgcgg  44340
agcaacggct acttcgcgcc aacggtcacc tgcaggcgca ttcaatgcgc gccagaagcg  44400
cgcagaagtc aggcacgccc atgctggcgc accggacact ctacagtaca tgtccggtgc  44460
gccaccggac atcaaggcgg gcccagaagg cagaactcca acggtcaaat tccaacggct  44520
ttggtgacat ggctggcgca ccggactgtc cggtgcacca tacgacagac agcctccacc  44580
aacggtcatg tttggtggtt ggggctataa ataccccaac caccccacca ttcattgcat  44640
ccaagttttc cagcttccaa ccactataca agagctagca ttcattgcaa agcacaccaa  44700
aagagatcaa atcctctccc aactccacac aaagccttag tgattagaga gagtgatttg  44760
tagtgttcat ttgagctctt gcgcttggat cgcttctttt ctttggcatt ctttcttgtg  44820
atcaaacact cacttgtaat tgaggcaaga gacaccaatt gtgtggtggt ccttgcgggg  44880
agtttgattc ccaagtgatt tgagaagaga agctcactcg gtccaaggga ccgtttgaga  44940
gagggaaggg ttgaaagaga cccggccttt gtggcctcct caacggggag taggtttgag  45000
agaaccgaac ctcggtaaaa caaatccacg cgtctcactt cattattcgc ttgcgatttg  45060
ttttcacgcc ctctctcgga ctcgttctta tttctaacgc taacccggct tgtagttgtg  45120
tttatatttg taaatttcag tttcgcccta ttcacccccc ctctaggcga ctatcaaata  45180
gccagtgctt tttggtctgc gagttcctgc acttggttaa tcaactgtgt cgcttgatct  45240
tctacttgtt tgcacgagaa ggtcaaagcc actttcgaag ctattagttc agaacacaca  45300
acatctagct aaatacatca ccagtttgaa gtcattgatt gtattcttga tatcatcttt  45360
attcttgaat gtcatttgtg ccagttcatt taactcttgt gctgcaaacc aacctgacat  45420
cgtcaattca tttaatctct caatctcagt ttcctttttt tgtttcacat tgaagctccc  45480
taattgttgc ttctcgatgt gcagtggcct gattagctac aagaagctct tgttccatgg  45540
actcgatctc tggaccgcac tatcgttgcc tcagccccta ggtcgtgctg ccctctggcc  45600
tcctcatcgt acaattcacc aacatctcca atgtaagtgc agcaggttca gtaatgaact  45660
cagaagtggc atcagaatac tccaagagtt ttttgatctt tttgcctgga tatataccaa  45720
gggaaatgca ttcaaaactc ctatagatga cgaatcccat ctctccctct tttctcggac  45780
acggatcccc aggtccgtct ccgtgcttta ctcatttgtt ttttacaagt tcagatccac  45840
ttgcgtactc acacggtgga catctgttat gcacatgtgt aaaccagcat aagtccttac  45900
actcgaaaat gcatgtgtta tttagcttga gaataaataa aattattagc aaggagaaaa  45960
caaaaaaata ggactaaaca atagagtcac attggtttaa attagtacct agaagtaaaa  46020
aaagatgatc taaattagat acatcatacc aaataccata ttactattcc agttaccccg  46080
tctactatgc ctagatatca aattcttgaa ggttggcctt ctcattttca gtaatagcct  46140
gacgaaagta gagtatgttt gtatgagcaa ttatgctgct cactactgcc ttgcgctata  46200
ataggccact actgatttta catgcttttt ctacattaga tagctcacaa acatgctacc  46260
tcaaaaaaat gatggcaaag gggagccaca aaatgtcaat tattttgtca agtattagca  46320
gttttcttgt gtatgtgatc agactaacac tgcatgtctt tgttttcctg taaaactatg  46380
tatgatgaaa ccatggtgtg attgtattgg ctggccttac cctgttttgt tgcaatgcat  46440
tcgttgttgt acaggtaata tgttgaaaca caattcattg catatgacaa ttctgttttt  46500
tctttctaga atattgacat attgtttgat cattattttc taagcaataa tcatggctat  46560
tcttatagta ttgcataata ccttttttctt ttcgaaccct agcgcattga ttctttagtg  46620
aagtgattat agtgattcca gcgggagagt agggtgggga gcagagggtt gattctggac  46680
```

```
tgatttcggt ggagattaaa tggggagcag tgaggagcat gtttttttag atcccaccag  46740
aatatgtgcg ccattttgct atttggctga ggagtgatgc tcagggagaa tccgttctca  46800
ggagctgtgc caaatgtcgc cttaggtttt atgatatgac ctgacttctg tgttaatatt  46860
tgttagatct ttattttatt tgaggttaca aaggtggtgt tctcaagcta gaaacaaagt  46920
tgtggctagg tcaaaactag atgatgctct tgaaccgtgt cttttgactc tgttacttgt  46980
tgcaggtttg atgttcacta atatgttgtt caactttgag caggtcagca attgactggt  47040
gttgctggta gcctggcata tctggcacct gaggttctac taggaaatta ctcccaaaag  47100
gtagatgtat gggctgccgg ggtgcttctg catgttctgt tgatgggcac tcttccgttc  47160
caaggaaaat ctatcgaagc tatctttgat gttataaaga ctgctgaact tgactttcac  47220
aatagtcagt gggcatctgt gtcacttctt gcttatgatc tcattggtcg aatgcttaat  47280
cgagaggtct cttcaaggcc cgatgccgaa gatgttctcc gtaagttcaa gcacccttgt  47340
aacttgtgct ttatatatat atataatata tatatatata tgattctcaa tttatcattg  47400
acttttccta atggctttca acacagggca cccatgggtc ttattctaca ctgattgcct  47460
gcagaaagct gaattctcta acctatggga tactaacaaa actgcagctc ccatgattca  47520
tcgggagata gtcaggtttg gttactgcga gtcttcatct tcaaaatcct caagtgacaa  47580
ctctgaagag cgagatgaat gcggtatagt tgatgcactg gcgacaacaa taacacaggt  47640
gaggatctca gagcccaaga ggagtcggct gttcagccta cccaacgggt tgttgccgcc  47700
aagcaggaac agtctccgaa catgaagatg atgaatccgt gtgtggcttt ctaacttgac  47760
ctacctagct cccatcccca tgcatgtata aacgagataa acgagctctg tgattttata  47820
gatggaaaat tttcaccgtg gttgatgttt tgcgattgct agctcgctga gcctgcaatc  47880
ctctgtaaat atatcattgt tgtcatcatt tttgtacatc gatgacaccg taattgattc  47940
gatt                                                               47944
```

<210> SEQ ID NO 2
<211> LENGTH: 1524
<212> TYPE: DNA
<213> ORGANISM: Artificial Sequence
<220> FEATURE:
<223> OTHER INFORMATION: cDNA

<400> SEQUENCE: 2

```
atggggagca gtgaggagca tgttttttta gatcccacca gaatatgtgc atccgtgtca    60
cttcttgctc atgatctcat tggccgaatg cttaatcgag aggtctcttc aaggcccaat   120
gccaaagaag ttctccctcc catgattcat cgggagatag tcaggtttgg ttactgtgag   180
tcttcatctt caaaatcctc aagtgacaac tctgaagagc gagatgaatg cggtatagtt   240
gatgcactgg tgacaacaat aacacagatt cggaagatgg acttggaggc aaggagccta   300
cagcctagca ttaaggctgg tttgcttgca aagctgaggg agtataaatc tgacctcaac   360
aacgtcaaga tgggtctatc cgcagagagg aagaagcaga agctctccga gatccaatcc   420
ggcgttgagg aagctgaatc gctgattcag aaaatggacc tggaggcaag gagcctacag   480
cctagcatta aggctggttt gcttgcaaag ccgagggatt ataaatctga cctcaacaac   540
gtcaagagtg agctcaagag gatatctgcg cccaatgcca gtggcctgat tagctacaag   600
aagctcttgt tccatggact cgatctctgg accgcactat cgttgcctca gcccctaggt   660
cgtgctgccc tctggcctcc tcatcgtaca attcaccaac atctccaatg tcagcaattg   720
```

```
actggtgttg ctggtagcct ggcatatctg gcacctgagg ttctactagg aaattactcc    780

caaaaggtag atgtatgggc tgccggggtg cttctgcatg ttctgttgat gggcactctt    840

ccgttccaag gaaaatctat cgaagctatc tttgatgtta taaagactgc tgaacttgac    900

tttcacaata gtcagtgggc atctgtgtca cttcttgctt atgatctcat tggtcgaatg    960

cttaatcgag aggtctcttc aaggcccgat gccgaagatg ttctccggca cccatgggtc   1020

ttattctaca ctgattgcct gcagaaagct gaattctcta acctatggga tactaacaaa   1080

actgcagctc ccatgattca tcgggagata gtcaggtttg gttactgcga gtcttcatct   1140

tcaaaatcct caagtgacaa ctctgaagag cgagatgaat gcggtatagt tgatgcactg   1200

gcgacaacaa taacacaggt gaggatctca gagcccaaga ggagtcggct gttcagccta   1260

cccaacgggt tgttgccgcc aagcaggaac agtctccgaa catgaagatg atgaatccgt   1320

gtgtggcttt ctaacttgac ctacctagct cccatcccca tgcatgtata aacgagataa   1380

acgagctctg tgattttata gatggaaaat tttcaccgtg gttgatgttt tgcgattgct   1440

agctcgctga gcctgcaatc ctctgtaaat atatcattgt tgtcatcatt tttgtacatc   1500

gatgacaccg taattgattc gatt                                          1524
```

<210> SEQ ID NO 3
<211> LENGTH: 1082
<212> TYPE: DNA
<213> ORGANISM: Artificial Sequence
<220> FEATURE:
<223> OTHER INFORMATION: cDNA

<400> SEQUENCE: 3

```
cctgcccttc cattcttccc ccgctgcccc cggtcaacgt cacgaacccg ggcctcgtgc     60

cgctcgtcgt ggccacactg ttcgacgagc gagtcacaga gctgctgagc gtgctcgctg    120

atgcggcggt ggggcgacca ggcaggtggt ccatcggcga agcgccatgg tcgtcgtcgg    180

ggggcacgaa ccaggcggtg tacgcgcgcc gcgcgcccgg ctcttcatcg cctccacccg    240

ctccagcgtc tccaccactt ccttcatcga gggccgactg cttggctcgc tggccaggca    300

gccgagcatt agttgcgccg cttggaacgc ctgcttttgt tgatcgtttg ttttggtctg    360

atttcagtgg gtctatccgc agagaggaag aagcagaagc tctccgagat ccaatccggc    420

gttgaggaag ctgaatcgct gattcagaaa atggacctgg aggcaaggag cctacagcct    480

agcattaagg ctggtttgct tgcaaagccg agggattata aatctgacct caacaacgtc    540

aagagtgagc tcaagaggat atctgcgccc aatgccagat tcggaagatg gacctggaag    600

caaggagcct acaacctagc attaagagtg agctcaagag gatatctgcg cccattgcca    660

ggcaggctac ccgggaggag ctcctggagt ctggaatggc tgatactctc gcagtgagct    720

aatgctagga cttgactgtg tctacgagac tgctcctaac aataaactga agaaagcaaa    780

agaaatcatt caacgtattc gccgaagaga actctacaag atatggtagt cctgggagga    840

agagccatcg ccgctatgta tggcagaacc acccgcgaaa gcaacctctc tggtctcgcg    900

tagccagagc aggagcagct cgcttgcgcg gtcgcggcgc tggcggccgg ccccgcgtac    960

gagcgcctgc aggaagccag gaacccatcc gaacaaggtt gcaatcatga taagcagata   1020

gagcaagcat atgatgatat tttgaattcg tcgaagcata ctttggccag catgatggag   1080

ct                                                                  1082
```

<210> SEQ ID NO 4
<211> LENGTH: 2321

<212> TYPE: DNA
<213> ORGANISM: Artificial Sequence
<220> FEATURE:
<223> OTHER INFORMATION: cDNA

<400> SEQUENCE: 4

```
tgaggagcat gttttttag atcccaccag aatatgtgca tccgtgtcac ttcttgctca     60

tgatctcatt ggccgaatgc ttaatcgaga ggtctcttca aggcccaatg ccaaagaagt    120

tctccgtaag ttcaagcacc cttgtaactt gtgctttata tatatgattc tcaatttatc    180

attgactttt cctaatggct ttcaacacag ggcaccatgg gtcttattct acactgattg    240

cccgcagaaa gctgaattct ctaacatatg ggatactaac aaaactgcag ctcccatgat    300

tcatcgggag atagtcaggt ttggttactg tgagtcttca tcttcaaaat cctcaagtga    360

caactctgaa gagcgagatg aatgcggtat agttgatgca ctggtgacaa caataacaca    420

ggtgaggatc tcagagccca agaggagtcg gctgttcagc ctacccaacg ggttgttgcc    480

gccaagcagg aacagtctcc gaacatgaag atgatgaatc cgtgtgtggc tttctaactt    540

gacctaccta gctcccatcc ccatgcatgt ataaacgaca tttggggaat gggtagaaaa    600

gcagagatta gggattttcg tttccgtcgg tgcagttttg gtgttccaat ggagttgcga    660

gatgtttatg tgccttagtc ttcaatttgg gggttggggg aaaagtaatt ttatgttttt    720

gttttgtgtc tgcagattcg gaagatggac ttggaggcaa ggagcctaca gcctagcatt    780

aaggctggtt tgcttgcaaa gctgagggag tataaatctg acctcaacaa cgtcaagagt    840

gagctcaaga ggatatttgc gcccaatgcc aggcaggcta cccgggagga gctcctagag    900

tttggaatgg ctgatactct cgctgtgagc taatgctagg acttgactgt gtctacgaga    960

ctgctcctaa caataaactg aagaaagcaa aagaaatcat tcaacgtatt cgccgaagag   1020

aactctacaa ggtagtatga tgctttaatt gctcatatac aagtgtcatt ttgtcatgtc   1080

attacacatg gttaggatac atacttaagt ttctaacgta ggcgtccaca caacggattg   1140

gtgcacggtt ctgccgatgt atcccacgca cgtgcatgga aggaggcagg caccccttccc  1200

cgccgccccg gatctcgcgc cagcccccgc cctaccccgc ctgcccttcc attcttcccc   1260

cgctgccccc ggtcaacgtc acgaacccgg gcctcgtgcc gctcgtcgtg gccacactgt   1320

tcgacgagcg agtcacagag ctgctgagcg tgctcgctga tgcggcggtg gggcgaccag   1380

gcaggtggtc catcggcgaa gcgccatggt cgtcgtcggg gggcacgaac caggcggtgt   1440

acgcgcgccg cgcgcccggc tcttcatcgc ctccacccgc tccagcgtct ccaccacttc   1500

cttcatcgag ggccgactgc ttggctcgct ggccaggcag ccgagcatta gttgcgccgc   1560

ttggaacgcc tgcttttgtt gatcgtttgt tttggtctga tttcagtggg tctatccgca   1620

gagaggaaga agcagaagct ctccgagatc caatccggcg ttgaggaagc tgaatcgctg   1680

attcagaaaa tggacctgga ggcaaggagc ctacagccta gcattaaggc tggtttgctt   1740

gcaaagccga gggattataa atctgacctc aacaacgtca agagtgagct caagaggata   1800

tctgcgccca atgccagatt cggaagatgg acctggaagc aaggagccta caacctagca   1860

ttaagagtga gctcaagagg atatctgcgc ccattgccag gcaggctacc cgggaggagc   1920

tcctggagtc tggaatggct gatactctcg cagtgagcta atgctaggac ttgactgtgt   1980

ctacgagact gctcctaaca ataaactgaa gaaagcaaaa gaaatcattc aacgtattcg   2040

ccgaagagaa ctctacaaga tatggtagtc ctgggaggaa gagccatcgc cgctatgtat   2100

ggcagaacca cccgcgaaag caacctctct ggtctcgcgt agccagagca ggagcagctc   2160
```

```
gcttgcgcgg tcgcggcgct ggcggccggc cccgcgtacg agcgcctgca ggaagccagg   2220

aacccatccg aacaaggttg caatcatgat aagcagatag agcaagcata tgatgatatt   2280

ttgaattcgt cgaagcatac tttggccagc atgatggagc t                        2321
```

<210> SEQ ID NO 5
<211> LENGTH: 1082
<212> TYPE: DNA
<213> ORGANISM: Artificial Sequence
<220> FEATURE:
<223> OTHER INFORMATION: cDNA

<400> SEQUENCE: 5

```
cctgcccttc cattcttccc ccgctgcccc cggtcaacgt cacgaacccg ggcctcgtgc     60

cgctcgtcgt ggccacactg ttcgacgagc gagtcacaga gctgctgagc gtgctcgctg    120

atgcggcggt ggggcgacca ggcaggtggt ccatcggcga agcgccatgg tcgtcgtcgg    180

ggggcacgaa ccaggcggtg tacgcgcgcc gcgcgcccgg ctcttcatcg cctccacccg    240

ctccagcgtc tccaccactt ccttcatcga gggccgactg cttggctcgc tggccaggca    300

gccgagcatt agttgcgccg cttggaacgc ctgcttttgt tgatcgtttg ttttggtctg    360

atttcagtgg gtctatccgc agagaggaag aagcagaagc tctccgagat ccaatccggc    420

gttgaggaag ctgaatcgct gattcagaaa atggacctgg aggcaaggag cctacagcct    480

agcattaagg ctggtttgct tgcaaagccg agggattata aatctgacct caacaacgtc    540

aagagtgagc tcaagaggat atctgcgccc aatgccagat tcggaagatg gacctggaag    600

caaggagcct acaacctagc attaagagtg agctcaagag gatatctgcg cccattgcca    660

ggcaggctac ccgggaggag ctcctggagt ctggaatggc tgatactctc gcagtgagct    720

aatgctagga cttgactgtg tctacgagac tgctcctaac aataaactga agaaagcaaa    780

agaaatcatt caacgtattc gccgaagaga actctacaag atatggtagt cctgggagga    840

agagccatcg ccgctatgta tggcagaacc acccgcgaaa gcaacctctc tggtctcgcg    900

tagccagagc aggagcagct cgcttgcgcg gtcgcggcgc tggcggccgg ccccgcgtac    960

gagcgcctgc aggaagccag gaacccatcc gaacaaggtt gcaatcatga taagcagata   1020

gagcaagcat atgatgatat tttgaattcg tcgaagcata ctttggccag catgatggag   1080

ct                                                                  1082
```

<210> SEQ ID NO 6
<211> LENGTH: 3646
<212> TYPE: DNA
<213> ORGANISM: Zea mays

<400> SEQUENCE: 6

```
atggcacact ttgatgaact agaggataaa acaacagatt atgttgattt atcggttcaa     60

gaatttgctc ttaagcaacc tcaatgtggc atggcttata attactatgg aaatttaagg    120

ctttatgtag tagccaataa agctgaattg gcctcttcaa tatttgaaat cgataaggta    180

aacaaaggcg gagttaatgc atctatgcca gtgaccactt ccactcctaa ttcgaatcaa    240

aattcatgaa ccggttatgg aacaaataga gaatcaagtt tcggtgaggt ataatacgat    300

tcccctaacc catggaattt acctagtaaa aatcctgtag ttaatagtgt actagtaact    360

tctgtcaccg acttgaataa agctttgaat gagtataaaa atgagatgtc taaatttatt    420

gagaatagct tggtgtatag attaagccta gtagaaacac ttataacaag ttgtatgctt    480

caattttttt tgattttttt ggaagctact catagttgga gggtaccaaa tttacaaaaa    540
```

```
aaaattggtg attataatag taaatctacc atagaacatg ttagcttgtt tcttgctctg    600
agaggtgaag ctagtagcat gaaaattgaa tgtgcgttat ttttcttttt cacttactgg    660
tacaattttt gcatggttta tgttgttgcc ctgcttgttg tattggttca tgggctggtc    720
tgtgaaataa tttggcgata gccattttct tttttgagat acattgcttt tgctatatat    780
atctagatat ggtgcatatt taaatgcata ataaaaatgt aaaaatctaa aacgtcttat    840
aatttaggac agatgaaagt actagatatt agacattttt agtgttttta ttaaaatgga    900
atatgtaccg cctttgatgc tacaactttt acttagcttt taaaacacac cattctaaat    960
tgtaaaaaaa tattaaaaat gtgttttgca agatgaatat actaaccttt gttatgataa   1020
tagttttcat atgttaatgg aacaagctaa aaagtttggc aaagtatagt cctatagctt   1080
ccatttcgac tcagagagag tatgttgtat ccactaaccg tgtacacaag atagcccaac   1140
taattaatta ttttgtgagc tatcacccaa ccttctgttt atcatggatt catggaaaaa   1200
tgtaattgcc atcattacac taaaaactaa aacttatgaa ggagaaccat tgtcttgcta   1260
tatatgagat gacaaaattt tccaaagaag agagaagccg gcagaaccca tcctgtttca   1320
aatctcttct actacttaag tttctaacgt aggcgtccac aaaacggatt ggtgcacggt   1380
tctgccgatg tctcccacac acgcgcatgg aaggaggcag gcacccttcc ccgccgcccc   1440
ggatctcgcg ccagccccag ccctaccccg cctgcccttc cattcttccc cagccgcccc   1500
ccggtcaacg tcacgaaccc gggcctcgtg ccgttcgccg tggccacgcg gttcgacgag   1560
cgggtcacgg agctgctgag cgcgctcgct gacgcggcgg cggggcgacc aggcaggtgg   1620
gccatcggcg aagcgccatg gtcgtcgtcg gggggcagga accaggcggt gtacgcgcgc   1680
cgcgcgcccg gctcttcatc gcctccaccc gctccagcgt ctccaccacc tccttcatcg   1740
agggccgact gcgaggctcg ccggccaggc agccgagcgt cagttgcgcc gcttggaacg   1800
cctgcttttg ttgatcgttt gttttggtct gatttcggtg ggtctatccg cagagaggaa   1860
gaagcagaag ctctccgaga tccaatccgg cgttgaggaa gctgaatcgc tggtaaatag   1920
atgccgcgac acgttctggt ttggggatcc ccttggctaa caggacatac gacatttggg   1980
gaatgggtag aaaagcagag attagggatt tttcgtttcc gtcggtgcag ttttggtgtt   2040
ccaacggagt tgcgagatgt ttatgtgcct tagtcttcaa tttgggggtt gggggaaaag   2100
taattttatg tttttgtttt gtgtctgcag attcagaaaa tggacctgga ggcaaggagc   2160
ctacagccta gcattaaggc tagtttgctt gcaaagctga gggagtataa atctgacctc   2220
aacaacgtca agagtgagct caagaggata tctgcgccca atgccaggca ggctacccgg   2280
gaggagctcc tggagtctgg aatggctgat actctcgcag tgagctaatg ataggacttg   2340
actgtgtcta cgagactgct cctaacaata aactgaagaa agcaaaagaa atcattcaac   2400
gtattcgccg aagagaactc tacaaggtag tatgatgctt taattgctca tatacaagtg   2460
tcattttgtc atgtcattac acatggttag gatacatagg agattctgtt ttttaacaca   2520
tagttgtccc atgtccatga attcatttga attaatttac tcttcgcaat cttatacatt   2580
aaaatcgtgt tacctattac atcacaactt catgagagca tgcttgttct gtgtagatat   2640
ggtagtcctg ggaggaagag ccatcgccgc tatgtatggc agaaccaccc gcgaaagcaa   2700
cctctctggt ctcgcatagc cagagcagga gcagctcgct tgcgcggccg cagcgctggc   2760
ggtcggcccc gcgtacgagc gcctgcaggt aggccagctt ctgctgcaat gcccgaatct   2820
cggcgtccac gcgcagcagc gtcgtcgcct cctcctccgt cagctcaccc agcttggcca   2880
```

```
gcacccccgt cacccccgcg tccgccatgg ctgtcgccgg gaccgaaagg ctaaaactgt   2940

cacaatgacg taaagtttgg ttggtgttgg cggctcacgc aaaaccagac ctttccaagt   3000

tttactttag cggagttttt ttggaacgag agcaaagcag cacagtttca agaatgtggg   3060

gcaatttgaa tgttcgttcc tgctgcactg ctactgcttt tagaattgta gtatgcttca   3120

tcatttattt atttctaaaa aaacttgcat gaattctatc gtgactttta ttgagaaaat   3180

aatgtattca cgtatcttca tgtttctgat aaaggtattt gtatatgcat cggtgctaca   3240

tatgcgaata caagttttgt ttcaactctg aagtctcaag ttgaattcta aactccagtt   3300

tgttttctac tgtgctgctg caggaagcca ggaacccatc cgaacaaggt tgcaatcatg   3360

ataagcagat agagcaagca tatgatgata ttttgaattc gtcgaagcat actttggcca   3420

gcatgatgga gctgcaggag gttcagttat ttgcacacat tgtttttctt tcactcctat   3480

gattttcctc aatatgatca aaatgtttct tttgcaaata atgattgaaa tgtttctcat   3540

tgtactcaac ctcttaaact acctataggc tttgcttgag agtaatcagg ctacaaagga   3600

tgccaatggt attgctgctc tctatattgt tcttgttcta atgtaa                  3646
```

<210> SEQ ID NO 7
<211> LENGTH: 3646
<212> TYPE: DNA
<213> ORGANISM: Artificial Sequence
<220> FEATURE:
<223> OTHER INFORMATION: cDNA

<400> SEQUENCE: 7

```
atggcacact ttgatgaact agaggataaa acaacagatt atgttgattt atcggttcaa     60

gaatttgctc ttaagcaacc tcaatgtggc atggcttata attactatgg aaatttaagg    120

ctttatgtag tagccaataa agctgaattg gcctcttcaa tatttgaaat cgataaggta    180

aacaaaggcg gagttaatgc atctatgcca gtgaccactt ccactcctaa ttcgaatcaa    240

aattcatgaa ccggttatgg aacaaataga gaatcaagtt tcggtgaggt ataatacgat    300

tcccctaacc catggaattt acctagtaaa aatcctgtag ttaatagtgt actagtaact    360

tctgtcaccg acttgaataa agctttgaat gagtataaaa atgagatgtc taaatttatt    420

gagaatagct tggtgtatag attaagccta gtagaaacac ttataacaag ttgtatgctt    480

caattttttt tgattttttt ggaagctact catagttgga gggtaccaaa tttacaaaaa    540

aaaattggtg attataatag taaatctacc atagaacatg ttagcttgtt tcttgctctg    600

agaggtgaag ctagtagcat gaaaattgaa tgtgcgttat ttttcttttt cacttactgg    660

tacaattttt gcatggttta tgttgttgcc ctgcttgttg tattggttca tgggctggtc    720

tgtgaaataa tttggcgata gccattttct tttttgagat acattgcttt tgctatatat    780

atctagatat ggtgcatatt taaatgcata ataaaaatgt aaaaatctaa aacgtcttat    840

aatttaggac agatgaaagt actagatatt agacattttt agtgttttta ttaaaatgga    900

atatgtaccg cctttgatgc tacaactttt acttagcttt taaaacacac cattctaaat    960

tgtaaaaaaa tattaaaaat gtgttttgca agatgaatat actaaccttt gttatgataa   1020

tagttttcat atgttaatgg aacaagctaa aaagtttggc aaagtatagt cctatagctt   1080

ccatttcgac tcagagagag tatgttgtat ccactaaccg tgtacacaag atagcccaac   1140

taattaatta ttttgtgagc tatcacccaa ccttctgttt atcatggatt catggaaaaa   1200

tgtaattgcc atcattacac taaaaactaa aacttatgaa ggagaaccat tgtcttgcta   1260

tatatgagat gacaaaattt tccaaagaag agagaagccg gcagaaccca tcctgtttca   1320
```

```
aatctcttct actacttaag tttctaacgt aggcgtccac aaaacggatt ggtgcacggt   1380
tctgccgatg tctcccacac acgcgcatgg aaggaggcag gcacccttcc ccgccgcccc   1440
ggatctcgcg ccagccccag ccctaccccg cctgcccttc cattcttccc cagccgcccc   1500
ccggtcaacg tcacgaaccc gggcctcgtg ccgttcgccg tggccacgcg gttcgacgag   1560
cgggtcacgg agctgctgag cgcgctcgct gacgcggcgg cggggcgacc aggcaggtgg   1620
gccatcggcg aagcgccatg gtcgtcgtcg gggggcagga accaggcggt gtacgcgcgc   1680
cgcgcgcccg gctcttcatc gcctccaccc gctccagcgt ctccaccacc tccttcatcg   1740
agggccgact gcgaggctcg ccggccaggc agccgagcgt cagttgcgcc gcttggaacg   1800
cctgcttttg ttgatcgttt gttttggtct gatttcggtg ggtctatccg cagagaggaa   1860
gaagcagaag ctctccgaga tccaatccgg cgttgaggaa gctgaatcgc tggtaaatag   1920
atgccgcgac acgttctggt ttggggatcc ccttggctaa caggacatac gacatttggg   1980
gaatgggtag aaaagcagag attagggatt tttcgtttcc gtcggtgcag ttttggtgtt   2040
ccaacggagt tgcgagatgt ttatgtgcct tagtcttcaa tttgggggtt gggggaaaag   2100
taattttatg tttttgtttt gtgtctgcag attcagaaaa tggacctgga ggcaaggagc   2160
ctacagccta gcattaaggc tagtttgctt gcaaagctga gggagtataa atctgacctc   2220
aacaacgtca agagtgagct caagaggata tctgcgccca atgccaggca ggctacccgg   2280
gaggagctcc tggagtctgg aatggctgat actctcgcag tgagctaatg ataggacttg   2340
actgtgtcta cgagactgct cctaacaata aactgaagaa agcaaaagaa atcattcaac   2400
gtattcgccg aagagaactc tacaaggtag tatgatgctt taattgctca tatacaagtg   2460
tcattttgtc atgtcattac acatggttag gatacatagg agattctgtt ttttaacaca   2520
tagttgtccc atgtccatga attcatttga attaatttac tcttcgcaat cttatacatt   2580
aaaatcgtgt tacctattac atcacaactt catgagagca tgcttgttct gtgtagatat   2640
ggtagtcctg ggaggaagag ccatcgccgc tatgtatggc agaaccaccc gcgaaagcaa   2700
cctctctggt ctcgcatagc cagagcagga gcagctcgct tgcgcggccg cagcgctggc   2760
ggtcggcccc gcgtacgagc gcctgcaggt aggccagctt ctgctgcaat gcccgaatct   2820
cggcgtccac gcgcagcagc gtcgtcgcct cctcctccgt cagctcaccc agcttggcca   2880
gcaccccgt caccccgcg tccgccatgg ctgtcgccgg gaccgaaagg ctaaaactgt   2940
cacaatgacg taaagtttgg ttggtgttgg cggctcacgc aaaaccagac ctttccaagt   3000
tttactttag cggagttttt ttggaacgag agcaaagcag cacagtttca agaatgtggg   3060
gcaatttgaa tgttcgttcc tgctgcactg ctactgcttt tagaattgta gtatgcttca   3120
tcatttattt atttctaaaa aaacttgcat gaattctatc gtgactttta ttgagaaaat   3180
aatgtattca cgtatcttca tgtttctgat aaaggtattt gtatatgcat cggtgctaca   3240
tatgcgaata caagttttgt ttcaactctg aagtctcaag ttgaattcta aactccagtt   3300
tgttttctac tgtgctgctg caggaagcca ggaacccatc cgaacaaggt tgcaatcatg   3360
ataagcagat agagcaagca tatgatgata ttttgaattc gtcgaagcat actttggcca   3420
gcatgatgga gctgcaggag gttcagttat ttgcacacat tgtttttctt tcactcctat   3480
gattttcctc aatatgatca aaatgtttct tttgcaaata atgattgaaa tgtttctcat   3540
tgtactcaac ctcttaaact acctataggc tttgcttgag agtaatcagg ctacaaagga   3600
tgccaatggt attgctgctc tctatattgt tcttgttcta atgtaa                  3646
```

<210> SEQ ID NO 8
<211> LENGTH: 10605
<212> TYPE: DNA
<213> ORGANISM: Zea mays

<400> SEQUENCE: 8
aggaatctta aacatgtgga acaggtgctc aacacattta gcaactagtt gttgatgacc 60
cataactttg cagccttcat aatgcacaca attgatgcat caattgcata cctcctgtct 120
ttgtcaacat tttcaacacc ttttttcttc tcatcaacag gaggcgatgg aatccaaaaa 180
gagtgacaac aaaaatatta gtataataac taaactctaa gtctaccaaa cagtgaaaga 240
atagtgaaac aggaaatacc ttaattctta tcattatgtt aataaattta aaattgaact 300
aaaaaacatc attaggtgag atggatctat ttgtcggttc cctgttaagg atcttgtatt 360
tcacacaaga aagtgaatgg agcaaacaca cactacatca tctgacatgt ttagttgtgt 420
tgcaatttca aaatatctaa gcctgtcgga tccattgaac aatagtagta atgtggcatg 480
tcaaaaaatg tcaaacatgt taatatagca ccatttttg tgatgcagaa atgacccgag 540
attacctgat atgtcataac aacgagctca atagggttag catcaaactt cgcacttacg 600
ttgcaggttc ccatccatgt cagcttcatg tgcttcgttc ttgtttgatg gaactccttg 660
aaaacatcta cacatttcag tgcctcatga gactcgccat agcgagcggg gtggaggatg 720
gtgacaattt cggcagcctc gccgggggca gcactgcgac gagcgaggcg ggaggggtgg 780
caatctcgtg gggggagggc caggcacgac cgtccaacca cggcgggcgg agacacggta 840
tccatgtgag atatagccac ctcatctagc cttatctcca agattttaaa tcactgatca 900
tcataagcga tcagatggag gccagttcac atcgaccgac aggactgata ctaacaggac 960
catccacact tgcacatact ataaagatta ataagagatt acataagaac taagtagtga 1020
atcagacacc cattgctgac cttgttaatc agcccatcgc caatgaaggt gctgctgatc 1080
ttcttgaaca acctgtacaa tgcctcgacc ttgttcacgc tgactgcaag aatgacaagc 1140
agaggaaacc caaccaggca ggaaaatgat gaccaacact gaatagaaaa agtaaatgaa 1200
cacctccagc tatcaaaatt ttaaagcaat gtgaagtcct caaagaacca ggacaacact 1260
catgattttt tataactaag ggaattgttt atcatcaatt cattctaaaa tacaagacaa 1320
tcaaaagaac taagcaaagc atgagataca aaaattcaaa gcacatgtat agtgtcttgg 1380
taaaaaattt acaagatggt gaatgaattc aactcaggtt gtctacttca gcattagttt 1440
gcactgtcca gaaaaagaac aacagcaaga ttggaataat gctatggcca ccagaataaa 1500
aggtcagagc tgtcttttaa tgctaatatt gttcatgcca aacatttctt tgttagcttg 1560
tgaatttata cttggacact ggactgggcc ttgatcgacg ctggcaatat catgctgaac 1620
tctgaaggca ccaaaactgt tagctccttc cctcgtcaat ttgtcaattc aacatgtctg 1680
cttcaaaatg gttatgcgta ggttgaagaa aagttgggag tttacaaaat aatacaatgg 1740
gatgcctgtt ctatcatcta acttaagcca tgtatcaagg ttgcaagtta cataaaatac 1800
gcttatattc tgatggttgg aaccacacat tctacacgtt tcccaaaaca atgaaaaagg 1860
tagttgtcga aagatttaag catctaaagt gtccactctc tctgagagca tcaaaataaa 1920
gtagtacgtc ttatgtttta aactatttat tgaagtacca aactatacgg ctactaaaga 1980
tttatttaga tgagtaaacg aaataattta tggtatataa attaagaagg ggtgattagt 2040
catgaaaaat aaaatgtcac aattaccagc agcacgtgat tttctaaata atttaagcat 2100
gtgcggtgct cttccagata aaacttaggg gacgaccacc tagttcattg aaagagggga 2160

```
ataaaccaag ctccaacttt caagcttgtc aaggcttgtc attattaatt taaacaggac   2220
agccaattct cagacatgat gttccaaact gctaatgaat atataatgct caaaataaac   2280
aactaggttc ttaactgtca attacaccca caagatgcac ataattagaa aaggtaaaag   2340
agaaggcaaa tggaatacca ggaattatat gactactaaa tcatttattt agataagtag   2400
atgaaataat ttatggtaca taatataaga acgggtgatt agttatgaga aataaaaggt   2460
caccattacc agcagcatgt gttgttctaa ataatttaag cctgtgtggt attctttgag   2520
ataaaacata ggagacgacc acctaattca ttggaagagg ggaacagacg aagctccaac   2580
cttcgagctt gtcaaggctt ggcattatta atttaaacag gacagacaat gctcaatctg   2640
aactgccatt gtatctacaa tactcaaaat aaacaactag attctgaaca accagattat   2700
ttgtactcat tccatgtctc ataaacaagg aaaaaataac aaccagatta tttgtactca   2760
ttccatgtct cataaacttt gggcaccatc catccaacac atccaatcta aacacaccaa   2820
acgatgggga atggaaagag cagtattcga ttcaacaatg gcaaacaaat atcactgaat   2880
tagaccaaga ataaacctaa ttagacaacg acctcccaac catcattcgt caggctgtaa   2940
agaagataaa gctgccatgg ggcatggatc aagcagaaca ccagagatga atccaaacac   3000
acagaaaatc acgcgcgctg tctacaatga caacaagccc cacatttcat tgcagtacac   3060
tgggctacaa aggcacgtac aacaaagagc tagggaaaca ttgcggaggg cacgagagag   3120
cagctaactt gacaatatag cagactgagc ttgcactgtt agcaggcgag gaagggaatc   3180
atggggacgg agaatggggt ccatgcccgc gaaggagaag gcggacgccg ccacggtggc   3240
accggcgcac gcgcacacag ggaacccgca caggcagcca tggatgctgc ctcgccattg   3300
cgccggtcgt ctctgccacg ctcctctctc tctcccgctg catcgccgtg gatggggcaa   3360
gcagagagca gggactgcga cgatctgggc ggaggactcg ccttggagag cgcggacgca   3420
gacgggattc tagggagaga gcgaagacgg ggcgcgcgcg gcgctcgcgc ggcgtggtgg   3480
cggcgagatt agcgggggtg gggggagggc ggagccgtgg tgagggtgtg gacgccctcc   3540
ttaccctctt aagtagtagt agagatataa tccgttccaa aatatccatc cgttcaattt   3600
atatttcgtt tgatcttttt accctaaatt tgattgactc atcttattaa aaaagttcat   3660
aactattatt aatctttatt gagatatcat ttagcatata atatacttta agtgtggttt   3720
tagatttttt ttaaaaaaaa aaattcgcaa aaattaaatg aaacgaccca atcaaacttg   3780
aaaagtaaaa ctaattataa atttgaacgg aaggagtaag aggatgtttg aatgtactag   3840
agctaatagt tggttgcttt aaaatttgct agtagaatta gctagctaat aaatatctag   3900
ataactatta gctaatttgc taaaacagct aatagttgaa ctattagcta gattgtttgg   3960
atgtattcgg ctaattttaa tggctaacta ttagctatag tacaatattc aaacacctcc   4020
taattaaaat ggacaaatat ctcttctttt ggtcccttgc gttagatttt tcatatctcc   4080
ttatttagta taaaagaatc atcaaaaagt ggacaacccc tagtggaaca ccattttagt   4140
agtggttgca tgaaaccttt cgcgcaccag tttctatgtg tcactctaaa aatgggacag   4200
catgtacgta gtgcctatat atatacaagt catctatcgt tgcctcctca gttcatcact   4260
aatcacactt attgtgccct cgacgagtat ctatagctag ctcattaatc gattcggggg   4320
tgtgttgtcg aaggcggcaa tggcgagcta ctcgtcgcgg cgtccatgca atacctgtag   4380
cacgaaggcg atggccggga gcgtggtcgg cgagcccgtc gtgctggggc agagggtgac   4440
ggtgctgacg gtggacggcg gcggcgtccg gggtctcatc ccgggaacca tcctcgcctt   4500
```

```
cctggaggcc aggctgcagg agctggacgg accggaggcg aggctggcgg actacttcga   4560
ctacatcgcc ggaaccagca ccggcggtct catcaccgcc atgctcaccg cgcccggcaa   4620
ggacaagcgg cctctctacg ctgccaagga catcaaccac ttttacatgc agaactgccc   4680
gcgcatcttt cctcagaagt gagtccgatg ctgccgccat tgttcttgca tccatccagc   4740
atcgtacgta cgtcctctat acatctgcgg atcatcatgt gcgcatgttt gtggcatgca   4800
tgcatgcatg tgagcaggag caggcttgcg gccgccatgt ccgcgctgag gaagccaaag   4860
tacaacggca agtgcatgcg cagcctgatt aggagcatcc tcggcgagac gagggtaagc   4920
gagacgctga ccaacgtcat catccctgcc ttcgacatca ggctgctgca gcctatcatc   4980
ttctctacct acgacgtacg tacgtcgtca cgaatgattc atctgtacgt cgtcgcatgc   5040
gaatggctgc ctacgtacgc cgtgcgctaa catactcagc tctttcctat ctgctgcgcc   5100
aatttgcagg ccaagagcac gcctctgaag aacgctctgc tctcggacgt gtgcattggc   5160
acgtccgccg cgccgaccta cctcccggcg cactacttcc agactgaaga cgccaacggc   5220
aaggagcgcg aatacaacct catcgacggc ggtgtggcgg ccaacaaccc ggtaactgac   5280
tagctaactg gaaaacggac gcacagactc catgtccatg gcggcccaca aggtcgatgc   5340
taattgttgc ttatgtatgt cgcccgattg cacatgcgta gacgatggtt gcgatgacgc   5400
agatcaccaa aaagatgctt gccagcaagg acaaggccga ggagctgtac ccagtgaagc   5460
cgtcgaactg ccgcaggttc ctggtgctgt ccatcgggac ggggtcgacg tccgagcagg   5520
gcctctacac ggcgcggcag tgctcccggt ggggtatctg ccggtggctc cgcaacaacg   5580
gcatggcccc catcatcgac atcttcatgg cggccagctc ggacctggtg gacatccacg   5640
tcgccgcgat gttccagtcg ctccacagcg acggcgacta cctgcgcatc caggacaact   5700
cgctccgtgg cgccgcggcc accgtggacg cggcgacgcc ggagaacatg cggacgctcg   5760
tcgggatcgg ggagcggatg ctggcacaga gggtgtccag ggtcaacgtg gagacaggga   5820
ggtacgaacc ggtgactggc gaaggaagca atgccgatgc cctcggtggg ctcgctaggc   5880
agctctccga ggagaggaga acaaggctcg cgcgccgcgt ctctgccatc aacccaagag   5940
gctctagatg tgcgtcgtac gatatctaag acaagtggct ttactgtcag tcacatgctt   6000
gtaaataagt agactttatt ttaataaaac ataaaaatat atatatgttc ttgaatataa   6060
aattgataac caaattaaaa ttcgaaccat cacttataca taattttact ttattttta   6120
taaaacgtga acgggaagga ctaccgtgaa tgactataga accaatcata ctagtataaa   6180
atatatgatg acactacggg agagacaaac tttgtctggc gctaaatatt ttgccgagtg   6240
tgaattcacg ggcactaggc aaagatcttc tttgccgagt gttacgctgg gcaaagtaag   6300
acactaggta aatcagtcat ttgccgagtg tccgccacta ggcaaagcaa aacactggca   6360
aatcaaaagt ttacctagtg ccagacacta ggcaaaaaaa aaacgctcgg caaatcggaa   6420
gtttccctag tgccagacac tagacaaaga aaaacacttg ataaactagc gtcgtcagct   6480
aacaccatcc accaaccgtt aacgttgccg agtatctgac ttcgacactc ggcaaagaag   6540
gtctctttgc ctagtgtcgg tctggaacac taggcaaaga ggcactttac ctagtgtcgt   6600
attttgacac tcagtaaaat aattttttt ctttctgctt ccaaactttt tatgatgtgt   6660
tcctatagca cctagaacta catgtcaagt tttggtaaaa tttttgaagt ttttgctata   6720
tttacttaat ttattttatt taattgaatt tcttttgata attcaaattt gaactcggca   6780
aggtaagaag cgagggtagc ctggaaacac actttgccta gtgttacact cggtacagga   6840
gcctcccctg cctagtgctg cactcgacaa aagattcgcc tttgcctagc gctgcactcg   6900
```

```
gcacaggagt cgcctttgcc tagtgctgca ctaggcaaag cctccgttac cgtgccttcc   6960
atcgtcatgg aaacttttct tcgccgagtg acgtgtggca ctaggcaaag tttttgccga   7020
gtgcccgaga aatggcactc ggcaaggact ctttgccgat cccttcgttg ccgacttctt   7080
tttgccgagt gcaacactag gcaaaccatt tgccgagtgt aaaagaggct ttgcctagtg   7140
tctgtggcac taggcaaaga agacgagtcc tgtagtgaac ctagtaggcc agtgcgggac   7200
cattccaaaa aatacctata aaaataaatt taatattaaa ttaaacatat ggtccacgta   7260
ccaagatatt aaactcaaaa gaacaattat tacaatttat cttagctaaa aggccgagaa   7320
aaagtatatg ttaaaaagga gtgtgatccc atttttatag ctcgctcggt cgatcgcccg   7380
tccactttta ggtaacgagg tggtaccatg taggagtgtt gcgttgcgtg cgacttccta   7440
tcatgttggg cttaggtggc ttctcacgac ccaatgatag gcgagaagtg tggaagatga   7500
acaaacctac ttgtttcgtg cacgacgcat gtgtttgaac aacgagttag attagaaaaa   7560
aaatataatg actttttttt ttgcaaaagt gaggataatg aaaaccagaa aaactggtgc   7620
ttcataagag tagagatttg atggtaaata tagtagtaat gcaatggcta tactacacgc   7680
gagagtccaa tggcaagccg gtgtgttggg gcgaaggcga agacgctacc cttcgctcca   7740
ggcctttgtc aactcgctgc accaacagag gcaagatgac cggcgcggcc cacccttcgt   7800
cctcttcact gcaagacgaa ggcctacgac gaagtctctc catcccacgt cctcgcctta   7860
cctggaggcc cacgtgggat tcggcccatc gtaacaggcc ccgcacggac aggcgtgtta   7920
cgggtttgat ttgtaatagc ttttctgtaa tgacagtttg taaccctccc ttatgggaat   7980
attctgggga taatccaggt gtctgagggc ataagcgtcc ttacatcggg acgttgggcg   8040
ctcgggcacc tataaatacc cccgtacagt gcccttgaga ggctggatta acatagcaat   8100
tgccatctcg agttaaacct tgcttgcatc ctttccactc tcccgttgga tcaacttgcc   8160
caagagagct agttccaaca tttggcgccc accgttcgtg ctacgagcaa accacccgcg   8220
atggcaccca aaagagctag ttcgaaggca gccccatccg tcgacgaagc ggcgaaggca   8280
gcactgctag ctgagaaaaa gggcaaggcc ctcgcagaca acacccacca agaagctggc   8340
gaagacgaag cactcagtaa gagacagcgc aacgatcaac acactctcga aggcaccctc   8400
cgcacctaca gctccggagg ccaaccacaa gtaccacccc taggcttcgc tccactagag   8460
ggcgaggaca caacagagga cggcgaagtc atcggcgtct cagcagaaga acaactacag   8520
ttatgggccc tgcgcctcaa gaaccgcaac ctccaaaagc agaaagaaat cctcgaagcc   8580
aagcgccaac gcgtctccgc gcaagccaaa gtgcgttaga tgatacgaga cgaggagcag   8640
agggcccggg aactagagca agagattgcg ctcatgcaga gcgaaggaca gcatgatcta   8700
cagcatggcc cacccctcca gcagcgcgcg ccagctagag atttattcat tccccagcgc   8760
gggcccttca tcccacacgc cgcagctttc caaggcatca actaccttga tgagcgaagc   8820
cccctggcgc cgcaactcca agtgtcacct tggcccgcca acttcagggc agggagctac   8880
cccaagtaca atggcagcac cgacccagca caatacatca tgagctatca agtcgctgtc   8940
gcatcatccg gaggggacga cgccacaatg gccaagtcct tcatcatcgc cctcgaaggt   9000
ccggccttga cctggtacac caggttgccc ccactgtcca tcgactcctg gcgaagtctc   9060
cgggacaagt ttctgcttaa ctttcaaggg taccgcccag acatcgatgc cttggccaag   9120
ctgtcactct acaaacaaca agagaaagaa accctacggg agtactaccg caagttcctg   9180
gctctcaagt cgcaactgcc ctcggtcgac gaccaaatcg ccatacacta cgccatcagt   9240
```

```
ggccttcggg ctggcgtcct atacagtcac tgcatcaggt acccacccaa aaacctccaa   9300
gagctctatc agttgtttga aaagtacgcc agatccgaag agctccatca gcgcaaggtc   9360
gagtctcaaa gaaagcccaa ggaccctccg cagtctagcc aaacatggac aagaccttca   9420
cagtcagact ccggtcggga caaccgcagt cagcagcagg tgcataacat tgccaaccag   9480
caccccgcca gcgaagcccc tcgccgccaa gattatcccc ccagggccgc ggcaatggca   9540
cgcgtggtcg gggctgggga cgggcgcaac agccgtgcag atattactgc ctgttttcac   9600
ggcgaagact gcacgcaccc aaccaaggat tgtccggaaa cgaaggccac cagggacagg   9660
atgtctcggg cacaacccgc cgacaaccca agagttgtcg cgcacacata ccaacaccac   9720
cacccacaac catacaacca cggccccgcc cagcatctac ccaaccacgc atatcaacac   9780
caccaggagt tacaagtcat accacctcca cccccgcctc cgcatcaacc aaacatccac   9840
caccaaaatc accccaagca ccaaaacagg aagacttcgc tgatcagccg tatcgcggag   9900
tcattcacat gatcaccgga ggggtccagc attgactttg acacgaagcg acaaaagagg   9960
aatcactacc gaagcatcaa ccacgtcgcc atcaccggct cggtcgtgca aacgaagtgg  10020
tcacatgtgc cgctaacctt cgacgccaga gatgttgatc tgcgcagcgc accccacatt  10080
gatgccatgg taatcaactg cagtgtggca ggctgggacc tgcacaaagt cctagttgac  10140
aacggcagcc aggcggacat catcttcctc catgccttcg accgcatggg catcagccac  10200
agccctctca agccttcgaa caatccccta tatggcttcg gcggcaaggg caccttccct  10260
gtgggcaaga tagagctacc cctatccttc ggcgtagcac ccaatgcgcg aagcgaatag  10320
gtcacctttg acatcattga catggtctat ccctacaacg ccataatggg tcggggctct  10380
atcaacaaat ttgaagcggc aatccacgga ttatacctct gcatgaaaat tccgggtcca  10440
caatgcgtaa taacggtgta cgggaaccag cagactgcgc ataacattga gagagatttc  10500
gttcccgatc aacggaacgt acactgcctt acgacgcagc gcgaagtccc cgaggctacc  10560
tgcctagctg ccaacaaaaa tgaaaaggca cagctaaaaa gcaac                  10605
```

<210> SEQ ID NO 9
<211> LENGTH: 11001
<212> TYPE: DNA
<213> ORGANISM: Zea mays

<400> SEQUENCE: 9

```
aaatggccga agctattttg gatgaagcca tctctcgact attaaacgaa gctgcggaag     60
cagttttaaa agaagaatag ttgttattgt aaaaacattt ggaatgtaat atttgctgaa    120
caaagtgtgt aatattttta taatttgaat gtaatatata agctgctcgt aactcaattc    180
tttacgatgc atgaaacttt acgtacatac cgtttttgag ccttcggcga aaaaacacct    240
tcccttcttt tcatgcttcg tgaagaatat ccatacttcg taaaaacatt atgcttcata    300
agcaatagat ctctttttca tattagagtt gatgaagttg tacttgttca aaacttattg    360
tgccttggca ctgcttcttc gaaacaatct cgaagatcaa cattgtatcc ccttcttgtg    420
ttattgatgc aatatgatgt tatgctatgc aaaatgatgt gatgatgtta tgctatgcaa    480
aatgatattt atgtcgaaga tacataaaca ttcccacagt agagcacaca atctttttgc    540
cgtttatttt tcggcttcac cgcttatttt tcggtgtatc agcgctgact tttcgctgta    600
agcctccctt aggtgcttct tcgcctttta cttcggcggt atttgcgttg actttttgcg    660
cttcgcctta tacttcggtg gaatcagcgt ttatttctcg ctgtaagctc tgcattccct    720
ttggaacgac ttttgagcag aaaacttacg ctgcgctccc ttagaaatga ctttttgtaa    780
```

```
cttcggcaaa cttacgctgc gtttcataga acgacttttt tgtagtttcg gagatacttt    840
ctgtagccac aagttcttaa gaacgagttt tcatgcttca tcaacttttt gaattccgta    900
agtctgtgga gaagatatat tttcactatg acaaaaacaa agctgttaca agaaattgaa    960
aacaacaaga aaaacttagg ctttcaatga ttgttcttta ttaaaaagaa aaatgataac   1020
taatgcaaga actatttcag aagtaggata tctgttagta gatgtgcttt gactctggca   1080
caatactgtt gactgtgcga gcttcggact cctctctgaa gtctcgttgc tgatgagtgt   1140
gctggctccc ttctggctgc tggcctcgtt gtattggtgg tggaggtgga agctgttgcc   1200
aagatgcctg aggttggctt gccgaagcaa cagaagctgc aggatggtta cccttaccca   1260
catactctgg aatgtacggt gagtggtacg aagcagtatg cataacttgc ttcggctggc   1320
tctgttgggc tgcagtttct gctatctctt tctgtttctg gatggtgaca tggcacatcc   1380
tggtagtatg gcccttgtcc tcaccgcaga atagacaata aattttcctg ggctgatccc   1440
caaaccttcc tccgaagccc ctggctcctc tgccccttgg ggctggaggc cgaggataac   1500
tctgttgctg ccccgaagcc taggaggaat attgcggcct ctgttgctga cttcccctgt   1560
cgtcattctg agtggaatga attgatctga catgtctagg gtgtactctc cctccgaagc   1620
ccctggtcat ctcggagaat ctgtaagaag gcccccaaca cctctctttc ccattcgttt   1680
aggtgagaaa acacattggg gagcactagg gagttctttc ctagtgaggc gtctgtgatt   1740
tgataatcac aagattaagg atttcattag tgcatgtgta gtagcaagtg tgcatccacc   1800
ttcctcatta agcttgttta ggataagcca gagtttgtgc cggttactct tgatgttcaa   1860
caacaccaag atggcttggt ggtaattaag agcttggtga tctctcagtg gtgctcgtga   1920
gagtcccaac tcattgtgta ataaaagatt ataggtgatt caccatgccg gagtggtgaa   1980
taatcaaccc gtagagagca ttgagtcctt gaatggatcg atggggggct acacccttgt   2040
gtgggtcaag tcagagtttt agcagttctt gcacccatga tctcatcgtg aagcatagat   2100
aaatttaaat tcttttgaat tatttatata tgacaacact attcgtcgct ctaggtgact   2160
atcacctacc ctaaaatgac ttaacaaatc tttattaatt gttaagtcat tcacattttt   2220
gttaatccac tccaaagtca gggtgtttag tgtttttaca tccatgtctc cttagactca   2280
cggtgtctct cccagattct ctctcaccct cacctctctc tcactagcca ctagggaacg   2340
caacacccat cgatggctct tcgccccatg aaacgttcac acaatcgcaa ttgtcgaggc   2400
atgcatggct gggagagcag acatggaggc atacgtgcta gggttgcaca tgggcaagag   2460
ggtgggtgtg gctattcaga tatgcatggt gagcaagatg ggtgaggttg tgggcatgat   2520
gaggggataa ggaagaataa gatctctttt gttaggctgt ctccagcagc tatcgtatcc   2580
cattccctat cgcatcccct attttaaact ttactatgca aacaatgtaa tatatagtgc   2640
agattcccta ttttacacaa tgtgttgtag acaaccttgg agctcttgca taaaagctct   2700
agttttggct ctagctcctc tgagaaaaca atccccacca tgtttttagg aagaatccct   2760
gaagggcacc ccatttggtt ggaaatacat ctcctcctac aggattatgt ttgacttttt   2820
tttgcaatgt gggacccaca ggggagagga ggacgagaag gaaccggaga gcctattttt   2880
tgggctcctg gcttcgcttg gtttctaggg gcggctcctt cctattttca caaaggagct   2940
agtagaggag cctcccattt catgattttt tgaaggatct atttaaggag ccttgaaaga   3000
gccctaccaa ggtaggccta gaaataataa aggaggaaaa agagaaggta tcacaacttt   3060
tgtctacaac gtgaaaatgt ttggctaaat agataaaaca gtttgaattt tatcgattca   3120
```

```
attgtttatt gagggcatgt ttgggagggc tttagttcta gcttctttcg cgaaaaatcc   3180
agagccctac aaaatgacgt ttggtaaaac gacttcttcc gaaaaacacc caaaaaccca   3240
agatatttta tactacgaag gaaaggtcac acatcctagt tagcttcact ggttctagct   3300
ccttccaatt ttgcaaaaaa gtcacaaagg ataagccatt ttttcaaatg atttgtgaaa   3360
tgcctacgct aaaaagtcta cttttccaaa aaaactagag ctagagccgt ttttggcaag   3420
tcagaaccct accaaatagt ccctcagttt aagcaaagtg aggctatact gaagctaaat   3480
tatgccaaat tgggcctaca tctccatatt ttcaaccaaa tgctttaggg tttcttgtaa   3540
tcgacatgat ttgtttcttc ataaatagta tatggaccgc tccaaaatac tccatccgtt   3600
tcaatttata ttacgtttga tctttttacc ctaaatttga tcgactcgtc ttattaaaaa   3660
agttcataac tattaataat ctttactgtg atatcattta gcatataata tactttaagt   3720
gtagctttga tttttttttt gcaaaaatta aatgaaacga cccaatcaaa cttgataaaa   3780
aagtaaaact aattataaat ttggacataa ggagtaggag ggtgtttgaa tacactagag   3840
ttaatagtta gttgtcttaa aatttgctag tacaattagc tagctaacaa atatttaggt   3900
aactattagc taatttgcta aaaacagcta atagttgaac tattagttga actattagct   3960
agactgtttg gatgtattca actaatttta gcagctaact attagttata gtataatatt   4020
caaacacctc ctaattaaaa tggacaaata tctattccct tggtcccttg cgttagattt   4080
tccatatatc ctcatttagt ataaaaagaa tcatcaaaaa gtggacaacc cctagtggaa   4140
caccatttta gtagtggttg catgaaacct ttcgcgcatc agttactatg tgtcactcta   4200
aaaatggggc agcatgtacg cagtgcctat atttatacaa ggcatctatc gttgcctcct   4260
cagttcatca ctaatcacac ttattgtgcc ctcgacgagt atctagctag ctcattaatc   4320
gatcaatcgg ggtgtgcggt cgaaggcggc aatggcgagc tactcgtcgc ggcgtccatg   4380
caatacctgt agcacgaagg cgatggccgg gagcgtggtc ggcgagcccg tcgtgctggg   4440
gcagagggtg acggtgctga cggtggacgg cggcggcgtc cggggtctca tcccgggaac   4500
catcctcgcc ttcctggagg ccaggctgca ggagctggac ggaccggagg cgaggctggc   4560
ggactacttc gactacatcg ccggaaccag caccggcggt ctcatcaccg ccatgctcac   4620
cgcgcccggc aaggacaagc ggcctctcta cgctgccaag gacatcaact acttttacat   4680
ggagaactgc ccgcgcatct tccctcagaa gtgagtccga tgctgccgcc attgttctcg   4740
catccatcca gcatcgtacg tcctctatac atctgcggat gatcatttgc gcatgtttgt   4800
ggcatgcatg tgagcaggag caggcttgcg gccgccatgt ccgcgctgag gaagccaaag   4860
tacaacggca agtgcatgcg cagcctgatt aggagcatcc tcggcgagac gagggtaagc   4920
gagacgctga ccaacgtcat catccctgcc ttcgacatca ggctgctgca gcctatcatc   4980
ttctctacct acgacgtacg tacgtcgtca cgaatgattc atctgtacgt cgtcgcatgc   5040
gaatggctgc ctacgccgtg cgctaacata ctcagctctt tccgatctgc tgcgccaatt   5100
tgcaggccaa gagcacgcct ctgaagaacg cgctgctctc ggacgtgtgc attggcacgt   5160
ccgccgcgcc gacctacctc ccggcgcact acttccagac tgaagacgcc aacggcaagg   5220
agcgcgaata caacctcatc gacggcggtg tggcggccaa caacccggta actgactagc   5280
taactgcaaa acgaacgcac agactccatg tccatggcgg cccacaaggt cgatgctaat   5340
tgttgcttat gtatgtcgcc cgattgcaca tgcgtagacg atggttgcga tgacgcagat   5400
caccaaaaag atgcttgcca gcaaggacaa ggccgaggag ctgtacccag tgaacccgtc   5460
gaactgccgc aggttcctgg tgctgtccat cgggacgggg tcgacgtccg agcagggcct   5520
```

```
ctacacggcg cggcagtgct cccggtgggg catctgccgg tggctccgca acaacggcat   5580
ggccccccatc atcgacatct tcatggcggc cagctcggac ctggtggaca tccacgtcgc   5640
cgcgatgttc cagtcgctcc acagcgacgg cgactaccta cgcatccagg acaactcgct   5700
ccgtggcgcc gcggcaaccg tggacgcggc gacgccggag aacatgcgga cgctcgtcgg   5760
gatcggggag cggatgctgg cacagcgggt gtccagggtc aacgtggaga cagggagcga   5820
ggtacgaacc ggtgaccgga gaaggaagca atgccgatgc cctcggtggg ctcgctaggc   5880
agctctccga ggagaggaga acaaggctcg cgcgccgcgt ctctgccatc aaccccagaa   5940
gctctagatg tgcgccctac gatatctaag acaagtggct ttactgtcaa tcacatgctt   6000
gtaaataagt agactttatt ttaataaaat ataaatatat atatattctg ataaccaaga   6060
ttcgaaccct cacttataca caattttatc ttatttttta taaaatgaga atggaaagga   6120
ctaccgtgaa cgactataga accaatcata ctagtttaaa atgctcgtaa gctatgacga   6180
acctagtagg ccggtgctgg accattccaa aaaacctata aaaataaatt taatattaaa   6240
ttaaacatat ggtctatata tcagatatta aactcaaaag aataattatt ataatttatc   6300
ttagctaaaa ggttgagaaa ggtatgcgtt aaaaaagagt tttaacccat ttttatagct   6360
tatttgatcg cccgtccact tttagggagc gaggtggtac tatgcagaag tgttgcgctg   6420
tgtgcgactt actatcatgt tgggtttagg tggattctca cgacccaatg atagacgaga   6480
agtgtgggag atgaacaaac ctacgcattt cgcgtacgac acatgtgttt gaacaacgag   6540
ttagattgga aaaaatataa tgaccttttt tgcaaaaatg actacaatga aaaccaggaa   6600
aaccggtgct tcataggagt agagatttga cggtaaattg ttacgatcta ctggtatttg   6660
ctgcgaggat gtattcgctt ggtgaaaaca gaattacaga gtagcagtag cagggaagac   6720
agtagcgaga ggagaagaag aaacttgagg aagaagaaga taaatgtagt tgttacatcc   6780
tgccttcgcc gtaggtctca gcgagcatat atcttcaggt cctccattct gggccctgga   6840
atctcacatt ggccttacgc tggcgtgttc ctcttctcgg cccaactgta gtcttctctt   6900
gaggcccacc agtctccaca ttcctttgtt gctgctatag ctcctcggac acggctgctt   6960
ccgcctgctg ctgcacctgg atgtcttctg aagtcgactt gcgtggaggg acagtgctgc   7020
cattcccctc ccgataacac gctgcttgtc cccaagcagg cgctcgaggg aacctctgac   7080
gaagtggaat caggtcctcc caagttgcca gagatggatg caactcagac cacagaatca   7140
accgttgtga tgctccatta ggcccccatc ggcattgtag tactcgttca ggaatttggt   7200
ggttgtcaag gcgatcagga agctgtgcca ccaccactaa agaacccact gccttcttga   7260
gttgtgaaac atggaacacg ggatggatag tagaagtaac tggaagctcc agcctgtaag   7320
caacagatcc caacttagca gcaactggaa atggcccaaa aagcgaaaat ctagcttctg   7380
atttgcccga ggtgcaagcg atgactgcac ataaggctgc ataacagcct tctcttgcag   7440
ccactctccg aggataggca caggagtgga atccaaaatg tcaatgccaa aatgcttggg   7500
tgcataacca tatagcacct caaatggaga cattttcaat gctgaatgcc aactagaatt   7560
gtaccaaaat tctgccaagt acaaccagtc aatccatttg tgaggacaag catgcacaaa   7620
acatctcaaa aaggtctcaa ggcactgatt aactctcttt gtttgtccat cggattgagg   7680
gtgataggaa gaactcatat tcagtgatac accagccagg gtaaacaatg atttccagag   7740
ctgactagta aagattttat cgcgatcaga gaccatagca gatggcatac catgcaggcg   7800
ataaatgtgt tgcataaagg ccttggccac cactgcagct gtgaaggggt gtttaagggg   7860
```

```
aatgaaatgt ccaaacttgg agaatttgtc aaccacgaca agaatacaat ttttacctcc   7920
ggacacaagc aagccttcaa caaaatccat agtgatcgtt tgccaagctc ctgaaggcac   7980
atgaagaggt tggagtaggc ctgggtattt cactctctca ggtttagctt gctgacaagt   8040
ggcacatgct gcaatgaact ggatgacaga tttcttcatg ttcggccagg caaacaactg   8100
cttcagccga tggtaagcga ctgctatacc cgagtgaccc ccaacagcag aactatggag   8160
agcagacaat atagactgtt gaagtgtatg attgttacca acccaaatac ggcctttaaa   8220
cttaagcaac ccttcttgaa gagtaaaatg aggaacaaca tcttggtcaa caaccaactt   8280
agataacaag gtcttagccg aagggtccaa caaatatcca tccattacca aacgagtcca   8340
ctatggtgaa cagactgaga gagcatgtaa tgtgatagca tgttgtcttc tcgacaaggc   8400
gtcagcaact ctattttcat gtccatgctt gtatacaatc ttatattgca accccaaaag   8460
tttagtaaag acttttgctg ccatggagtg ttaagccatt gctcattcaa atgcaccaaa   8520
ctcttttggt cagtataaat aacaaactcc ccatgaagta agtaagctcg ccattgttcc   8580
accgcgacca atatggctaa gtactccttc tcataggttg ataagccttg agtcttaaca   8640
ccaagaggtt tgctgagaac gctaatggat gaccattctg caaaagtaca gctcccaccc   8700
cattcttgca agcatcggtc tcaatagcaa aaggttggtg aaagttggat aatgctaaca   8760
ccggggctga gatcacagct tgcttcaagg tattgaagga gatttcttga tcttgagtcc   8820
aaacatagaa cacccctttc tttcacagtg catttagagg tttggcaata atagcaaaat   8880
gactgacaaa tcgcctataa taacccgcca aaccaaggaa gctccttaac tctttaacat   8940
tggagggcac aggccagttc aacacagcat caacctttgc aggatcagta tccactccag   9000
cagcactgat cacatgaccc aagtaagcaa tagatgtttg agcaaattta cacttagact   9060
tcttgacaaa ccagtggtct ttttggagaa tggtgagaac ttgggccaag tgagatacgt   9120
gatcgtcaaa tgacctgctg tagactaaga tgctatcaaa gaagactaca acacacttcc   9180
tcaacaaaag ggccaaagaa gagttcatag cgccctgaaa ggtaccaggt gctcccgaca   9240
atccaaaagg catgactcaa aactcaaatt gaccatgatg tgtctagaac gctgttttaa   9300
actcttccct aggcttcaac ctcacccgat gataccctga agccaagtcc aatgtggtga   9360
accaacatgc accatgcaac tcatccatta actgttcaaa gatggggatg gaaaacgggc   9420
tttgaccgtt aaagcattca aatagcgata atccacacaa aactgaaaag tgccatcctt   9480
ctttctcacc aacagcacag gagaattaaa agatgatgca ctgggtctga taatccccga   9540
ctgaaccatt tctgccacct gacgttcaat ttcatctttc ggagctggtg ggtatcgata   9600
gggtctgata ttaactgggc tggcaccagc aaccaatggt atactatgat cacaacttct   9660
ttctagaggt aaggacatag gtttagcaaa aaccgactga aactggttca acagctgaac   9720
aatttcagga ggaagggtag cctcatcagt cagagcaaca gacacttgag atagggaaat   9780
ctgaaccaac aattcgtcaa ccggctctac agtttcccct tgcaagagca cttgcacacc   9840
atgataaggg atcaacatcc atcgttgttt ccaatgcact tccataggac tgaaagtctc   9900
taaccaatca agtcccaata tcacatcaaa ggattgtaat ggcaacacct tcagatcaaa   9960
ggaaaaccca tacccctaaa ttgtccattg agcttgagta aacacttggg agcaagtcat  10020
aacaccttca ttagccactt taacctggag acaagttggt accaaagtaa tgtcggttaa  10080
cctggaaatc atagtgtgac tgataaaaga gtgtgaactg cttgaatcca caagaataac  10140
gatttcatac tcctgtatag accctctcaa caaaatggat cctttggccc ttgatcttga  10200
aacagcctca gcagatagag ccaagaagag ttgttcctcg tggactgaat cttctgatgg  10260
```

agaagactca ttcagaaatg caggcataag atcccagact tcctgcaggg catgaagttg 10320
aactgtagta ttgcagacat gtcccctatg ccatttttca gcacaacggt cacaaagacc 10380
acgtgcatga cgataagcac ggagtgcagc cagtttttca tcagtgcttc gatcagtctg 10440
catgagacgc tgcttaggta aggatctcgg cgcactggca cttgctgcag cagtagttgg 10500
ttgaggaaga ggcagggtcg tcttgtgctg ggatttcgac caaataccac gatcaccctt 10560
gcagaattca ctccgcatag gtggagcagc gacctcatcc tgcaaaaaag cgagggaaca 10620
ggcaatatcc agatccatcg acctttgaag cataacaaca gcacgcatat catcgcaaag 10680
accatccaca aaccgtgtaa caaaatataa cggatcaacc ccagactcat acacagagag 10740
ttgatctacg agagaagaaa attgttcaat atattgagtt aaactaccta actatttgat 10800
gcgaaataag tggtgcaaca acagctgata ctggtcctta ccaaaccgtt cgttcatcaa 10860
ttgacacaag agaggccaag acaaacgggg atgacgaaac ataactgaca gaaaccagca 10920
cgctactgta ggcgacaagt gcatagaggc aattttgacc catgaattca gatcaacttg 10980
atatatatca aagtaattct t 11001

<210> SEQ ID NO 10
<211> LENGTH: 1284
<212> TYPE: DNA
<213> ORGANISM: Artificial Sequence
<220> FEATURE:
<223> OTHER INFORMATION: cDNA

<400> SEQUENCE: 10
atggcgagct actcgtcgcg gcgtccatgc aatacctgta gcacgaaggc gatggccggg 60
agcgtggtcg gcgagcccgt cgtgctgggg cagagggtga cggtgctgac ggtggacggc 120
ggcggcgtcc ggggtctcat cccgggaacc atcctcgcct tcctggaggc caggctgcag 180
gagctggacg gaccggaggc gaggctggcg gactacttcg actacatcgc cggaaccagc 240
accggcggtc tcatcaccgc catgctcacc gcgcccggca aggacaagcg gcctctctac 300
gctgccaagg acatcaacca cttttacatg cagaactgcc cgcgcatctt tcctcagaag 360
agcaggcttg cggccgccat gtccgcgctg aggaagccaa agtacaacgg caagtgcatg 420
cgcagcctga ttaggagcat cctcggcgag acgagggtaa gcgagacgct gaccaacgtc 480
atcatccctg ccttcgacat caggctgctg cagcctatca tcttctctac ctacgacgcc 540
aagagcacgc ctctgaagaa cgctctgctc tcggacgtgt gcattggcac gtccgccgcg 600
ccgacctacc tcccggcgca ctacttccag actgaagacg ccaacggcaa ggagcgcgaa 660
tacaacctca tcgacggcgg tgtggcggcc aacaacccga cgatggttgc gatgacgcag 720
atcaccaaaa agatgcttgc cagcaaggac aaggccgagg agctgtaccc agtgaagccg 780
tcgaactgcc gcaggttcct ggtgctgtcc atcgggacgg ggtcgacgtc cgagcagggc 840
ctctacacgg cgcggcagtg ctcccggtgg ggtatctgcc ggtggctccg caacaacggc 900
atggccccca tcatcgacat cttcatggcg gccagctcgg acctggtgga catccacgtc 960
gccgcgatgt tccagtcgct ccacagcgac ggcgactacc tgcgcatcca ggacaactcg 1020
ctccgtggcg ccgcggccac cgtggacgcg gcgacgccgg agaacatgcg gacgctcgtc 1080
gggatcgggg agcggatgct ggcacagagg gtgtccaggg tcaacgtgga gacagggagg 1140
tacgaaccgg tgactggcga aggaagcaat gccgatgccc tcggtgggct cgctaggcag 1200
ctctccgagg agaggagaac aaggctcgcg cgccgcgtct ctgccatcaa cccaagaggc 1260

```
tctagatgtg cgtcgtacga tatc                                           1284


<210> SEQ ID NO 11
<211> LENGTH: 1140
<212> TYPE: DNA
<213> ORGANISM: Artificial Sequence
<220> FEATURE:
<223> OTHER INFORMATION: cDNA

<400> SEQUENCE: 11

atggcgagct actcgtcgcg gcgtccatgc aatacctgta gcacgaaggc gatggccggg      60

agcgtggtcg gcgagcccgt cgtgctgggg cagagggtga cggtgctgac ggtggacggc     120

ggcggcgtcc ggggtctcat cccgggaacc atcctcgcct tcctggaggc caggctgcag     180

gagctggacg gaccggaggc gaggctggcg gactacttcg actacatcgc cggaaccagc     240

accggcggtc tcatcaccgc catgctcacc gcgcccggca aggacaagcg gcctctctac     300

gctgccaagg acatcaacta cttttacatg gagaactgcc cgcgcatctt ccctcagaag     360

agcaggcttg cggccgccat gtccgcgctg aggaagccaa agtacaacgg caagtgcatg     420

cgcagcctga ttaggagcat cctcggcgag acgagggtaa gcgagacgct gaccaacgtc     480

atcatccctg ccttcgacat caggctgctg cagcctatca tcttctctac ctacgacgcc     540

aagagcacgc ctctgaagaa cgcgctgctc tcggacgtgt gcattggcac gtccgccgcg     600

ccgacctacc tcccggcgca ctacttccag actgaagacg ccaacggcaa ggagcgcgaa     660

tacaacctca tcgacggcgg tgtggcggcc aacaacccga cgatggttgc gatgacgcag     720

atcaccaaaa agatgcttgc cagcaaggac aaggccgagg agctgtaccc agtgaacccg     780

tcgaactgcc gcaggttcct ggtgctgtcc atcgggacgg ggtcgacgtc cgagcagggc     840

ctctacacgg cgcggcagtg ctcccggtgg ggcatctgcc ggtggctccg caacaacggc     900

atggccccca tcatcgacat cttcatggcg gccagctcgg acctggtgga catccacgtc     960

gccgcgatgt tccagtcgct ccacagcgac ggcgactacc tacgcatcca ggacaactcg    1020

ctccgtggcg ccgcggcaac cgtggacgcg gcgacgccgg agaacatgcg gacgctcgtc    1080

gggatcgggg agcggatgct ggcacagcgg gtgtccaggg tcaacgtgga gacagggagc    1140


<210> SEQ ID NO 12
<211> LENGTH: 16619
<212> TYPE: DNA
<213> ORGANISM: Zea mays

<400> SEQUENCE: 12

atcttttatt ggtttgagtt gaacctatat gcacctgtag aatataatct agagcaaact      60

agttagtcca attatttgtg ttgggcattc aaccaccaaa attatttata ggaaaaggtt     120

aaaccctatt tccctttcat ccgggccctt gcggcggacc gtccgcgaca ccagggtgag     180

ccttggacag gaacactgca aaaacacaag ttaacactac ggatcgtccg atggagaagc     240

gagcaccgtc cgagaccaag cacggaccgt ccggcctcag gcgcgaatcg cccggtcgtt     300

gaaaaaccag aaaaacccga aggtgacggg ttcggtaaaa tgcattttta gcgtccttgc     360

ggatcgtcct gggtgcacgg tcggaccgtc cacgactgct ttatctgaca tttgacgacg     420

cattaaaagc tctatagccg ttactcctga ccgttgtgat ttcagtcgtt gatgtgcagg     480

ggtacggacc gtccgcggtc ggtagaaaat gagcaacgac taggaagtgg ttggaggcta     540

taaatacaag agaaaattcc tggtatgcca tcagatttta tactcatccc ttgtgtgcca     600

ctgagtggca tataagtata ttttttgtg tctatgacat gtggggccag tggcatacaa      660
```

```
ggaatgagta tatttttcag tggcatacag ggaattggcc ctaaatacaa ccccaaccac    720
ctccattcaa atgatccaag cactccactc attcacattc aatacaggag ctagcaatac    780
attccaagac acactcaaag ctttcaatct ctcaaagtcc cacaatttag acaagtgatc    840
attagtgctt agtgacttga gagagtgtga tctatgtgtt atttgtcgct cttgttgctt    900
ggctttcaca attgggcttt cttcatctct ttctcaacct tctaagtgaa ttataaagca    960
agcaagagac acctaatttt gtggtgatcc ttgtggggtc ttagtgaccc gtgtgattaa   1020
gaagaagcac tcgaccggtc taagtgaccg actgagagag ggaaagggtt ggaatagacc   1080
cggactttgt ggcctcctta acggggacta ggttctttgg aatcaaacct cggtaaacaa   1140
atcgctgtgt ttatttgtgt tgattttcac tcgatttgtt tcccctccct tcctctctct   1200
aaaattccct tgctcatatt gttgtgagtt ggctctcaaa gttatctgca ttgattgggc   1260
aactacttgc aaggataact atcttccgca ctccgaatta tttctgacat taaccccggg   1320
cataatgtgt gttttaagtg tataattttc atgtttcgcc tatttacccc cctctaggcg   1380
actttcaaat gttctccttc acttgtgatg tctacaacca taatcagctc aacatttgga   1440
ctatcaccct tgaacactta tgttgaactt taaaagttgt gcactaagca cttgtccaac   1500
acttaacaca cttgtcagtc ctttaattgg gttgtcatct aaaccaccaa aaaccacaaa   1560
gagatctttc accggggtcc gtggttcatg gccgtactgc tcggtctcaa gatttttatt   1620
ataaaatcac tagagctcta ctatttatgg ttcggtgtgc catcgaaccg tctccaacgg   1680
gtacatccaa cgagcgccag cacaccaacg actagttgac gtggtctacg gtccagaggc   1740
tcatcagact tgtcaggagg ctcgtcgact ggtctggtgc cacacccgtc gacttgggat   1800
cgaacaagaa tgatggcaag aggacgaagc gcatcaagaa gatcatctac tacgactcct   1860
cttacccttc acacaaggac gacgattcca cctcctccaa gaaaaatacg gttaaacaag   1920
gttactctaa gacatctttt atttattctc gcattcctta caatttcaat gctcatttgc   1980
tttctattca tcttggcaag cctgctcgct ttgatgggag gactattctt ggtggagcca   2040
taaaatgcgt agccatattt ttttgctcca ccctagcatt tgggatgtcg tagacaatgt   2100
aatgcaattg ctaggtagcg atgataaaaa ttataatact attattgccc aataatctat   2160
tcataatagc gcccaagcta aagaggtgcg ctaagggatc ctttttatag cccaaagagg   2220
tccataggcg ttgctccttc cttctaaaca tcgatgaaat tgtgttgtct gcgaggacat   2280
caaaccgggt ctgtgcacac cttctccggg atctgatttg gtgctttcct taactgattc   2340
acagcggacc gatccgatgc accaccggac cgtctgccac atcagctagt cgttggcctt   2400
caaactccac cgggaagtag ccgttggagg cggtccggtg cgccattgga ccgtgcaaag   2460
tgaagggtcg atgattttta taaataaaat ctcgagacct caaagttcag ctctgtaggc   2520
ggtccggtgc acatggacct ggttcgatgc attaggtcgc ctaacactaa gttctatgcc   2580
ctgcggactt gatccggtgc accaccagac gagtccgatg aggcctagaa caacccaagt   2640
aaggctgttt tgagcctaac ttcttcaaat ccttttggct attcttggga gctttccaac   2700
aacttagaca aacataatta gcacatattc caattgatta ggtgtggaga actcaccttt   2760
tactttgtcg ttcaccatga tttgcatttt ggcttaatct aagtattcga accacttttc   2820
tcacaggata gagttagagt tcaaataaag tgctaaacac atagtattag acacatgcaa   2880
cttatctaag taatcaaacc tcatgatttt acccttttgt ccaaagctgc acactttagc   2940
cttcatttta gttctttagg atctagtact ttcaaattga cttcaagtgc ttgtgctcgt   3000
```

```
actcatatca aattagttag tccatgttgt tgtgctaaac acttaatcac taaaacatgt   3060
agaaatggtt atctaacaca tttttctttc ataagtaaaa caggagattt atattgtaga   3120
tgttattgtt tgttgatgaa atttgaaata agagatataa gagcaactcg aaaagcctag   3180
ctaaatcgat ttgtatcggt aaaaatagaa aactgatgat taaaatagga tccaacaaac   3240
tctctttgct cctctctatg ctatcctgct cagcatcacg tcgaggtctc tagccatatt   3300
tgctgagctc acctgcctcg ccatcttcat tctctcgtgc atcctcaccg tccctgcgcc   3360
ttgccgtcgt tgcagctcac tgtcccacgc cctgctgtcg ccatgcctcg ccgaccctgc   3420
ggctcacctt accgcgcctc gtcatcgtcg cggctcgccg tctcgtgcct cgccaacccc   3480
gctccttgac gtcctcacgg cttacagtcc ccatcgtcct cgtggctcca cgcctcgcca   3540
tatttgcggt tcactgtcca cgtgccctgc catcctagag cccgacatcg atatgtcaaa   3600
tgagacagga gaaaaagaaa tgaacatgtg attataatca gtgatttgaa tattgataga   3660
taagatttga agagtctgtt gtgtcatatc accttttat gaaactcttt attttttaga    3720
gtttttataa aactctaaat ttagctaaaa ttatatctag tcttttagag ttactctaac   3780
aagagatgag atagcgagct ggcgagctgc tggagacagc cgagagtaga gatagtagag   3840
gagactagaa actccattag gcctagccca gagtcagcta gggatgccgc ccgatccact   3900
acgtactgaa agcgatcccg gcccatgaac gctagtgggt tgtaattcgg cttacccaag   3960
tacccagccg ttcctccaca cctctgcact acccgaaacc cacgcccaac ggccgtttcc   4020
cgcacccct  atccgggaag gaagaaagcc agaactcacc cctgcttcgt ctggcggcgc   4080
cgtttcccgc acgcgatgcc gtcgacggcg gaggatttcc cggcgataag gaagctgggg   4140
aagctcttcc ggcttaccga agtgtacctc tggtaagtct cctgtctccc ctacccgctt   4200
ctcagcgtag ggtttgccgt ttgcgaggag tacgtctcct caaactactc tctcttcctg   4260
cagggacgat tcgtatggcg ctggacctca cgatggacag aagaacgggc gctcggcgga   4320
ggctgctctc gtggtacggt ctctgacccg ctttggtgta gctcactctt aagctttctg   4380
agttgggggt gcgcttgtgc ttcgactagt agatggctaa tttcgtcggg ctactggtaa   4440
tttcttggta tctgcattgt cgagaaagaa ggcccgacgc ataatttcat gcttgcccaa   4500
gagtctactt aacacaagga attggttttg tggcgtggtt tgtgcattgc gcccaaactg   4560
tagcctgtac aaaatgttaa tcgtcgcgtg cattttaaac aaagttttgt attatacgac   4620
aaaataccct cggcacattt gttacagact accgataagt gcatacctat ttctcctagt   4680
tctatcagga aataatcctg gacctcgaaa tgacagcctc gtctggctag aaccctacta   4740
aacattttga gtgatcactt ttcattactc attttcttga tgaaagcaca ttactgacat   4800
ggaagtttgc tacataagac ataacacttc cttgtagtgc tttatttaat tattgaccga   4860
tgatcttttt ggaaaattaa gctgtattaa acaattgtag cttcggtgat gattgttgga   4920
ttaagcatta gtctgctgca gtcctcttct tgattctgat atgacagtta tttgttgatt   4980
aaaataatga tggtttgctt tacacttcga tctcctttga gaggaaaaca tgtgaaggtg   5040
tggactagat catgtataga ccaacagcat tatcttatta aaacacttct aaataactta   5100
gcaatttcat aaccattttt acacttctga ggaattcatc ttgtcgtgaa agagtcaatt   5160
aacttagctg cttagcagac tgtgtcaagc ttattacttg tatgttgtgc cctacaaatt   5220
actatgaggt ttataatgta catagcaatt tgacgacctt caacttttca ggactctcat   5280
acagataaaa catgcaatga agcatccaat agcactgaca aaggttagat gtatttttct   5340
tgtattctag tatcttcctt ggtcaatttt ctttacagag gatgttacaa tgtactctac   5400
```

```
tttttttgtg tggaaacaac ccactagaga aaaaaaatca cttcatttga gaaatcttaa   5460
gaatctgaac tctgaagctc agcatgcttc cacaccacca cttttcaggc cactgtctct   5520
tcattggagt aaatgacgct tcttttagag agaaagagag gggggggggt ctgtttataa   5580
ttgaatcaag agattttatt ggtcacctga tttctgttgc atgacgtggg acctggatag   5640
acttcagatt tgccttagtt gataagttca ccggcactag tgaaagaaaa gtatatggta   5700
caggtactct tatgaacagg caaccactta gcaattcagc atctaataga gaaggaccaa   5760
gtcttcaact aaagtcacaa tataccttta gtactattag aggggctgac cctccttgtc   5820
tagtgcttgt gagatcatag gagatggggc gtggtggtta agattgtgga tcatattcgc   5880
caagctccca gggtcaatgt gattgaggga tgtggtatgc tacttgtgaa agggttcaaa   5940
aaggccagga tgacattgtt cctacattcc tggaatgggg atgacacccc caggacaagg   6000
aaggtggcac agttccacgt tcctggtgac atgttgtgta tcaaatggga ggccaaatca   6060
ccacgggatt actctaggaa gggaagatga tgttgataat ttgagtcatt gttgcaacat   6120
ctgttcatgg tttcatgcct cattttataa gtcatattgc ccacacataa cattgtaata   6180
gtaaaatcaa caccagttat tttacgtttt cccttgtatg tcaaccgatt tcttactgtg   6240
tatatgatct gtctatcaat aggccatttc tttgttgaag atttggaatt ggtcaatctc   6300
atgggttctt tggggcttcc tgtttcattc agcacaagta aagtggtcag ttgctcacat   6360
agtgtgacac catgttactg ttccctaccg gttccattgc ttaattcctt tatgcattgc   6420
agaacaagaa cacatgcaac aagggaaaga aaaaaggaag acaagcaccg ctcaaagcag   6480
caaacactca aatcaatgat gctgtgagga tatgtatcaa tactgaagat agagaaaatt   6540
ctgttgaatc attggatgct atggagcaaa cgcactcatg caatttattt gtgacaccac   6600
tgggtcaaaa tgaaccctcc cgtgatgaca ctgacaagag gcttagggaa gacagctctt   6660
gtgttgaaga acaagaagag tctggctgta gcaccatcta ctctgctggc aaagcccctg   6720
gctgtgatgc taaaaatcat ctcactgaac ttggggcttt tgagctttct gataacttgg   6780
ccaactcagc aaaagaagaa tactcaattc aagaaaatca agcttatgaa agtgtgttgc   6840
tagattctga agagatgtca aggaatgact gtgttgatga tgaatctaca cattcctgtg   6900
ttggcattta tcaggatgaa agagtgtcca caaggggaga tcaaacatct gaagaaactc   6960
tatcagtacc ccatgattac aatgatgttg gcagagaagc tagtctaagt ttggcagagc   7020
catcatctat tgatgagcat gcacaaagct ctgccaacaa cttttactat gactatggtg   7080
aatggagggt tatctgggat ccattctata atcggtatta tttttacaac atccagacac   7140
aagagtccac atggtgtcct cctgaaggac tggaggattt tgcatcatat tgtagcccag   7200
ataccactaa agagctagct gaactgggat ctcagtgttc aagcatggca ccacaagaga   7260
acagtaaaaa ccctagtctc gtcctttgca gttgacatta cgaatagtta tatgcactac   7320
gataaaaact ttctacaata tgtaacactt gagcatgtgg caatgggtgt aaacatttaa   7380
taataaggta gtgaaatcca ttacacacag tattgaattt tgcactacaa atgctgaagg   7440
agaaacctaa attgtcaatg ctttttggtg acattaatta ttgccattga tttcctgctt   7500
gtaggtgctt catttatctg tctccaattt actcatatgc tagcttcttg tttgggacta   7560
aaggctttgc tgttgtttta gtatgtcaca catttctctt taatctcacc atcacagatc   7620
tggctactca tgtcaatcat ttagaagcac aggagcaaga tcactgcatt catgatttat   7680
ctgacattcc tgttgaaaag ccaatatatc aaaggtaggg aataccaaac tgtacaatgt   7740
```

-continued

```
tgaacaagtt attgtttttt tttgttaatt ctgttcatct atgcagtatg ataactacct   7800
ctgacaaagc acagcacact gaaaataagt acagcgattc aacaactact gtgttagaga   7860
tgaaccagga agttgctagc accaaaacga aaaagagagt aaggagatct cgatcgtgta   7920
aggcgataat atatggcatc tgctttctag gagtttgttc ctgttacaat tttaggttgc   7980
gcatttacac aatagtttct tggtttcttt gagcaaatgc agctttgcat gactgctaca   8040
ttgcctactt atgtctaggt aacttttctt tgcaaactgc aaagttatgt ctaggtaact   8100
atgccttcta gaaaacctcc ttgttagcta tgtattagtg agacttgcct aatatttatt   8160
ttcttgtggt ccgttcttgt gctctttgta catatttgcc aataaccatt ttaattgttc   8220
tacagatcat tcatgccaag acatggcagg gaacgtctct aatgacatca tcaagtactg   8280
ggctcagcgg tattcacttt tctcactttt tgatagtggt ataaagatgg atgaagtagg   8340
gtggttttca gttacgccag agccaattgc aaagcatcat gcatctcgtg tgggtgcggg   8400
agtaatgatt gattgtttca caggagttgg tggaaatgcc atccaatttg ccaaaaagta   8460
cgtcaatgtt atcttgcaat tgagttatgt gatggtctaa tgtatcattt gcttgaacac   8520
ttcctgttta gtagcaactg ttatttttct tatgtcacga gaatgcaatg gctatatcac   8580
cttaagcagt atgctatgtc cactgtccag tttaactaag gcatctgctt ccagtaatat   8640
gcaaggctct tcttactttt gctgttattt aatatatgga agtgtcctta cggaggtgtt   8700
attgtggaca ttttgagcat gttcatcatg tcacttgagt tagtagagcc agccttagtt   8760
gtttgcagtg taggtggatt tattttatgt tatcaatgtt tcttctacag tactaagact   8820
attgttccac attaactatg tctccttttc caggtgcaag catgtaattg cagttgatat   8880
tgatccacaa aagattgatt gcgcgcatca taatgcatcc atttatggag taaatgatca   8940
catagatttc attgtaggtg attttataca tatagctcct catctgaagg taatgccttt   9000
ttcttggaat tattactttt aagtttctca acacgtcact tctattagct atatgttttt   9060
gtagctgttt gcgagagtga atttattgtt gacattgttc tcatttgccc acccatttta   9120
ggataggggc ttggtactac aaatatcttg atacttcaag tcctacaaaa agaaatttat   9180
gtttcatatt ttttccattt gaacgtcgag attttatggt cccatggagt tctccctatt   9240
tttcgatgat gcccatcttt tggcagtacc ttctttgtgt acacaataaa tgggaggata   9300
ttttctgcag ggagaaactg ctttcatgtc gcctccttgg ggtggccctg actatgccaa   9360
agttgatgtt tatgatatga aaagcatgct tattccttgt gatgggttag ttccttgttt   9420
ctattttaag agagtaattt ctttcagttt gcactcactg atgtttactt actttgtgag   9480
taaaacgcac cagagatcca ttaaccttta aggaggtgtt atctatgtcc atcaacactc   9540
aaactgcatt tttgggttcc taaacttttt aagtgattca ccggagttcc gtaccccttc   9600
gtttatattt gtattttgca gaaacctcac tctgttttat ttctccttcg catgtagggg   9660
tggtaatgga tcacgattca aacgtttctc cacgattcgt ttgagccctt aattaatttt   9720
agtacaaaaa taaatagaaa tagagataga gcctgatcct aatatgattt gatcctcaaa   9780
ttttatagcg tagaatttag agcccattac catttaccac ccctattcac atgcctaccc   9840
ctctccatct tctggattga atgttccaac ctaatttaca ctcgtagttt ctttgatctg   9900
ccaatcaaat ccagagccta attgctataa cattagaacg aacacgccat attaccagaa   9960
tactcgatgc agatatggat agaagcgagg cgctaagcgc agccagcctt ggcttcttgc  10020
tctgcaggcc gatcagggcg ccagccaaag ccaaccatgc gcgcacgtga ctgcaatgct  10080
actctctctt cgcctttgcc atcgtcgtcg caggatgtta cgttgtgctt atgctggctc  10140
```

```
ccacgagtgc cgccgcccag agcgagctga gcgcacgcag ccactgcttg tggttcacga  10200
gcgtgagcat gccctcacca cctgctgctg cgcccttgct gcttgcttgc ttgccggtgg  10260
tgtacattat ggacggatta aattgaatgg atttacctgt tccagaaaaa gatctgatcg  10320
acgatgggat gctatcttgt atggctccgg atcaatgaag attaatggaa caaccaatcg  10380
aaggctcaga gcaggctagt tggtgcccgg aagactctgg ccagaagatg gaaatgggta  10440
agcgtgtgaa ggaaaaaaga aatagagggg gatttctaca aaaaacaaac ataatgaaga  10500
ggtatggatt tcaggtgaac cacttaaaaa ataaaaaggg catacccagt gccgtaggct  10560
tcccgcactg tgcggggtcg tctggggaag ggtatcttta agcgtcaagt cttacccgca  10620
taatatgcag aggctggggc tcgaacccgg gacctttcgg ttatagacgg taggctctac  10680
cgccgcacca agcccgccct tgaaccattt aaaaaattta ggactcaaaa atacagtttg  10740
acagttgatg gacctagatg acacctcctt aaaaaattta atggacctat ggtgcatttt  10800
aatcttttgt tgatcgacta tactcaatgt tgaactcttt aggtactctc tttttaaact  10860
cggaaccatg atagcttcaa gagtagtgat gtttcttcct cgcaacattg acctaaacca  10920
attggcggac atgtccttgt ctgtggatcc cccgtgggca gttgaggtaa gcccattttt  10980
gctgattttg tgccaagctg acgtttccta tagatgtcac agtggtctct ctctctgcag  11040
gtcgagaaga acttcctcaa cggaaagctg aaagccataa cagcttactt tgaagaacag  11100
gatcgttgaa ccaagcatcg gcgctggtga tacaaatcat cttgttagct atgactcacg  11160
acaaattttt gtggtgaccc taaacagaac ctttgtgttc ggagacagaa agaagcggtt  11220
tatcatcttc accgagcata gataatttat ttgcagagat gagtcattgg tatcatacaa  11280
aagcagctca gcttatctca attcacagca agtgaaactg tcgaaggaaa actacaaggc  11340
tgacagtcga acgcgtggga gttagcttaa ttttgcctta tgataagcaa gcatgcttcc  11400
tggtttattt catacagcta ctagtagttt cagctgcaac agttgtgcgt tggtgtgcgt  11460
gtgattctca catatctggt cctgcggatg tgagtgatgc aaatgtatgt gtcatcatcc  11520
catgtaaggg tttgtttgtt tgctctcaat ctatgtagat tgagtgggat taagtgagtt  11580
taaatctcag acaagtcaaa aaaaaatgtt ttcaatctca tccaatccac atatgatagt  11640
aatacccgag taaggcttag atgtaatagt tggaataaga aaaacaagtc agccattttg  11700
aagttttgtc cttggagttc tattaaaagg cattactgat aaatctccaa cagatttgca  11760
gttgaagcaa catgtgaaac atatttatca tgttaaaaca atttgcctta gtattcgatt  11820
atgccatgaa atctgacatt tccttacaca tcccagttta tcattgtcaa ctgtctttag  11880
gaatgtattg tatctgctgt ttttacttgt atatgtatgt tattttttgt cgttgtatgt  11940
atatgtttta ttataaacat ggccactaag gttgttctat tcgttaaaat aacacagatc  12000
tataaacgac taaacaagct tcttgggata aagaatcata tggaggctgg attttcgagg  12060
agtctggtgc actgttttgc taatgatcag cccccccccc cccccccctct aaaaataaag  12120
aaaatactgg atttcctgtt catttattac attcatatgt aaatgcttct gtccttttct  12180
atatctgggc tggacttttt gtgtgctcgt cactcaagtt ggttagtgtg gttaatttta  12240
ttatgctccg tgctctttcc taccgaactt ggtctttgtt agtatcatta tcagtcagtt  12300
atattttctc ctcttgatgc ttcatctaat ctatttttgc aaagttgtca tgttatgtac  12360
tatatgatct tttacaaggt ttttgacttt tcaaattatt gtgtcgtata ttatttgtac  12420
tcagattgtg cttacaactt tagtttatct atactttaag ggtgtttggg tttctatggg  12480
```

```
ctaatttata atcccttcat tttattctat tttcgtacct aaattgtcaa gcacgaaaac  12540
gaaaataaag ttttaacttt tatatttagc agtttataca ctaaaataga ataaaataga  12600
tgaagtaaaa attagtcctc agaaaccaaa catctcctaa atgtctagta atagtcgcct  12660
gaactgtaga gcgcccaaca cgcgccaccc tgatttggtg tcttaaaatg gcatgtgtat  12720
ataggtggaa tgggtttgac gagactgtaa ctactttttc ttaattaaat tatagatgga  12780
cttaactttt ctatatgcat tttaaatata tttttctata tttttggtgg gctgagttac  12840
agtttatgtc aatataaatt acaacagacc gaatctaaaa ttttattata aaatgtatgc  12900
accaaccgtt gactaaaaag ataaaatttg gacacctaca ttttagcaag tcacctgcta  12960
atatatatct atactaggta agtgtccgtg cgttgcaacg aaaacatata ataatacgat  13020
aacttatata taaaatatgt gttatactgt tatgagaaaa agtttcacct gtcctatttt  13080
tatcaatatg acaacagagg atcaatataa ggccttggca tggcttcaga agttcagatt  13140
aacgaattat ggagcaagag caactatttc tggtgtttca gtagaaagaa tggggatatg  13200
tgtttatctc tctcatacat gttacacaat gtgctataga atgacacctc taggccgctg  13260
ctacaactac agagaataaa ttatggatca tgggtgccct actaagttag ctacacgtaa  13320
aatctggggc gattgacccc ctaatgcttc atcttggaga tctcactaaa atacaccttc  13380
cgcacaaacc gagccttgat aaagctcgcg atcttcgtgt cctgatcttt agtgcagaca  13440
actgcaaggg aaattattgt gccggtcagc aagagtggaa aatgtcagca gaaacacaag  13500
aatggaaaat tatatgatgt gcaagtagga cggcacccta tttaactaaa ggtgtgtttg  13560
gttcagtttt ctgaaccaat tcgttgccaa aaaatctaaa atctcacaca aacggtacaa  13620
catcagaata gatttttaaa agtttataga tttctcaagt tcaattcaaa atcaccatct  13680
accccaaatt tttcagatta ctattattca tgttacaact atcactcttg tagtatctac  13740
cattgatagt tgttttaatc aaatatattt tagctttctc acaatcctca gctcgaaaca  13800
gattttcatg gctcacagtt ggattcatat tttcataaat ctataggtgt gaaccaaata  13860
gaccctaaaa catcatgttg taatgttcca aaaaaatcat cacaaaaaac atgtatgcaa  13920
cacacctaag tgcaacaaca ctaacctgca ggagcgttgg cgtaggctgg actcttgtgt  13980
gtctgcaatg tggaaacctg cattgtaaat ggttaggtaa atgcttcgct taaaaatggc  14040
agtaaatgct tcactaaaaa tgcttccacg tgctcatgat caagtaggtt ttatgttcaa  14100
tctgcagttc tacacaagtg cgattcattt tgatactcat ttctatttac tttcagagct  14160
cgtgctaact gtcataaagt gcaatgcatc tatgactgcc aattgatatt gtgctcctgc  14220
cataaagtgc actgcatcgt gctaactgta cactaatctg tgaggatcta agaccaatat  14280
ttgtttacgt tttctccttt agtatcctat aaaaacaaca cgcctagaca acccaaaaaa  14340
tgtgtcccaa taggaatatc agattctgac gctggcagca atctcgaatg ataatatttt  14400
ttccaaacaa gcgaggtccc taaatagaag cggcaacaga taaaaactaa agataaaaac  14460
taaagagtac agatgattgg catcacatcg ggaatgaaat atgcctaaca tatcaatttg  14520
catattagat tatttgctga gaacaataac gaaaacatat ttagttgttc atcacaagtt  14580
accttagatt ttgctgttca aggtcctttg ggtcttcttt ctgctagaac atacaagggt  14640
atttcagatt tgcaaacaag gaaaagcaag aacttcaatg atacatcatt gtaaaaccaa  14700
gtttccgatt taaataaaga tgatgcttgc ggtcaacaca ttcacaaatg taaatgtgtg  14760
aaatcgttca aacataaggc ttatgtggtc atgctcaggt agtatgtaca gacctaaaaa  14820
caaggtatat gacaacagta ccagccacta aacacacatg gttaatcact aaaacaattc  14880
```

```
tccgattaac caggaaaact atagcagcca ctagaactat acaggtttct accagtaatt  14940

gcttcactaa aaaatgcccc catgtgtaaa ttttcaggtg gtttgtacag acataaaaac  15000

aagggtatag gactacttct tgtgctaaaa taaaagctgg cactaaacag tgtatccagt  15060

tcatcaggaa aacagtttta gtgattaatc actaaaacaa tacccatggt gcaaattatc  15120

tgattaacca tgtacatacc agtaattgct tcataaaaaa tgcccccaat ttgctcatgt  15180

ttaaggaata tgtatagaac taaaaacaag ggtatatgat aacaatacca gccactaaac  15240

acacatggtt aatcactaaa acaattctct gacaactcct ataaaaagat agcaaccacc  15300

agaaataaac cgcccacgac atccctaatt gtagtcacta aaaactggta gcagtaattg  15360

gttcactaaa aaatgaccat aatcacgaaa actataacag tcaccagaac tatataggtt  15420

tcattagtaa ttgcttcact aaaaaatgtc cccatgtgta aattttcatg tcgtatgtat  15480

agacctaaaa acaagggtat atgactactt gctatgctaa aacaatagct agcactaaac  15540

agtgtattca gttaatcatc caaacaattt tgtgattaat cactaaaaca atacccatgg  15600

agcaaattat atgagaataa gatctcgtcg ttcctattgt gaagaatata ctactacctc  15660

cagtttcaaa ttacaatttc aaattacaag ttgtttagaa catccacaag gtaattgcga  15720

agaatatact aattgctcta gtttcaaatt agaagttgtt tagagaaaag gtgttcctta  15780

atagtctagt tttagaagct acatccaact ggtaaacata aattgcagaa accttttatg  15840

tggaagcctc cgtcattgag tctgtcccct ttagctgtaa gtagttttct aaatattgtt  15900

agtcaggctt agttgtttga gactctgttt ccattcgtga ccatgggaac tgtgaaatgt  15960

gtagaagatg ctcatgctca tgcatatgca tcgaattgtt ttgtaaagtc atcttaatgc  16020

tcaaacagtt tttttatctg ccccagctgt acactgcttt ctgaattatg tcatttaggc  16080

ttagctgtcc gagataattt catttgtgat gaaggtaacc ggagcatctg tccttttgtt  16140

ttaaacataa atattttgat agcttaactt gtgcgtcatt ttatcatgta ctaacatggt  16200

atatagatgg cacttagcag taacattcct gacttatgtg attgtcctgt tagaatgctt  16260

ctgcaatata atgggcttat gctaatctgt ttggaatccc atgatgaata acaattatgg  16320

atgttgggca ttttgtattt ttatgatgta ggcttaacat attttcttct ctgctcagcc  16380

ctgccggtgg agacctctat ttatagctat aatccagcca tatctagtga actaacagat  16440

ctattcctat ctctagtgct tatcccctta acagatttat tttcctatct ctatttcttt  16500

gatgttactt gctgcaggtg ctatccccca ctgatgcatt atatgacaat cactcgaaga  16560

atcagatgct aattaattgt tttatacttg accattgcta attaagtact ccattttttt   16619
```

<210> SEQ ID NO 13
<211> LENGTH: 17274
<212> TYPE: DNA
<213> ORGANISM: Zea mays

<400> SEQUENCE: 13

```
caaccctttc cctctctcaa acggtcactt agaccgagtg aggcttcttc cttaatctca     60

tgggtcactt agaccccgca aggatcacca cacaattggt gtctcttgcc tcgcttacaa    120

agcacttgag agtaagaagt gagaaagaaa agaaagccaa gccaagcaaa caagagcaac    180

aaagaaacac aaatgatcct ttaacaagtt ctaatgcgct agagttgaat cgagaacttt    240

gagtggatcg atcacttgaa ttgtgtcttt gcagtggagt ctattgctct tgtattgaat    300

gcaatgtgtt gaatgcttgg atggttagag tggaggtggt tgggggtatt tatagccctc    360
```

```
aaccaccaaa caactgttgg ggaggggttg ctgtcgatgg gcgcaccgga cagtccggtg    420
cgccagcaac gtcacccaac cgttagggtt cgagcgcaga cgactgttgg agctttgtct    480
tcttgtgcca ccgaacagtc aggtgccgca ccggacaggc actgttcact gtccggtgcg    540
cctctgacgg ctgctctaac ttctgcgcgc actggtcgca cactgtagcg ttcgcaggtg    600
tccgttgcag tcgaccattg tgctggaagc cgttgctccg tttggtgcat cggacagtct    660
ggtggcacac cggacagtct ggtgaattat agcggagtgc ggcctgagaa acccgaaggt    720
ggagagttcg gagttgtacg gtcctggtgc atcggacact gttcggtgcg ccagaccagg    780
gcacctttgg tttctttgtt cctttgcttt tgaaccctaa ctttgatctt ttattggttt    840
gagttgaacc tatatgcacc tgtagaatat aatctagagc aaactagtta gtccaattat    900
ttgtgttggg cattcaacca ccaaaattat ttataggaaa aggttaaacc ctatttccct    960
ttcatccggg cccttgcggc ggaccgtccg cgacaccagg gtgagccttg gacaggaaca   1020
ctgcaaaaac acaagttaac actacggatc gtccgatgga gaagcgagca ccgtccgaga   1080
ccaagcacgg accgtccggc ctcaggcgcg aatcgcccgg tcgttgaaaa accagaaaaa   1140
cccgaaggtg acgggttcgg taaaatgcat ttttagcgtc cttgcggatc gtcctgggtg   1200
cacggtcgga ccgtccacga ctgctttatc tgacatttga cgacgcatta aaagctctat   1260
agccgttact cctgaccgtt gtgatttcag tcgttgatgt gcaggggtac ggaccgtccg   1320
cggtcggtag aaaatgagca acgactagga agtggttgga ggctataaat acaaccccaa   1380
ccacctccat tcaaatgatc caagcactcc actcattcac attcaataca ggagctagca   1440
atacattcca agacacactc aaagctttca atctctcaaa gtcccacaat ttagacaagt   1500
gatcattagt gcttagtgac ttgagagagt gtgatctatg tgttatttgt cgctcttgtt   1560
gcttggcttt cacaattggg ctttcttcat ctctttctca accttctaag tgaattataa   1620
agcaagcaag agacacctaa ttttgtggtg atccttgtgg ggtcttagtg acccgtgtga   1680
ttaagaagaa gcactcgacc ggtctaagtg accgactgag agagggaaag ggttggaata   1740
gacccggact ttgtggcctc cttaacgggg actaggttct ttggaatcaa acctcggtaa   1800
acaaatcgct gtgtttattt gtgttgattt tcactcgatt tgtttcccct cccttcctct   1860
ctctaaaatt cccttgctca tattgttgtg agttggctct caaagttatc tgcattgatt   1920
gggcaactac ttgcaaggat aactatattc cgcactccga attatttctg acattaaccc   1980
cgggcataat gtgtgtttta agtgtataat tttcatgttt cgcctattta cccccctcta   2040
ggcgactttc aaatgttctc cttcacttgt gatgtctaca accataatca gctcaacatt   2100
tggactatca cccttgaaca cttatgttga actttaaaag ttgtgcacta agcacttgtc   2160
caacacttaa cacacttgtc agtcctttaa ttgggttgtc atctaaacca ccaaaaacca   2220
caaagagatc tttcaccggg gtccgtggtt catggccgta ctgctcggtc tcaagatttt   2280
tattataaaa tcactagagc tctactattt atggttcggt gtgccatcga accgtctcca   2340
acgggtacat ccaacgagcg ccagcacacc aacgactagt tgacgtggtc tacggtccag   2400
aggctcatca gacttgtcag gaggctcgtc gactggtctg gtgccacacc cgtcgacttg   2460
ggatcgaaca agaatgatgg caagaggacg aagcgcatca agaagatcat ctactacgac   2520
tcctcttacc cttcacacaa ggacgacgat tccacctcct ccaagaaaaa tacggttaaa   2580
caaggttact ctaagacatc ttttatttat tctcgcattc cttacaattt caatgctcat   2640
ttgctttcta ttcatcttgg caagcctgct cgctttgatg ggaggactat tcttggtgga   2700
gccataaaat gcgtagccat attttttgc tccaccctag catttgggat gtcgtagaca   2760
```

```
atgtaatgca attgctaggt agcgatgata aaaattataa tactattatt gcccaataat   2820
ctattcataa tagcgcccaa gctaaagagg tgcgctaagg gatccttttt atagcccaaa   2880
gaggtccata ggcgttgctc cttccttcta aacatcgatg aaattgtgtt gtctgcgagg   2940
acatcaaacc gggtctgtgc acaccttctc cgggatctga tttggtgctt tccttaactg   3000
attcacagcg gaccgatccg atgcaccacc ggaccgtctg ccacatcagc tagtcgttgg   3060
ccttcaaact ccaccgggaa gtagccgttg gaggcggtcc ggtgcgccat tggaccgtgc   3120
aaagtgaagg gtcgatgatt tttataaata aaatctcgag acctcaaagt tcagctctgt   3180
aggcggtccg gtgcacatgg acctggttcg atgcattagg tcgcctaaca ctaagttcta   3240
tgccctgcgg acttgatccg gtgcaccacc agacgagtcc gatgaggcct agaacaaccc   3300
aagtaaggct gttttgagcc taacttcttc aaatcctttt ggctattctt gggagctttc   3360
caacaactta gacaaacata attagcacat attccaattg attaggtgtg gagaactcac   3420
cttttacttt gtcgttcacc atgatttgca ttttggctta atctaagtat tcgaaccact   3480
tttctcacag gatagagtta gagttcaaat aaagtgctaa acacatagta ttagacacat   3540
gcaacttatc taagtaatca aacctcatga ttttaccctt ttgtccaaag ctgcacactt   3600
tagccttcat tttagttctt taggatctag tactttcaaa ttgacttcaa gtgcttgtgc   3660
tcgtactcat atcaaattag ttagtccatg ttgttgtgct aaacacttaa tcactaaaac   3720
atgtagaaat ggttatctaa cacatttttc tttcataagt aaaacaggag atttatattg   3780
tagatgttat tgtttgttga tgaaatttga aataagagat ataagagcaa ctcgaaaagc   3840
ctagctaaat cgatttgtat cggtaaaaat agaaaactga tgattaaaat aggatccaac   3900
aaactctctt tgctcctctc tatgctatcc tgctcagcat cacgtcgagg tctctagcca   3960
tatttgctga gctcacctgc ctcgccatct tcattctctc gtgcatcctc accgtccctg   4020
cgccttgccg tcgttgcagc tcactgtccc acgccctgct gtcgccatgc ctcgccgacc   4080
ctgcggctca ccttaccgcg cctcgtcatc gtcgcggctc gccgtctcgt gcctcgccaa   4140
ccccgctcct tgacgtcctc acggcttaca gtccccatcg tcctcgtggc tccacgcctc   4200
gccatatttg cggttcactg tccacgtgcc ctgccatcct agagcccgac atcgatatgt   4260
caaatgagac aggagaaaaa gaaatgaaca tgtgattata atcagtgatt tgaatattga   4320
tagataagat ttgaagagtc tgttgtgtca tatcaccttt ttatgaaact ctttattttt   4380
tagagttttt ataaaactct aaatttagct aaaattatat ctagtctttt agagttactc   4440
taacaagaga tgagatagcg agctggcgag ctgctggaga cagccgagag tagagatagt   4500
agaggagact agaaactcca ttaggcctag cccagagtca gctagggatg ccgcccgatc   4560
cactacgtac tgaaagcgat cccggcccat gaacgctagt gggttgtaat tcggcttacc   4620
caagtaccca gccgttcctc cacacctctg cactacccga aacccacgcc caacggccgt   4680
ttcccgcacc ccctatccgg gaaggaagaa agccagaact cacccctgct tcgtctggcg   4740
gcgccgtttc ccgcacgcga tgccgtcgac ggcggaggat ttcccggcga taaggaagct   4800
ggggaagctc ttccggctta ccgaagtgta cctctggtaa gtctcctgtc tcccctaccc   4860
gcttctcagc gtagggtttg ccgtttgcga ggagtacgtc tcctcaaact actctctctt   4920
cctgcaggga cgattcgtat ggcgctggac ctcacgatgg acagaagaac gggcgctcgg   4980
cggaggctgc tctcgtggta cggtctctga cccgctttgg tgtagctcac tcttaagctt   5040
tctgagttgg gggtgcgctt gtgcttcgac tagtagatgg ctaatttcgt cgggctactg   5100
```

```
gtaatttctt ggtatctgca ttgtcgagaa agaaggcccg acgcataatt tcatgcttgc   5160
ccaagagtct acttaacaca aggaattggt tttgtggcgt ggtttgtgca ttgcgcccaa   5220
actgtagcct gtacaaaatg ttaatcgtcg cgtgcatttt aaacaaagtt ttgtattata   5280
cgacaaaata ccctcggcac atttgttaca gactaccgat aagtgcatac ctatttctcc   5340
tagttctatc aggaaataat cctggacctc gaaatgacag cctcgtctgg ctagaaccct   5400
actaaacatt ttgagtgatc acttttcatt actcattttc ttgatgaaag cacattactg   5460
acatggaagt ttgctacata agacataaca cttccttgta gtgctttatt taattattga   5520
ccgatgatct ttttggaaaa ttaagctgta ttaaacaatt gtagcttcgg tgatgattgt   5580
tggattaagc attagtctgc tgcagtcctc ttcttgattc tgatatgaca gttatttgtt   5640
gattaaaata atgatggttt gctttacact tcgatctcct ttgagaggaa aacatgtgaa   5700
ggtgtggact agatcatgta tagaccaaca gcattatctt attaaaacac ttctaaataa   5760
cttagcaatt tcataaccat ttttacactt ctgaggaatt catcttgtcg tgaaagagtc   5820
aattaactta gctgcttagc agactgtgtc aagcttatta cttgtatgtt gtgccctaca   5880
aattactatg aggtttataa tgtacatagc aatttgacga ccttcaactt ttcaggactc   5940
tcatacagat aaaacatgca atgaagcatc caatagcact gacaaaggtt agatgtattt   6000
ttcttgtatt ctagtatctt ccttggtcaa ttttctttac agaggatgtt acaatgtact   6060
ctactttttt tgtgtggaaa caacccacta gagaaaaaaa atcacttcat ttgagaaatc   6120
ttaagaatct gaactctgaa gctcagcatg cttccacacc accacttttc aggccactgt   6180
ctcttcattg gagtaaatga cgcttctttt agagagaaag agaggggggg ggggtctgtt   6240
tataattgaa tcaagagatt ttattggtca cctgatttct gttgcatgac gtgggacctg   6300
gatagacttc agatttgcct tagttgataa gttcaccggc actagtgaaa gaaaagtata   6360
tggtacaggt actcttatga acaggcaacc acttagcaat tcagcatcta atagagaagg   6420
accaagtctt caactaaagt cacaatatac ctttagtact attagagggg ctgaccctcc   6480
ttgtctagtg cttgtgagat cataggagat ggggcgtggt ggttaagatt gtggatcata   6540
ttcgccaagc tcccagggtc aatgtgattg agggatgtgg tatgctactt gtgaaagggt   6600
tcaaaaaggc caggatgaca ttgttcctac attcctggaa tggggatgac acccccagga   6660
caaggaaggt ggcacagttc cacgttcctg gtgacatgtt gtgtatcaaa tgggaggcca   6720
aatcaccacg ggattactct aggaagggaa gatgatgttg ataatttgag tcattgttgc   6780
aacatctgtt catggtttca tgcctcattt tataagtcat attgcccaca cataacattg   6840
taatagtaaa atcaacacca gttattttac gttttccctt gtatgtcaac cgatttctta   6900
ctgtgtatat gatctgtcta tcaataggcc atttctttgt tgaagatttg gaattggtca   6960
atctcatggg ttctttgggg cttcctgttt cattcagcac aagtaaagtg gtcagttgct   7020
cacatagtgt gacaccatgt tactgttccc taccggttcc attgcttaat tcctttatgc   7080
attgcagaac aagaacacat gcaacaaggg aaagaaaaaa ggaagacaag caccgctcaa   7140
agcagcaaac actcaaatca atgatgctgt gaggatatgt atcaatactg aagatagaga   7200
aaattctgtt gaatcattgg atgctatgga gcaaacgcac tcatgcaatt tatttgtgac   7260
accactgggt caaaatgaac cctcccgtga tgacactgac aagaggctta gggaagacag   7320
ctcttgtgtt gaagaacaag aagagtctgg ctgtagcacc atctactctg ctggcaaagc   7380
ccctggctgt gatgctaaaa atcatctcac tgaacttggg gcttttgagc tttctgataa   7440
cttggccaac tcagcaaaag aagaatactc aattcaagaa aatcaagctt atgaaagtgt   7500
```

```
gttgctagat tctgaagaga tgtcaaggaa tgactgtgtt gatgatgaat ctacacattc   7560
ctgtgttggc atttatcagg atgaaagagt gtccacaagg ggagatcaaa catctgaaga   7620
aactctatca gtaccccatg attacaatga tgttggcaga gaagctagtc taagtttggc   7680
agagccatca tctattgatg agcatgcaca aagctctgcc aacaactttt actatgacta   7740
tggtgaatgg agggttatct gggatccatt ctataatcgg tattattttt acaacatcca   7800
gacacaagag tccacatggt gtcctcctga aggactggag gattttgcat catattgtag   7860
cccagatacc actaaagagc tagctgaact gggatctcag tgttcaagca tggcaccaca   7920
agagaacagt aaaaacccta gtctcgtcct ttgcagttga cattacgaat agttatatgc   7980
actacgataa aaactttcta caatatgtaa cacttgagca tgtggcaatg ggtgtaaaca   8040
tttaataata aggtagtgaa atccattaca cacagtattg aattttgcac tacaaatgct   8100
gaaggagaaa cctaaattgt caatgctttt tggtgacatt aattattgcc attgatttcc   8160
tgcttgtagg tgcttcattt atctgtctcc aatttactca tatgctagct tcttgtttgg   8220
gactaaaggc tttgctgttg ttttagtatg tcacacattt ctctttaatc tcaccatcac   8280
agatctggct actcatgtca atcatttaga agcacaggag caagatcact gcattcatga   8340
tttatctgac attcctgttg aaaagccaat atatcaaagg tagggaatac caaactgtac   8400
aatgttgaac aagttattgt ttttttgtt aattctgttc atctatgcag tatgataact   8460
acctctgaca aagcacagca cactgaaaat aagtacagcg attcaacaac tactgtgtta   8520
gagatgaacc aggaagttgc tagcaccaaa acgaaaaaga gagtaaggag atctcgatcg   8580
tgtaaggcga taatatatgg catctgcttt ctaggagttt gttcctgtta caattttagg   8640
ttgcgcattt acacaatagt ttcttggttt ctttgagcaa atgcagcttt gcatgactgc   8700
tacattgcct acttatgtct aggtaacttt tctttgcaaa ctgcaaagtt atgtctaggt   8760
aactatgcct tctagaaaac ctccttgtta gctatgtatt agtgagactt gcctaatatt   8820
tattttcttg tggtccgttc ttgtgctctt tgtacatatt tgccaataac cattttaatt   8880
gttctacaga tcattcatgc caagacatgg cagggaacgt ctctaatgac atcatcaagt   8940
actgggctca gcggtattca cttttctcac tttttgatag tggtataaag atggatgaag   9000
tagggtggtt ttcagttacg ccagagccaa ttgcaaagca tcatgcatct cgtgtgggtg   9060
cgggagtaat gattgattgt ttcacaggag ttggtggaaa tgccatccaa tttgccaaaa   9120
agtacgtcaa tgttatcttg caattgagtt atgtgatggt ctaatgtatc atttgcttga   9180
acacttcctg tttagtagca actgttattt ttcttatgtc acgagaatgc aatggctata   9240
tcaccttaag cagtatgcta tgtccactgt ccagtttaac taaggcatct gcttccagta   9300
atatgcaagg ctcttcttac ttttgctgtt atttaatata tggaagtgtc cttacggagg   9360
tgttattgtg gacattttga gcatgttcat catgtcactt gagttagtag agccagcctt   9420
agttgtttgc agtgtaggtg gatttatttt atgttatcaa tgtttcttct acagtactaa   9480
gactattgtt ccacattaac tatgtctcct tttccaggtg caagcatgta attgcagttg   9540
atattgatcc acaaaagatt gattgcgcgc atcataatgc atccatttat ggagtaaatg   9600
atcacataga tttcattgta ggtgatttta tacatatagc tcctcatctg aaggtaatgc   9660
ctttttcttg gaattattac ttttaagttt ctcaacacgt cacttctatt agctatatgt   9720
ttttgtagct gtttgcgaga gtgaatttat tgttgacatt gttctcattt gcccacccat   9780
tttaggatag gggcttggta ctacaaatat cttgatactt caagtcctac aaaaagaaat   9840
```

```
ttatgtttca tattttttcc atttgaacgt cgagatttta tggtcccatg gagttctccc   9900
tatttttcga tgatgcccat cttttggcag taccttcttt gtgtacacaa taaatgggag   9960
gatattttct gcagggagaa actgctttca tgtcgcctcc ttggggtggc cctgactatg  10020
ccaaagttga tgtttatgat atgaaaagca tgcttattcc ttgtgatggg ttagttcctt  10080
gtttctattt taagagagta atttctttca gtttgcactc actgatgttt acttactttg  10140
tgagtaaaac gcaccagaga tccattaacc tttaaggagg tgttatctat gtccatcaac  10200
actcaaactg catttttggg ttcctaaact ttttaagtga ttcaccggag ttccgtaccc  10260
cttcgtttat atttgtattt tgcagaaacc tcactctgtt ttatttctcc ttcgcatgta  10320
ggggtggtaa tggatcacga ttcaaacgtt tctccacgat tcgtttgagc ccttaattaa  10380
ttttagtaca aaaataaata gaaatagaga tagagcctga tcctaatatg atttgatcct  10440
caaattttat agcgtagaat ttagagccca ttaccattta ccacccctat tcacatgcct  10500
acccctctcc atcttctgga ttgaatgttc caacctaatt tacactcgta gtttctttga  10560
tctgccaatc aaatccagag cctaattgct ataacattag aacgaacacg ccatattacc  10620
agaatactcg atgcagatat ggatagaagc gaggcgctaa gcgcagccag ccttggcttc  10680
ttgctctgca ggccgatcag ggcgccagcc aaagccaacc atgcgcgcac gtgactgcaa  10740
tgctactctc tcttcgcctt tgccatcgtc gtcgcaggat gttacgttgt gcttatgctg  10800
gctcccacga gtgccgccgc ccagagcgag ctgagcgcac gcagccactg cttgtggttc  10860
acgagcgtga gcatgccctc accacctgct gctgcgccct tgctgcttgc ttgcttgccg  10920
gtggtgtaca ttatggacgg attaaattga atggatttac ctgttccaga aaaagatctg  10980
atcgacgatg ggatgctatc ttgtatggct ccggatcaat gaagattaat ggaacaacca  11040
atcgaaggct cagagcaggc tagttggtgc ccggaagact ctggccagaa gatggaaatg  11100
ggtaagcgtg tgaaggaaaa aagaaataga gggggatttc tacaaaaaac aaacataatg  11160
aagaggtatg gatttcaggt gaaccactta aaaataaaaa gggcataccc agtgccgtag  11220
gcttcccgca ctgtgcgggg tcgtctgggg aagggtatct ttaagcgtca agtcttaccc  11280
gcataatatg cagaggctgg ggctcgaacc cgggaccttt cggttataga cggtaggctc  11340
taccgccgca ccaagcccgc ccttgaacca tttaaaaaat ttaggactca aaaatacagt  11400
ttgacagttg atggacctag atgacacctc cttaaaaatt ttaatggacc tatggtgcat  11460
tttaatcttt tgttgatcga ctatactcaa tgttgaactc tttaggtact ctctttttaa  11520
actcggaacc atgatagctt caagagtagt gatgtttctt cctcgcaaca ttgacctaaa  11580
ccaattggcg gacatgtcct tgtctgtgga tcccccgtgg gcagttgagg taagcccatt  11640
tttgctgatt ttgtgccaag ctgacgtttc ctatagatgt cacagtggtc tctctctctg  11700
caggtcgaga agaacttcct caacggaaag ctgaaagcca taacagctta ctttgaagaa  11760
caggatcgtt gaaccaagca tcggcgctgg tgatacaaat catcttgtta gctatgactc  11820
acgacaattt tttgtggtga ccctaaacag aacctttgtg ttcggagaca gaaagaagcg  11880
gtttatcatc ttcaccgagc atagataatt tatttgcaga gatgagtcat tggtatcata  11940
caaaagcagc tcagcttatc tcaattcaca gcaagtgaaa ctgtcgaagg aaaactacaa  12000
ggctgacagt cgaacgcgtg ggagttagct taattttgcc ttatgataag caagcatgct  12060
tcctggttta tttcatacag ctactagtag tttcagctgc aacagttgtg cgttggtgtg  12120
cgtgtgattc tcacatatct ggtcctgcgg atgtgagtga tgcaaatgta tgtgtcatca  12180
tcccatgttt gtttgtttgc tctcaatcta tgtagattga gtgggattaa gtgagtttaa  12240
```

```
atctcagaca agtcaaaaaa aaatgttttc aatctcatcc aatccacata tgatagtaat  12300
acccgagtaa ggcttagatg taatagttgg aataagaaaa acaagtcagc cattttgaag  12360
ttttgtcctt ggagttctat taaaaggcat tactgataaa tctccaacag atttgcagtt  12420
gaagcaacat gtgaaacata tttatcatgt taaaacaatt tgccttagta ttcgattatg  12480
ccatgaaatc tgacatttcc ttacacatcc cagtttatca ttgtcaactg tctttaggaa  12540
tgtattgtat ctgctgtttt tacttgtata tgtatgttat tttttgtcgt tgtatgtata  12600
tgttttatta taaacatggc cactaaggtt gttctattcg ttaaaataac acagatctat  12660
aaacgactaa acaagcttct tgggataaag aatcatatgg aggctggatt ttcgaggagt  12720
ctggtgcact gttttgctaa tgatcagacc cccccccccc ctctaaaaat aaagaaaata  12780
ctggatttcc tgttcattta ttacattcat atgtaaatgc ttctgtcctt ttctatatct  12840
gggctggact ttttgtgtgc tcgtcactca agttggttag tgtggttaat tttattatgc  12900
tccgtgctct ttcctaccga acttggtctt tgttagtatc attatcagtc agttatattt  12960
tctcctcttg atgcttcatc taatctattt ttgcaaagtt gtcatgttat gtactatatg  13020
atcttttaca aggtttttga cttttcaaat tattgtgtcg tatattattt gtactcagat  13080
tgtgcttaca actttagttt atctatactt taaggggtgt ttggtttcta tgagctaatt  13140
tataatccct tcattttatt ctattttcgt acctaaattg tcaagcacga aaacgaaaat  13200
aaagttttaa cttttatatt tagcagttta tacactaaaa tagaataaaa tagatgaagt  13260
aaaaattagt cctcagaaac caaacatctc ctaaatgtct agtaatagtc gcctgaactg  13320
tagagcgccc aacacgcgcc accctgattt ggtgtcttaa aatggcatgt gtatataggt  13380
ggaatgggtt tgacgagact gtaactactt tttcttaatt aaattataga tggacttaac  13440
ttttctatat gcattttaaa tatatttttc tatattttttg gtgggctgag ttacagttta  13500
tgtcaatata aattacaaca gaccgaatct aaaattttat tataaaatgt atgcaccaac  13560
cgttgactaa aaagataaaa tttggacacc tacattttag caagtcacct gctaatatat  13620
atctatacta ggtaagtgtc cgtgcgttgc aacgaaaaca tataataata cgataactta  13680
tatataaaat atgtgttata ctgttatgag aaaaagtttc acctgtccta tttttatcaa  13740
tatgacaaca gaggatcaat ataaggcctt ggcatggctt cagaagttca gattaacgaa  13800
ttatggagca agagcaacta tttctggtgt ttcagtagaa agaatgggga tatgtgttta  13860
tctctctcat acatgttaca caatgtgcta tagaatgaca cctctaggcc gctgctacaa  13920
ctacagagaa taaattatgg atcatgggtg ccctactaag ttagctacac gtaaaatctg  13980
gggcgattga ccccctaatg cttcatcttg gagatctcac taaaatacac cttccgcaca  14040
aaccgagcct tgataaagct cgcgatcttc gtgtcctgat ctttagtgca gacaactgca  14100
agggaaatta ttgtgccggt cagcaagagt ggaaaatgtc agcagaaaca caagaatgga  14160
aaattatatg atgtgcaagt aggacggcac cctatttaac taaaggtgtg tttggttcag  14220
ttttctgaac caattcgttg ccaaaaaatc taaaatctca cacaaacggt acaacatcag  14280
aatagatttt taaaagttta tagatttctc aagttcaatt caaaatcacc atctacccca  14340
aatttttcag attactatta ttcatgttac aactatcact cttgtagtat ctaccattga  14400
tagttgtttt aatcaaatat attttagctt tctcacaatc ctcagctcga aacagatttt  14460
catggctcac agttggattc atattttcat aaatctatag gtgtgaacca aatagaccct  14520
aaaacatcat gttgtaatgt tccaaaaaaa tcatcacaaa aaacatgtat gcaacacacc  14580
```

```
taagtgcaac aacactaacc tgcaggagcg ttggcgtagg ctggactctt gtgtgtctgc  14640
aatgtggaaa cctgcattgt aaatggttag gtaaatgctt cgcttaaaaa tggcagtaaa  14700
tgcttcacta aaaatgcttc cacgtgctca tgatcaagta ggttttatgt tcaatctgca  14760
gttctacaca agtgcgattc attttgatac tcatttctat ttactttcag agctcgtgct  14820
aactgtcata aagtgcaatg catctatgac tgccaattga tattgtgctc ctgccataaa  14880
gtgcactgca tcgtgctaac tgtacactaa tctgtgagga tctaagacca atatttgttt  14940
acgttttctc ctttagtatc ctataaaaac aacacgccta gacaacccaa aaaatgtgtc  15000
ccaataggaa tatcagattc tgacgctggc agcaatctcg aatgataata tttttttccaa  15060
acaagcgagg tccctaaata gaagcggcaa cagataaaaa ctaaagataa aaactaaaga  15120
gtacagatga ttggcatcac atcgggaatg aaatatgcct aacatatcaa tttgcatatt  15180
agattatttg ctgagaacaa taacgaaaac atatttagtt gttcatcaca agttacctta  15240
gattttgctg ttcaaggtcc tttgggtctt ctttctgcta gaacatacaa gggtatttca  15300
gatttgcaaa caaggaaaag caagaacttc aatgatacat cattgtaaaa ccaagtttcc  15360
gatttaaata aagatgatgc ttgcggtcaa cacattcaca aatgtaaatg tgtgaaatcg  15420
ttcaaacata aggcttatgt ggtcatgctc aggtagtatg tacagaccta aaaacaaggt  15480
atatgacaac agtaccagcc actaaacaca catggttaat cactaaaaca attctccgat  15540
taaccaggaa aactatagca gccactagaa ctatacaggt ttctaccagt aattgcttca  15600
ctaaaaaatg cccccatgtg taaattttca ggtggtttgt acagacataa aaacaagggt  15660
ataggactac ttcttgtgct aaaataaaag ctggcactaa acagtgtatc cagttcatca  15720
ggaaaacagt tttagtgatt aatcactaaa acaataccca tggtgcaaat tatctgatta  15780
accatgtaca taccagtaat tgcttcataa aaaatgcccc caatttgctc atgtttaagg  15840
aatatgtata gaactaaaaa caagggtata tgataacaat accagccact aaacacacat  15900
ggttaatcac taaaacaatt ctctgacaac tcctataaaa agatagcaac caccagaaat  15960
aaaccgccca cgacatccct aattgtagtc actaaaaact ggtagcagta attggttcac  16020
taaaaaatga ccataatcac gaaaactata acagtcacca gaactatata ggtttcatta  16080
gtaattgctt cactaaaaaa tgtccccatg tgtaaatttt catgtcgtat gtatagacct  16140
aaaaacaagg gtatatgact acttgctatg ctaaaacaat agctagcact aaacagtgta  16200
ttcagttaat catccaaaca attttgtgat taatcactaa aacaataccc atggagcaaa  16260
ttatatgaga ataagatctc gtcgttccta ttgtgaagaa tatactacta cctccagttt  16320
caaattacaa tttcaaatta caagttgttt agaacatcca caaggtaatt gcgaagaata  16380
tactaattgc tctagtttca aattacaagt tgtttagaga aaaggtgttc cttaatagtc  16440
tagttttaga agctacatcc aactggtaaa cataaattgc agaaaccttt tatgtggaag  16500
cctccgtcat tgagtctgtc ccctttagct gtaagtagtt ttctaaatat tgttagtcag  16560
gcttagttgt ttgagactct gtttccattc gtgaccatgg gaactgtgaa atgtgtagaa  16620
gatgctcatg ctcatgcata tgcatcgaat tgttttgtaa agtcatctta atgctcaaac  16680
agttttttta tctgccccag ctgtacactg ctttctgaat tatgtcattt aggcttagct  16740
gtccgagata atttcatttg tgatgaaggt aaccggagca tctgtccttt tgttttaaac  16800
ataaatattt tgatagctta acttgtgcgt cattttatca tgtactaaca tggtatatag  16860
atggcactta gcagtaacat tcctgactta tgtgattgtc ctgttagaat gcttctgcaa  16920
tataatgggc ttatgctaat ctgtttggaa tcccatgatg aataacaatt atggatgttg  16980
```

```
ggcattttgt atttttatga tgtaggctta acatattttc ttctctgctc agccctgccg  17040
gtggagacct ctatttatag ctataatcca gccatatcta gtgaactaac agatctattc  17100
ctatctctag tgcttatccc cttaacagat ttattttcct atctctattt ctttgatgtt  17160
acttgctgca ggtgctatcc cccactgatg cattatatga caatcactcg aagaatcaga  17220
tgctaattaa ttgttttata cttgaccatt gctaattaag tactccattt ttta        17274
```

<210> SEQ ID NO 14
<211> LENGTH: 1767
<212> TYPE: DNA
<213> ORGANISM: Artificial Sequence
<220> FEATURE:
<223> OTHER INFORMATION: cDNA

<400> SEQUENCE: 14

```
atgggttctt tggggcttcc tgtttcattc agcacaagta aagtgaacaa gaacacatgc     60
aacaagggaa agaaaaaagg aagacaagca ccgctcaaag cagcaaacac tcaaatcaat    120
gatgctgtga ggatatgtat caatactgaa gatagagaaa attctgttga atcattggat    180
gctatggagc aaacgcactc atgcaattta tttgtgacac cactgggtca aaatgaaccc    240
tcccgtgatg acactgacaa gaggcttagg gaagacagct cttgtgttga agaacaagaa    300
gagtctggct gtagcaccat ctactctgct ggcaaagccc ctggctgtga tgctaaaaat    360
catctcactg aacttggggc ttttgagctt tctgataact tggccaactc agcaaaagaa    420
gaatactcaa ttcaagaaaa tcaagcttat gaaagtgtgt tgctagattc tgaagagatg    480
tcaaggaatg actgtgttga tgatgaatct acacattcct gtgttggcat ttatcaggat    540
gaaagagtgt ccacaagggg agatcaaaca tctgaagaaa ctctatcagt accccatgat    600
tacaatgatg ttggcagaga agctagtcta agtttggcag agccatcatc tattgatgag    660
catgcacaaa gctctgccaa caacttttac tatgactatg gtgaatggag ggttatctgg    720
gatccattct ataatcggta ttatttttac aacatccaga cacaagagtc cacatggtgt    780
cctcctgaag gactggagga ttttgcatca tattgtagcc cagataccac taaagagcta    840
gctgaactgg gatctcagtg ttcaagcatg gcaccacaag agaacaatct ggctactcat    900
gtcaatcatt tagaagcaca ggagcaagat cactgcattc atgatttatc tgacattcct    960
gttgaaaagc caatatatca aagtatgata actacctctg acaaagcaca gcacactgaa   1020
aataagtaca gcgattcaac aactactgtg ttagagatga accaggaagt tgctagcacc   1080
aaaacgaaaa agagagtaag gagatctcga tcgtatcatt catgccaaga catggcaggg   1140
aacgtctcta atgacatcat caagtactgg gctcagcggt attcactttt ctcacttttt   1200
gatagtggta taaagatgga tgaagtaggg tggttttcag ttacgccaga gccaattgca   1260
aagcatcatg catctcgtgt gggtgcggga gtaatgattg attgtttcac aggagttggt   1320
ggaaatgcca tccaatttgc caaaaagtgc aagcatgtaa ttgcagttga tattgatcca   1380
caaaagattg attgcgcgca tcataatgca tccatttatg gagtaaatga tcacatagat   1440
ttcattgtag gtgattttat acatatagct cctcatctga agggagaaac tgctttcatg   1500
tcgcctcctt ggggtggccc tgactatgcc aaagttgatg tttatgatat gaaaagcatg   1560
cttattcctt gtgatgggta ctctcttttt aaactcggaa ccatgatagc ttcaagagta   1620
gtgatgtttc ttcctcgcaa cattgaccta aaccaattgg cggacatgtc cttgtctgtg   1680
gatcccccgt gggcagttga ggtcgagaag aacttcctca acggaaagct gaaagccata   1740
```

```
acagcttact ttgaagaaca ggatcgt                                        1767


<210> SEQ ID NO 15
<211> LENGTH: 1767
<212> TYPE: DNA
<213> ORGANISM: Artificial Sequence
<220> FEATURE:
<223> OTHER INFORMATION: cDNA

<400> SEQUENCE: 15

atgggttctt tggggcttcc tgtttcattc agcacaagta aagtgaacaa gaacacatgc      60

aacaagggaa agaaaaaagg aagacaagca ccgctcaaag cagcaaacac tcaaatcaat     120

gatgctgtga ggatatgtat caatactgaa gatagagaaa attctgttga atcattggat     180

gctatggagc aaacgcactc atgcaattta tttgtgacac cactgggtca aaatgaaccc     240

tcccgtgatg acactgacaa gaggcttagg gaagacagct cttgtgttga agaacaagaa     300

gagtctggct gtagcaccat ctactctgct ggcaaagccc ctggctgtga tgctaaaaat     360

catctcactg aacttggggc ttttgagctt tctgataact tggccaactc agcaaaagaa     420

gaatactcaa ttcaagaaaa tcaagcttat gaaagtgtgt tgctagattc tgaagagatg     480

tcaaggaatg actgtgttga tgatgaatct acacattcct gtgttggcat ttatcaggat     540

gaaagagtgt ccacaagggg agatcaaaca tctgaagaaa ctctatcagt accccatgat     600

tacaatgatg ttggcagaga agctagtcta agtttggcag agccatcatc tattgatgag     660

catgcacaaa gctctgccaa caacttttac tatgactatg gtgaatggag ggttatctgg     720

gatccattct ataatcggta ttatttttac aacatccaga cacaagagtc cacatggtgt     780

cctcctgaag gactggagga ttttgcatca tattgtagcc cagataccac taaagagcta     840

gctgaactgg gatctcagtg ttcaagcatg gcaccacaag agaacaatct ggctactcat     900

gtcaatcatt tagaagcaca ggagcaagat cactgcattc atgatttatc tgacattcct     960

gttgaaaagc caatatatca aagtatgata actacctctg acaaagcaca gcacactgaa    1020

aataagtaca gcgattcaac aactactgtg ttagagatga accaggaagt tgctagcacc    1080

aaaacgaaaa agagagtaag gagatctcga tcgtatcatt catgccaaga catggcaggg    1140

aacgtctcta atgacatcat caagtactgg gctcagcggt attcactttt ctcacttttt    1200

gatagtggta taaagatgga tgaagtaggg tggttttcag ttacgccaga gccaattgca    1260

aagcatcatg catctcgtgt gggtgcggga gtaatgattg attgtttcac aggagttggt    1320

ggaaatgcca tccaatttgc caaaaagtgc aagcatgtaa ttgcagttga tattgatcca    1380

caaaagattg attgcgcgca tcataatgca tccatttatg gagtaaatga tcacatagat    1440

ttcattgtag gtgattttat acatatagct cctcatctga agggagaaac tgctttcatg    1500

tcgcctcctt ggggtggccc tgactatgcc aaagttgatg tttatgatat gaaaagcatg    1560

cttattcctt gtgatgggta ctctcttttt aaactcggaa ccatgatagc ttcaagagta    1620

gtgatgtttc ttcctcgcaa cattgaccta aaccaattgg cggacatgtc cttgtctgtg    1680

gatcccccgt gggcagttga ggtcgagaag aacttcctca acggaaagct gaaagccata    1740

acagcttact ttgaagaaca ggatcgt                                        1767


<210> SEQ ID NO 16
<211> LENGTH: 434
<212> TYPE: PRT
<213> ORGANISM: Zea mays

<400> SEQUENCE: 16
```

```
Met Gly Ser Ser Glu Glu His Val Phe Leu Asp Pro Thr Arg Ile Cys
1               5                   10                  15

Ala Ser Val Ser Leu Leu Ala His Asp Leu Ile Gly Arg Met Leu Asn
            20                  25                  30

Arg Glu Val Ser Ser Arg Pro Asn Ala Lys Glu Val Leu Pro Pro Met
        35                  40                  45

Ile His Arg Glu Ile Val Arg Phe Gly Tyr Cys Glu Ser Ser Ser Ser
    50                  55                  60

Lys Ser Ser Ser Asp Asn Ser Glu Glu Arg Asp Glu Cys Gly Ile Val
65                  70                  75                  80

Asp Ala Leu Val Thr Thr Ile Thr Gln Ile Arg Lys Met Asp Leu Glu
                85                  90                  95

Ala Arg Ser Leu Gln Pro Ser Ile Lys Ala Gly Leu Leu Ala Lys Leu
            100                 105                 110

Arg Glu Tyr Lys Ser Asp Leu Asn Asn Val Lys Met Gly Leu Ser Ala
        115                 120                 125

Glu Arg Lys Lys Gln Lys Leu Ser Glu Ile Gln Ser Gly Val Glu Glu
    130                 135                 140

Ala Glu Ser Leu Ile Gln Lys Met Asp Leu Glu Ala Arg Ser Leu Gln
145                 150                 155                 160

Pro Ser Ile Lys Ala Gly Leu Leu Ala Lys Pro Arg Asp Tyr Lys Ser
                165                 170                 175

Asp Leu Asn Asn Val Lys Ser Glu Leu Lys Arg Ile Ser Ala Pro Asn
            180                 185                 190

Ala Ser Gly Leu Ile Ser Tyr Lys Lys Leu Leu Phe His Gly Leu Asp
        195                 200                 205

Leu Trp Thr Ala Leu Ser Leu Pro Gln Pro Leu Gly Arg Ala Ala Leu
    210                 215                 220

Trp Pro Pro His Arg Thr Ile His Gln His Leu Gln Cys Gln Gln Leu
225                 230                 235                 240

Thr Gly Val Ala Gly Ser Leu Ala Tyr Leu Ala Pro Glu Val Leu Leu
                245                 250                 255

Gly Asn Tyr Ser Gln Lys Val Asp Val Trp Ala Ala Gly Val Leu Leu
            260                 265                 270

His Val Leu Leu Met Gly Thr Leu Pro Phe Gln Gly Lys Ser Ile Glu
        275                 280                 285

Ala Ile Phe Asp Val Ile Lys Thr Ala Glu Leu Asp Phe His Asn Ser
    290                 295                 300

Gln Trp Ala Ser Val Ser Leu Leu Ala Tyr Asp Leu Ile Gly Arg Met
305                 310                 315                 320

Leu Asn Arg Glu Val Ser Ser Arg Pro Asp Ala Glu Asp Val Leu Arg
                325                 330                 335

His Pro Trp Val Leu Phe Tyr Thr Asp Cys Leu Gln Lys Ala Glu Phe
            340                 345                 350

Ser Asn Leu Trp Asp Thr Asn Lys Thr Ala Ala Pro Met Ile His Arg
        355                 360                 365

Glu Ile Val Arg Phe Gly Tyr Cys Glu Ser Ser Ser Ser Lys Ser Ser
    370                 375                 380

Ser Asp Asn Ser Glu Glu Arg Asp Glu Cys Gly Ile Val Asp Ala Leu
385                 390                 395                 400

Ala Thr Thr Ile Thr Gln Val Arg Ile Ser Glu Pro Lys Arg Ser Arg
                405                 410                 415
```

```
Leu Phe Ser Leu Pro Asn Gly Leu Leu Pro Pro Ser Arg Asn Ser Leu
            420                 425                 430

Arg Thr


<210> SEQ ID NO 17
<211> LENGTH: 143
<212> TYPE: PRT
<213> ORGANISM: Zea mays

<400> SEQUENCE: 17

Met Leu Asn Arg Glu Val Ser Ser Arg Pro Asn Ala Lys Glu Val Leu
1               5                   10                  15

Arg Lys Phe Lys His Pro Cys Asn Leu Cys Phe Ile Tyr Met Ile Leu
            20                  25                  30

Asn Leu Ser Leu Thr Phe Pro Asn Gly Phe Gln His Arg Ala Pro Trp
        35                  40                  45

Val Leu Phe Tyr Thr Asp Cys Pro Gln Lys Ala Glu Phe Ser Asn Ile
    50                  55                  60

Trp Asp Thr Asn Lys Thr Ala Ala Pro Met Ile His Arg Glu Ile Val
65                  70                  75                  80

Arg Phe Gly Tyr Cys Glu Ser Ser Ser Ser Lys Ser Ser Ser Asp Asn
                85                  90                  95

Ser Glu Glu Arg Asp Glu Cys Gly Ile Val Asp Ala Leu Val Thr Thr
            100                 105                 110

Ile Thr Gln Val Arg Ile Ser Glu Pro Lys Arg Ser Arg Leu Phe Ser
        115                 120                 125

Leu Pro Asn Gly Leu Leu Pro Pro Ser Arg Asn Ser Leu Arg Thr
    130                 135                 140


<210> SEQ ID NO 18
<211> LENGTH: 162
<212> TYPE: PRT
<213> ORGANISM: Zea mays

<400> SEQUENCE: 18

Met Glu Gly Gly Arg His Pro Ser Pro Pro Pro Arg Ile Ser Arg Gln
1               5                   10                  15

Pro Pro Pro Tyr Pro Ala Cys Pro Ser Ile Leu Pro Pro Leu Pro Pro
            20                  25                  30

Val Asn Val Thr Asn Pro Gly Leu Val Pro Leu Val Val Ala Thr Leu
        35                  40                  45

Phe Asp Glu Arg Val Thr Glu Leu Leu Ser Val Leu Ala Asp Ala Ala
    50                  55                  60

Val Gly Arg Pro Gly Arg Trp Ser Ile Gly Glu Ala Pro Trp Ser Ser
65                  70                  75                  80

Ser Gly Gly Thr Asn Gln Ala Val Tyr Ala Arg Arg Ala Pro Gly Ser
                85                  90                  95

Ser Ser Pro Pro Pro Ala Pro Ala Ser Pro Pro Leu Pro Ser Ser Arg
            100                 105                 110

Ala Asp Cys Leu Ala Arg Trp Pro Gly Ser Arg Ala Leu Val Ala Pro
        115                 120                 125

Leu Gly Thr Pro Ala Phe Val Asp Arg Leu Phe Trp Ser Asp Phe Ser
    130                 135                 140

Gly Ser Ile Arg Arg Glu Glu Glu Ala Glu Ala Leu Arg Asp Pro Ile
145                 150                 155                 160

Arg Arg
```

<210> SEQ ID NO 19
<211> LENGTH: 87
<212> TYPE: PRT
<213> ORGANISM: Zea mays

<400> SEQUENCE: 19

```
Met Asp Leu Glu Ala Arg Ser Leu Gln Pro Ser Ile Lys Ala Gly Leu
1               5                   10                  15

Leu Ala Lys Pro Arg Asp Tyr Lys Ser Asp Leu Asn Asn Val Lys Ser
            20                  25                  30

Glu Leu Lys Arg Ile Ser Ala Pro Asn Ala Arg Phe Gly Arg Trp Thr
        35                  40                  45

Trp Lys Gln Gly Ala Tyr Asn Leu Ala Leu Arg Val Ser Ser Arg Gly
    50                  55                  60

Tyr Leu Arg Pro Leu Pro Gly Arg Leu Pro Gly Arg Ser Ser Trp Ser
65                  70                  75                  80

Leu Glu Trp Leu Ile Leu Ser
                85
```

<210> SEQ ID NO 20
<211> LENGTH: 279
<212> TYPE: PRT
<213> ORGANISM: Zea mays

<400> SEQUENCE: 20

```
Met Ala His Phe Asp Glu Leu Glu Asp Lys Thr Thr Asp Tyr Val Asp
1               5                   10                  15

Leu Ser Val Gln Glu Phe Ala Leu Lys Gln Pro Gln Cys Gly Met Ala
            20                  25                  30

Tyr Asn Tyr Tyr Gly Asn Leu Arg Leu Tyr Val Val Ala Asn Lys Ala
        35                  40                  45

Glu Leu Ala Ser Ser Ile Phe Glu Ile Asp Lys Ala Ser Thr Lys Arg
    50                  55                  60

Ile Gly Ala Arg Phe Cys Arg Cys Leu Pro His Thr Arg Met Glu Gly
65                  70                  75                  80

Gly Arg His Pro Ser Pro Pro Pro Arg Ile Ser Arg Gln Pro Gln Pro
                85                  90                  95

Tyr Pro Ala Cys Pro Ser Ile Leu Pro Gln Pro Pro Pro Glu Arg Lys
            100                 105                 110

Lys Gln Lys Leu Ser Glu Ile Gln Ser Gly Val Glu Glu Ala Glu Ser
        115                 120                 125

Leu Ile Gln Lys Met Asp Leu Glu Ala Arg Ser Leu Gln Pro Ser Ile
    130                 135                 140

Lys Ala Ser Leu Leu Ala Lys Leu Arg Glu Tyr Lys Ser Asp Leu Asn
145                 150                 155                 160

Asn Val Lys Ser Glu Leu Lys Arg Ile Ser Ala Pro Asn Ala Arg Gln
                165                 170                 175

Ala Thr Arg Glu Glu Leu Leu Glu Ser Gly Met Ala Asp Thr Leu Ala
            180                 185                 190

Pro Glu Gln Glu Gln Leu Ala Cys Ala Ala Ala Ala Leu Ala Val Gly
        195                 200                 205

Pro Ala Tyr Glu Arg Leu Gln Glu Ala Arg Asn Pro Ser Glu Gln Gly
    210                 215                 220

Cys Asn His Asp Lys Gln Ile Glu Gln Ala Tyr Asp Asp Ile Leu Asn
225                 230                 235                 240
```

```
Ser Ser Lys His Thr Leu Ala Ser Met Met Glu Leu Gln Glu Ala Leu
                245                 250                 255

Leu Glu Ser Asn Gln Ala Thr Lys Asp Ala Asn Gly Ile Ala Ala Leu
            260                 265                 270

Tyr Ile Val Leu Val Leu Met
        275


<210> SEQ ID NO 21
<211> LENGTH: 428
<212> TYPE: PRT
<213> ORGANISM: Zea mays

<400> SEQUENCE: 21

Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Gly Val Arg Gly Leu Ile Pro
        35                  40                  45

Gly Thr Ile Leu Ala Phe Leu Glu Ala Arg Leu Gln Glu Leu Asp Gly
    50                  55                  60

Pro Glu Ala Arg Leu Ala Asp Tyr Phe Asp Tyr Ile Ala Gly Thr Ser
65                  70                  75                  80

Thr Gly Gly Leu Ile Thr Ala Met Leu Thr Ala Pro Gly Lys Asp Lys
                85                  90                  95

Arg Pro Leu Tyr Ala Ala Lys Asp Ile Asn His Phe Tyr Met Gln Asn
            100                 105                 110

Cys Pro Arg Ile Phe Pro Gln Lys Ser Arg Leu Ala Ala Ala Met Ser
        115                 120                 125

Ala Leu Arg Lys Pro Lys Tyr Asn Gly Lys Cys Met Arg Ser Leu Ile
    130                 135                 140

Arg Ser Ile Leu Gly Glu Thr Arg Val Ser Glu Thr Leu Thr Asn Val
145                 150                 155                 160

Ile Ile Pro Ala Phe Asp Ile Arg Leu Leu Gln Pro Ile Ile Phe Ser
                165                 170                 175

Thr Tyr Asp Ala Lys Ser Thr Pro Leu Lys Asn Ala Leu Leu Ser Asp
            180                 185                 190

Val Cys Ile Gly Thr Ser Ala Ala Pro Thr Tyr Leu Pro Ala His Tyr
        195                 200                 205

Phe Gln Thr Glu Asp Ala Asn Gly Lys Glu Arg Glu Tyr Asn Leu Ile
    210                 215                 220

Asp Gly Gly Val Ala Ala Asn Asn Pro Thr Met Val Ala Met Thr Gln
225                 230                 235                 240

Ile Thr Lys Lys Met Leu Ala Ser Lys Asp Lys Ala Glu Glu Leu Tyr
                245                 250                 255

Pro Val Lys Pro Ser Asn Cys Arg Arg Phe Leu Val Leu Ser Ile Gly
            260                 265                 270

Thr Gly Ser Thr Ser Glu Gln Gly Leu Tyr Thr Ala Arg Gln Cys Ser
        275                 280                 285

Arg Trp Gly Ile Cys Arg Trp Leu Arg Asn Asn Gly Met Ala Pro Ile
    290                 295                 300

Ile Asp Ile Phe Met Ala Ala Ser Ser Asp Leu Val Asp Ile His Val
305                 310                 315                 320

Ala Ala Met Phe Gln Ser Leu His Ser Asp Gly Asp Tyr Leu Arg Ile
```

```
                325                 330                 335

Gln Asp Asn Ser Leu Arg Gly Ala Ala Ala Thr Val Asp Ala Ala Thr
            340                 345                 350

Pro Glu Asn Met Arg Thr Leu Val Gly Ile Gly Glu Arg Met Leu Ala
        355                 360                 365

Gln Arg Val Ser Arg Val Asn Val Glu Thr Gly Arg Tyr Glu Pro Val
    370                 375                 380

Thr Gly Glu Gly Ser Asn Ala Asp Ala Leu Gly Gly Leu Ala Arg Gln
385                 390                 395                 400

Leu Ser Glu Glu Arg Arg Thr Arg Leu Ala Arg Arg Val Ser Ala Ile
                405                 410                 415

Asn Pro Arg Gly Ser Arg Cys Ala Ser Tyr Asp Ile
            420                 425


<210> SEQ ID NO 22
<211> LENGTH: 401
<212> TYPE: PRT
<213> ORGANISM: Zea mays

<400> SEQUENCE: 22

Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Gly Val Arg Gly Leu Ile Pro
        35                  40                  45

Gly Thr Ile Leu Ala Phe Leu Glu Ala Arg Leu Gln Glu Leu Asp Gly
    50                  55                  60

Pro Glu Ala Arg Leu Ala Asp Tyr Phe Asp Tyr Ile Ala Gly Thr Ser
65                  70                  75                  80

Thr Gly Gly Leu Ile Thr Ala Met Leu Thr Ala Pro Gly Lys Asp Lys
                85                  90                  95

Arg Pro Leu Tyr Ala Ala Lys Asp Ile Asn His Phe Tyr Met Gln Asn
            100                 105                 110

Cys Pro Arg Ile Phe Pro Gln Lys Ser Arg Leu Ala Ala Ala Met Ser
        115                 120                 125

Ala Leu Arg Lys Pro Lys Tyr Asn Gly Lys Cys Met Arg Ser Leu Ile
    130                 135                 140

Arg Ser Ile Leu Gly Glu Thr Arg Ala Lys Ser Thr Pro Leu Lys Asn
145                 150                 155                 160

Ala Leu Leu Ser Asp Val Cys Ile Gly Thr Ser Ala Ala Pro Thr Tyr
                165                 170                 175

Leu Pro Ala His Tyr Phe Gln Thr Glu Asp Ala Asn Gly Lys Glu Arg
            180                 185                 190

Glu Tyr Asn Leu Ile Asp Gly Gly Val Ala Ala Asn Asn Pro Thr Met
        195                 200                 205

Val Ala Met Thr Gln Ile Thr Lys Lys Met Leu Ala Ser Lys Asp Lys
    210                 215                 220

Ala Glu Glu Leu Tyr Pro Val Lys Pro Ser Asn Cys Arg Arg Phe Leu
225                 230                 235                 240

Val Leu Ser Ile Gly Thr Gly Ser Thr Ser Glu Gln Gly Leu Tyr Thr
                245                 250                 255

Ala Arg Gln Cys Ser Arg Trp Gly Ile Cys Arg Trp Leu Arg Asn Asn
            260                 265                 270
```

```
Gly Met Ala Pro Ile Ile Asp Ile Phe Met Ala Ala Ser Ser Asp Leu
        275                 280                 285

Val Asp Ile His Val Ala Ala Met Phe Gln Ser Leu His Ser Asp Gly
    290                 295                 300

Asp Tyr Leu Arg Ile Gln Asp Asn Ser Leu Arg Gly Ala Ala Ala Thr
305                 310                 315                 320

Val Asp Ala Ala Thr Pro Glu Asn Met Arg Thr Leu Val Gly Ile Gly
                325                 330                 335

Glu Arg Met Leu Ala Gln Arg Val Ser Arg Val Asn Val Glu Thr Gly
            340                 345                 350

Arg Tyr Glu Pro Val Thr Gly Glu Gly Ser Asn Ala Asp Ala Leu Gly
        355                 360                 365

Gly Leu Ala Arg Gln Leu Ser Glu Glu Arg Arg Thr Arg Leu Ala Arg
    370                 375                 380

Arg Val Ser Ala Ile Asn Pro Arg Gly Ser Arg Cys Ala Ser Tyr Asp
385                 390                 395                 400

Ile


<210> SEQ ID NO 23
<211> LENGTH: 380
<212> TYPE: PRT
<213> ORGANISM: Zea mays

<400> SEQUENCE: 23

Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Gly Val Arg Gly Leu Ile Pro
        35                  40                  45

Gly Thr Ile Leu Ala Phe Leu Glu Ala Arg Leu Gln Glu Leu Asp Gly
    50                  55                  60

Pro Glu Ala Arg Leu Ala Asp Tyr Phe Asp Tyr Ile Ala Gly Thr Ser
65                  70                  75                  80

Thr Gly Gly Leu Ile Thr Ala Met Leu Thr Ala Pro Gly Lys Asp Lys
                85                  90                  95

Arg Pro Leu Tyr Ala Ala Lys Asp Ile Asn Tyr Phe Tyr Met Glu Asn
            100                 105                 110

Cys Pro Arg Ile Phe Pro Gln Lys Ser Arg Leu Ala Ala Ala Met Ser
        115                 120                 125

Ala Leu Arg Lys Pro Lys Tyr Asn Gly Lys Cys Met Arg Ser Leu Ile
    130                 135                 140

Arg Ser Ile Leu Gly Glu Thr Arg Val Ser Glu Thr Leu Thr Asn Val
145                 150                 155                 160

Ile Ile Pro Ala Phe Asp Ile Arg Leu Leu Gln Pro Ile Ile Phe Ser
                165                 170                 175

Thr Tyr Asp Ala Lys Ser Thr Pro Leu Lys Asn Ala Leu Leu Ser Asp
            180                 185                 190

Val Cys Ile Gly Thr Ser Ala Ala Pro Thr Tyr Leu Pro Ala His Tyr
        195                 200                 205

Phe Gln Thr Glu Asp Ala Asn Gly Lys Glu Arg Glu Tyr Asn Leu Ile
    210                 215                 220

Asp Gly Gly Val Ala Ala Asn Asn Pro Thr Met Val Ala Met Thr Gln
225                 230                 235                 240
```

```
Ile Thr Lys Lys Met Leu Ala Ser Lys Asp Lys Ala Glu Glu Leu Tyr
                245                 250                 255

Pro Val Asn Pro Ser Asn Cys Arg Arg Phe Leu Val Leu Ser Ile Gly
            260                 265                 270

Thr Gly Ser Thr Ser Glu Gln Gly Leu Tyr Thr Ala Arg Gln Cys Ser
        275                 280                 285

Arg Trp Gly Ile Cys Arg Trp Leu Arg Asn Asn Gly Met Ala Pro Ile
    290                 295                 300

Ile Asp Ile Phe Met Ala Ala Ser Ser Asp Leu Val Asp Ile His Val
305                 310                 315                 320

Ala Ala Met Phe Gln Ser Leu His Ser Asp Gly Asp Tyr Leu Arg Ile
                325                 330                 335

Gln Asp Asn Ser Leu Arg Gly Ala Ala Ala Thr Val Asp Ala Ala Thr
            340                 345                 350

Pro Glu Asn Met Arg Thr Leu Val Gly Ile Gly Glu Arg Met Leu Ala
        355                 360                 365

Gln Arg Val Ser Arg Val Asn Val Glu Thr Gly Ser
    370                 375                 380


<210> SEQ ID NO 24
<211> LENGTH: 589
<212> TYPE: PRT
<213> ORGANISM: Zea mays

<400> SEQUENCE: 24

Met Gly Ser Leu Gly Leu Pro Val Ser Phe Ser Thr Ser Lys Val Asn
1               5                   10                  15

Lys Asn Thr Cys Asn Lys Gly Lys Lys Lys Gly Arg Gln Ala Pro Leu
            20                  25                  30

Lys Ala Ala Asn Thr Gln Ile Asn Asp Ala Val Arg Ile Cys Ile Asn
        35                  40                  45

Thr Glu Asp Arg Glu Asn Ser Val Glu Ser Leu Asp Ala Met Glu Gln
    50                  55                  60

Thr His Ser Cys Asn Leu Phe Val Thr Pro Leu Gly Gln Asn Glu Pro
65                  70                  75                  80

Ser Arg Asp Asp Thr Asp Lys Arg Leu Arg Glu Asp Ser Ser Cys Val
                85                  90                  95

Glu Glu Gln Glu Glu Ser Gly Cys Ser Thr Ile Tyr Ser Ala Gly Lys
            100                 105                 110

Ala Pro Gly Cys Asp Ala Lys Asn His Leu Thr Glu Leu Gly Ala Phe
        115                 120                 125

Glu Leu Ser Asp Asn Leu Ala Asn Ser Ala Lys Glu Glu Tyr Ser Ile
    130                 135                 140

Gln Glu Asn Gln Ala Tyr Glu Ser Val Leu Leu Asp Ser Glu Glu Met
145                 150                 155                 160

Ser Arg Asn Asp Cys Val Asp Asp Glu Ser Thr His Ser Cys Val Gly
                165                 170                 175

Ile Tyr Gln Asp Glu Arg Val Ser Thr Arg Gly Asp Gln Thr Ser Glu
            180                 185                 190

Glu Thr Leu Ser Val Pro His Asp Tyr Asn Asp Val Gly Arg Glu Ala
        195                 200                 205

Ser Leu Ser Leu Ala Glu Pro Ser Ser Ile Asp Glu His Ala Gln Ser
    210                 215                 220

Ser Ala Asn Asn Phe Tyr Tyr Asp Tyr Gly Glu Trp Arg Val Ile Trp
225                 230                 235                 240
```

```
Asp Pro Phe Tyr Asn Arg Tyr Tyr Phe Tyr Asn Ile Gln Thr Gln Glu
                245                 250                 255

Ser Thr Trp Cys Pro Pro Glu Gly Leu Glu Asp Phe Ala Ser Tyr Cys
            260                 265                 270

Ser Pro Asp Thr Thr Lys Glu Leu Ala Glu Leu Gly Ser Gln Cys Ser
        275                 280                 285

Ser Met Ala Pro Gln Glu Asn Asn Leu Ala Thr His Val Asn His Leu
    290                 295                 300

Glu Ala Gln Glu Gln Asp His Cys Ile His Asp Leu Ser Asp Ile Pro
305                 310                 315                 320

Val Glu Lys Pro Ile Tyr Gln Ser Met Ile Thr Thr Ser Asp Lys Ala
                325                 330                 335

Gln His Thr Glu Asn Lys Tyr Ser Asp Ser Thr Thr Thr Val Leu Glu
            340                 345                 350

Met Asn Gln Glu Val Ala Ser Thr Lys Thr Lys Lys Arg Val Arg Arg
        355                 360                 365

Ser Arg Ser Tyr His Ser Cys Gln Asp Met Ala Gly Asn Val Ser Asn
    370                 375                 380

Asp Ile Ile Lys Tyr Trp Ala Gln Arg Tyr Ser Leu Phe Ser Leu Phe
385                 390                 395                 400

Asp Ser Gly Ile Lys Met Asp Glu Val Gly Trp Phe Ser Val Thr Pro
                405                 410                 415

Glu Pro Ile Ala Lys His His Ala Ser Arg Val Gly Ala Gly Val Met
            420                 425                 430

Ile Asp Cys Phe Thr Gly Val Gly Gly Asn Ala Ile Gln Phe Ala Lys
        435                 440                 445

Lys Cys Lys His Val Ile Ala Val Asp Ile Asp Pro Gln Lys Ile Asp
    450                 455                 460

Cys Ala His His Asn Ala Ser Ile Tyr Gly Val Asn Asp His Ile Asp
465                 470                 475                 480

Phe Ile Val Gly Asp Phe Ile His Ile Ala Pro His Leu Lys Gly Glu
                485                 490                 495

Thr Ala Phe Met Ser Pro Pro Trp Gly Gly Pro Asp Tyr Ala Lys Val
            500                 505                 510

Asp Val Tyr Asp Met Lys Ser Met Leu Ile Pro Cys Asp Gly Tyr Ser
        515                 520                 525

Leu Phe Lys Leu Gly Thr Met Ile Ala Ser Arg Val Val Met Phe Leu
    530                 535                 540

Pro Arg Asn Ile Asp Leu Asn Gln Leu Ala Asp Met Ser Leu Ser Val
545                 550                 555                 560

Asp Pro Pro Trp Ala Val Glu Val Glu Lys Asn Phe Leu Asn Gly Lys
                565                 570                 575

Leu Lys Ala Ile Thr Ala Tyr Phe Glu Glu Gln Asp Arg
            580                 585


<210> SEQ ID NO 25
<211> LENGTH: 589
<212> TYPE: PRT
<213> ORGANISM: Zea mays

<400> SEQUENCE: 25

Met Gly Ser Leu Gly Leu Pro Val Ser Phe Ser Thr Ser Lys Val Asn
1               5                   10                  15

Lys Asn Thr Cys Asn Lys Gly Lys Lys Lys Gly Arg Gln Ala Pro Leu
```

```
            20                  25                  30

Lys Ala Ala Asn Thr Gln Ile Asn Asp Ala Val Arg Ile Cys Ile Asn
        35                  40                  45

Thr Glu Asp Arg Glu Asn Ser Val Glu Ser Leu Asp Ala Met Glu Gln
    50                  55                  60

Thr His Ser Cys Asn Leu Phe Val Thr Pro Leu Gly Gln Asn Glu Pro
65                  70                  75                  80

Ser Arg Asp Asp Thr Asp Lys Arg Leu Arg Glu Asp Ser Ser Cys Val
                85                  90                  95

Glu Glu Gln Glu Glu Ser Gly Cys Ser Thr Ile Tyr Ser Ala Gly Lys
            100                 105                 110

Ala Pro Gly Cys Asp Ala Lys Asn His Leu Thr Glu Leu Gly Ala Phe
        115                 120                 125

Glu Leu Ser Asp Asn Leu Ala Asn Ser Ala Lys Glu Glu Tyr Ser Ile
    130                 135                 140

Gln Glu Asn Gln Ala Tyr Glu Ser Val Leu Leu Asp Ser Glu Glu Met
145                 150                 155                 160

Ser Arg Asn Asp Cys Val Asp Asp Glu Ser Thr His Ser Cys Val Gly
                165                 170                 175

Ile Tyr Gln Asp Glu Arg Val Ser Thr Arg Gly Asp Gln Thr Ser Glu
            180                 185                 190

Glu Thr Leu Ser Val Pro His Asp Tyr Asn Asp Val Gly Arg Glu Ala
        195                 200                 205

Ser Leu Ser Leu Ala Glu Pro Ser Ser Ile Asp Glu His Ala Gln Ser
    210                 215                 220

Ser Ala Asn Asn Phe Tyr Tyr Asp Tyr Gly Glu Trp Arg Val Ile Trp
225                 230                 235                 240

Asp Pro Phe Tyr Asn Arg Tyr Tyr Phe Tyr Asn Ile Gln Thr Gln Glu
                245                 250                 255

Ser Thr Trp Cys Pro Pro Glu Gly Leu Glu Asp Phe Ala Ser Tyr Cys
            260                 265                 270

Ser Pro Asp Thr Thr Lys Glu Leu Ala Glu Leu Gly Ser Gln Cys Ser
        275                 280                 285

Ser Met Ala Pro Gln Glu Asn Asn Leu Ala Thr His Val Asn His Leu
    290                 295                 300

Glu Ala Gln Glu Gln Asp His Cys Ile His Asp Leu Ser Asp Ile Pro
305                 310                 315                 320

Val Glu Lys Pro Ile Tyr Gln Ser Met Ile Thr Thr Ser Asp Lys Ala
                325                 330                 335

Gln His Thr Glu Asn Lys Tyr Ser Asp Ser Thr Thr Thr Val Leu Glu
            340                 345                 350

Met Asn Gln Glu Val Ala Ser Thr Lys Thr Lys Lys Arg Val Arg Arg
        355                 360                 365

Ser Arg Ser Tyr His Ser Cys Gln Asp Met Ala Gly Asn Val Ser Asn
    370                 375                 380

Asp Ile Ile Lys Tyr Trp Ala Gln Arg Tyr Ser Leu Phe Ser Leu Phe
385                 390                 395                 400

Asp Ser Gly Ile Lys Met Asp Glu Val Gly Trp Phe Ser Val Thr Pro
                405                 410                 415

Glu Pro Ile Ala Lys His His Ala Ser Arg Val Gly Ala Gly Val Met
            420                 425                 430

Ile Asp Cys Phe Thr Gly Val Gly Gly Asn Ala Ile Gln Phe Ala Lys
        435                 440                 445
```

```
Lys Cys Lys His Val Ile Ala Val Asp Ile Asp Pro Gln Lys Ile Asp
    450                 455                 460

Cys Ala His His Asn Ala Ser Ile Tyr Gly Val Asn Asp His Ile Asp
465                 470                 475                 480

Phe Ile Val Gly Asp Phe Ile His Ile Ala Pro His Leu Lys Gly Glu
                485                 490                 495

Thr Ala Phe Met Ser Pro Pro Trp Gly Gly Pro Asp Tyr Ala Lys Val
            500                 505                 510

Asp Val Tyr Asp Met Lys Ser Met Leu Ile Pro Cys Asp Gly Tyr Ser
        515                 520                 525

Leu Phe Lys Leu Gly Thr Met Ile Ala Ser Arg Val Val Met Phe Leu
    530                 535                 540

Pro Arg Asn Ile Asp Leu Asn Gln Leu Ala Asp Met Ser Leu Ser Val
545                 550                 555                 560

Asp Pro Pro Trp Ala Val Glu Val Glu Lys Asn Phe Leu Asn Gly Lys
                565                 570                 575

Leu Lys Ala Ile Thr Ala Tyr Phe Glu Glu Gln Asp Arg
            580                 585


<210> SEQ ID NO 26
<211> LENGTH: 13229
<212> TYPE: DNA
<213> ORGANISM: Zea mays
<220> FEATURE:
<221> NAME/KEY: misc_feature
<222> LOCATION: (10689)..(10788)
<223> OTHER INFORMATION: n is a, c, g, or t

<400> SEQUENCE: 26

ccccgcgcgg ccaaccctct ctaagagggc cctggtcctt ccttttatag tcgtaaggag      60

tggatccagg tgtacaacgg gggtgtagca gagtgctacg tgtctagcgg gggagagcta     120

gcgccctaag tacatgccga tgtggcagcc ggagagatct tggcacccag cgagtgtgat     180

gtcgtggcca tcggaggagc gacggagcct ggcggaggga cagctgttgg agcggttgag     240

tccttgctga cgtcctcctg cttccgtaag agagctgaga gccgccgtcg tcacagagct     300

tgcggggcgc catcattgcc tatctggcgg agctagccag ataggacacc ggtcttgttc     360

tctgcggccc gagtcggctc ggggcagggt gatgatggcg cttcctgttg acgtgactgg     420

cctgcgccct aggtcgggcg acgtggaggc tcctccgaag ccgaggtcga gtctgtcttc     480

catggtcgag gccgagcccg agcccctggg tcgggcgagg cggaggtcgt tcggcagagg     540

ccagggcgga gtccgagccc tggggtcggg cgaagcggag ttcgtcgtct tctggggctg     600

agcccgagtc cgagccctgg gtcgggcgga gcggagttcg ccgtcttccg ggactttagc     660

ccgagtccga gccctgggtc gggcggagcg gagttcgccg tcttccgggg cttagcccga     720

gtccgagccc tgggtcgggc ggagcggagt tcgccgtctt ccgggactta ccccgagtcc     780

gagccctggg gtcgggcgga gcttcctatg gtgcctttgg cagggcctga ctgcccgtca     840

gtctcactct gtcgagtggc actgcagtcg gagtggcgca ggcggcgctg tccttctgcc     900

aggccggtca gtggagcggc gaagtgacgg cggtcacttc ggctctgccg gagggcgtgt     960

gtcaggataa aggtgtcagg ccacctttgc gttaaatgct cctgcgattc ggtcggtcgg    1020

tgcggcgatt tagtcagggt tgcttcttag cgaaggcaag gcctcgggcg agccggagat    1080

gtgtccgccg ttggaggggg gcctcgggcg agacggaaat cctccggggt cggctgccct    1140

tgtccgaggc taggctcggg cgaggcgtga tcgagtcgct cgaatggact gatccttgac    1200
```

```
ttaatcgcac ccatcgggcc tttgcagctt tatgctgatg ggggttacca gctgagaatt   1260
aggcgtcttg agggtacccc taattatggt ccccgacaac cacaaacgcc cacgtcgtgc   1320
gcgtggaggt aaggctatct gcattcatca tactttaaac tagttgggtg cccgtgcgtt   1380
gcaacagata tcatataaat tcatgtgttt tgctacgcga cacgagggat cggtattatt   1440
agtagtcatt tttctattgg acctagtgag gtactcgtac gttgctacgg agatcatata   1500
aatccatgtg ttttgctacg cgacacgagg gatcggtatt attagaagtc attttctatt   1560
ggacctagtg aggtacctgt atgtgcccgt acgttaccac gagagttaaa acctagtata   1620
aaacataaat acagaatgac aaacatcatt atgatataca aattcgtgta acaaaatatc   1680
actgtagcac taatattcaa taaaatgtag caactcactg ctcactaatg atgtgtccag   1740
ggtaagtggg taaagcacgg tagacgtctt cttttgactt agtacaatgc tcgtgtgttg   1800
agacggtgca caattattcg ataaaatgtt tgagcacaag tgcacaacga ttacataaaa   1860
ttgaaaaata cttatattaa caaagtctaa ttgtctcaaa ttctttttgc caacaaccaa   1920
ttcactgtgt tgcgatgata cacaataata tttcatgaat gactcaggca atccacctaa   1980
gtgggtaacc caaaagcaca ccaatgtgat gcctacacgt gaacatctaa cctctattac   2040
tacaatagtc ttgttggaaa tttacaactc atctagaatt tcaaaatact caaaattatt   2100
tagactctct ctaaaccgga gcatacaaaa tagatcaggc agttttaacg gaaacatgta   2160
tgactctcac catcctgtgc agcgctgctc gaataccaga aagtcccagc tcagccaata   2220
ctgcatcaag ttctgctagt tccttttttt catctccttt ttagacaact gtctttctgt   2280
ctctttgggt ggcgcagcta gggcccacaa ctgtcttgat agcaggttcg gctggggcat   2340
ctttcggatc atgctttagg ttcatcctca gctccatcat caacctcaaa atcaagatcc   2400
ttgtcatcac tctcaatgtc ctgcaacata tatagaagta catctaagaa cactatcaga   2460
gaggctaact ataatgacaa tcagccaaac atgctccatc cccctcgaga tgagtaaatt   2520
atacttccac ttaatagttt agttttgatg caaaaattat gacaaaaaac aagtagaaca   2580
ataaccagag tttgctatga caaacatgca gcacctgtca tgtataacca tttccaaatc   2640
acttgcttac ccaagatata gaaaaacttg gaacaagtcc ctatccaagg tacatatttt   2700
ttatttttgt ttagcaggtg gtcagctctg aaaattttct gtcaaggtga agtttgcctt   2760
atgacttgct catagcaggg tctgctttga actcctccac tgggaatgca atgtcgtgat   2820
cccacagacc gatcaaatgg gattcaaatt taggctgtgc tatatcgcgc tctgaatcta   2880
gtgataatgc gtctatcctt ggtttcttgg gagaatgttg catgatctct gggtagtcat   2940
ctaagcttgg aggtgaatca gaaagtttct gaccctcaga agctttaatt gatccaccaa   3000
gcttttgttg ctcctcaatg atcatctgca agtatattcc ttgtgcttta attgttagtt   3060
gcagttgtct ttgaacctga aaacataact tatttagaca agcaaaagaa agttggcaag   3120
gaaaatttag attgatcttg aagctaaaaa ggactcataa actacaagca ataagacaaa   3180
acaggagaac tgccaacaat agattattga caactaagca ttactacaac catgagaaga   3240
aaccactgtt aggtgtaacg tgacagttaa taagtgaata ttgagaatgg gccaaaatat   3300
cagcttgtag aagtagcccc aactaagtag gacttctggt catagtagga ttgtcggtaa   3360
actaaaatga tgtaaaaaac agaaatctct actacttatt aagtaagcaa tagtagtctg   3420
cctccctcgt tctgccgttc tgccatccat cgatctggac cgttcatatc gcatcgtgcg   3480
tctgcgtctc ccacactcta tctccctcca ccgcacgacc acccaatccc taaccttccc   3540
```

```
ccacacgttc ctctctctct cgcgttgccc gccccctgcc cctgccgcga tagaatgcct   3600
cgcggcctcc accgccgacg cggcctccac cgcttccctt cctccctttg cctccaccgc   3660
ccctccccca acgtcgtcgc caccgccgct ctagggcctc gacgcaggca gcttgggaac   3720
cgccctcggc ctcggtgtcg cacggcccca cgaggaccga ccttgccgca tggcggttgt   3780
ggaggcgtgc gaccccgcaa ggatcgacat ctcgtccaag acagcagccc cctcagagcg   3840
gacgacgcag cttatctctg gtggaaggca cgtagccacg cccccactcc ctcctcgtgc   3900
tcccgccgac gcctgcctcg cgctcctcgt cgaccgtctc tccctctcct ccgtcgttgc   3960
atctcgcctc tcgcgcacgc acaaaggtga gtctcccctc ccccgactca cccctctagg   4020
tctctgattc ttctcatcgg cgagcaagga cggaggagct ggcggaggag ctgtcgaata   4080
taacctaatt atgtcggtct cgggtgggat ttggctattt tgggcgccat ggcctaggtg   4140
agcgtacaga tctggttctg cattttgttt tcttatctgt caatcatgtt ttttcatatt   4200
actgcaggtg ggtctgatta aatattacag acatgttttg cttcgaagcc ctacacctgt   4260
ccatctaatt ttaggaactg acgattgaca cagctttgtt gtggcgctat ttagtataag   4320
ttatagaaat cggatctttg gctctcatct gcttgtagtt gcaacattga ggtagaacct   4380
gggtgggtct gattgctcat tgctgtgata tatgtctgga aaagcagagt tatagtttgg   4440
aaactagcgc gtagtacatg tcggtttctt taagtaattg cttatgctct gttgttttga   4500
tttccagatg ccccaaatgt gctgaactta agctatcgcg tgagaacaca actttctggt   4560
aagtggcaag ctcctccgtt tcttatttta ccgcattgga agttggaaca ccatgatagc   4620
tctcaggacg aatgagtatc agctaatttt attgttttaa caatagagca taaaacctta   4680
tgcatatttt aaaggttcat gtatcattta gttatggcct tatgaggaag cttcatcatc   4740
atatctgtag ataccttgat tcgtggggat ggtaattttt tgtattcttg ttcttttgat   4800
ttttgaagga aacacatctt ataatacgat agcacccatt ggaagtcctc gcatacagtg   4860
cagggtagaa ttatgcttca tgtgttgccc cttcaccacg atatgccaaa ttgaatgtag   4920
tttcatcagt tatgctcaat tatggatgtt cagaggcatc caatttcagt gtgtactgca   4980
atacttgggt ccacctatag ttgatagatg ttctgtattt tgttttctta taaattagat   5040
ttggcttgca ttatattgtt ctcttttgga acagagtcac tctccgacag ctcatcgccg   5100
cctgcttcga ccgcctgtac acaaggttta agaagcgctc tgcgaacttc cacggccgcg   5160
ccgtgctgct tctagctatt tacctttttc tatgatgcaa atgtttatat gcatactatg   5220
ttacttgaga aacattaaag tacttgatgt acctaaacac attttgttta gtgatgtata   5280
gtgatatagc attattgtct atattaatat ttatattgct ggtagcttct actttaattg   5340
atctcaatgg ggcatttggg tggctagcaa ttcacattga taatttaaaa gtgaatttca   5400
ggtgtacatt tgatggcctc cgatatggtg ctgccttcaa ttctctacaa tgcgcgagaa   5460
tgctgctcag gagggtatta atggctcaac acagatgacc tcctcggagt catgtttcta   5520
attatctaca ctatgattct ccttctgttg ataaaatatt gttttattgt gctgtgagct   5580
aatgataaca gtgatggtaa gtaaatatgg tccatgcata ttctcatcat agatggctga   5640
aaaactccga gtgctgctac gctaccagag tcttcatgtg catacttact tcaagaactc   5700
aaggtacata gttttctcaa cagaagaata tgtatctgtt tgattccagc tgaattgctt   5760
actaaactca gtgtgtcact ttaaatgata tgggatgaag ttgggcaaga ccaaagtgaa   5820
agtgggagaa tacccgaaga acttcttgtt ggacgaactt ggagaaacca atactaaaac   5880
tcagtgtcaa ccgcttgcaa caggcaattt aggtcgatgt gctcgcacgc tgtgtgacca   5940
```

```
tgtctgagca ctccccaccc acccaatcgc ttcccacgtc atgccgccac gtcgagaatt   6000

tgtacacaac tcaggttgcc cattttactc tgttattgaa cctcgctttt ctgtagaccc   6060

aggtatgcta gaagtaggta atggtagcat gaccttagca gagtatcgct cacattttag   6120

catttgggtt gtcatgaagg taagttttca ctgagattgg accgatgttg tgtcatcata   6180

ttttgagtaa agggtttgac cgaagaattt tgaaaaataa aagactgtag ttcattgaag   6240

gtgataactg gtatgcaagt attactatta atgattctcc acttactgat attacatttg   6300

gataagagga aggagatatc ctaattctaa tgggttaact gctagcagtt ccttatgtac   6360

tgttatgctt caggcccctt tattaattgc ctcatgtgga aagagggtgt gatgatcttt   6420

tgttgttttt gtagcgagaa gctcaaagaa ggggaagaca tctacatcta tcagtaagtg   6480

atccagttta gtagatgaat caccgctatg ggtgtttttc tattcttgaa taggcatgtg   6540

gttctattga tggttgtttg atgtttggta tattgtgttc tgactgtagg ggtgacaaat   6600

ccttttgcag catggagtgc agagaaaatt tcatggtaga cgagatggaa ggtgagccag   6660

agagtatgta taatcagatc aattttagac ttttttttcac taaccactta tccatagcac   6720

acttgtgttt atttgagata tgtgtcgtca ttttgtgttc atcggctatt gctatgaaga   6780

tgaccacagg gttaattctt gtttatgagt tcatcctcta gaatgtattg ggttgtcgcc   6840

aagaaaaaac acacgaagac ataaattcaa ataatttctg gtgctgtgga gtattcataa   6900

ttgtgtgctt ttgttgaatc cttcatgtac cataattctt actgcttgca agccctttta   6960

gaatgtgact ttaggatgta gaatttggtg aaaggagaca agaaattatt ctctaaacta   7020

ctatttttat aggcaaggga ggctggaagc accttttttg catgggagct gcatggagag   7080

aacttattgg tagaaaacaa actttgacca gattcttgaa tgtgccaagg gaaaaaggta   7140

ttaattggga ccttctattt atacaaggga aaaaggtatt ttttatacaa ttgctcttcc   7200

ttctcatgta tggcaacttc ctgttttgta gagattgagc gcccttcctc actgtttgaa   7260

ctttactcat cctcatgaaa ctgtgatgct acctgtagga gcggtttgtt caaggaggga   7320

atgactttta gaccctaata acttgtctac acttaagata aaaattgttg tcattgctat   7380

ggttacctcc tttagtgtcg taaactcaga ataatcatag atccctttgt tgcttacaca   7440

ttattcatgt tctacaagct attgagattt tgactagccg ctacatttta gtgcaggttt   7500

tcataatttc ttacctttat atctacattt tagatttcct cccttttgac actacatttt   7560

agccgctcac tcggaagctt tccatccctg ctggagtact cagcccataa aggtaaatgc   7620

atgcctttac ctgcctgaaa tgcattgtct ttcttttcaa ccgtgaatgt gaattggatc   7680

catcattcat gtgcacacac aaggccggtt tgaatttgga atgcactgtt gttctgcctg   7740

tgatccactt ggtggttttt atttgcgttc acatattaaa aaatatatta taccctgatt   7800

ctgagtcaaa ctttggttag acctggattt gttgattagt ttccgttgtt gtgatctgtt   7860

gaacaaacta taggttaggt gagttatcag attcttagat ctgtcctgta cggttgtgat   7920

ctgttgaaca aactataggt taggtgagtt atcagattct tagatctgtc ttgtacgtct   7980

gatctctacc atgttacaaa catctgaaag ttaataataa tcactactac attcacacct   8040

atcttgtatg gatttgctgt tgaaattgca gaatgcttcc caacttgtgc atttttatta   8100

catccccaca acttcatcgt atagtccaga catcctttgt ttgtgtagca aaatagatgt   8160

gcaattgttt cattgtaaca atgtcctgta tattaacctc ggcggctctg gtgctttctg   8220

caggcttctc attcttattt gcatggcctg taactgctgc acagcgcgct acggctggcg   8280
```

```
tagcggcagc aactgctggt atgaacagga tccgtccacc ctcattagcg acgatgaagt   8340
gacacccaat tctaggcgcg gacgtacgat ggcgccctcg cgcgggatat cgggctgagt   8400
gatgagacgc tgctgccatt ggggttccag gcgcgcctga ccgctcccac tcctaggccc   8460
ggcatgtctc tccgacgcta cctaccggtg ctggtgaaac gcaaacttaa aatcgtgcat   8520
tgcaagatgt tgccttctct ttatgtctcc tctactctac gcctacgagc tttctttgtt   8580
tataactttt tctgtggttt cgctttcaac aagctcaagc ggtcaacaga tcaacttaga   8640
caaaatgcag atgcagtgga aatattaagg aagaccagat tccctcatgt tcatggagca   8700
ggtgaaaaga agtcaccaga gacaattctg gatcatgaga ctatgagagg actttggcaa   8760
caaatgttcg gtttggactt ctctgggtgg ttctatgata ctttataatt tcttttggct   8820
tatgtgtcat ttcagaagat atgaaaatag ctaagcattg tcaataatat tagcttcctt   8880
gtttcttgtt aacctaagat gactgcccta tttcacttgt tttttctagc tgtggtagta   8940
ggtcattaga gtagttccct tcaatcgtag cactcagcca tgttgtaaat ggtttacttc   9000
tattgtgaat cgtgtttttc ttttttaatg gtggggttag tggaaaatct ggacgtatcc   9060
gcgaatggtg gagaagcaca caaaacaaca attatatgca aaaactaaac tatgttttct   9120
ttctttctat ggtatatgaa tttagtacct tgataatcac aatgattaga gtctgtttgt   9180
atttatatta aaacataact gcttaggagg tgtatgagga ggataacgag atgtgcagtg   9240
cgcgcaacag taagcagact accatgactt ggttgctctt caagtgtgca agtgtgtcta   9300
tggattgtat ggttctttgg tttttgttgt tcgctaaggt gcaaagtagg aagaaaatac   9360
ggccctgacc ctgcaagtgg ggaatgtatc gtttttgctg gaactgaaat atgcggtgtt   9420
ctttttttatg cactaatatt ttgttgaata ttttgtatac cgttgcaacg cacgggcatc   9480
tacctagtaa attaatagtt ttcaataaaa gacctcgagt ttctcatgta gtcgcttctg   9540
aacctccatt tacatcttta gtgccttaaa aatcgtgcca atgtttccat atatcaaatc   9600
acggtgatca acaattaaac aaaataactc ttaaccaaaa aaatggaagt gtcacgcact   9660
catgaactac agatgtcaat agctaacata taaacaggct caagccttcc ttcaaggata   9720
ccaggttgtt ctaagcagca tctctatatt tagagaggaa gacttgtctc gattcatctc   9780
ttcctgagac cccactcatg tgggtagttc taccttttttt atgaatacag atgcaacatc   9840
aacatataaa caggctcatg cctcagatac tactctcaat tggtctactg aaattctatt   9900
gcatttatga cgaatgcagt tacagattta aaagtaaagg acgagtacag ctgcatgatg   9960
aaaagtaaac agaacggtaa ctgcaaattt acttcagaca tgctgctgct ttgatgagat  10020
cggaacaggg ttgttgctca caatctgtgg atttaaagcc tgcaacacat gtcacaattt  10080
aatcatgagg ttcactaaga caacattaca caaaagaggt gttggtactg agaacataaa  10140
agatcatgtc atccttgtct gaaaggaagt gcattccaac taagaacaaa gatcactgct  10200
tctcaatgaa gcaaggctac gacatgatgc atatttagct caaattaccc aagcaagtgt  10260
ttattaaaat aaaagcatgc atcttagaca tcagcaatag gttatctaag acgtcaatgc  10320
atatttagcc cagttttaga caacaatgca tatttagcta aaatattaaa catgcaatgc  10380
ctctttagct caaatttcag accacagtat taaccggtgg tgctacactt gaagaacaag  10440
cttatctgga gaagcagccc acatccagtc ctgaaggcaa atcagatgtt tgaacaaaat  10500
cagtgcttag ccaaatctag aaaccacaac cactcgaacg ctgactcaga tggtagagcc  10560
atcacaccaa tggtgctacc atcagtaaaa taatagaatc aatttgtttt tccttactga  10620
tacagtaccc ttcgaataat tgtttataag caattgaact tgctgcccaa tgtattatag  10680
```

```
tcttggtcnn nnnnnnnnnn nnnnnnnnnn nnnnnnnnnn nnnnnnnnnn nnnnnnnnnn  10740
nnnnnnnnnn nnnnnnnnnn nnnnnnnnnn nnnnnnnnnn nnnnnnnntt agagacatat  10800
agagtagtat agataaggat aatggacagt agtacttgaa gttaatacat aaaacttgca  10860
gctaataaac aaacatagta ctattttagt taacatacaa caattttcca gctcttcttt  10920
gcacttatag catttttagt acctacacac aacctgaact gaacaccatc aagaacagta  10980
ctgcatttgg aagtttgaat aaaaatggtg tccaattaac agttttctaa tattgtaact  11040
taattattga atggtgcaat agggtgttca cttgttgaat tggttgataa tcttgtgtgg  11100
gctttaaata taacattgtt agtgaatgct aaataattct gcactcttgg aatggtcaag  11160
ctgagaatga gccagagatt aactggtgcg aacctgggaa gcctgcaggg atggaggtcc  11220
ttcttgggag taaggatggg ttcttgacga agaagattaa gagctatagc acatgccgaa  11280
gtgatcctac aaagccacgt gcattgcaat gcctttcacc actgatagca ggtcatgtaa  11340
gatacatcat ttaaccatct ggatatgtgt taatgttaga caactaattt ataaaatttt  11400
cgattcaggt gggcaatgga attgtttgtt gaatgagagt aatgtttatt attggtaaag  11460
tatcacaatt cagtctgatt caggtgggca tggtaaaatg aagtgcatct gccaaaaagt  11520
aaggtaagta actaagtatc ttttggatgt ttggaggatc agatgttgtt gcagaatgtt  11580
tattgactaa ttgcaagtca aatgaattaa aggggaaaac agataagcac taagattttt  11640
atatgaaagc tgtgtgagtc aacctgctaa gagctctaaa tgtcctgtcc cagaagtagt  11700
ggcggagcca gcccaaattt gaagcctatc gactcagaaa attcatccat gccaaccaaa  11760
caaatagaat aattacctta tctgttgcac gggtgtgaag gagctggaga tgcagatcag  11820
gtgtcacaaa ttctataacc aaattgcata atgcataagc aatcaaacaa tacaccccta  11880
attctttagg ctaaacgaac tgcactaagc ctatgtttca gatttcaaga ttactattgg  11940
attgtgttca tcacaccaat aggttaagta ccaacatgct aatcaataag aacagtaaag  12000
gggcattacc tacaacaaat gttacgtcta aatagaacta acttggaggc aatgtaagct  12060
ctgaatgtcc gaaacattga aacaaagtct gaactctgaa attgtctccc taatcctcac  12120
ctcatcccat ctgtgtcgat ggatggtggg tgcctcgcct gagctgttgt gtggtgccgc  12180
ggacgaggtg agcgcttgtg tagaatgaag atggggtcgc agagcgacgt ggccgacggc  12240
ggaccgatga tggagagggt actttttact ttcattaaca gatcatcaag caaaataaaa  12300
tagtaatgag caattgagcc cagatcacat ttgtaatcat ctagcatgta agcactattt  12360
tttaatttga tacccctcat tcagagtttt tgcacaaact tagaactgga ggctgaaagt  12420
aagcaaattg acttcatctt ttagtttgat gaagatcaaa tgaatttaaa agcttgagaa  12480
gatgaaaaga tctcatatgt atgaccaaga gatgatagca aatggcttca agccaataaa  12540
gtcacgagag atgaaagcaa ataggttcac atgcaggata caacagaaag ttatgtatac  12600
aggaacaaat gctaatagaa ctatgcattt atcatatttt agaaactgta gcccttgttc  12660
atcctacccc caatgagtat tcctatcagt acacatgtag gctagcattt ttttagttgt  12720
aatacttgct tagctacaga tcactggcta gctgaaaaaa acctaagtag caacagtgga  12780
acagtttgag tatagctgta tgaaaaaggc tatctgaata atagcaatat ttggattcat  12840
gttcatttca agaacttcac cattgggaaa actccaacgg tactaccatt tgattgctgc  12900
aatgtttgta atgataaaga gatctcactt actcacttgt ggtaccatag aaacctgcaa  12960
aaaagaggaa aataatataa attggtgtaa aaattaagga attcatagta caaatatgat  13020
```

```
cgactttata ggaccaccct tttgttaaat ttttcagtgt caacaggaag gtgtgattca  13080

ggcctttgtg gatcaagtca gcacagaacc ttggcttctt cattcggtag aatgatgaca  13140

agactaccga atgatgacaa gacttttaaa aatatcctgt tgaaaatgca tttaccatgt  13200

cagctgtgtt accaagacgg gtaattact                                   13229


<210> SEQ ID NO 27
<211> LENGTH: 1515
<212> TYPE: DNA
<213> ORGANISM: Artificial Sequence
<220> FEATURE:
<223> OTHER INFORMATION: cDNA

<400> SEQUENCE: 27

atggcggttg tggaggcgtg cgaccccgca aggatcgaca tctcgtccaa gacagcagcc     60

ccctcagagc ggacgacgca gcttatctct ggtggaaggc acgtagccac gcccccactc    120

cctcctcgtg ctcccgccga cgcctgcctc gcgctcctcg tcgaccgtct ctccctctcc    180

tccgtcgttg catctcgcct ctcgcgcacg cacaaagatg ccccaaatgt gctgaactta    240

agctatcgcg tgagaacaca actttctgct tctactttaa ttgatctcaa tggggcattt    300

gggtggctag caattcacat tgataattta aaagtgaatt tcaggtgtac atttgatggc    360

ctccgatatg gtgctgcctt caattctcta caatgcgcga gaatgctgct caggaggatg    420

gctgaaaaac tccgagtgct gctacgctac cagagtcttc atgtgcatac ttacttcaag    480

aactcaagcg agaagctcaa agaaggggaa gacatctaca tctatcaggg tgacaaatcc    540

ttttgcagca tggagtgcag agaaaatttc atggtagacg agatggaagg caagggaggc    600

tggaagcacc ttttttgcat gggagctgca tggagagaac ttattggtag aaaacaaact    660

ttgaccagat tcttgaatgt gccaagggaa aaaggtatta attgggacct tctatttata    720

caagggaaaa aggcgcggac gtacgatggc gccctcgcgc gggatatcgg gctgagtgat    780

gagacgctgc tgccattggg gttccaggcg cgcctgaccg ctcccactcc taggcccggc    840

atgtctctcc gacgctacct accggtgctg gtgaaacgca aacttaaaat cgtgcattgc    900

aagatgttgc cttctcttta tgtctcctct actctacgcc tacgagcttt ctttgtttat    960

aactttttct gtggtttcgc tttcaacaag ctcaagcggt caacagatca acttagacaa   1020

aatgcagatg cagtggaaat attaaggaag accagattcc ctcatgttca tggagcaggt   1080

gaaaagaagt caccagagac aattctggat catgagacta tgagaggact ttggcaacaa   1140

atgttcggtt tggacttctc tgggtggttc tatgatactt tataatttct tttggcttat   1200

gtgtcatttc agaagatatg aaaatagcta agcattgtca ataatattag cttccttgtt   1260

tcttgttaac ctaagatgac tgccctattt cacttgtttt ttctagctgt ggtagtaggt   1320

cattagagta gttcccttca atcgtagcac tcagccatgt tgtaaatggt ttacttctat   1380

tgtgaatcgt gtttttcttt tttaatggtg gggttagtgg aaaatctgga cgtatccgcg   1440

aatggtggag aagcacacaa aacaacaatt atatgcaaaa actaaactat gttttctttc   1500

tttctatggt atatg                                                    1515


<210> SEQ ID NO 28
<211> LENGTH: 2229
<212> TYPE: DNA
<213> ORGANISM: Artificial Sequence
<220> FEATURE:
<223> OTHER INFORMATION: cDNA

<400> SEQUENCE: 28
```

```
attgatctca atggggcatt tgggtggcta gcaattcaca ttgataattt aaaagtgaat     60
ttcaggtgta catttgatgg cctccgatat ggtgctgcct tcaattctct acaatgcgcg    120
agaatgctgc tcaggagggt attaatggct caacacagat gacctcctcg gagtcatgtt    180
tctaattatc tacactatga ttctccttct gttgataaaa tattgtttta ttgtgctgtg    240
agctaatgat aacagtgatg gtaagtaaat atggtccatg catattctca tcatagatgg    300
ctgaaaaact ccgagtgctg ctacgctacc agagtcttca tgtgcatact tacttcaaga    360
actcaagttg ggcaagacca aagtgaaagt gggagaatac ccgaagaact tcttgttgga    420
cgaacttgga gaaaccaata ctaaaactca gtgtcaaccg cttgcaacag gcaatttagg    480
tcgatgtgct cgcacgctgt gtgaccatgt ctgagcactc cccacccacc caatcgcttc    540
ccacgtcatg ccgccacgtc gagaatttgt acacaactca ggttgcccat tttactctgt    600
tattgaacct cgcttttctg tagacccagg tatgctagaa gtaggtaatg gtagcatgac    660
cttagcagag tatcgctcac attttagcat ttgggttgtc atgaaggtaa gttttcactg    720
agattggacc gatgttgtgt catcatattt tgagtaaagg gtttgaccga agaattttga    780
aaaataaaag actgtagttc attgaaggtg ataactggta tgcaagtatt actattaatg    840
attctccact tactgatatt acatttggat aagaggaagg agatatccta attctaatgg    900
gttaactgct agcagttcct tatgtactgt tatgcttcag gcccctttat taattgcctc    960
atgtggaaag agggtgtgat gatcttttgt tgtttttgta gcgagaagct caaagaaggg   1020
gaagacatct acatctatca gggtgacaaa tccttttgca gcatggagtg cagagaaaat   1080
ttcatggtag acgagatgga aggcaaggga ggctggaagc acctttttg  catgggagct   1140
gcatggagag aacttattgg tagaaaacaa actttgacca gattcttgaa tgtgccaagg   1200
gaaaaaggta ttaattggga ccttctattt atacaaggga aaaaggtatt ttttatacaa   1260
ttgctcttcc ttctcatgta tggcaacttc ctgttttgta gagattgagc gcccttcctc   1320
actgtttgaa ctttactcat cctcatgaaa ctgtgatgct acctgtagga gcggtttgtt   1380
caaggaggga atgactttta gaccctaata acttgtctac acttaagata aaaattgttg   1440
tcattgctat ggttacctcc tttagtgtcg taaactcaga ataatcatag atccctttgt   1500
tgcttacaca ttattcatgt tctacaagct attgagattt tgactagccg ctacatttta   1560
gtgcaggttt tcataatttc ttacctttat atctacattt tagatttcct cccttttgac   1620
actacatttt agccgctcac tcggaagctt tccatccctg ctggagtact cagcccataa   1680
aggcttctca ttcttatttg catggcctgt aactgctgca cagcgcgcta cggctggcgt   1740
agcggcagca actgctggta tgaacaggat ccgtccaccc tcattagcga cgatgaagtg   1800
acacccaatt ctaggcgcgg acgtacgatg gcgccctcgc gcgggatatc gggctgagtg   1860
atgagacgct gctgccattg gggttccagg cgcgcctgac cgctcccact cctaggcccg   1920
gcatgtctct ccgacgctac ctaccggtgc tggtgaaacg caaacttaaa atcgtgcatt   1980
gcaagatgtt gccttctctt tatgtctcct ctactctacg cctacgagct ttctttgttt   2040
ataacttttt ctgtggtttc gctttcaaca agctcaagcg gtcaacagat caacttagac   2100
aaaatgcaga tgcagtggaa atattaagga agaccagatt ccctcatgtt catggagcag   2160
gtgaaaagaa gtcaccagag acaattctgg atcatgagac tatgagagga ctttggcaac   2220
aaatgttcg                                                           2229
```

<210> SEQ ID NO 29

<211> LENGTH: 579
<212> TYPE: DNA
<213> ORGANISM: Artificial Sequence
<220> FEATURE:
<223> OTHER INFORMATION: cDNA

<400> SEQUENCE: 29

```
aagttttcac tgagattgga ccgatgttgt gtcatcatat tttgagtaaa gggtttgacc     60
gaagaatttt gaaaaataaa agactgtagt tcattgaagg tgataactgg tatgcaagta    120
ttactattaa tgattctcca cttactgata ttacatttgg ataagaggaa ggagatatcc    180
taattctaat gggttaactg ctagcagttc cttatgtact gttatgcttc aggccccttt    240
attaattgcc tcatgtggaa agagggtgtg atgatctttt gttgtttttg tagcgagaag    300
ctcaaagaag ggaagacat ctacatctat cagggtgaca aatccttttg cagcatggag    360
tgcagagaaa atttcatggt agacgagatg gaaggcaagg gaggctggaa gcaccttttt    420
tgcatgggag ctgcatggag agaacttatt ggtagaaaac aaactttgac cagattcttg    480
aatgtgccaa gggaaaaagg tattaattgg gaccttctat ttatacaagg gaaaaaggta    540
tttttatac aattgctctt ccttctcatg tatggcaac                            579
```

<210> SEQ ID NO 30
<211> LENGTH: 2512
<212> TYPE: DNA
<213> ORGANISM: Zea mays

<400> SEQUENCE: 30

```
cccgctacct gttcaccgcg cgccagcgaa acctccgcac gcccactgcc catctgttcc     60
ccgtgcgcca gcgaaacatc cgcacgcccg cggcccgcct gttccccgcg catcccgctg    120
cacgacttct gctaccgcaa cggccaccca cgcacgcccg cctgttcacc gcgcatcccg    180
ctgacctccc cttcacgctc gcacacgctc cgttccccca ccccaccgca atccccgacg    240
ctataagagc ggtaaccaac tccatctccc tggtgccacg cattgttgag ttcttaaggt    300
gcgtttcgtt gaggacttgt tcatttttgt tggtcatgta ttccatttta ctgctctacc    360
attttgtgga ataaagggag gaatgttttc actagaagag ttcatcaatc ttatgttggt    420
ttcttggatc agttttgctc tatggctaaa tggtcgaatt gagcctattt cattataaag    480
ttagcgagcg aataattgtt cagcctcttc ctagaactca ttaccagtag aatcagttac    540
taactgcttt tctttttctt ggattagaat ggctggggct atctctcacc atgcgctagc    600
attttcacaa tcccactggt gcagtgcgaa gaactctaga ttcggaaaga ggacgggcaa    660
tgctcgcctg gtttatctaa aaggaagatg tggttcaggc agcagaaaac tgggtttgat    720
gtgggcctcg agctcgcagt cttctgtcat ggagccgacg cacctaccat ctgatggcaa    780
cagcagccac accccaaaaa aatcaagtaa ttttaacgac ctcctatggt ggttatttgt    840
ttttaatttg agaaaactat ccatttgaca catttaactt tgggcttctc agaatttggg    900
ggcatataat aagatctgct aatctgttat ctctatgtcg ttgtaggtga aagcgctctt    960
atattgattt ggcatggtga atccctgtgg aacgagaaaa atctatttcc tggctgcatc   1020
gatgtacccc tgacaccgaa gggtgttgag gaggccattg aggcaggtaa aaggatatgc   1080
aatatcccaa tcgatgtgat atatacttca tcactgattt gtgctcagat gaccgcaatg   1140
cttgccatga tgcagcatcg acgcaagaag gtttgtgtct ttcctttgaa attccagtaa   1200
tttcttctag catttgtatg aacttgccgg agaaatcatg ctttgctggt gatatatgta   1260
tttatagatc ctagttatca cgcataatga gagtgaacaa gctcacaggt ggagtcagat   1320
```

```
atacagtgag gagacaatga aacagtccat tcctgtcatc acagcttggc aattgaatga   1380

acggatgtaa tactttctcc atactctttg atttgctaat tactccctct gtctcaaaat   1440

agtattaatt ttagctcttg atttttatgt ctatattcaa atagatgatg ataaatctag   1500

attctagaca caaatataaa acatatacat caagtattat atgaatctat taatttacta   1560

agaccaattt taatttggga cagagggagt atacgattat aatagttgtt tgactgtgct   1620

tctctttaaa tatcccttga catttctagg tatggtgagc tacaaggcct taacaagcaa   1680

gaaactgtag atcgatttgg caaagaacaa gttcatgagt ggcgccgcag ttatgatatt   1740

cctccgccaa atggagaaag tctagagaag tgtgctgaga gagctgttgc ttatttcaaa   1800

gatcaggcac atctagcaag gccactttac actaattgaa agatacactt tttacttggg   1860

ttattggtct tgctgcagta ttggtatgca tgctaaaggt tattcttgaa tcgatgaatt   1920

cctctactat gggatgcaga aatgcatgtg cttagttttc tttctattgt gctagctcat   1980

atcaaattta taacctgaat tttttattta tgttcgactc taaaaaacag ttttttctag   2040

ctcgatttga cctatagtaa tttttccgta atagattatt ccacaacttg tggctggaaa   2100

acatgtgatg gttgctgcac atgggaattc acttcgttca attataatgc atctggacaa   2160

attaacttct cagaaggtaa ttcactgtcg tttttgtctt tccatcaaaa aggactcggc   2220

taaacagaac atgtagcatt atgttaagtt tgggagtgag cctttcgtcc cttcaggtaa   2280

taagccttga gctgtctact ggcattccca tgctttacat attcaaagag ggaaagttta   2340

ttcgacgtgg gactccagta ggaccttcgg aggccagtgt ttatgcttat accagggtaa   2400

gattctttcc cccacatgtt ctaccatagg acgatactcc agtttacaaa ccttatctgt   2460

acagaccaaa cgatttgctg agcacattac atttcagaac aaattggcct ag           2512
```

<210> SEQ ID NO 31
<211> LENGTH: 1005
<212> TYPE: DNA
<213> ORGANISM: Artificial Sequence
<220> FEATURE:
<223> OTHER INFORMATION: cDNA

<400> SEQUENCE: 31

```
atggctgggg ctatctctca ccatgcgcta gcattttcac aatcccactg gtgcagtgcg     60

aagaactcta gattcggaaa gaggacgggc aatgctcgcc tggtttatct aaaaggaaga    120

tgtggttcag gcagcagaaa actgggtttg atgtgggcct cgagctcgca gtcttctgtc    180

atggagccga cgcacctacc atctgatggc aacagcagcc acaccccaaa aaaatcaagt    240

gaaagcgctc ttatattgat ttggcatggt gaatccctgt ggaacgagaa aaatctattt    300

cctggctgca tcgatgtacc cctgacaccg aagggtgttg aggaggccat tgaggcaggt    360

aaaaggatat gcaatatccc aatcgatgtg atatatactt catcactgat ttgtgctcag    420

atgaccgcaa tgcttgccat gatgcagcat cgacgcaaga agatcctagt tatcacgcat    480

aatgagagtg aacaagctca caggtggagt cagatataca gtgaggagac aatgaaacag    540

tccattcctg tcatcacagc ttggcaattg aatgaacgga tgtatggtga gctacaaggc    600

cttaacaagc aagaaactgt agatcgattt ggcaaagaac aagttcatga gtggcgccgc    660

agttatgata ttcctccgcc aaatggagaa agtctagaga agtgtgctga gagagctgtt    720

gcttatttca aagatcagat tattccacaa cttgtggctg gaaaacatgt gatggttgct    780

gcacatggga attcacttcg ttcaattata atgcatctgg acaaattaac ttctcagaag    840
```

```
gtaataagcc ttgagctgtc tactggcatt cccatgcttt acatattcaa agagggaaag    900

tttattcgac gtgggactcc agtaggacct tcggaggcca gtgtttatgc ttataccagg    960

accaaacgat ttgctgagca cattacattt cagaacaaat tggcc                   1005


<210> SEQ ID NO 32
<211> LENGTH: 394
<212> TYPE: PRT
<213> ORGANISM: Zea mays

<400> SEQUENCE: 32

Met Ala Val Val Glu Ala Cys Asp Pro Ala Arg Ile Asp Ile Ser Ser
1               5                   10                  15

Lys Thr Ala Ala Pro Ser Glu Arg Thr Thr Gln Leu Ile Ser Gly Gly
            20                  25                  30

Arg His Val Ala Thr Pro Pro Leu Pro Pro Arg Ala Pro Ala Asp Ala
        35                  40                  45

Cys Leu Ala Leu Leu Val Asp Arg Leu Ser Leu Ser Ser Val Val Ala
    50                  55                  60

Ser Arg Leu Ser Arg Thr His Lys Asp Ala Pro Asn Val Leu Asn Leu
65                  70                  75                  80

Ser Tyr Arg Val Arg Thr Gln Leu Ser Ala Ser Thr Leu Ile Asp Leu
                85                  90                  95

Asn Gly Ala Phe Gly Trp Leu Ala Ile His Ile Asp Asn Leu Lys Val
            100                 105                 110

Asn Phe Arg Cys Thr Phe Asp Gly Leu Arg Tyr Gly Ala Ala Phe Asn
        115                 120                 125

Ser Leu Gln Cys Ala Arg Met Leu Leu Arg Arg Met Ala Glu Lys Leu
    130                 135                 140

Arg Val Leu Leu Arg Tyr Gln Ser Leu His Val His Thr Tyr Phe Lys
145                 150                 155                 160

Asn Ser Ser Glu Lys Leu Lys Glu Gly Glu Asp Ile Tyr Ile Tyr Gln
                165                 170                 175

Gly Asp Lys Ser Phe Cys Ser Met Glu Cys Arg Glu Asn Phe Met Val
            180                 185                 190

Asp Glu Met Glu Gly Lys Gly Gly Trp Lys His Leu Phe Cys Met Gly
        195                 200                 205

Ala Ala Trp Arg Glu Leu Ile Gly Arg Lys Gln Thr Leu Thr Arg Phe
    210                 215                 220

Leu Asn Val Pro Arg Glu Lys Gly Ile Asn Trp Asp Leu Leu Phe Ile
225                 230                 235                 240

Gln Gly Lys Lys Ala Arg Thr Tyr Asp Gly Ala Leu Ala Arg Asp Ile
                245                 250                 255

Gly Leu Ser Asp Glu Thr Leu Leu Pro Leu Gly Phe Gln Ala Arg Leu
            260                 265                 270

Thr Ala Pro Thr Pro Arg Pro Gly Met Ser Leu Arg Arg Tyr Leu Pro
        275                 280                 285

Val Leu Val Lys Arg Lys Leu Lys Ile Val His Cys Lys Met Leu Pro
    290                 295                 300

Ser Leu Tyr Val Ser Ser Thr Leu Arg Leu Arg Ala Phe Phe Val Tyr
305                 310                 315                 320

Asn Phe Phe Cys Gly Phe Ala Phe Asn Lys Leu Lys Arg Ser Thr Asp
                325                 330                 335

Gln Leu Arg Gln Asn Ala Asp Ala Val Glu Ile Leu Arg Lys Thr Arg
            340                 345                 350
```

```
Phe Pro His Val His Gly Ala Gly Glu Lys Lys Ser Pro Glu Thr Ile
        355                 360                 365

Leu Asp His Glu Thr Met Arg Gly Leu Trp Gln Gln Met Phe Gly Leu
    370                 375                 380

Asp Phe Ser Gly Trp Phe Tyr Asp Thr Leu
385                 390


<210> SEQ ID NO 33
<211> LENGTH: 128
<212> TYPE: PRT
<213> ORGANISM: Zea mays

<400> SEQUENCE: 33

Met Tyr Cys Tyr Ala Ser Gly Pro Phe Ile Asn Cys Leu Met Trp Lys
1               5                   10                  15

Glu Gly Val Met Ile Phe Cys Cys Phe Cys Ser Glu Lys Leu Lys Glu
            20                  25                  30

Gly Glu Asp Ile Tyr Ile Tyr Gln Gly Asp Lys Ser Phe Cys Ser Met
        35                  40                  45

Glu Cys Arg Glu Asn Phe Met Val Asp Glu Met Glu Gly Lys Gly Gly
    50                  55                  60

Trp Lys His Leu Phe Cys Met Gly Ala Ala Trp Arg Glu Leu Ile Gly
65                  70                  75                  80

Arg Lys Gln Thr Leu Thr Arg Phe Leu Asn Val Pro Arg Glu Lys Gly
                85                  90                  95

Ile Asn Trp Asp Leu Leu Phe Ile Gln Gly Lys Lys Val Phe Phe Ile
            100                 105                 110

Gln Leu Leu Phe Leu Leu Met Tyr Gly Asn Phe Leu Phe Cys Arg Asp
        115                 120                 125


<210> SEQ ID NO 34
<211> LENGTH: 335
<212> TYPE: PRT
<213> ORGANISM: Zea mays

<400> SEQUENCE: 34

Met Ala Gly Ala Ile Ser His His Ala Leu Ala Phe Ser Gln Ser His
1               5                   10                  15

Trp Cys Ser Ala Lys Asn Ser Arg Phe Gly Lys Arg Thr Gly Asn Ala
            20                  25                  30

Arg Leu Val Tyr Leu Lys Gly Arg Cys Gly Ser Gly Ser Arg Lys Leu
        35                  40                  45

Gly Leu Met Trp Ala Ser Ser Ser Gln Ser Ser Val Met Glu Pro Thr
    50                  55                  60

His Leu Pro Ser Asp Gly Asn Ser Ser His Thr Pro Lys Lys Ser Ser
65                  70                  75                  80

Glu Ser Ala Leu Ile Leu Ile Trp His Gly Glu Ser Leu Trp Asn Glu
                85                  90                  95

Lys Asn Leu Phe Pro Gly Cys Ile Asp Val Pro Leu Thr Pro Lys Gly
            100                 105                 110

Val Glu Glu Ala Ile Glu Ala Gly Lys Arg Ile Cys Asn Ile Pro Ile
        115                 120                 125

Asp Val Ile Tyr Thr Ser Ser Leu Ile Cys Ala Gln Met Thr Ala Met
    130                 135                 140

Leu Ala Met Met Gln His Arg Arg Lys Lys Ile Leu Val Ile Thr His
145                 150                 155                 160
```

```
Asn Glu Ser Glu Gln Ala His Arg Trp Ser Gln Ile Tyr Ser Glu Glu
                165                 170                 175

Thr Met Lys Gln Ser Ile Pro Val Ile Thr Ala Trp Gln Leu Asn Glu
            180                 185                 190

Arg Met Tyr Gly Glu Leu Gln Gly Leu Asn Lys Gln Glu Thr Val Asp
        195                 200                 205

Arg Phe Gly Lys Glu Gln Val His Glu Trp Arg Arg Ser Tyr Asp Ile
    210                 215                 220

Pro Pro Pro Asn Gly Glu Ser Leu Glu Lys Cys Ala Glu Arg Ala Val
225                 230                 235                 240

Ala Tyr Phe Lys Asp Gln Ile Ile Pro Gln Leu Val Ala Gly Lys His
                245                 250                 255

Val Met Val Ala Ala His Gly Asn Ser Leu Arg Ser Ile Ile Met His
            260                 265                 270

Leu Asp Lys Leu Thr Ser Gln Lys Val Ile Ser Leu Glu Leu Ser Thr
        275                 280                 285

Gly Ile Pro Met Leu Tyr Ile Phe Lys Glu Gly Lys Phe Ile Arg Arg
    290                 295                 300

Gly Thr Pro Val Gly Pro Ser Glu Ala Ser Val Tyr Ala Tyr Thr Arg
305                 310                 315                 320

Thr Lys Arg Phe Ala Glu His Ile Thr Phe Gln Asn Lys Leu Ala
                325                 330                 335
```

<210> SEQ ID NO 35
<211> LENGTH: 637
<212> TYPE: DNA
<213> ORGANISM: Artificial Sequence
<220> FEATURE:
<223> OTHER INFORMATION: cDNA

<400> SEQUENCE: 35

```
gctacgtgcc ttccaccaga gataagctgc gtcgtccgct ctgagggggc tgctgtcttg     60

gacgagatgt cgatccttgc ggggtcgcac gcctccacaa ccgccatgcg gcaaggttca    120

aagacaactg caactaacaa ttaaagcaca aggaatatac ttgcagatga tcattgagga    180

gcaacaaaag cttggtggat caattaaagc ttctgaggga cattgagagt gatgacaagg    240

atcttgattt tgaggttgat gatggagctg aggatgaacc taaagcatga tccgaaagat    300

gccccagccg aacctgctat caagacagtt gtggccctag ctgcgccacc caaagagaca    360

gaaagacagt tgtctaaaaa ggagatgaaa aaaaggaact agcagaactt gatgcagtat    420

tggctgagct gggactttct ggtattcgag cagcgctgca caggatggtg agagtcatac    480

atgtttccgt taaaactgcc tgatctattt tgtatgctcc ggtttagaga gagtctaaat    540

aattttgagt attttgaaat tctagatgag ttgtaaattt ccaacaagac tattgtagta    600

atagaggtta gatgttcacg tgtaggcatc acattgg                             637
```

<210> SEQ ID NO 36
<211> LENGTH: 691
<212> TYPE: DNA
<213> ORGANISM: Artificial Sequence
<220> FEATURE:
<223> OTHER INFORMATION: cDNA

<400> SEQUENCE: 36

```
tatagggaga gcggccgcca gatcttccgg atggctcgag tttttcagca agatgctacg     60

tgccttccac cagagataag ctgcgtcgtc cgctctgagg gggctgctgt cttggacgag    120
```

atgtcgatcc ttgcggggtc gcacgcctcc acaaccgcca tgcggcaagg ttcaaagaca 180
actgcaacta acaattaaag cacaaggaat atacttgcag atgatcattg aggagcaaca 240
aaagcttggt ggatcaatta aagcttctga gggacattga gagtgatgac aaggatcttg 300
attttgaggt tgatgatgga gctgaggatg aacctaaagc atgatccgaa agatgcccca 360
gccgaacctg ctatcaagac agttgtggcc ctagctgcgc cacccaaaga gacagaaaga 420
cagttgtcta aaaaggagat gaaaaaaagg aactagcaga acttgatgca gtattggctg 480
agctgggact ttctggtatt cgagcagcgc tgcacaggat ggtgagagtc atacatgttt 540
ccgttaaaac tgcctgatct attttgtatg ctccggttta gagagagtct aaataatttt 600
gagtattttg aaattctaga tgagttgtaa atttccaaca agactattgt agtaatagag 660
gttagatgtt cacgtgtagg catcacattg g 691

<210> SEQ ID NO 37
<211> LENGTH: 2146
<212> TYPE: DNA
<213> ORGANISM: Artificial Sequence
<220> FEATURE:
<223> OTHER INFORMATION: cDNA

<400> SEQUENCE: 37
atgagaagaa tcagagacct agaggggtga gtcgggggag gggagactca cctttgtgcg 60
tgcgcgagag gcgagatgca acgacggagg agagggagag acggtcgacg aggagcgcga 120
ggcaggcgtc ggcgggagca cgaggaggga gtgggggcgt ggctacgtgc cttccaccag 180
agataagctg cgtcgtccgc tctgaggggg ctgctgtctt ggacgagatg tcgatccttg 240
cggggtcgca cgcctccaca accgccatgc ggcaaggtcg gtcctcgtgg ggccgtgcga 300
caccgaggcc gagggcggtt cccaagctgc ctgcgtcgag gccctagagc ggcggtggcg 360
acgacgttgg gggagggggcg gtggaggcaa agggaggaag ggaagcggtg gaggccgcgt 420
cggcggtgga ggccgcgagg cattctatcg cggcaggggc agggggcggg caacgcgaga 480
gagagaggaa cgtgtggggg aaggttaggg attgggtggt cgtgcggtgg agggagatag 540
agtgtgggag acgcagacgc acgatgcgat atgaacggtc cagatcgatg gatggcagaa 600
cggcagaacg agggaggcag actactattg cttacttaat aagtagtaga gatttctgtt 660
ttttacatca ttttagttta ccgacaatcc tactatgacc agaagtccta cttagttggg 720
gctacttcta caagctgata ttttggccca ttctcaatat tcacttatta actgtcacgt 780
tacacctaac agtggtttct tctcatggtt gtagtaatgc ttagttgtca ataatctatt 840
gttggcagtt ctcctgtttt gtcttattgc ttgtagttta tgagtccttt ttagcttcaa 900
gatcaatcta aattttcctt gccaactttc ttttgcttgt ctaaataagt tatgttttca 960
ggttcaaaga caactgcaac taacaattaa agcacaagga atatacttgc agatgatcat 1020
tgaggagcaa caaaagcttg gtggatcaat taaagcttct gagggtcaga aactttctga 1080
ttcacctcca agcttagatg actacccaga gatcatgcaa cattctccca agaaaccaag 1140
gatagacgca ttatcactag attcagagcg cgatatagca cagcctaaat ttgaatccca 1200
tttgatcggt ctgtgggatc acgacattgc attcccagtg gaggagttca aagcagaccc 1260
tgctatgagc aagtcataag gcaaacttca ccttgacaga aaattttcag agctgaccac 1320
ctgctaaaca aaaataaaaa atatgtacct tggataggga cttgttccaa gtttttctat 1380
atcttgggta agcaagtgat ttggaaatgg ttatacatga caggtgctgc atgtttgtca 1440

```
tagcaaactc tggttattgt tctacttgtt ttttgtcata atttttgcat caaaactaaa   1500

ctattaagtg gaagtataat ttactcatct cgagggggat ggagcatgtt tggctgattg   1560

tcattatagt tagcctctct gatagtgttc ttagatgtac ttctatatat gttgcaggac   1620

attgagagtg atgacaagga tcttgatttt gaggttgatg atggagctga ggatgaacct   1680

aaagcatgat ccgaaagatg ccccagccga acctgctatc aagacagttg tgggccctag   1740

ctgcgccacc caaagagaca gaaagacagt tgtctaaaaa ggagatgaaa aaaaggaact   1800

agcagaactt gatgcagtat tggctgagct gggactttct ggtattcgag cagcgctgca   1860

caggatggtg agagtcatac atgtttccgt taaaactgcc tgatctattt tgtatgctcc   1920

ggtttagaga gagtctaaat aattttgagt attttgaaat tctagatgag ttgtaaattt   1980

ccaacaagac tattgtagta atagaggtta gatgttcacg tgtaggcatc acattggtgt   2040

gcttttgggt tacccactta ggtggattgc ctgagtcatt catgaaatat tattgtgtat   2100

catcgcaaca cagtgaattg gttgttggca aaaagaattt gagaca                  2146
```

```
<210> SEQ ID NO 38
<211> LENGTH: 637
<212> TYPE: DNA
<213> ORGANISM: Artificial Sequence
<220> FEATURE:
<223> OTHER INFORMATION: cDNA

<400> SEQUENCE: 38

gctacgtgcc ttccaccaga gataagctgc gtcgtccgct ctgagggggc tgctgtcttg     60

gacgagatgt cgatccttgc ggggtcgcac gcctccacaa ccgccatgcg gcaaggttca    120

aagacaactg caactaacaa ttaaagcaca aggaatatac ttgcagatga tcattgagga    180

gcaacaaaag cttggtggat caattaaagc ttctgaggga cattgagagt gatgacaagg    240

atcttgattt tgaggttgat gatggagctg aggatgaacc taaagcatga tccgaaagat    300

gccccagccg aacctgctat caagacagtt gtggccctag ctgcgccacc caaagagaca    360

gaaagacagt tgtctaaaaa ggagatgaaa aaaaggaact agcagaactt gatgcagtat    420

tggctgagct gggactttct ggtattcgag cagcgctgca caggatggtg agagtcatac    480

atgtttccgt taaaactgcc tgatctattt tgtatgctcc ggtttagaga gagtctaaat    540

agttttgagt attttgaaat tctagatgag ttgtaaattt ccaacaagac tattgtagta    600

atagaggtta gatgttcacg tgtaggcatc acattgg                             637
```

```
<210> SEQ ID NO 39
<211> LENGTH: 55
<212> TYPE: PRT
<213> ORGANISM: Zea mays

<400> SEQUENCE: 39

Met Ala Arg Val Phe Gln Gln Asp Ala Thr Cys Leu Pro Pro Glu Ile
1               5                   10                  15

Ser Cys Val Val Arg Ser Glu Gly Ala Ala Val Leu Asp Glu Met Ser
            20                  25                  30

Ile Leu Ala Gly Ser His Ala Ser Thr Thr Ala Met Arg Gln Gly Ser
        35                  40                  45

Lys Thr Thr Ala Thr Asn Asn
    50                  55
```

```
<210> SEQ ID NO 40
<211> LENGTH: 56
```

<212> TYPE: PRT
<213> ORGANISM: Zea mays

<400> SEQUENCE: 40

```
Met Thr Arg Ile Leu Ile Leu Arg Leu Met Met Glu Leu Arg Met Asn
1               5                   10                  15

Leu Lys His Asp Pro Lys Asp Ala Pro Ala Glu Pro Ala Ile Lys Thr
            20                  25                  30

Val Val Ala Leu Ala Ala Pro Pro Lys Glu Thr Glu Arg Gln Leu Ser
        35                  40                  45

Lys Lys Glu Met Lys Lys Arg Asn
    50                  55
```

<210> SEQ ID NO 41
<211> LENGTH: 1327
<212> TYPE: DNA
<213> ORGANISM: Zea mays

<400> SEQUENCE: 41

```
tattgttgcc tcctcctcat ctcatcacta gtcactcaac cgcaattgat tgaaaattgt     60

gttcatcatc tcgttggatc gatcataatt ctttcatttc tggcctcgac aagtatcgag    120

ctcattaatc catcaatcca atgtgtgttc tgtcgaaggc gacaatggtg agctacttat    180

cgcggcgtcc atttaatggc tgcagcacaa aggcgatgga cgtgatcgtg gtcgacaaga    240

ccatcgtgcc ggggggggag gggggtagag ggtgacggtg ctgatgatgg atggcgatgg    300

tatccggggt ctcatcccgg aaaccattct tgccttcctc gaggcgaggg tgcaggatct    360

ggacaggctg gaggcgaggc tcgcagacta cttcgactac atcgccagga ccggtgggct    420

cgtcatcacg ctgctcactt cgcccggcaa ggacaagcgg cctctctacg ttgccaagaa    480

catcaaccac ttgttcttgc atccattcac atcgccctaa tcacatcaat gtatagagga    540

ctatgatgga tggatgcaag aacaatgacg ccagatggaa ttcacttttg agggaagaca    600

tgtgggctgt tctccatgta gaagtggttg atgtccttgg caacgtagag agaccgcttg    660

tttttgccgg tcccgatgaa catggcggtg atgatctcat cggtgctatt cctagtgatg    720

tagtcgaagt agtccgcgag ccttgccttc gtcccgtcca actcctacgg catggcctcg    780

aggaaggtga ggatggttcc cgagatgaga ccccagatgg cgcctctgtc caccgttatc    840

actgtcaccc tcggttcaac acgacgggct catcgaccat gctcccggcc atcgccttcg    900

tgctgcatgt gttgcatgga cgccttgatg agtagctcac cgttgccgcc tttgaccaag    960

cacacaccca attgatcgat taatgaacta gatactcatt gaggccacga atgaaagaat   1020

tatcatcaaa ccaacaaatg acggacacaa ttttcaatcg attatggatg agtgtgagta   1080

gtgatgagct gaggaagatg caatgataga tcgattgtgt acatatatag gcactgcgta   1140

cgtgctgccc ctttttggag tgacaaatag gaactagcgc gcgtattttt gcatacaacc   1200

actactaaat aagagatata tgtaaaattt aacgcaaggg atatagggaa gagatatttg   1260

tccattgcaa tgtattttga agctgtccac atatactatt tatgaagaaa cggattatgc   1320

caagtat                                                             1327
```

<210> SEQ ID NO 42
<211> LENGTH: 714
<212> TYPE: DNA
<213> ORGANISM: Zea mays

<400> SEQUENCE: 42

```
atcattacat aacttatgct atattttccc gagtatgtcc taacatcttc cacagtgttt     60

ttatgggctc cttagaagtt ccagcccagg ggcctgaaac tattaaagtt ccaactgctc    120

attatgaatt tggtgccaat tttttagatc caaagttaat gctcattgga agggtgataa    180

cagatggaag gcttaatgct cgcgtgaaat gtgatttgac agacaatctc acgctgaaag    240

taaatgcaca gcttacccaa gaggcacatt actcacaagg aatgtttaac tttgactaca    300

aggttgacgt ttctgacaag tcagacgtaa cgagggcgtc cacaccgcgg ctccgccgga    360

catcgcaaca atctccccgc cccagctctc ctctccctgc gccgaggcca caatccctgc    420

cgccccggct ctcctcgtcc ccaaatcttg cacgcggtcg taatccccgc cgcctcgctc    480

tcctcgcccc tagatcgccg cctccactat cgctgatata ccagaccaag caggtagagc    540

agaccaagat gtcgctcgag gaggccaagc tggagatggc cacgctgctg cagcagcagg    600

cgagcaagtc atgcatggta ctaagtcctg catggtacta atggttgtaa tgtagtgatg    660

aaatagctag attaaaataa caaaatttat gtatggctag gatcacaaat agat          714
```

```
<210> SEQ ID NO 43
<211> LENGTH: 460
<212> TYPE: DNA
<213> ORGANISM: Zea mays

<400> SEQUENCE: 43

ccagcccagg ggcctgaaac tattaaagtt ccaactgctc attatgaatt tggtgccaat     60

tttttagatc caaagttaat gctcattgga agggtgataa cagatggaag gcttaatgct    120

cgcgtgaaat gtgatttgac agacaatctc acgctgaaag taaatgcaca gcttacccaa    180

gaggcacatt actcacaagg aatgtttaac tttgactaca aggacgtaac gagggcgtcc    240

acaccgcggc tccgccggac atcgcaacaa tctccccgcc ccagctctcc tctccctgcg    300

ccgaggccac aatccctgcc gccccggctc tcctcgtccc caaatcttgc acgcggtcgt    360

aatccccgcc gcctcgctct cctcgcccct agatcgccgc ctccactatc gctgatatac    420

cagaccaagc aggtagagca gaccaagatg tcgctcgagg                          460
```

```
<210> SEQ ID NO 44
<211> LENGTH: 192
<212> TYPE: PRT
<213> ORGANISM: Zea mays

<400> SEQUENCE: 44

Met Gly Ser Leu Glu Val Pro Ala Gln Gly Pro Glu Thr Ile Lys Val
1               5                   10                  15

Pro Thr Ala His Tyr Glu Phe Gly Ala Asn Phe Leu Asp Pro Lys Leu
            20                  25                  30

Met Leu Ile Gly Arg Val Ile Thr Asp Gly Arg Leu Asn Ala Arg Val
        35                  40                  45

Lys Cys Asp Leu Thr Asp Asn Leu Thr Leu Lys Val Asn Ala Gln Leu
    50                  55                  60

Thr Gln Glu Ala His Tyr Ser Gln Gly Met Phe Asn Phe Asp Tyr Lys
65                  70                  75                  80

Val Asp Val Ser Asp Lys Ser Asp Val Thr Arg Ala Ser Thr Pro Arg
                85                  90                  95

Leu Arg Arg Thr Ser Gln Gln Ser Pro Arg Pro Ser Ser Pro Leu Pro
            100                 105                 110

Ala Pro Arg Pro Gln Ser Leu Pro Pro Arg Leu Ser Ser Ser Pro Asn
        115                 120                 125
```

```
Leu Ala Arg Gly Arg Asn Pro Arg Arg Leu Ala Leu Leu Ala Pro Arg
    130                 135                 140

Ser Pro Pro Pro Leu Ser Leu Ile Tyr Gln Thr Lys Gln Val Glu Gln
145                 150                 155                 160

Thr Lys Met Ser Leu Glu Glu Ala Lys Leu Glu Met Ala Thr Leu Leu
                165                 170                 175

Gln Gln Gln Ala Ser Lys Ser Cys Met Val Leu Ser Pro Ala Trp Tyr
            180                 185                 190


<210> SEQ ID NO 45
<211> LENGTH: 127
<212> TYPE: PRT
<213> ORGANISM: Zea mays

<400> SEQUENCE: 45

Met Leu Ile Gly Arg Val Ile Thr Asp Gly Arg Leu Asn Ala Arg Val
1               5                   10                  15

Lys Cys Asp Leu Thr Asp Asn Leu Thr Leu Lys Val Asn Ala Gln Leu
            20                  25                  30

Thr Gln Glu Ala His Tyr Ser Gln Gly Met Phe Asn Phe Asp Tyr Lys
        35                  40                  45

Asp Val Thr Arg Ala Ser Thr Pro Arg Leu Arg Arg Thr Ser Gln Gln
    50                  55                  60

Ser Pro Arg Pro Ser Ser Pro Leu Pro Ala Pro Arg Pro Gln Ser Leu
65                  70                  75                  80

Pro Pro Arg Leu Ser Ser Ser Pro Asn Leu Ala Arg Gly Arg Asn Pro
                85                  90                  95

Arg Arg Leu Ala Leu Leu Ala Pro Arg Ser Pro Pro Pro Leu Ser Leu
            100                 105                 110

Ile Tyr Gln Thr Lys Gln Val Glu Gln Thr Lys Met Ser Leu Glu
        115                 120                 125


<210> SEQ ID NO 46
<211> LENGTH: 2979
<212> TYPE: DNA
<213> ORGANISM: Helianthus annuus

<400> SEQUENCE: 46

atgaataaca tcaatcttgt aatagtttcg cttgtaatcg cgattgtagc catccaaccc      60

cttgcgcaag agcaaaccga tgtaggtgag gcaaatttcg tcactgttct tagcatcgat     120

ggtgggggtg ttcgtggcat tgttcccgcc accttgcttg cttttcttga atccaaaatt     180

caggtactcg aacttaaaat gcacatgtgc atcatattac aagctgtaac ttattattga     240

aatgtgccgt ctcttcggat aggaaataga tgggccagat gcacgaattg cggattattt     300

tgatgtaata gccggaacaa gcacaggagg gctgatgaca actatgcttg cagctcctaa     360

tgagaaaaat cgtcccatgt tcgccgcaaa agacattacc aacttctact ttcaacattc     420

gcctaggatc ttccctaaaa tagggtaaac tctaactagt ttccggatct ataagatcat     480

cattaaatac aagtttcatt ttctttttcg aatcaaatac agacacacat ttgatgaggc     540

gcaaccttat ccttctcaaa acgaagcctg cgaaatgggg tattctccta caaagacttt     600

tgtaattcat gttctagtgg gtgtttggat gtgcgtttta aaactgatta ttatttacat     660

gtagtttctg aagaaaataa aacagttatt caaacacttt ttgttaataa ttctactaga     720

aaaaaaaaat ccttgtcagg aaattaatta aaaaaaagtt accatctatt aaagttcttt     780
```

```
cttactaatc aaaagttttt aaattttatt atcatgttat tataactaaa catacacatc    840
caaacactat ctcataccac atgattacac aagtctatta tttgaatatg ctaacttagt    900
attttcatat aataagtttt taaaacgcca catccaaaac ccttgattct tattttacat    960
tgtgtagcta aaacagtgtt tatacataaa aacaatcagt tatataaatc aaagcattat   1020
ttaactaaag taagctcggt tcaaactcga taagagaatt aatatatacg agtcgagttc   1080
ctgttgacca gatttcgcta gtgttaagtt tcgagttcaa aattgtatat gaacttgaac   1140
ctgtgtatca tcatacttga catttaaacc ataatgttgt tgaataaata aagtgatttt   1200
attttgtagt cggaccaaat tcatgaattc ggtagtaacc gtacttggtg aggccaccgg   1260
accaaagtat gatggtaaat atcttcgagc catggcaaag atgatgttaa aaaacctcac   1320
tattaaagat acgttgacga atgttgtcat acctgctttc gacattaggc ggcttcaacc   1380
tgttatcttc tcctctgctc aagtaattaa actcgttttt tatatttata gcagttctct   1440
atttaaaatt gattgtgtat cataaaatgg tttctgtttg atacgtttag ggaaaagagg   1500
tcgcgtggaa aaatgctttg ctagcagacg tatgcattag taccgcggcg gcaccaacat   1560
ttttcccgcc atactatttt gagactagag acgtcgatgg aaccaagcac acttttgatc   1620
taatcgatgg cggggtagct gcaaacaatc cggtagttac atttcaacaa tattgagttt   1680
gcattttatt tttaggacaa gtagtcacat tagggtgaag ggtgtgttca agctcatccc   1740
gaaggtggga gcggtgttcc cactcgtacc tcatggcgca ttttcttctt tgttgcagct   1800
ccaattttaa aaagccaccc cgccttttcc attccatagc gccacgtcaa ctgggaaatg   1860
gtgttcccac tggtattgga gatttggagg cgctacgcca cctctgtcat cccgaagcca   1920
caccctccac ccttaggagt gttatcggtt cagttttcgg tttatacagt ttaaaggttt   1980
ttttttggtt gaaaccaaaa accgaactga actgaacgga attcgggtag ttcacaactg   2040
aaccaaaaac tgaatccata ttcggttttc tgtttgaccg aataatcatt atttgttatt   2100
tgattgtgcg aggttaaata agattgagca aaaattgtaa ttaattggat ttggctaaat   2160
gacaatttaa ataaccgtta tttgttatcc gattcaaacc gaacacccaa ctcgatttgg   2220
tttaataccg aaccgacaac cggatacgta attcagttcg ctattaaaag gttcgggttt   2280
ggtagggttt aacccatttg aaatcgaatc ttcagagaaa gggttcgcta atgtcaccca   2340
cataaccaaa gaaatcttgt ttaaatgtta atggcagaca catttggcta tcacacatat   2400
aaccaaagaa gcggtgatgg ggaaatacag gttctctggc ccggaggttt tcgacggaag   2460
acggatgctt gtgctttcac tcggcactgg tacgcagacg tacaatgact tatatactgc   2520
acaaaaggct gcaaaatggg ggttgcttag ttggatcttt accaatggta ctgcgccaat   2580
cctccgcatt tttggtgatg ccatgtcaga tatggtcgac atccatgtgt caactatatt   2640
ccaatcgttg caagtcgaaa aaaactatct gcgtattcag gtataactaa gaacatataa   2700
atataatgtt gtataggtta catgtttagt aacaaggagt ttttttatgg gcaggaagat   2760
aacttgaaag gggaagcaac tgcaatggat atttcatcac ctgagaacat gagggcgcta   2820
gaggacattg gcaagaaatt gttgaagaaa ccgttgtcga gattggatgt ggagacaggc   2880
aagcttgaac cagttaaagg agaaggtacg aatgctgatg cattagcacg tttcgccact   2940
ttgctttgtg ccgaacgaaa gcgccgcaat ccagcttaa                           2979
```

<210> SEQ ID NO 47
<211> LENGTH: 1302
<212> TYPE: DNA
<213> ORGANISM: Artificial Sequence
<220> FEATURE:
<223> OTHER INFORMATION: cDNA

<400> SEQUENCE: 47

```
atgaataaca tcaatcttgt aatagtttcg cttgtaatcg cgattgtagc catccaaccc     60

cttgcgcaag agcaaaccga tgtaggtgag gcaaatttcg tcactgttct tagcatcgat    120

ggtgggggtg ttcgtggcat tgttcccgcc accttgcttg cttttcttga atccaaaatt    180

caggaaatag atgggccaga tgcacgaatt gcggattatt ttgatgtaat agccggaaca    240

agcacaggag ggctgatgac aactatgctt gcagctccta atgagaaaaa tcgtcccatg    300

ttcgccgcaa aagacattac caacttctac tttcaacatt cgcctaggat cttccctaaa    360

ataggacaca catttgatga ggcgcaacct tatccttctc aaaacgaagc ctgcgaaatg    420

ggtcggacca aattcatgaa ttcggtagta accgtacttg gtgaggccac cggaccaaag    480

tatgatggta aatatcttcg agccatggca aagatgatgt taaaaaacct cactattaaa    540

gatacgttga cgaatattgt catacctgct ttcgacatca ggcggcttca acctgttatc    600

ttctcctctg ctcaaggaaa agaggtcgcg tggaaaaatg ctttgctagc agacgtatgc    660

attagtaccg cggcggcacc aacgtttttc ccgccatact attttgagac tagagatgtc    720

gatggaacca agcacacttt tgatctaatc gatggcgggg tagctgcaaa caatccgaca    780

catttggcta tcacacatat aaccaaagaa gcggtgatgg ggaaatacag gttctctggc    840

ccggaggttt tcgacggcag acggatgctt gtgctttcac tcggcactgg tacgcagacg    900

tacaatgact tatacactgc acaaaaggct gcaaaatggg ggttgcttag ttggatcttt    960

accaatggta ctgcgccaat cctccgcatt tttggtgatg ccatgtcaga tatggtcgac   1020

atccatgtgt caactatatt ccaatcgttg caagtcgaaa aaaactatct gcgtattcag   1080

gaagataact tgaaagggga agcaactgca atggatattt catcacccga gaacatgagg   1140

gcgctagagg acattggcaa gaaattgttg aagaaaccgt tgtcgagatt ggatgtggag   1200

acaggcaagc ttgaaccagt taaaggagaa ggtacgaatg ctgatgcatt agcacgtttc   1260

gccactttgc tttgtgccga acgaaagcgc cgcaatccag ct                      1302
```

<210> SEQ ID NO 48
<211> LENGTH: 433
<212> TYPE: PRT
<213> ORGANISM: Helianthus annuus

<400> SEQUENCE: 48

```
Met Asn Asn Ile Asn Leu Val Ile Val Ser Leu Val Ile Ala Ile Val
1               5                   10                  15

Ala Ile Gln Pro Leu Ala Gln Glu Gln Thr Asp Val Gly Glu Ala Asn
            20                  25                  30

Phe Val Thr Val Leu Ser Ile Asp Gly Gly Gly Val Arg Gly Ile Val
        35                  40                  45

Pro Ala Thr Leu Leu Ala Phe Leu Glu Ser Lys Ile Gln Glu Ile Asp
    50                  55                  60

Gly Pro Asp Ala Arg Ile Ala Asp Tyr Phe Asp Val Ile Ala Gly Thr
65                  70                  75                  80

Ser Thr Gly Gly Leu Met Thr Thr Met Leu Ala Ala Pro Asn Glu Lys
                85                  90                  95

Asn Arg Pro Met Phe Ala Ala Lys Asp Ile Thr Asn Phe Tyr Phe Gln
            100                 105                 110

His Ser Pro Arg Ile Phe Pro Lys Ile Gly His Thr Phe Asp Glu Ala
```

```
        115                 120                 125

Gln Pro Tyr Pro Ser Gln Asn Glu Ala Cys Glu Met Gly Arg Thr Lys
    130                 135                 140

Phe Met Asn Ser Val Val Thr Val Leu Gly Glu Ala Thr Gly Pro Lys
145                 150                 155                 160

Tyr Asp Gly Lys Tyr Leu Arg Ala Met Ala Lys Met Met Leu Lys Asn
                165                 170                 175

Leu Thr Ile Lys Asp Thr Leu Thr Asn Ile Val Ile Pro Ala Phe Asp
            180                 185                 190

Ile Arg Arg Leu Gln Pro Val Ile Phe Ser Ser Ala Gln Gly Lys Glu
        195                 200                 205

Val Ala Trp Lys Asn Ala Leu Leu Ala Asp Val Cys Ile Ser Thr Ala
    210                 215                 220

Ala Ala Pro Thr Phe Phe Pro Pro Tyr Tyr Phe Glu Thr Arg Asp Val
225                 230                 235                 240

Asp Gly Thr Lys His Thr Phe Asp Leu Ile Asp Gly Gly Val Ala Ala
                245                 250                 255

Asn Asn Pro Thr His Leu Ala Ile Thr His Ile Thr Lys Glu Ala Val
            260                 265                 270

Met Gly Lys Tyr Arg Phe Ser Gly Pro Glu Val Phe Asp Gly Arg Arg
        275                 280                 285

Met Leu Val Leu Ser Leu Gly Thr Gly Thr Gln Thr Tyr Asn Asp Leu
    290                 295                 300

Tyr Thr Ala Gln Lys Ala Ala Lys Trp Gly Leu Leu Ser Trp Ile Phe
305                 310                 315                 320

Thr Asn Gly Thr Ala Pro Ile Leu Arg Ile Phe Gly Asp Ala Met Ser
                325                 330                 335

Asp Met Val Asp Ile His Val Ser Thr Ile Phe Gln Ser Leu Gln Val
            340                 345                 350

Glu Lys Asn Tyr Leu Arg Ile Gln Glu Asp Asn Leu Lys Gly Glu Ala
        355                 360                 365

Thr Ala Met Asp Ile Ser Ser Pro Glu Asn Met Arg Ala Leu Glu Asp
    370                 375                 380

Ile Gly Lys Lys Leu Leu Lys Lys Pro Leu Ser Arg Leu Asp Val Glu
385                 390                 395                 400

Thr Gly Lys Leu Glu Pro Val Lys Gly Glu Gly Thr Asn Ala Asp Ala
                405                 410                 415

Leu Ala Arg Phe Ala Thr Leu Leu Cys Ala Glu Arg Lys Arg Arg Asn
            420                 425                 430

Pro
```

<210> SEQ ID NO 49
<211> LENGTH: 1795
<212> TYPE: DNA
<213> ORGANISM: Artificial Sequence
<220> FEATURE:
<223> OTHER INFORMATION: TILLING mutant D74N

<400> SEQUENCE: 49

```
agttcatcac taatcacact tattgtgccc tcgacgagta tctatagcta gctcattaat      60

cgattcgggg gtgtgttgtc gaaggcggca atggcgagct actcgtcgcg gcgtccatgc     120

aatacctgta gcacgaaggc gatggccggg agcgtggtcg gcgagcccgt cgtgctgggg     180

cagagggtga cggtgctgac ggtggacggc ggcggcgtcc ggggtctcat cccgggaacc     240
```

```
atcctcgcct tcctggaggc caggctgcag gagctggacg gaccggaggc gaggctggcg    300
gactacttca actacatcgc cggaaccagc accggcggtc tcatcaccgc catgctcacc    360
gcgcccggca aggacaagcg gcctctctac gctgccaagg acatcaacca cttttacatg    420
cagaactgcc cgcgcatctt tcctcagaag tgagtccgat gctgccgcca ttgttcttgc    480
atccatccag catcgtacgt acgtcctcta tacatctgcg gatcatcatg tgcgcatgtt    540
tgtggcatgc atgcatgcat gtgagcagga gcaggcttgc ggccgccatg tccgcgctga    600
ggaagccaaa gtacaacggc aagtgcatgc gcagcctgat taggagcatc ctcggcgaga    660
cgagggtaag cgagacgctg accaacgtca tcatccctgc cttcgacatc aggctgctgc    720
agcctatcat cttctctacc tacgacgtac gtacgtcgtc acgaatgatt catctgtacg    780
tcgtcgcatg cgaatggctg cctacgtacg ccgtgcgcta acatactcag ctctttccta    840
tctgctgcgc caatttgcag gccaagagca cgcctctgaa gaacgctctg ctctcggacg    900
tgtgcattgg cacgtccgcc gcgccgacct acctcccggc gcactacttc cagactgaag    960
acgccaacgg caaggagcgc gaatacaacc tcatcgacgg cggtgtggcg gccaacaacc   1020
cggtaactga ctagctaact ggaaaacgga cgcacagact ccatgtccat ggcggcccac   1080
aaggtcgatg ctaattgttg cttatgtatg tcgcccgatt gcacatgcgt agacgatggt   1140
tgcgatgacg cagatcacca aaaagatgct tgccagcaag gacaaggccg aggagctgta   1200
cccagtgaag ccgtcgaact gccgcaggtt cctggtgctg tccatcggga cggggtcgac   1260
gtccgagcag ggcctctaca cggcgcggca gtgctcccgg tggggtatct gccggtggct   1320
ccgcaacaac ggcatggccc ccatcatcga catcttcatg gcggccagct cggacctggt   1380
ggacatccac gtcgccgcga tgttccagtc gctccacagc gacggcgact acctgcgcat   1440
ccaggacaac tcgctccgtg gcgccgcggc caccgtggac gcggcgacgc cggagaacat   1500
gcggacgctc gtcgggatcg gggagcggat gctggcacag agggtgtcca gggtcaacgt   1560
ggagacaggg aggtacgaac cggtgactgg cgaaggaagc aatgccgatg ccctcggtgg   1620
gctcgctagg cagctctccg aggagaggag aacaaggctc gcgcgccgcg tctctgccat   1680
caacccaaga ggctctagat gtgcgtcgta cgatatctaa gacaagtggc tttactgtca   1740
gtcacatgct tgtaaataag tagactttat tttaataaaa cataaaaata tatat        1795
```

```
<210> SEQ ID NO 50
<211> LENGTH: 1284
<212> TYPE: DNA
<213> ORGANISM: Artificial Sequence
<220> FEATURE:
<223> OTHER INFORMATION: TILLING mutant D74N

<400> SEQUENCE: 50

atggcgagct actcgtcgcg gcgtccatgc aatacctgta gcacgaaggc gatggccggg     60
agcgtggtcg gcgagcccgt cgtgctgggg cagagggtga cggtgctgac ggtggacggc    120
ggcggcgtcc ggggtctcat cccgggaacc atcctcgcct tcctggaggc caggctgcag    180
gagctggacg gaccggaggc gaggctggcg gactacttca actacatcgc cggaaccagc    240
accggcggtc tcatcaccgc catgctcacc gcgcccggca aggacaagcg gcctctctac    300
gctgccaagg acatcaacca cttttacatg cagaactgcc cgcgcatctt tcctcagaag    360
agcaggcttg cggccgccat gtccgcgctg aggaagccaa agtacaacgg caagtgcatg    420
cgcagcctga ttaggagcat cctcggcgag acgagggtaa gcgagacgct gaccaacgtc    480
atcatccctg ccttcgacat caggctgctg cagcctatca tcttctctac ctacgacgcc    540
```

```
aagagcacgc ctctgaagaa cgctctgctc tcggacgtgt gcattggcac gtccgccgcg    600

ccgacctacc tcccggcgca ctacttccag actgaagacg ccaacggcaa ggagcgcgaa    660

tacaacctca tcgacggcgg tgtggcggcc aacaacccga cgatggttgc gatgacgcag    720

atcaccaaaa agatgcttgc cagcaaggac aaggccgagg agctgtaccc agtgaagccg    780

tcgaactgcc gcaggttcct ggtgctgtcc atcgggacgg ggtcgacgtc cgagcagggc    840

ctctacacgg cgcggcagtg ctcccggtgg ggtatctgcc ggtggctccg caacaacggc    900

atggccccca tcatcgacat cttcatggcg gccagctcgg acctggtgga catccacgtc    960

gccgcgatgt tccagtcgct ccacagcgac ggcgactacc tgcgcatcca ggacaactcg   1020

ctccgtggcg ccgcggccac cgtggacgcg gcgacgccgg agaacatgcg gacgctcgtc   1080

gggatcgggg agcggatgct ggcacagagg gtgtccaggg tcaacgtgga gacagggagg   1140

tacgaaccgg tgactggcga aggaagcaat gccgatgccc tcggtgggct cgctaggcag   1200

ctctccgagg agaggagaac aaggctcgcg cgccgcgtct ctgccatcaa cccaagaggc   1260

tctagatgtg cgtcgtacga tatc                                          1284
```

```
<210> SEQ ID NO 51
<211> LENGTH: 428
<212> TYPE: PRT
<213> ORGANISM: Artificial Sequence
<220> FEATURE:
<223> OTHER INFORMATION: TILLING mutant D74N

<400> SEQUENCE: 51

Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Gly Val Arg Gly Leu Ile Pro
        35                  40                  45

Gly Thr Ile Leu Ala Phe Leu Glu Ala Arg Leu Gln Glu Leu Asp Gly
    50                  55                  60

Pro Glu Ala Arg Leu Ala Asp Tyr Phe Asn Tyr Ile Ala Gly Thr Ser
65                  70                  75                  80

Thr Gly Gly Leu Ile Thr Ala Met Leu Thr Ala Pro Gly Lys Asp Lys
                85                  90                  95

Arg Pro Leu Tyr Ala Ala Lys Asp Ile Asn His Phe Tyr Met Gln Asn
            100                 105                 110

Cys Pro Arg Ile Phe Pro Gln Lys Ser Arg Leu Ala Ala Ala Met Ser
        115                 120                 125

Ala Leu Arg Lys Pro Lys Tyr Asn Gly Lys Cys Met Arg Ser Leu Ile
    130                 135                 140

Arg Ser Ile Leu Gly Glu Thr Arg Val Ser Glu Thr Leu Thr Asn Val
145                 150                 155                 160

Ile Ile Pro Ala Phe Asp Ile Arg Leu Leu Gln Pro Ile Ile Phe Ser
                165                 170                 175

Thr Tyr Asp Ala Lys Ser Thr Pro Leu Lys Asn Ala Leu Leu Ser Asp
            180                 185                 190

Val Cys Ile Gly Thr Ser Ala Ala Pro Thr Tyr Leu Pro Ala His Tyr
        195                 200                 205

Phe Gln Thr Glu Asp Ala Asn Gly Lys Glu Arg Glu Tyr Asn Leu Ile
    210                 215                 220
```

```
Asp Gly Gly Val Ala Ala Asn Asn Pro Thr Met Val Ala Met Thr Gln
225                 230                 235                 240

Ile Thr Lys Lys Met Leu Ala Ser Lys Asp Lys Ala Glu Glu Leu Tyr
                245                 250                 255

Pro Val Lys Pro Ser Asn Cys Arg Arg Phe Leu Val Leu Ser Ile Gly
            260                 265                 270

Thr Gly Ser Thr Ser Glu Gln Gly Leu Tyr Thr Ala Arg Gln Cys Ser
        275                 280                 285

Arg Trp Gly Ile Cys Arg Trp Leu Arg Asn Asn Gly Met Ala Pro Ile
    290                 295                 300

Ile Asp Ile Phe Met Ala Ala Ser Ser Asp Leu Val Asp Ile His Val
305                 310                 315                 320

Ala Ala Met Phe Gln Ser Leu His Ser Asp Gly Asp Tyr Leu Arg Ile
                325                 330                 335

Gln Asp Asn Ser Leu Arg Gly Ala Ala Ala Thr Val Asp Ala Ala Thr
            340                 345                 350

Pro Glu Asn Met Arg Thr Leu Val Gly Ile Gly Glu Arg Met Leu Ala
        355                 360                 365

Gln Arg Val Ser Arg Val Asn Val Glu Thr Gly Arg Tyr Glu Pro Val
    370                 375                 380

Thr Gly Glu Gly Ser Asn Ala Asp Ala Leu Gly Gly Leu Ala Arg Gln
385                 390                 395                 400

Leu Ser Glu Glu Arg Arg Thr Arg Leu Ala Arg Arg Val Ser Ala Ile
                405                 410                 415

Asn Pro Arg Gly Ser Arg Cys Ala Ser Tyr Asp Ile
            420                 425
```

```
<210> SEQ ID NO 52
<211> LENGTH: 1795
<212> TYPE: DNA
<213> ORGANISM: Artificial Sequence
<220> FEATURE:
<223> OTHER INFORMATION: TILLING mutant G78R

<400> SEQUENCE: 52

agttcatcac taatcacact tattgtgccc tcgacgagta tctatagcta gctcattaat     60

cgattcgggg gtgtgttgtc gaaggcggca atggcgagct actcgtcgcg gcgtccatgc    120

aatacctgta gcacgaaggc gatggccggg agcgtggtcg gcgagcccgt cgtgctgggg    180

cagagggtga cggtgctgac ggtggacggc ggcggcgtcc ggggtctcat cccgggaacc    240

atcctcgcct tcctggaggc caggctgcag gagctggacg gaccggaggc gaggctggcg    300

gactacttcg actacatcgc cagaaccagc accggcggtc tcatcaccgc catgctcacc    360

gcgcccggca aggacaagcg gcctctctac gctgccaagg acatcaacca cttttacatg    420

cagaactgcc cgcgcatctt tcctcagaag tgagtccgat gctgccgcca ttgttcttgc    480

atccatccag catcgtacgt acgtcctcta tacatctgcg gatcatcatg tgcgcatgtt    540

tgtggcatgc atgcatgcat gtgagcagga gcaggcttgc ggccgccatg tccgcgctga    600

ggaagccaaa gtacaacggc aagtgcatgc gcagcctgat taggagcatc ctcggcgaga    660

cgagggtaag cgagacgctg accaacgtca tcatccctgc cttcgacatc aggctgctgc    720

agcctatcat cttctctacc tacgacgtac gtacgtcgtc acgaatgatt catctgtacg    780

tcgtcgcatg cgaatggctg cctacgtacg ccgtgcgcta acatactcag ctctttccta    840

tctgctgcgc caatttgcag gccaagagca cgcctctgaa gaacgctctg ctctcggacg    900
```

```
tgtgcattgg cacgtccgcc gcgccgacct acctcccggc gcactacttc cagactgaag    960

acgccaacgg caaggagcgc gaatacaacc tcatcgacgg cggtgtggcg gccaacaacc   1020

cggtaactga ctagctaact ggaaaacgga cgcacagact ccatgtccat ggcggcccac   1080

aaggtcgatg ctaattgttg cttatgtatg tcgcccgatt gcacatgcgt agacgatggt   1140

tgcgatgacg cagatcacca aaaagatgct tgccagcaag gacaaggccg aggagctgta   1200

cccagtgaag ccgtcgaact gccgcaggtt cctggtgctg tccatcggga cggggtcgac   1260

gtccgagcag ggcctctaca cggcgcggca gtgctcccgg tggggtatct gccggtggct   1320

ccgcaacaac ggcatggccc ccatcatcga catcttcatg gcggccagct cggacctggt   1380

ggacatccac gtcgccgcga tgttccagtc gctccacagc gacggcgact acctgcgcat   1440

ccaggacaac tcgctccgtg gcgccgcggc caccgtggac gcggcgacgc cggagaacat   1500

gcggacgctc gtcgggatcg gggagcggat gctggcacag agggtgtcca gggtcaacgt   1560

ggagacaggg aggtacgaac cggtgactgg cgaaggaagc aatgccgatg ccctcggtgg   1620

gctcgctagg cagctctccg aggagaggag aacaaggctc gcgcgccgcg tctctgccat   1680

caacccaaga ggctctagat gtgcgtcgta cgatatctaa gacaagtggc tttactgtca   1740

gtcacatgct tgtaaataag tagactttat tttaataaaa cataaaaata tatat        1795
```

```
<210> SEQ ID NO 53
<211> LENGTH: 1284
<212> TYPE: DNA
<213> ORGANISM: Artificial Sequence
<220> FEATURE:
<223> OTHER INFORMATION: TILLING mutant G78R

<400> SEQUENCE: 53
```

```
atggcgagct actcgtcgcg gcgtccatgc aatacctgta gcacgaaggc gatggccggg     60

agcgtggtcg gcgagcccgt cgtgctgggg cagagggtga cggtgctgac ggtggacggc    120

ggcggcgtcc ggggtctcat cccgggaacc atcctcgcct tcctggaggc caggctgcag    180

gagctggacg gaccggaggc gaggctggcg gactacttcg actacatcgc cagaaccagc    240

accggcggtc tcatcaccgc catgctcacc gcgcccggca aggacaagcg gcctctctac    300

gctgccaagg acatcaacca cttttacatg cagaactgcc cgcgcatctt tcctcagaag    360

agcaggcttg cggccgccat gtccgcgctg aggaagccaa agtacaacgg caagtgcatg    420

cgcagcctga ttaggagcat cctcggcgag acgagggtaa gcgagacgct gaccaacgtc    480

atcatccctg ccttcgacat caggctgctg cagcctatca tcttctctac ctacgacgcc    540

aagagcacgc ctctgaagaa cgctctgctc tcggacgtgt gcattggcac gtccgccgcg    600

ccgacctacc tcccggcgca ctacttccag actgaagacg ccaacggcaa ggagcgcgaa    660

tacaacctca tcgacggcgg tgtggcggcc aacaacccga cgatggttgc gatgacgcag    720

atcaccaaaa agatgcttgc cagcaaggac aaggccgagg agctgtaccc agtgaagccg    780

tcgaactgcc gcaggttcct ggtgctgtcc atcgggacgg ggtcgacgtc cgagcagggc    840

ctctacacgg cgcggcagtg ctcccggtgg ggtatctgcc ggtggctccg caacaacggc    900

atggccccca tcatcgacat cttcatggcg gccagctcgg acctggtgga catccacgtc    960

gccgcgatgt tccagtcgct ccacagcgac ggcgactacc tgcgcatcca ggacaactcg   1020

ctccgtggcg ccgcggccac cgtggacgcg gcgacgccgg agaacatgcg gacgctcgtc   1080

gggatcgggg agcggatgct ggcacagagg gtgtccaggg tcaacgtgga gacagggagg   1140

tacgaaccgg tgactggcga aggaagcaat gccgatgccc tcggtgggct cgctaggcag   1200
```

```
ctctccgagg agaggagaac aaggctcgcg cgccgcgtct ctgccatcaa cccaagaggc   1260

tctagatgtg cgtcgtacga tatc                                          1284


<210> SEQ ID NO 54
<211> LENGTH: 428
<212> TYPE: PRT
<213> ORGANISM: Artificial Sequence
<220> FEATURE:
<223> OTHER INFORMATION: TILLING mutant G78R

<400> SEQUENCE: 54

Met Ala Ser Tyr Ser Ser Arg Arg Pro Cys Asn Thr Cys Ser Thr Lys
1               5                   10                  15

Ala Met Ala Gly Ser Val Val Gly Glu Pro Val Val Leu Gly Gln Arg
            20                  25                  30

Val Thr Val Leu Thr Val Asp Gly Gly Gly Val Arg Gly Leu Ile Pro
        35                  40                  45

Gly Thr Ile Leu Ala Phe Leu Glu Ala Arg Leu Gln Glu Leu Asp Gly
    50                  55                  60

Pro Glu Ala Arg Leu Ala Asp Tyr Phe Asp Tyr Ile Ala Arg Thr Ser
65                  70                  75                  80

Thr Gly Gly Leu Ile Thr Ala Met Leu Thr Ala Pro Gly Lys Asp Lys
                85                  90                  95

Arg Pro Leu Tyr Ala Ala Lys Asp Ile Asn His Phe Tyr Met Gln Asn
            100                 105                 110

Cys Pro Arg Ile Phe Pro Gln Lys Ser Arg Leu Ala Ala Ala Met Ser
        115                 120                 125

Ala Leu Arg Lys Pro Lys Tyr Asn Gly Lys Cys Met Arg Ser Leu Ile
    130                 135                 140

Arg Ser Ile Leu Gly Glu Thr Arg Val Ser Glu Thr Leu Thr Asn Val
145                 150                 155                 160

Ile Ile Pro Ala Phe Asp Ile Arg Leu Leu Gln Pro Ile Ile Phe Ser
                165                 170                 175

Thr Tyr Asp Ala Lys Ser Thr Pro Leu Lys Asn Ala Leu Leu Ser Asp
            180                 185                 190

Val Cys Ile Gly Thr Ser Ala Ala Pro Thr Tyr Leu Pro Ala His Tyr
        195                 200                 205

Phe Gln Thr Glu Asp Ala Asn Gly Lys Glu Arg Glu Tyr Asn Leu Ile
    210                 215                 220

Asp Gly Gly Val Ala Ala Asn Asn Pro Thr Met Val Ala Met Thr Gln
225                 230                 235                 240

Ile Thr Lys Lys Met Leu Ala Ser Lys Asp Lys Ala Glu Glu Leu Tyr
                245                 250                 255

Pro Val Lys Pro Ser Asn Cys Arg Arg Phe Leu Val Leu Ser Ile Gly
            260                 265                 270

Thr Gly Ser Thr Ser Glu Gln Gly Leu Tyr Thr Ala Arg Gln Cys Ser
        275                 280                 285

Arg Trp Gly Ile Cys Arg Trp Leu Arg Asn Asn Gly Met Ala Pro Ile
    290                 295                 300

Ile Asp Ile Phe Met Ala Ala Ser Ser Asp Leu Val Asp Ile His Val
305                 310                 315                 320

Ala Ala Met Phe Gln Ser Leu His Ser Asp Gly Asp Tyr Leu Arg Ile
                325                 330                 335

Gln Asp Asn Ser Leu Arg Gly Ala Ala Ala Thr Val Asp Ala Ala Thr
```

```
            340                 345                 350

Pro Glu Asn Met Arg Thr Leu Val Gly Ile Gly Glu Arg Met Leu Ala
        355                 360                 365

Gln Arg Val Ser Arg Val Asn Val Glu Thr Gly Arg Tyr Glu Pro Val
    370                 375                 380

Thr Gly Glu Gly Ser Asn Ala Asp Ala Leu Gly Gly Leu Ala Arg Gln
385                 390                 395                 400

Leu Ser Glu Glu Arg Arg Thr Arg Leu Ala Arg Arg Val Ser Ala Ile
                405                 410                 415

Asn Pro Arg Gly Ser Arg Cys Ala Ser Tyr Asp Ile
            420                 425


<210> SEQ ID NO 55
<211> LENGTH: 13516
<212> TYPE: DNA
<213> ORGANISM: Zea mays

<400> SEQUENCE: 55

tcttgctata tatgagatga caaaattttc caaagaagag agaagccggc agaacccatc     60

ctgtttcaaa tctcttctac tacttaagtt tctaacgtag gcgtcgacaa aacggattgg    120

tgcacggttc tgccgatgtc tcccacacac gcgcatggaa ggaggcaggc acccttcccc    180

gccgccccgg atctcgcgcc agccccagcc ctaccccgcc tgcccttcca ttcttcccca    240

gccgcccccc ggtcaacgtc acgaacccgg gcctcgtgcc gttcgccgtg gccacgcggt    300

tcgacgagcg ggtcacggag ctgctgagcg cgctcgctga cgcggcggcg gggcgaccag    360

gcaggtgggc catcggcgaa gcgccatggt cgtcgtcggg gggcaggaac caggcggtgt    420

acgcgcgccg cgcgcccggc tcttcatcgc ctccacccgc tccagcgtct ccaccacctc    480

cttcatcgag ggccgactgc gaggctcgcc ggccaggcag ccgagcgtca gttgcgccgc    540

ttggaacgcc tgcttttgtt gatcgtttgt tttggtctga tttcggtggg tctatccgca    600

gagaggaaga agcagaagct ctccgagatc caatccggcg ttgaggaagc tgaatcgctg    660

gtaaatagat gccgcgacac gttctggttt ggggatcccc ttggctaaca ggacatacga    720

catttgggga atgggtagaa aagcagagat tagggatttt tcgtttccgt cggtgcagtt    780

ttggtgttcc aacggagttg cgagatgttt atgtgcctta gtcttcaatt tgggggttgg    840

gggaaaagta attttatgtt tttgttttgt gtctgcagat tcagaaaatg gacctggagg    900

caaggagcct acagcctagc attaaggcta gtttgcttgc aaagctgagg gagtataaat    960

ctgacctcaa caacgtcaag agtgagctca agaggatatc tgcgcccaat gccaggcagg   1020

ctacccggga ggagctcctg gagtctggaa tggctgatac tctcgcagtg agctaatgat   1080

aggacttgac tgtgtctacg agactgctcc taacaataaa ctgaagaaag caaaagaaat   1140

cattcaacgt attcgccgaa gagaactcta caaggtagta tgatgcttta attgctcata   1200

tacaagtgtc attttgtcat gtcattacac atggttagga tacataggag attctgtttt   1260

ttaacacata gttgtcccat gtccatgaat tcatttgaat taatttactc ttcgcaatct   1320

tatacattaa aatcgtgtta cctattacat cacaacttca tgagagcatg cttgttctgt   1380

gtagatatgg tagtcctggg aggaagagcc atcgccgcta tgtatggcag aaccacccgc   1440

gaaagcaacc tctctggtct cgcatagcca gagcaggagc agctcgcttg cgcggccgca   1500

gcgctggcgg tcggccccgc gtacgagcgc ctgcaggtag gccagcttct gctgcaatgc   1560

ccgaatctcg gcgtccacgc gcagcagcgt cgtcgcctcc tcctccgtca gctcacccag   1620
```

-continued

```
cttggccagc acccccgtca cccccgcgtc cgccatggct gtcgccggga ccgaaaggct   1680
aaaactgtca caatgacgta aagtttggtt ggtgttggcg gctcacgcaa aaccagacct   1740
ttccaagttt tactttagca gagttttttt ggaacgagag caaagcagca cagtttcaag   1800
aatgtggggc aatttgaatg ttcgttcctg ctgcactgct actgctttta gaattgtagt   1860
atgcttcatc atttatttat ttctaaaaaa acttgcatga attctatcgt gacttttatt   1920
gagaaaataa tgtattcacg tatcttcatg tttctgataa aggtatttgt atatgcatcg   1980
gtgctacata tgcgaataca agttttgttt caactctgaa gtctcaagtt gaattctaaa   2040
ctccagtttg ttttctactg tgctgctgca ggaagccagg aacccatccg aacaaggttg   2100
caatcatgat aagcagatag agcaagcata tgatgatatt ttgaattcgt cgaagcatac   2160
tttggccagc atgatggagc tgcaggaggt tcagttattt gcacacattg tttttctttc   2220
actcctatga ttttcctcaa tatgatcaaa atgtttcttt tgcaaataat gattgaaatg   2280
tttctcattg tactcaacct cttaaactac ctataggctt tgcttgagag taatcaggct   2340
acaaaggatg ccaatggtat tgctgctctc tatattgttc ttgttctaat gtaaaaacta   2400
caacacaact ctttacttga tcccagaaat tccttctgcc tcaaatggag acaatgacga   2460
gtggtcagaa gtacagagat tgcagacaag gtaaattttg caatagaaat aactaaccaa   2520
ccattagtgc ttgaaaaaaa ctggactggt gactggggca cgtggtttca tcaacatttg   2580
gacctcaacg gtctaatcag tataacttag aagttggcta gctcttgaaa aacactgcat   2640
gacactaagc atttgtttat tttcagctgc ttgcacccct atgatttcaa gtaactactt   2700
gtctacttgt gataatcacc tgaatatgag tatttgaaat gcttatcacg tctcggcaat   2760
tgcatttctt ttatgcgtaa ctgaagtctg ctctagcttc ctaatagagt tcattttttta   2820
atacagaaac cactttgaga tagccacaat atagtaaaag tggcagctaa ggtactaaaa   2880
acacccatgc aaataagaaa aaaaatgaat cttgtatttt aattttgtta aatacctcta   2940
tagtttggcg atatattatg ttaccatcct gcttgtagcc tgtaggtcat tttatatgag   3000
ccatcaaatt gcgatgacag ttgccacaaa tccagtttca tatgaaggta ttagctgtgt   3060
aacaagctaa ctgctgctct ctgcccaata agttattcaa ttggattagt aggttgcatc   3120
caaggttatt caattggatc agtaggttgc atccaaggta tactgctgct ctctgcccaa   3180
taagttattc aattcgatca gtaggttgcc tgttcccttc attttattaa aaaatacata   3240
ataatataat aagtacctgt ttgttctaaa aataatactt ctgtaaatga ggttattaat   3300
tttccttttg gtaataatgc aggttgatga tactgaagtc atcagttttt tgttgcaaac   3360
tgaaataatt tctctgtgct tgcgaaccat ggagatgggt agtgagctat ccaaaactgt   3420
atgtagctag ccatatattc tcattcaaat atcataattt atctcttctg cttaatactg   3480
gcaaaggtgt aatagttttt ttagtattga tttgtcacct gaagtttatc ttgtgcacta   3540
ctactttgcc atcatcagtt atctctagaa tactcttatc ctgtaccatc ttctctctga   3600
taagcctaaa tttgtacaat tcataagcct aaaaggtgac ttatataata tatacaagga   3660
ccctcaagag ttgtttggca attcagtgac tgtcctgggt cctgttttgg ggagcttctg   3720
gtagcttttg cttctccaaa agaaaagcta gaagctcccc ccaaacagag cagcttcttc   3780
aagccggtaa aagcttcaaa agctataatt atactaaaaa cagtgaagct ccctcagagc   3840
agcttcccag ctctccagga gatgcttttg gagaagctac agtttcccca aacagggccc   3900
tgctctgttg aaccccccctt cctgatacat atttgaatat gagtttatag tgtgtgtggg   3960
ggggtgtaag tagggggggta atgggttcta aattttatac tataaaaatt aaggatcaga   4020
```

```
ttagaattga gctctatttc tattcatttt tgaactaaaa ttaattaagg gctcaaatga   4080
attatgaaga agcattagga tcatgatcca ttaccacccc tacgtgtaag atgtttttttg   4140
gtggttgtgg ttgattttga attttaaggc cgcatatgtc tcatggacta cacaagctca   4200
tattcatcta catttgtagc cgtcactaac ttagccaaat atgcatatgt ggcggctgag   4260
agcacctaga gggggggggg gtgaataggt gatcctataa aaacttgaaa cataatgcca   4320
caaaacttga ttaggagtta gcacaataaa gccaagtgac tagagaggag ttcttgcaag   4380
acacgataac cacacgaaga tcaacacaga tagacacaat ggtttatccc gttgttcggc   4440
caagtccaac acttgcctac tccacgttgt ggcgtcccaa cggacgaggg ttgcaatcaa   4500
cccctctcaa gcggtccaag gacccacttg aataccacgg tgttttgctt agtttcacta   4560
tatcccgctt gcgaggaatc tacacaactt ggagcctctc gcccttacaa tttgatgttc   4620
acaaagaagc acgaaagtaa ggctgggatg agcaacgcac acaagacaca aaatcagagc   4680
acaacacgca cacaagtcac aacacgagct cacaaacacaa cccaaagagt tctctactca   4740
aatggagctc tagttgctat cacaaagaat cgaatacgcg gaattggagt cttggtgctt   4800
agaaacgctt agagaatgct tggtgtgttc ctccatgcgc ctaggggtcc cttttatagc   4860
cccaaggcag ctaggagccg ttgagagcat tccaggaagg caattcttgc cttctgtcgc   4920
ctggcgcacc ggacagtccg gtgcaccacc ggacactgtc cggtgcggat ttctttcctt   4980
ctttagcgaa gccgaccgtt ggagattcag agccgttggc gcaccggaca gtgtccggtg   5040
cacaccggac agtccggtgc cccttctga ccgttggctc tgccacgcgt cgcacgcgga   5100
ttacgcggcc gaccgttggc ccggccgact gttggctcac cggatagtcc ggtgcaccac   5160
cggacagtcc ggtgatttat agccgtacgc cgccgacgaa acccgagagc agccagttcg   5220
ccagagccag cctggcgcac cagacactgt ccggtgcacc cagactacgc agtcttggct   5280
gcacagccaa gtcttttcca aattggtctt tttctgtttc tagcacttag acacattaca   5340
ttagtatcca aaacaatgta ctaagtctta gaaacatacc tttactcttg atttgcactt   5400
tgtccatcat ttggcataga ttaacacatg accacttgtg ttggcactca atctccaaaa   5460
tacttagaaa tggcccaatg gcacatttcc ctttcaatct cccccttttt ggtgatttat   5520
gccaacacaa caaaaagcaa ctaaaagaag tgcaacatca atgcaaatga gaacaaaaaa   5580
ttgttttgat tcaaatttgg catatttgga tcattctttg ccaccacttg gttttgtttt   5640
tgcaaatcaa cctcaatttc ctatctctaa gtcaaacaca cttgttgaaa cataaagaga   5700
gttgttccat gagaaattga tcaaagattt caaaaactcc cccttttttc cataatcaaa   5760
cattctcccc acaagagacc aacttttgac agaagagaca ataagagaat tttgacaaac   5820
caaaaagctc tattctacta ttttcaaaat tctcaagtgg tagctgatcc atttattgct   5880
ttggccttat tttctccccc tttggcatca agcaccagaa cgggataaat cttggccctt   5940
aaaaccccat tgcctcacca aaatcttcaa ttaagagtaa aaaggcaata agagcatgaa   6000
gatgaacttg gagttagtta ctctttcatc ggagtgcagt ggaagtcttt catggtccaa   6060
gtccaacatt tcctttcaat ccacctttga gactaaatca agcaaactca agcacacagt   6120
tagtctcaag ggtcaagtt gtagcacaac tccccctaaa tatgtgcatt acttgcaaat   6180
ggacttgtga ggtccgggga gtgtttgtac aacttgagca ccatacataa acaacaaaat   6240
gcataaagga acatgatcaa ggcataaaac acatgtatgc tataaatcaa tccaagttcc   6300
gcgaatctaa gacatttagc tcactacgca gcctacaaaa ggtcttctca tctagaggct   6360
```

```
tggtaaagat atcggctagc tggttctcgg tgctaacatg aaacacttcg atatctccct   6420
tttgctggtg atctctcaaa aagtgatgcc ggatgtctat gtgcttagtg cggctgtgtt   6480
caacaggatt atccgccatg cggatggcac tctcattatc acataggagt gggactttgc   6540
tcagattgta gccaaagtcc ttgagggttt gcctcatcca aagtagttgc gcgcaacact   6600
gtcctgcggt aacgtactcg gcctcagcgg tggatagggc aacggaggtt tgtttcttag   6660
aattccacga caccagggac cttcctaaga attgacacgt ccccgatgta ctctttctat   6720
cgaccttaca tccaacatag tcggagtctg aatatccaat caagtcaaag gtagacccct   6780
ttggatacca gatcccgaag caaggcgtag cgactaaata tctaagaatt cgcttcacaa   6840
ccactaagtg acactccttt ggatcggatt gaaatctagc acacatgcat acacttagca   6900
taatatctgg tctactagca cataaataaa gtaaggaccc tatcatagac cggtatgcct   6960
tttgatcaac ggacttacct cctttgttga ggtcggtgtg tccgtcagtt cccattgtag   7020
tctttgcggg cttggcgttc ttcatcccaa actgctttag cagatcttgc gtgtacttcg   7080
tttgggagat gaaagtgccg tccttgagtt gcttcacttg gaacccaagg aagtagttca   7140
actcgcccat catcgacatc tcgaatttct gagtcatcac cctgctaaac tcttcacaag   7200
acttttggtt agtagaacca aatattatgt catcgacata aatttggcac acaaaaagat   7260
caccatcaca agtcttagtg aataaagttg gatcggcttt cccaaccttg aaagcattag   7320
caagtaaaaa gtctctaagg cattcatacc atgctcttgg ggcttgctta agtccataga   7380
gggccttaga gagcttacac acgtggtcgg ggtaccgttc atcctcgaag ccagggggtt   7440
gctccacgtg cacctcctcc ttgattagcc cgttgaggaa agcactcttc acatccattt   7500
ggaacaacct gaaggaatgg tgagcggcat aggctaacaa aatacgaata gactctagcc   7560
tagccacagg agcaaaagtc tcctcaaagt ccaaacctgc gacttgggca tagccttttg   7620
ccacaagtct cgccttgttc cttgtcacca ccctgtgctc gtcctgtttg ttgcggaaca   7680
cccacttggt tcccacaacg ttttgcttgg gacgaggcac cagtgtccaa acttcatttc   7740
gcttgaagtt gatgagctct tcctgcatgg ccaacaccca gtccggatct agcaaggcct   7800
cttctaccct gaaaggctca atagaagaga caaaagagta atgctcacaa aatttaacta   7860
atctagagcg agtagttact cccttgctaa tgtcacccaa aatctggtcg acgggatgat   7920
tcctttgaat cgtcgctcga acttgagttg aaggggcttg aggtgcttct tcctccataa   7980
catgatcatc ttgtgctccc ccttgatcac atgcctcctc ttgatgaacc tgttcatcgt   8040
cttgagttgg gggatgtacc aatgttgagg aagaaggttg atcttgctcc ttttgttcct   8100
gtggccgcac atctccaatc gtcatggtgc gtattgcggc cgttggaatg tcttcttcat   8160
ctacatcatt aagatcaaca acttgctctc ttggagagcc attagtctca tcaaatacaa   8220
cgtcgctaga gacttcaacc aaactcgatg atttgttgaa aaccctatac gcctttgtat   8280
ttgagtcata acctaacaaa aacccttcta cagctttggg agcaaactta gaatttctac   8340
ctttcttcac tagaatgtag catttactcc caaatacacg aaagtatgaa acattgggtt   8400
tgttaccggt taggagctca tacgaagtct tcttgaggag gtgatgaagg tagacccggt   8460
ttatggcgtg gcaagccgtg ttcacggctt ccgaccaaaa tcgctcgggg gtcttgaact   8520
ctccaagcat cgtcctcgcc atgtcaatga gcgtcctatt tttcctctct accacaccat   8580
tttgctgtgg tgtgtaggga gcggagaact cgtgcttgat tccttcctcc tcaaggtact   8640
cttctacttg aagattcttg aactccgacc cgttgtcgct ccttatcttc ttcaccttga   8700
gctcaaactc attttgagct ctccttagga agcgcttgag ggtcccttgg gtttcagatt   8760
```

```
tatcctgcaa aaagaatacc caagtgaagc gggaaaaatc atcaactata acaagaccat   8820
acttacttcc tcctaagctt aggtaggcga cgggcctgaa gaggtccata tgtagcaact   8880
ccaaaggtct tgatgtggtc atcacatttt tggtatgatg agagcttccc acttgtttac   8940
ctgcttgaca agctgcataa ggtctatctt tttcgaaagt aacatttgtt agtcctatca   9000
cgtgttctcc ctttagaagc ttgtgaaggt tcttcatccc cacatgtgct aagcggcgat   9060
gccacagcca gcccatgcta gtcttagcaa ttaagcatgc atctagaccg gcctcctctt   9120
ttgcaaaatc aactaagtag agtttgccgt ctaatacacc cttaaaagct aatgaaccat   9180
cactccttct aaagacggac acatctacat ttgtgaataa gcaattatat cccatattac   9240
aaagctaact cacagacaat aagttatatc caagagactc aactaaaaac acattagaaa   9300
tagagtgctc ggatgaaatg gcaatcttcc ctagtccttt gaccttgcct tgattcccgt   9360
caccgaatat gattgagtct tgggaatcct tgttcttgac gtaggaggtg aacatcttct   9420
tctcccccgt catgtggttt gtgcatccgc tgtcgataat ccagcttgat cccccggatg   9480
cataaacctg caaggcaaat taggcttggg tcttaggtac ccaactcttg ttgggtccta   9540
caaggttagt acaaatagcc ttagggaccc aaatgcaagt tttatctccc ttgcattttg   9600
cccctaattt tctagcaacc accttcttat cctttctaca aatatcaaag gaagcattta   9660
aagcatgata aattgtagaa ggttcattac ttgttttcct aggtacatga gcatttctcc   9720
taggcacatg atgaatgata tttttcctag ccaaatttct atcatgcata atagaagaac   9780
ttgaagcaaa cattgcattt gaatcataag catgtgaaat gacatcattg caacttctat   9840
catgatgaac attcctggaa tatctcctat catggtataa gaaagcatgg ttcttttgaa   9900
tactatttgc catagggggcc ttccctttct ccttgatgga gataggagcc ttatgacttg   9960
tcaagttctt ggcttccctc ttgaagccaa gcccatcctt aattgagggg tgtctaccaa  10020
ccgtgtaggc atcccttgca aattttagtt tatcaaaatc atttttgcta gtcttaagtt  10080
gagcattaag actagccact tcatctttta gtttagaaat gcaaactagg tgttcactac  10140
aagcatcaac attgaaatct ttacacctat tgcaaatcgt aacatgttct tcacgagagg  10200
ttaatttact agctatttct aacttagcac tcaaatcatc attaacactt tttaggctag  10260
agatagattc atggcatgta gacaattcac atgaaagcat ttcatttctt ttaatttcta  10320
aagcaagaga attttgtgct tctacaaact tatcatgttc ttcatacaaa agatcctctt  10380
gcttttctaa taatctattc ttatcattca aggcatcaat caactcattg atcttatcaa  10440
tcttagttct atctaagccc ttgaacaaac tagcatagtc tatttcatca tcgctagatt  10500
catcatcact agaagcataa gtagactttc gagtgtttac cttcttctcc tttgccatta  10560
agcatgtgtg atgctcgttg ggggaagagg aacgacttgt tgaaggccga ggcgacgagt  10620
ccttcgttgt cggagtcgga cgacgaacaa tccgagtccc actccttgcc aaggtgtgcc  10680
tcacccttag ccttcttata agccttcttc ttttccctct tcttctcttg ttcctggtca  10740
ctatcattat cgggacaatt agcgataaat gaccaatctt accacatttg aagcatgagc  10800
gcttcccctt cgtcttgttg ggatgctcct tgcgaccctt tagtgctgtc ttgaatcgct  10860
tgatgatgag ggccatttct tcttcattaa gcccgaccgc ctcaacttgc gccaccttgc  10920
taggtagcgc ctccttgctc ctcgttgctt tgagagccac agtttgaggc tcgtggattg  10980
ggccattcaa cgcatcatcg acgtatcttg cctccttgat catcatccgc ccgcttacga  11040
actttccaag tatttcttcg ggcgacatct tggtgtacct aggattttca cgaatattgt  11100
```

```
ttacaagatg tggatcaagg atagtgaagg accttagcat taggcggacg acgtcgtgat  11160
ccgtccatcg cgtgcttcca tagcttctta ttttgttgac gagggtcttg agccggttgt  11220
acgtttgggt tggctcttct cccctgatca ttgcgaatct cccaagttcg ccctccacca  11280
actccatctt ggtgagcatg gtgacatcgt tcccctcatg tgagatcttg agggtgtccc  11340
agatctgctt ggcgttatcc aagccgctca ccttatggta ttcatccctg cacaatgatg  11400
ctagaagaac agtagtagct tgtgcatttt tgtgaatttg ctcattgata aatatgggac  11460
tatcagtact atcaaattgc attccactct ctactatctc ccatatgctt ggatggagag  11520
agaacaagtg actacgcatt ttgtgactcc aaaatccgta gtcctctcca tcaaagtgag  11580
gaggtttacc aagtggaatg gagagtaaat gagcatttgt actttgcgga atacgagaat  11640
aatcaaaaga aaagtttgaa ttgactgttt tctttttctc gtagttgtcg tcgtcctttt  11700
gggaagaaga ggactcgtcg ctgtcgtcgt agtagacgat ctccttgatg caccttgttt  11760
tcttcttctt cctgtctttt cttttgtggc tcgagcccga gtcagtaggc ttgtcatctt  11820
ttggatcatt gacgaaggac tccttctcct tatcattgac caccatcccc ttgcccttag  11880
gatccatctc ttcgggcgat tagtccctta cgtgaagaga acgactcaga taccaattga  11940
gagcacctag agggggtga ataggtgatc ctataaaaac ttgaaactta atgccacaaa  12000
acttgattag gagttagcac aataaagcca agtgactaga gagttcttgc aagacacgat  12060
aaccacacaa agatcaacac agatagacac agtggtttat ctcgtggttc ggccaagtcc  12120
aacacttgcc tactccacgt tgtggcgtcc caacggacga gggttgcaat caacccctct  12180
caagcggtcc aaggacccac ttgaatacca cagtgttttg cttagtttca ctatatcccg  12240
cttgcgagga atctccacaa cttgtagcct ctcgccctta caatttgatg ttcacaaaga  12300
agcacgaaag taaggctggg atgagcaacg cacacaagac acaaaatcag agcacaacac  12360
gcacacaagt cacaactcga gctcacaaca caacccaaag agttctctac tcaaatggag  12420
ctctagttgc tatcacaaag aatcgaatgc gcggaattgg agtcttggtg cttaggaacg  12480
cttagagaat gctttgtgtg ttcctccata cgcctagggg tccctttat agccccaagg  12540
cagctaggag ccgttgagag cattccagga aggcaattct tgccttctgt cgcctggcgc  12600
accggacagt ccggtgcacc atcggacact gtccggtgca gatttctttc ctttttagc  12660
gaagccgacc gtcggagatt cagagccgtt ggcgcactgg acactgtccg atggacaccg  12720
gacagtccgg tgcccccttc tgaccgttgg ctctgccacg cgtcgcgcgc ggattacgcg  12780
gccgaccgtt ggctcgaccg actgttggct cactgaacag tccggtgcac caccggacag  12840
tccggtgatt tatagccgta cgccgccgac gaaacccgag agcagctagt tcgctagagc  12900
cagtctggcg caccagacat tgtccggtgc accaccggac agttcggtgc acccagactg  12960
cgcagagtct tggctgcaca gccaagtctt ttccaaattg gtcttttcct gtttctagca  13020
cttagacaca ttacattagt ctccaaaaca atgtactaag tattagaaac atacctttac  13080
tcttgatttg cactttgtcc atcatttggc atagattaac acatgaccac ttgtgttggc  13140
actcaatctc caaaatactt agaaatggcc caagggcaca tttccctttc agcggctagc  13200
aacaggtcct tggtttcttg ggttatttat tctcttttta tcgtgtttga atgttttcgt  13260
gttcatttgc ataacatctt aggtctacat cagtatatga attgagatca aatgtgaatt  13320
ggaccacaca agctcatatt catctacatt tgtagtcgtc actaacttag ccaaatatgc  13380
atatgtccgc ttctgatttc attgtgtctt ttcttcagga gtttggggat caaggagagg  13440
actccattat cttgtcaccg cgactgaagg agattagtac tcctgaccgc cccgctgccc  13500
```

tccgtttcct aggtac 13516

<210> SEQ ID NO 56
<211> LENGTH: 1026
<212> TYPE: DNA
<213> ORGANISM: Artificial Sequence
<220> FEATURE:
<223> OTHER INFORMATION: cDNA Snare T1

<400> SEQUENCE: 56
gcgcccggct cttcatcgcc tccacccgct ccagcgtctc caccacctcc ttcatcgagg 60
gccgactgcg aggctcgccg gccaggcagc cgagcgtcag ttgcgccgct tggaacgcct 120
gcttttgttg atcgtttgtt ttggtctgat ttcggtgggt ctatccgcag agaggaagaa 180
gcagaagctc tccgagatcc aatccggcgt tgaggaagct gaatcgctga ttcagaaaat 240
ggacctggag gcaaggagcc tacagcctag cattaaggct agtttgcttg caaagctgag 300
ggagtataaa tctgacctca acaacgtcaa gagtgagctc aagaggatat ctgcgcccaa 360
tgccaggcag gctacccggg aggagctcct ggagtctgga atggctgata ctctcgcagt 420
gagctaatga taggacttga ctgtgtctac gagactgctc ctaacaataa actgaagaaa 480
gcaaaagaaa tcattcaacg tattcgccga agagaactct acaagatatg gtagtcctgg 540
gaggaagagc catcgccgct atgtatggca gaaccacccg cgaaagcaac ctctctggtc 600
tcgcatagcc agagcaggag cagctcgctt gcgcggccgc agcgctggcg gtcggccccg 660
cgtacgagcg cctgcaggaa gccaggaacc catccgaaca aggttgcaat catgataagc 720
agatagagca agcatatgat gatattttga attcgtcgaa gcatactttg gccagcatga 780
tggagctgca ggaggctttg cttgagagta atcaggctac aaaggatgcc aatgaaattc 840
cttctgcctc aaatggagac aatgacgagt ggtcagaagt acagagattg cagacaaggt 900
aaattttgca atagaaataa ctaaccaacc attagtgctt gaaaaaaact ggactggtga 960
ctggggcacg tggtttcatc aacatttgga cctcaacggt ctaatcagta taacttagaa 1020
gttggc 1026

<210> SEQ ID NO 57
<211> LENGTH: 874
<212> TYPE: DNA
<213> ORGANISM: Artificial Sequence
<220> FEATURE:
<223> OTHER INFORMATION: cDNA Snare T1

<400> SEQUENCE: 57
gcgcccggct cttcatcgcc tccacccgct ccagcgtctc caccacctcc ttcatcgagg 60
gccgactgcg aggctcgccg gccaggcagc cgagcgtcag ttgcgccgct tggaacgcct 120
gcttttgttg atcgtttgtt ttggtctgat ttcggtgggt ctatccgcag agaggaagaa 180
gcagaagctc tccgagatcc aatccggcgt tgaggaagct gaatcgctga ttcagaaaat 240
ggacctggag gcaaggagcc tacagcctag cattaaggct agtttgcttg caaagctgag 300
ggagtataaa tctgacctca acaacgtcaa gagtgagctc aagaggatat ctgcgcccaa 360
tgccaggcag gctacccggg aggagctcct ggagtctgga atggctgata ctctcgcagt 420
gagctaatga taggacttga ctgtgtctac gagactgctc ctaacaataa actgaagaaa 480
gcaaaagaaa tcattcaacg tattcgccga agagaactct acaaggaagc caggaaccca 540
tccgaacaag gttgcaatca tgataagcag atagagcaag catatgatga tattttgaat 600

```
tcgtcgaagc atactttggc cagcatgatg gagctgcagg aggctttgct tgagagtaat    660

caggctacaa aggatgccaa tgaaattcct tctgcctcaa atggagacaa tgacgagtgg    720

tcagaagtac agagattgca gacaaggtaa attttgcaat agaaataact aaccaaccat    780

tagtgcttga aaaaaactgg actggtgact ggggcacgtg gtttcatcaa catttggacc    840

tcaacggtct aatcagtata acttagaagt tggc                                874
```

<210> SEQ ID NO 58
<211> LENGTH: 553
<212> TYPE: DNA
<213> ORGANISM: Zea mays

<400> SEQUENCE: 58

```
cgatgtgcag tggcctgatt agctacaaga agctcttgtt ccatggactc gatctctgga     60

ccgcactatc gttgcctcag cccctaggtc atgctgccct ctggcctcct catcgtacaa    120

ttcaccaaca tctccaatgt aagtgcagct ggttcagtaa tgaactcaga agtggcatca    180

gaatactcca agagtttttt gttctttttg cctggatata taccaaggga aatgcattca    240

aaactcctat agatgacgaa tcccatctct ccctcttttc tcggacacgg atccccaggt    300

ccgtctccgt gctttactca tttgtttttt acaagttcag atccacttgc gtactcacac    360

agtggacatc tgttatgcac atgtgtaaac cagcataaga attaggaatt atgctcattt    420

tatctaagaa gtccttacac tcgaaaatgc atgtgttatt tagcttgaga ataaataaaa    480

ttattagcaa ggagaaaaaa aataggacta aagaatagag tcacattggt ttaaattagt    540

acctagaagc aaa                                                       553
```

<210> SEQ ID NO 59
<211> LENGTH: 527
<212> TYPE: DNA
<213> ORGANISM: Artificial Sequence
<220> FEATURE:
<223> OTHER INFORMATION: cDNA Snare T2

<400> SEQUENCE: 59

```
gcttctcgat gtgcagtggc ctgattagct acaagaagct cttgttccat ggactcgatc     60

tctggaccgc actatcgttg cctcagcccc taggtcatgc tgccctctgg cctcctcatc    120

gtacaattca ccaacatctc caatgtaagt gcagctggtt cagtaatgaa ctcagaagtg    180

gcatcagaat actccaagag ttttttgttc tttttgcctg gatatatacc aagggaaatg    240

cattcaaaac tcctatagat gacgaatccc atctctccct cttttctcgg acacggatcc    300

ccaggtccgt ctccgtgctt tactcatttg ttttttacaa gttcagatcc acttgcgtac    360

tcacacagtg gacatctgtt atgcacatgt gtaaaccagc ataagaatta ggaattatgc    420

tcattttatc taagaagtcc ttacactcga aaatgcatgt gttatttagc ttgagaataa    480

ataaaattat tagcaaggag aaaaaaaata ggactaaaga atagagt                  527
```

<210> SEQ ID NO 60
<211> LENGTH: 9062
<212> TYPE: DNA
<213> ORGANISM: Zea mays

<400> SEQUENCE: 60

```
gttgcgagat gtttatgtgc cttagtcttc aatttggggg ttgggggaaa agtaatttta     60

tgtttttgtt ttgtgtctgc agattcggaa gatggacttg gaggcaagga gcctacagcc    120

tagcattaag gctggtttgc ttgcaaagct gagggagtat aaatctgacc tcaacaacgt    180
```

```
caagagtgag ctcaagagga tatttgcgcc caatgccagg caggctaccc gggaggagct    240
cctagagttt ggaatggctg atactctcgc tgtgagctaa tgctaggact tgactgtgtc    300
tacgagactg ctcctaacaa taaactgaag aaagcaaaag aaatcattca acgtattcgc    360
cgaagagaac tctacaaggt agtatgatgc tttaattgct catatacaag tgtcattttg    420
tcatgtcatt acacatggtt aggatacata cttaagtttc taacgtaggc gtccacacaa    480
cggattggtg cacggttctg ccgatgtatc ccacgcacgt gcatggaagg aggcaggcac    540
ccttccccgc cgccccggat ctcgcgccag cccccgccct accccgcctg cccttccact    600
cttcccccgc tgcccccggt caacgtcacg aacccgggcc tcgtgccgct cgtcgtggcc    660
acactgttcg acgagcgagt cacagagctg ctgagcgtgc tcgctgatgc ggcggtgggg    720
cgaccaggca ggtggtccat cggcgaagcg ccatggtcgt cgtcgggggg cacgaaccag    780
gcggtgtacg cgcgccgcgc gcccggctct tcatcgcctc cacccgctcc agcgtctcca    840
ccacttcctt catcgagggc cgactgcttg gctcgctggc caggcagccg agcattagtt    900
gcgccgcttg gaacgcctgc ttttgttgat cgtttgtttt ggtctgattt cagtgggtct    960
atccgcagag aggaagaagc agaagctctc cgagatccaa tccggcgttg aggaagctga   1020
atcgctggta aatagatgtc gcgacgcgtt ctgttttggg gatccccttg gctaacggga   1080
catacgacat ttggggaatg ggtagaaaag cagagattag ggatttttcg tttccgtcgg   1140
tgcagttttg gtgttccaac agagttgcga gatgtttatg tgccttagtc ttcaatttgg   1200
gggttggggg aaaagtaatt ttatgttttt gttttgtgtc tgcagattca gaaaatggac   1260
ctggaggcaa ggagcctaca gcctagcatt aaggctggtt tgcttgcaaa gccgagggat   1320
tataaatctg acctcaacaa cgtcaagagt gagctcaaga ggatatctgc gcccaatgcc   1380
aggtaggcta cccgggagga gctcgtggag tctagaatgg ctgatactct cgcagtgagc   1440
taatgctagg acttgactgt gtctacgaga ctgctcctaa taataaactg aagaaagcaa   1500
aagaaatcat tcaacgtatt cgccgaagag aactctacaa ggtagtatga tgctttaatt   1560
gctcatatac aagtgtcatt ttgtcatgtc attacacatg gttaggatac atacttaagt   1620
ttctaacgta ggcatccaca caatggattg gtgcacggtt ctgccgatgt atcccacgca   1680
cgcgcatgga aggaggcagg caccccttccc tgccgccccg gatctcgcgc cagccatcgc  1740
cctaccccgc ctgcccttcc actcttcccc ctgaaagtcg cctagagggg gggtgaatag   1800
ggcgaatctg aaatttacaa acttaagcac aactacaagc cgggttaacg ttagaaatat   1860
aaacgagtcc gagagagagg gcgcaaaaca aatcatgagc aaataaagag tgagacacga   1920
tgatttgttt taccgaggtt cggttcttgc aaacctactc cccgttgagg tggtcacaaa   1980
gaccgggtct ctttcaaccc tttccctctc tcaaacggtc acttagaccg agtgagcttc   2040
tcttctcaat caaacgaaac acaaagttcc cgcaaggacc accacacaat tggtgtctct   2100
tgccttggtt acaattgagt ttgatcacaa gaagaatgag aaagaaaaga agcgatccaa   2160
gcgcaagagc tcaaatgaac acaaatgtcg ctctctctag tcactatttg atttggagtg   2220
attccggact tgggagagga tttgatcttt tggagtgtct agaattgaat gctatagctc   2280
ttgtaatatg ttgaaggtgg gaaacttgga tgccattgaa tgtggggtgg ttggggtatt   2340
tatagcccca aaacaccaaa aaaggccgtt ggaaggctgc tctcgcatgg cgcaccggac   2400
agtccggtgc gccagccacg tcagcagacc gttggggttc gaccgttgga gctctgactt   2460
gtggggcctc tgggctgtcc ggtggtgcac cggacaggtc ctgtaggatg tctggtgcgc   2520
```

```
caactgcacg tgctctgtcc tctgcgcgcg caggcgcgca ttaaatgcgt tgtagtcaac   2580
cgttgcgcgc gaagtagcca ttgctctgct ggcacaccgg acagtccggt gaattatagc   2640
ggagcgccct ctgattttcc cgaaggtagc gagttcagct tcgagtgccc tggtgcaccg   2700
gacactgtcc ggtgcgccaa accagggtgc cttccgggat gtcttttgct ctctttgttt   2760
gaaccctttc ttggtctttt tattggctta ttgtgaacct ttgacacctg taaaacttat   2820
agactagagc aaactagtta gtccaattat ttgtgttgga caattcaacc accaaaatca   2880
attaggaaat aggtgtgagc ctaattccct ttcaatctcc cccttttttgg tgattgatgc   2940
caacacaaac caaagcaagt atagaagtgc ataattgaac tagtttgcat aatgtaagtg   3000
caaaggttac ttagaattga accaataaat attttcataa gttatgcatg gattgtttct   3060
ttattttcat cattttggac cacgcttgca ccacatgttt tgtttttgca aatccttttg   3120
taaatagtca aaggtaaatg aataagattt tgagaagcat tttcaaaatt tgaaattttc   3180
tcccccctgtt tcaaatgctt ttcctttgac ttaaacaaaa ctccccccctc aaaaatccta   3240
ctcatagtgt tcaagagggt tttaagatat caattttgaa aatgctactt tctcccccctt   3300
ttgaatataa taagatatca attgaaaaat tcatcatttt aaaacctttt gaaaatgggt   3360
ggtggtgcgg tccttttgct ttgggctaat actttctccc cctttggcat gaatcgccaa   3420
aaacgaatac ttgagtgaaa tataagcccc tttaactact ttctcctgct ttggcgaaca   3480
taatatgagt gaagattata ccaaagttgg agagttgctt gaagcgacgg tgaaggatga   3540
gttatggagt ggaggttaag cctttgtctt cgccgaagat tccaattccc tttcaataca   3600
cctatgactt ggtttgaaat atacttgaaa acacattagt catagcacat gaaagagata   3660
tgatcaaagg tatattaatg agctatgtat gcaagacatc aaaagaaatt cctagaatca   3720
agaatattta gctcgtgtct aagtttgttc atctagtggc ttggtaaaga tatcggctaa   3780
ttgttcctta gtgttaatat aggcaatctc gatatctccc ttttttttggt gatcccttag   3840
gaaatgatac cgaatggcta tgtgtttagt gcggctatgc tcaacgggat tatccgccat   3900
gcggattgca ctctcattat cacatagaag aggaactttg gttaattttt aaccatagtc   3960
cctaagggtt tgcctcatcc aaagtaattg tgcgcaacaa tggcctgcgg caatatactc   4020
ggcttcggcg gtagaaagag ctacggaatt ttgcttcttt gaagcccaag acaccaggga   4080
ccttcccaag aactggcaag tccccgatgt actctttcta ttaattttac accccgccca   4140
atcggcatcc gaataaccaa tcaaatcaaa tgtggatccc gtaggatacc aaagcccaaa   4200
cttaggagta tgaactaaat atctcaagat tcgttttacg gccgtaaggt gagcttcctt   4260
agggtcggct tggaatcttg cacacatgca tacggaaagc ataatatccg gtcgagatgc   4320
acataaatag agtaaagagc ctatcatcga ccggtatacc ttttgatcga cggatttacc   4380
tcccgtgtcg aggtcgagat gcccattggt tcccatgggt gtcttgatgg gtttggcatc   4440
cttcatccca tacttgttta gaatgtcttg aatgtacttc gtttggctaa tgaaggtgcc   4500
ctcttagcgt tgcttcactt gaaatcacaa gaagtacttc aactccccca tcatagacat   4560
ctcgaatttc tgtgtcatga tcctactaaa ttcctcacat gtagattcat tagtagaccc   4620
aaatataata tcatcaacat aaatttggca tacaaacaaa tcattgtcaa gagttttagt   4680
aaataaagta ggatcggcct ttccgacttt gaaaccatta gtgataagga aatctctaag   4740
gcattcatac catgctcttg ggcttgcttt gagcccataa agcgccttag agagtttata   4800
tacgtgatta gggtactcac tatcttcaaa gccgggaggt tgctcaacat agacctcttc   4860
cttgattggt ccgttgagga aggcactttt cacgtccatt tgataaagct tgaagccatg   4920
```

```
gtaagtagca taggcaagta atatgcgaat tgactcaagc ctagctacgg gtgcataggt   4980
ttcaccaaaa tccaaacctt cgacttgtga ataacccttg gccacaagtc gggctttgtt   5040
ccttgtcacc acaccatgct catcttgttt gttgcggaag acccacttgg ttcctacaac   5100
attttgatta ggacgtggaa ctaagtgaca tacctcattc ctagtgaagt tgttgagctc   5160
ctcttgcatc gccaccaccc aatctgaatc ctgtagtgct tcctctaccc tttgtggctc   5220
aatagaggaa acaaaagagt aatgttcaca aaaatgagca acacgagatc gagtagttac   5280
ccccttttga atatcgccga ggatggtgtt cacggggtga tctcgttgga ttgcttggtg   5340
gactcttggg tgtggcggtc ttggttcttc atcctccttg tcttgatcat ttgcatctcc   5400
cccttgatta ttgccgtcat cttgaggtgg ctcatcttct tgatcttctc ctttatcatc   5460
ttgagcctca tcctcatttt gagttggtgg agatgcttgc gtggaggagg atggttgatc   5520
ttgtgcattt ggaggctctt tggattcctt aggacacaca tccccaatgg acatgttcct   5580
tagcgcgacg cacggagcct cttcatcacc tatctcatca agatcaactt gctctacttg   5640
agagccgtta gtttcatcaa acacaatgtc accagaaact tcaactagtc ccgaggactt   5700
gttaaagact ctatatgccc ttgtgtttga atcataccct agtaaaaagc cttctacagc   5760
cttaggagca aatttagatt ttctacctct tttaacaaga atgaagcatt tgctaccaaa   5820
gactctaaaa tatgaaacat tgggctttta ccggttagga gttcatatga tgtcttcttg   5880
aggattcggt gtagatataa ccggttgatg gtgtagcaag cggtgttgac cgcctcgatc   5940
caaaaccgat ccgaagtctt gtactcatca agcatggttc ttgccatgtc caatagagtt   6000
cgattcttcc tctccactac accattttgt tgtggggtgt agggagaaga gaactcatgc   6060
ttgatgccct cctcctcaag gaagccttcg atttgagaat tcttgaactc cgtcccgttg   6120
tcgcttctaa tctttttgat tcttaagccg aactcatttt gagcccatct caagaatccc   6180
tttaaggtct cttgggtatg agatttttcc tgcaaaaaga atacccaagt gaagcgagta   6240
taatcatcca caataactag atagtactta ctcccgccga tgcttatgta agctatcggg   6300
ccgaataggt ccatatgtag gagctcgagt ggcctgtcag tcatcatgat gttcttgtgt   6360
ggatgatgag taccaacttg cttccctgtc tgacatgcgc tacaaatcct atctttctca   6420
aagtgaacat ttgttagtcc caaaatgtgt tctcccttta gaagcttgtg aagattcttc   6480
attccaacat gtgctagtcg gtgatgccag agccagccca tgttagtctt agcaattaag   6540
caagtgtcga gttcagctct atcaaaatct accaagtata gctgaccctc taacactccc   6600
ttaaatgcta ctgaatcatc acttcttcta aagacagtaa cacctatatc tgtaaaaaga   6660
cagttgtagc ccattttaca taattgcgaa actgaaagca agttgtaatc taaagaatct   6720
acaagaaaca cattggaaat ggaatggtca ggagatatag caattttacc caatcctttg   6780
accaaacctt ggtttccatc cccgaatgtg atcgctcttt ggggatcttg gtttttctca   6840
taggaggaga acattttctt ctcccctgtc atatggtttg tgcacccgct atcgatgatc   6900
caacttgggc ccccggatgc ataaacctac aaaacaagtt tagttcttga ttttaggtac   6960
ccaaatggtt ttgggtcctt tgacattaga tacaagaact ttgggtaccc aaacacaagt   7020
ctttgatccc ttgtgtttgc ccccaacata cttggcaact atcttgtcgg atttgttagt   7080
taaaacataa gatgcatcaa aagttttgaa tgaaatgtta tgatcatttg atgcagcagg   7140
agttttcttc ttaggcaatt ttgcacgggt tgattgccta gagctagatg tctcaccctt   7200
atacataaaa gcatgattat ggccagagtg agacttccta gaatgaattc tcctaatttt   7260
gctctcggga taaccggcag ggtacaaaat gtaaccctca ttatcctgag gcatgggagc   7320
```

```
cttgccctta acaaagtttg acaatctttt aggagaggca ttaagtttga cattgtttcc   7380
cttttggaag ccaatgccat ccttgatgcc agggcgtctc ccactataga gcatgcttct   7440
agcaaattta aatttttcat tttttaagtc atgctcggca attttagcat ctaattttgc   7500
tatatgatta ttttgttgtt taattaaagc catatgatca tgaatagcat caatgttaat   7560
atctctacat ctagtgcaaa taatgacatg ctcaatggca gatgtagagg gtttgcaaga   7620
attaagttca acaatcttag cacgtaaaat atcattgtta tttctaagat cagaaatgga   7680
agcattgcaa acatctaatt ctttagcctt agcaatcaat ttttcatttt caaccctaag   7740
gctagcaaga gagacattca attcttcaat cttagcaagc aaattaacat tatcatctct   7800
aagattggga attgaaacat cacaaatatt agaatcaacc ttagcaatta gtttagtatt   7860
tttatttcta aggatggtaa tagtatcatg gcaagtgctt agctcactag ataatttttc   7920
acatttttct acttctagag cataagcatt tttaacctta acatgcttct tattttcctt   7980
aattaggaag tcctcttgaa agtccaagag atcatctttc tcatgaatag cactaattaa   8040
ttcatttagt ttttcctgta gttgcatgtt taggttggca aaaagggtac gcaaattatc   8100
ctcctcatca ctagcattat cttcatcact agaggatgca tatttagtgg aggattttga   8160
ttttaccttc ttctttttgc cgtcctttgc catgaggcac ttgtggccga cgttggggaa   8220
gaggagccct ttggtgacgg cgatgttggc ggcgtcctcg tcggatgagg agtcggagga   8280
actctcgtcg gagtcccact cgcggcacac atgggcatcg ccgcccttct tcttgtaata   8340
cctcctcttt tctctcctct tgcccttctt gtcgtcgccc ctgtcactat cactagataa   8400
aggacattta acaatgaaat gaccgggctt accacacttg tagcacaccc ttttggaaca   8460
aggcttgtaa tctttcccct tcctttgttt gaggatttgg tggaagctct tgatgatgag   8520
cgccattttc tagttgtcga gcttagaggc gtcgatgggt tgtctacttg atgtagactc   8580
ctctttcttc tcctctgtcg ccttgaatgc gaccggttgt gcttcgggcg tggagggacc   8640
gtcgtgctcg ataattttct ttgagccttt gatcatcaac tcaaagctca caaagtttcc   8700
tattacttcc tcgggagtca ttagtgtata tctaggatta ccacgaatta attgaacttg   8760
cgtagggtta aggaacacaa gtgatctaag aataacctta accatttcat ggtcatccca   8820
tttttgctc ccgaggttgc gcacttggtt caccaaggtc ttgagccggt tgtacatatc   8880
ttgtggctcc tcccccttggc gaagccggaa gcgaccgagc tccccctcga tcgtctcccg   8940
cttggtgatc ttggttacct cgtctccttc gtgcgcggtc tttagcacgt cccagatatc   9000
ctttgcactc ttcaaccctt gcaccttatt atactcctct cgacttggat ttgaaatgtt   9060
gg                                                                  9062
```

<210> SEQ ID NO 61
<211> LENGTH: 1082
<212> TYPE: DNA
<213> ORGANISM: Artificial Sequence
<220> FEATURE:
<223> OTHER INFORMATION: cDNA Snare T3

<400> SEQUENCE: 61

```
cctgcccttc cactcttccc ccgctgcccc cggtcaacgt cacgaacccg ggcctcgtgc     60
cgctcgtcgt ggccacactg ttcgacgagc gagtcacaga gctgctgagc gtgctcgctg    120
atgcggcggt ggggcgacca ggcaggtggt ccatcggcga agcgccatgg tcgtcgtcgg    180
ggggcacgaa ccaggcggtg tacgcgcgcc gcgcgcccgg ctcttcatcg cctccacccg    240
ctccagcgtc tccaccactt ccttcatcga gggccgactg cttggctcgc tggccaggca    300
```

```
gccgagcatt agttgcgccg cttggaacgc ctgcttttgt tgatcgtttg ttttggtctg    360

atttcagtgg gtctatccgc agagaggaag aagcagaagc tctccgagat ccaatccggc    420

gttgaggaag ctgaatcgct gattcagaaa atggacctgg aggcaaggag cctacagcct    480

agcattaagg ctggtttgct tgcaaagccg agggattata aatctgacct caacaacgtc    540

aagagtgagc tcaagaggat atctgcgccc aatgccagat tcggaagatg gacctggaag    600

caaggagcct acaacctagc attaagagtg agctcaagag gatatctgcg cccattgcca    660

ggcaggctac ccgggaggag ctcctggagt ctggaatggc tgatactctc gcagtgagct    720

aatgctagga cttgactgtg tctacgagac tgctcctaac aataaactga agaaagcaaa    780

agaaatcatt caacgtattc gccgaagaga actctacaag atatggtagt cctgggagga    840

agagccatcg ccgctatgta tggcagaacc acccgcgaaa gcaacctctc tggtctcgcg    900

tagccagagc aggagcagct cgcttgcgcg gtcgcggcgc tggcggccgg ccccgcgtac    960

gagcgcctgc aggaagccag gaacccatcc gaacaaggtt gcaatcatga taagcagata   1020

gagcaagcat atgatgatat tttgaattcg tcgaagcata ctttggccag catgatggag   1080

ct                                                                  1082
```

<210> SEQ ID NO 62
<211> LENGTH: 1154
<212> TYPE: DNA
<213> ORGANISM: Artificial Sequence
<220> FEATURE:
<223> OTHER INFORMATION: cDNA Snare T3

<400> SEQUENCE: 62

```
cctgcccttc cactcttccc ccgctgcccc cggtcaacgt cacgaacccg ggcctcgtgc     60

cgctcgtcgt ggccacactg ttcgacgagc gagtcacaga gctgctgagc gtgctcgctg    120

atgcggcggt ggggcgacca ggcaggtggt ccatcggcga agcgccatgg tcgtcgtcgg    180

ggggcacgaa ccaggcggtg tacgcgcgcc gcgcgcccgg ctcttcatcg cctccacccg    240

ctccagcgtc tccaccactt ccttcatcga gggccgactg cttggctcgc tggccaggca    300

gccgagcatt agttgcgccg cttggaacgc ctgcttttgt tgatcgtttg ttttggtctg    360

atttcagtgg gtctatccgc agagaggaag aagcagaagc tctccgagat ccaatccggc    420

gttgaggaag ctgaatcgct gattcagaaa atggacctgg aggcaaggag cctacagcct    480

agcattaagg ctggtttgct tgcaaagccg agggattata aatctgacct caacaacgtc    540

aagagtgagc tcaagaggat atctgcgccc aatgccagac tgctcctaat aataaactga    600

agaaagcaaa agaaatcatt caacgtattc gccgaagaga actctacaag attcggaaga    660

tggacctgga agcaaggagc ctacaaccta gcattaagag tgagctcaag aggatatctg    720

cgcccattgc caggcaggct acccgggagg agctcctgga gtctggaatg gctgatactc    780

tcgcagtgag ctaatgctag gacttgactg tgtctacgag actgctccta acaataaact    840

gaagaaagca aaagaaatca ttcaacgtat tcgccgaaga gaactctaca agatatggta    900

gtcctgggag gaagagccat cgccgctatg tatggcagaa ccacccgcga aagcaacctc    960

tctggtctcg cgtagccaga gcaggagcag ctcgcttgcg cggtcgcggc gctggcggcc   1020

ggccccgcgt acgagcgcct gcaggaagcc aggaacccat ccgaacaagg ttgcaatcat   1080

gataagcaga tagagcaagc atatgatgat attttgaatt cgtcgaagca tactttggcc   1140

agcatgatgg agct                                                     1154
```

```
<210> SEQ ID NO 63
<211> LENGTH: 107
<212> TYPE: PRT
<213> ORGANISM: Zea mays

<400> SEQUENCE: 63

Met Ile Gly Leu Asp Cys Val Tyr Glu Thr Ala Pro Asn Asn Lys Leu
1               5                   10                  15

Lys Lys Ala Lys Glu Ile Ile Gln Arg Ile Arg Arg Arg Glu Leu Tyr
            20                  25                  30

Lys Glu Ala Arg Asn Pro Ser Glu Gln Gly Cys Asn His Asp Lys Gln
        35                  40                  45

Ile Glu Gln Ala Tyr Asp Asp Ile Leu Asn Ser Ser Lys His Thr Leu
    50                  55                  60

Ala Ser Met Met Glu Leu Gln Glu Ala Leu Leu Glu Ser Asn Gln Ala
65                  70                  75                  80

Thr Lys Asp Ala Asn Glu Ile Pro Ser Ala Ser Asn Gly Asp Asn Asp
                85                  90                  95

Glu Trp Ser Glu Val Gln Arg Leu Gln Thr Arg
            100                 105


<210> SEQ ID NO 64
<211> LENGTH: 131
<212> TYPE: PRT
<213> ORGANISM: Zea mays

<400> SEQUENCE: 64

Met Cys Ser Gly Leu Ile Ser Tyr Lys Lys Leu Leu Phe His Gly Leu
1               5                   10                  15

Asp Leu Trp Thr Ala Leu Ser Leu Pro Gln Pro Leu Gly His Ala Ala
            20                  25                  30

Leu Trp Pro Pro His Arg Thr Ile His Gln His Leu Gln Cys Lys Cys
        35                  40                  45

Ser Trp Phe Ser Asn Glu Leu Arg Ser Gly Ile Arg Ile Leu Gln Glu
    50                  55                  60

Phe Phe Val Leu Phe Ala Trp Ile Tyr Thr Lys Gly Asn Ala Phe Lys
65                  70                  75                  80

Thr Pro Ile Asp Asp Glu Ser His Leu Ser Leu Phe Ser Arg Thr Arg
                85                  90                  95

Ile Pro Arg Ser Val Ser Val Leu Tyr Ser Phe Val Phe Tyr Lys Phe
            100                 105                 110

Arg Ser Thr Cys Val Leu Thr Gln Trp Thr Ser Val Met His Met Cys
        115                 120                 125

Lys Pro Ala
    130


<210> SEQ ID NO 65
<211> LENGTH: 162
<212> TYPE: PRT
<213> ORGANISM: Zea mays

<400> SEQUENCE: 65

Met Glu Gly Gly Arg His Pro Ser Pro Pro Pro Arg Ile Ser Arg Gln
1               5                   10                  15

Pro Pro Pro Tyr Pro Ala Cys Pro Ser Ile Leu Pro Pro Leu Pro Pro
            20                  25                  30

Val Asn Val Thr Asn Pro Gly Leu Val Pro Leu Val Val Ala Thr Leu
        35                  40                  45
```

-continued

```
Phe Asp Glu Arg Val Thr Glu Leu Leu Ser Val Leu Ala Asp Ala Ala
    50                  55                  60

Val Gly Arg Pro Gly Arg Trp Ser Ile Gly Glu Ala Pro Trp Ser Ser
65                  70                  75                  80

Ser Gly Gly Thr Asn Gln Ala Val Tyr Ala Arg Arg Ala Pro Gly Ser
                85                  90                  95

Ser Ser Pro Pro Pro Ala Pro Ala Ser Pro Pro Leu Pro Ser Ser Arg
            100                 105                 110

Ala Asp Cys Leu Ala Arg Trp Pro Gly Ser Arg Ala Leu Val Ala Pro
        115                 120                 125

Leu Gly Thr Pro Ala Phe Val Asp Arg Leu Phe Trp Ser Asp Phe Ser
    130                 135                 140

Gly Ser Ile Arg Arg Glu Glu Glu Ala Glu Ala Leu Arg Asp Pro Ile
145                 150                 155                 160

Arg Arg
```

HAPLOID INDUCERS

CROSS-REFERENCE TO RELATED APPLICATIONS

This application is a U.S. National Phase of International Patent Application No. PCT/EP2015/076469, filed Nov. 12, 2015, which published as International Application No. WO 2016/075255 A1, on May 19, 2016 and claims priority to German Patent Application No. 102014016667.8, filed Nov. 12, 2014, all of which applications are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Apr. 11, 2017, is named KWS0220PCT_ST25_en.txt, and is 307,875 bytes in size.

FIELD OF THE INVENTION

The present invention relates to the field of the modification of plants by means of molecular biology methods and marker technology and genetic engineering. It relates to the provision of technical means such as nucleic acids and vectors, as well as methods and uses for the production and identification of non-transgenic and transgenic plant haploid inductors, and the improvement of existing plant haploid inductors.

BACKGROUND OF THE INVENTION

Typically, in the production of hybrid plants, two breeding lines as parents are crossed with one another, the descendants of which generate, in part, a strongly increased yield relative to the parent lines, due to the known heterosis effect. The breeding lines may be obtained via multiple selfing steps, which, however, takes multiple generations and therefore is connected with an enormous time cost. Modern plant breeding already increasingly transitioned many years ago to generating the breeding lines via haploid induction and the subsequent chromosome duplication in a much shorter amount of time. A technical requirement for this is a functioning haploid induction system, which also simultaneously promises a sufficient efficiency, in order to be economically usable.

For example, for maize (*Zea mays*), a maternal in vivo induction system is known in which the plants to be induced are pollinated with pollen of the inductor. Up to 10% of the descendants that are thereby generated then contain only the simple (haploid) chromosome set of the seed parent. A few such inductors are presently available for maize hybrid breeding. However, these are all to be ascribed to the single line "Stock 6," described by Coe, 1959. One example of such a known inductor is the RWS (Rober et al., 2005) line. In the past, multiple QTL studies for the identification of the inductor-relevant loci were conducted on these lines. A main-QTL at chromosome 1 (bin 1.04) in maize was already identified in 1997 by Deimling et al. More precise mapping was performed by Barret et al. 2008 in the range between 66.96 MB and 68.11 MB on chromosome 1, by Prigge et al. 2012 in the range between 62.9 MB and 70.8 MB, and following this by Dong et al. 2013 in the range between 68.18 MB and 68.43 MB which, according to public annotation, contains three genes. All position information refers to the reference genome of B73, Version AGPv02. The functionality of the locus appears to have already been demonstrated on its own by Dong et al. 2014 by achieving an induction rate of 5%. However, an incorrect fine mapping cannot be excluded, since no unambiguous delimitation of the QTL is possible due to the lack of information of flanking markers in the recurrent parent.

Furthermore, WO 2012/030893 discloses an inductor-relevant locus on chromosome 1 in maize that, however, differs markedly from the preceding locus and is localized in more detail at the telomere. There is no overlap in the genome regions considered.

Overall, the molecular and development-specific mechanisms, which the in vivo haploid induction in maize lines which resulted from "Stock 6," are largely unknown today. For example, it is conceivable that a fertilization occurs, but it subsequently leads to a chromosome elimination which then allows haploid descendants to emerge. For example, such a mechanism has been described by Ravi & Chan (2010) in a system with the histone protein CenH3. On the other hand, however, the fertilization may also fail, and the development of the haploid egg cells occurs in the triploid endosperm. Without the understanding of the underlying maternal in vivo haploid induction suitability of an inductor genotype derived from "Stock 6" and the knowledge about the responsible genes, a targeted improvement of this maize inductor genotype or the transfer of the induction suitability to non-inductor genotypes, or the targeted mediation of the in vivo haploid induction capability in maize non-inductors, is practically impossible.

Furthermore, for some cultivated plants, no efficiently (and, therefore, economically) applicable system for the production of haploid and double-haploid plants is known at all—for example, for sorghum, rye, or sunflower.

There is also a need for the provision of genetic elements such as genes or regulatory elements that are usable in transgenic and/or non-transgenic approaches, in order to enable haploid development, or an improved efficiency in haploid development, via in vivo induction.

SUMMARY OF THE INVENTION

The present invention was produced before the background of the prior art described in the preceding, wherein it is an object of the present invention to provide means and methods which may be used to produce an in vivo haploid inductor and/or to produce a haploid plant.

According to the invention, the achievement of the posed object takes place by means of a nucleic acid which, after transcription or expression in a plant, is suitable for mediating the property of a haploid inductor or for increasing the induction capability of a haploid inductor. The nucleic acid according to the invention may be used as a trans-gene. On the other hand, an endogenous DNA sequence in the genome of a plant, or in the genome of a plant haploid inductor, which is identical to one of the nucleic acids according to the invention, may also be modified such that the property of a haploid inductor is mediated, or the induction capability of the haploid inductor is increased, after transcription or expression of the endogenous DNA sequence. The nucleic acid of the present invention is preferably an isolated nucleic acid which is extracted from its natural or original environment (genetic context). A nucleic acid may be double-stranded or single-stranded, and linear or circular. It may thereby be genomic DNA, synthetic DNA, cDNA, or an RNA type (for example, lncRNA, siRNA, or miRNA), wherein the nucleobase uracil occurs in RNA instead of the nucleobase thymine.

In a preferred embodiment of the present invention, the nucleic acid according to the invention, or an RNA encoded from the nucleic acid, or a protein or polypeptide encoded from the nucleic acid, has an influence on the pollen tube growth in a plant, on the energy metabolism of a pollen of a plant, and/or on the activity of the centromere—preferably, in a generative cell which develops into a pollen, for example.

The nucleic acid according to the invention may be characterized in that the nucleic acid, or an RNA encoded from the nucleic acid, or a protein or polypeptide encoded from the nucleic acid, is suitable or may be used for accelerating or promoting the pollen tube growth (for example, in a pollen of a plant), in comparison with a pollen of a wild-type plant in which the nucleic acid according to the invention, or an RNA encoded from the nucleic acid, or a protein or polypeptide encoded from the nucleic acid, is used as described in the following. For example, the nucleic acid according to the invention encodes for a protein which is involved in the transport of macromolecules, or affects this transport, in the pollen tube of a pollen of a plant. Belonging to these are, for example, SNAREv proteins which, for example, mediate the transport of pectins or phospholipids, e.g., at the tip of the pollen tube (Kato et al., 2010).

Furthermore, enzymes of the phospholipase class—especially, phospholipase A2 or patatin phospholipase—are in the position to promote the growth of the pollen tube (Kim et al., 2011), whereas enzymes of the inositol polyphosphate-5-phosphatase class, such as inositol-1,4,5-triphosphate-5-phosphatase, may inhibit the growth of the pollen tube (Wang et al., 2012). The nucleic acid according to the invention may be used as a transgene for the purpose of accelerated pollen tube growth, wherein it then—for example, by means of an over-expression approach—increases the expression rate of a pollen tube growth-promoting gene or the transcription rate of an RNA such as an lncRNA—which positively regulates (activates) a pollen tube growth-promoting gene or negatively regulates (inhibits) pollen tube growth-inhibiting genes—in a plant or a part thereof, in comparison to a wild-type plant or corresponding part thereof, and/or the expression rate of a pollen tube growth-inhibiting gene is reduced—by means of an RNAi approach or miRNA approach (Fire et al., 1998)—in a plant or a part thereof, in comparison to a wild-type plant or corresponding part thereof. On the other hand, an endogenous DNA sequence in the genome of a plant or in a genome of a plant haploid inductor which is identical to the nucleic acid according to the invention, or a regulatory sequence of the endogenous DNA sequence, may also be modified, e.g., via mutagenization or "genome editing." This modification may increase or reduce the transcription or expression rate of the endogenous DNA sequence, or the activity or stability of the protein or polypeptide encoded by the endogenous DNA sequence, in a plant, in comparison to a non-mutagenized wild-type plant. For example, the expression rate of an endogenous pollen tube growth-promoting gene, or the transcription rate of an endogenous RNA such as an lncRNA which positively regulates (activates) a pollen tube growth-promoting gene or negatively regulates (inhibits) a pollen tube growth-inhibiting gene, may thus be increased in a plant, in comparison to a non-mutagenized wild-type plant or a wild-type plant modified via "genome editing," or the expression rate of an endogenous pollen tube growth-inhibiting gene, or the transcription rate of an RNA such as an lncRNA which negatively regulates (inhibits) a pollen tube growth-promoting gene or positively regulates (activates) a pollen tube growth-inhibiting gene, may thus be reduced in a plant, in comparison to a non-mutagenized wild-type plant or a wild-type plant modified via "genome editing." Moreover, the activity or stability of a pollen tube growth-promoting protein or polypeptide encoded by the endogenous DNA sequence may be increased in a plant, in comparison to a non-mutagenized wild-type plant or a wild-type plant modified via "genome editing," or the activity or stability of a pollen tube growth-inhibiting protein or polypeptide encoded by the endogenous DNA sequence may be reduced in a plant, in comparison to a non-mutagenized wild-type plant or a wild-type plant modified via "genome editing."

In a further example, the nucleic acid according to the invention may be characterized in that, via the use of the nucleic acid, or of an RNA encoded by the nucleic acid, or of a protein or polypeptide encoded by the nucleic acid, the energy metabolism of a pollen in a plant may be negatively affected in comparison to a wild-type plant. For example, this may take place via a phosphoglycerate mutase, or a mitochondrial transporter or mitochondrial import receptor. For this purpose, the nucleic acid according to the invention may be used as a transgene in an over-expression approach, or in an RNAi approach, or in an miRNA approach (Fire et al., 1998). On the other hand, an endogenous DNA sequence in the genome of a plant or in a genome of a plant haploid inductor which is identical to the nucleic acid according to the invention, or a regulatory sequence of the endogenous DNA sequence, may also be modified, e.g., via mutagenization or "genome editing." This modification may increase or reduce the transcription or expression rate of the endogenous DNA sequence, or the activity or stability of the protein or polypeptide encoded by the endogenous DNA sequence, in the plant, in comparison to a non-mutagenized wild-type plant or wild-type plant modified via "genome editing."

In another example, the nucleic acid according to the invention may also be characterized in that, via the use of the nucleic acid or of an RNA encoded by the nucleic acid or of a protein or polypeptide encoded by the nucleic acid, the activity of the centromere in a plant is modified—in particular, in the early embryogenesis, and preferably in a generative cell of the plant which develops into a pollen, for example—in comparison to a wild-type plant, which may lead to the elimination of the inductor genome, for example. The activity of the centromere may be modified via chromatin modification of DNA or at the histone level—moreover, also via transcription, RNA interactions, or RNA binding. A change in the activity of the centromere may take place via a methyl transferase such as an RNA methyl transferase, for example. For this purpose, the nucleic acid according to the invention is used as a transgene, wherein it then increases—by means of an overexpression approach—the expression rate of a chromatin-modifying gene or the transcription rate of an RNA (such as an lncRNA), which positively regulates (activates) a chromatin-modifying gene in a plant, in comparison to a wild-type plant. On the other hand, an endogenous DNA sequence in the genome of a plant or in a genome of a plant haploid inductor, which is identical to the nucleic acid according to the invention, or a regulatory sequence of the endogenous DNA sequence, may also be modified, e.g., via mutagenization or "genome editing." This modification may increase or reduce the transcription or expression rate of the endogenous DNA sequence, or the activity or stability of the protein or polypeptide encoded by the endogenous DNA sequence, in a plant, in comparison to the non-mutagenized wild-type plant or wild-type plant modified via "genome editing." The expression rate of an endogenous chromatin-modifying gene or the transcription rate of an endogenous RNA (such as an lncRNA), which positively regulates (activates) a chromatin-modifying gene, may thus also be increased in a plant, in comparison to the non-mutagenized wild-type plant or wild-type plant modified via "genome editing." Moreover, the activity or stability of a chromatin-modified protein encoded by the endogenous DNA sequence may be increased in a plant, in comparison to the non-mutagenized wild-type plant or wild-type plant modified via "genome editing."

Uses of the nucleic acid according to the invention, or of an RNA encoded by the nucleic acid, or of a protein or polypeptide encoded by the nucleic acid, that are stated in the preceding are not exclusive or limiting, but rather are to be understood only as examples. Numerous additional technical means and methods are known to a person skilled in the art from the prior art, with which he may effect the above-described changes in the expression or transcription rate according to the invention of the nucleic acid or of the identical endogenous DNA sequence, or the above-described changes in the stability and activity of the protein or polypeptide encoded by the nucleic acid according to the invention or the endogenous DNA sequence.

In an especially preferred embodiment of the present invention, the nucleic acid which, after transcription or expression in a plant, is suitable for mediating the property of a haploid inductor or for increasing the induction capability of a haploid inductor may be a nucleic acid that includes a nucleotide sequence which (i) is a sequence selected from SEQ ID Nos: 1, 2, 3, 4, 5, 6, 7, 8, 9, 10, 11, 12, 13, 14, 15, 42, 43, 46, 47, 49, 50, 52, 53, 55, 56, 57, 58, 59, 60, 61, and/or 62, or has a functional fragment of these, or
(ii) is complementary to a sequence from (i), or
(iii) is at least 80%, 82%, 84%, 86%, 88%—preferably, at least 90%, 91%, 92%, 93%, 94%, 95%, 96%, or, especially preferably, at least 97%, 97.5%, 98%, 98.5%, 99%, or 99.5% —identical to a sequence from (i), or
(iv) encodes for a protein with the amino acid sequence selected from SEQ ID Nos: 16, 17, 18, 19, 20, 21, 22, 23, 24, 25, 44, 45, 48, 51, 54, 63, 64, and/or 65, or a functional part of the protein, or
(v) encodes for a homolog, analog, or ortholog of the protein according to (iv), or a functional part thereof, or
(vi) hybridizes with a sequence from (ii) under stringent conditions.

This nucleic acid may encode for a protein or a functional portion thereof, wherein the protein or the functional portion thereof has the functionality of a SNARE protein—especially, of a SNAREv protein—of a phospholipase—especially, a phospholipase A2 or a patatin phospholipase—a methyl transferase—especially, an RNA methyl transferase or a mitochondrial import receptor (see Table 1). A use of the nucleic acid may take place as described above, i.e., in order to mediate the property of a haploid inductor or to increase the induction capability of a haploid inductor in a plant, is, for example, for transgenically or endogenously increasing the expression rate of the nucleic acid or the activity or stability of the encoded protein or of the encoded part of the protein. Since this nucleic acid, or an RNA encoded by the nucleic acid or a protein or polypeptide encoded by the nucleic acid, has a positive effect an the haploid induction capability of a plant, in the following, a nucleic acid which is defined here is designated as an induction-promoting nucleic acid. Additional methods and uses of the induction-promoting nucleic acid, as well as substances which comprise the induction-promoting nucleic acid, are disclosed further below.

In a further, especially preferred embodiment of the present invention, the nucleic acid which is suitable—after transcription or after expression in a plant—for mediating the property of a haploid inductor or for increasing the induction capability of a haploid inductor may be a nucleic acid that comprises a nucleotide sequence that (i) has a sequence selected from SEQ ID Nos: 26, 27, 28, 29, 30, and/or 31, or a functional fragment thereof, or
(ii) is complementary to a sequence from (i), or
(iii) is at least 80%, 82%, 84%, 86%, 88%—preferably, at least 90%, 91%, 92%, 93%, 94%, 95%, 96%, or, especially preferably, at least 97%, 97.5%, 98%, 98.5%, 99%, or 99.5%—identical to a sequence from (i).
(iv) encodes for a protein with the amino acid sequence selected from SEQ ID Nos: 32, 33, and/or 34, or a functional part of the protein, or
(v) encodes for a homolog, analog, or ortholog of the protein according to (iv), or a functional part thereof, or
(vi) hybridizes with a sequence from (ii) under stringent conditions.

Such a nucleic acid may encode for a protein or a functional portion thereof, wherein the protein or the functional portion thereof has the functionality of an inositol polyphosphate-5-phosphatase—especially, of an inositol-1,4,5-triphosphate-5-phosphatase—or of a phosphoglycerate mutase (see Table 1). A use of the nucleic acid may take place as described above, i.e., in order to mediate the property of a haploid inductor or to increase the induction capability of a haploid inductor in a plant, is, for example, for transgenically or endogenously reducing the expression rate of the nucleic acid or the activity or stability of the encoded protein or of the encoded part of the protein. Since this nucleic acid, or an RNA encoded by the nucleic acid or a protein or polypeptide encoded by the nucleic acid, has a negative effect on the haploid induction capability of a plant, in the following, a nucleic acid which is defined here is designated as an induction-inhibiting nucleic acid. Additional methods and uses of the induction-inhibiting nucleic acid, as well as substances which comprise the induction-inhibiting nucleic acid, are disclosed further below.

In another especially preferred embodiment of the present invention, the nucleic acid which—after transcription or expression in a plant—is suitable for mediating the property of a haploid inductor or for increasing the induction capability of a haploid inductor may be a nucleic acid that encodes for an RNA that has a double-stranded portion, wherein at least one strand of the double-stranded portion has a nucleotide sequence which is homologous or identical to at least 14, 15, 16, 17, 18, 19, 20, 21, 22, 23, 24, or 25—preferably, to at least 30, 35, 40, 45, 50, 60, 70, 80, 90, 100, 120, or 140, and, especially preferably, to at least 160, 180, 200, 250, 300, 350, 400, 450, 500, 600, 700, 800, 900, or 1000—successive nucleotides of a coding sequence of a nucleic acid that (i) has a sequence selected from SEQ ID Nos: 26, 27, 28, 29, 30, and/or 31, or a fragment thereof in a sense or anti-sense orientation, or
(ii) is complementary to a sequence from (i), or
(iii) is at least 80%, 82%, 84%, 86%, or 88%—preferably, at least 90%, 91%, 92%, 93%, 94%, 95%, or 96%, or, especially preferably, at least 97%, 97.5%, 98%, 98.5%, 99%, or 99.5%—identical to a sequence from (i), or (iv) encodes for a protein with the amino acid sequence selected from SEQ ID Nos: 32, 33, and/or 34, or a part of the protein, or
(v) encodes for a homolog, analog, or ortholog of the protein according to (iv), or a part thereof, or
(vi) hybridizes with a sequence from (ii) under stringent conditions. In post-transcriptional gene silencing, as described in, for example, the RNAi approach or miRNA approach (Fire et al., 1998), such a nucleic acid may be used to suppress the expression of the induction-inhibiting nucleic acid described above. The dsRNA-encoding nucleic acid may also be a nucleic acid which encodes for a long, non-coding RNA (lncRNA). The lncRNA-encoding nucleic acid then preferably comprises a nucleotide sequence that
(a) has a sequence selected from SEQ ID Nos: 35, 36, 37, and/or 38, or a fragment thereof, or
(b) is complementary to a sequence from (a), or
(c) is at least 80%, 82%, 84%, 86%, or 88%—preferably, at least 90%, 91%, 92%, 93%, 94%, 95%, or 96%, or, especially preferably, at least 97%, 97.5%, 98%, 98.5%, 99%, or 99.5%—identical to a sequence from (a), or
(d) encodes for a polypeptide with the amino acid sequence of SEQ ID Nos: 40 or 41, or a part of the polypeptide, or
(e) hybridizes with a sequence (b) under stringent conditions. This lncRNA, designated in the following as lncRNA 1, may serve for expression or translation regulation of an inositol polyphosphate-5-phosphatase such as an inositol-1,4,5-triphosphate-5-phosphatase. Furthermore, the lncRNA-encoding nucleic acid may preferably comprises a nucleotide sequence that
(w) has a sequence of the SEQ ID No: 39, or a fragment thereof, or
(x) is complementary to a sequence from (w), or
(y) is at least 80%, 82%, 84%, 86%, or 88%—preferably, at least 90%, 91%, 92%, 93%, 94%, 95%, or 96%, or, especially preferably, at least 97%, 97.5%, 98%, 98.5%, 99%, or 99.5%—identical to a sequence from (w), or
(z) hybridizes with a sequence from (x) under stringent conditions. This lncRNA, designated in the following as lncRNA 2, may serve for expression or translation regulation of a phospholipase—especially, of the phospholipase A2 or the patatin phospholipase.

In a further especially preferred embodiment of the present invention, the nucleic acid which—after transcription or expression in a plant—is suitable for mediating the property of a haploid inductor or for increasing the induction capability of a haploid inductor may be a nucleic acid that encodes for an RNA that has a double-stranded portion, wherein at least one strand of the double-stranded portion has a nucleotide sequence which is homologous or identical to at least 14, 15, 16, 17, 18, 19, 20, 21, 22, 23, 24, or 25—preferably to at least 30, 35, 40, 45, 50, 60, 70, 80, 90, 100, 120, or 140, and, especially preferably, to at least one 160, 180, 200, 250, 300, 350, 400, 450, 500, 600, 700, 800, 900, or 1000—successive nucleotides of an intron sequence of a nucleic acid that
(i) has a sequence selected from SEQ ID Nos: 1, 6, 8, 9, 12, 13, 26, 30, 42, 43, 46, 55, 58, and/or 60, or a fragment thereof in a sense or anti-sense orientation, or
(ii) is complementary to a sequence from (i), or
(iii) is at least 80%, 82%, 84%, 86%, or 88%—preferably, at least 90%, 91%, 92%, 93%, 94%, 95%, or 96%, or, especially preferably, at least 97%, 97.5%, 98%, 98.5%, 99%, or 99.5%—identical to a sequence from (i), or
(iv) encodes for a protein with the amino acid sequence selected from SEQ ID Nos: 16, 17, 18, 19, 20, 21, 22, 23, 24, 25, 44, 45, 48, 63, 64, and/or 65, or from SEQ ID Nos: 32, 33, and/or 34, or a part of the protein, or
(v) encodes for a homolog, analog, or ortholog of the protein according to (iv), or a part thereof, or
(vi) hybridizes with a sequence from (ii) under stringent conditions. In transcriptional gene silencing, as, for example, in the RdDM approach (Shibuya et al., 2009), such a nucleic acid may be used to activate the expression of the induction-inducing nucleic acid described above, or to suppress the expression of the induction-inhibiting nucleic acid described above. The dsRNA-encoding nucleic acid may also be a nucleic acid which encodes for a long, non-coding RNA (lncRNA). The lncRNA-encoding nucleic acid then preferably comprises a nucleotide sequence that
(a) has a sequence selected from SEQ ID Nos: 35, 36, 37, and/or 38, or a fragment thereof, or
(b) is complementary to a sequence from (a), or
(c) is at least 80%, 82%, 84%, 86%, or 88%—preferably, at least 90%, 91%, 92%, 93%, 94%, 95%, or 96%, or, especially preferably, at least 97%, 97.5%, 98%, 98.5%, 99%, or 99.5%—identical to a sequence from (a), or
(d) encodes for a polypeptide with the amino acid sequence of SEQ ID Nos: 40 or 41, or a part of the polypeptide, or
(e) hybridizes with a sequence from (b) under stringent conditions. This lncRNA, designated in the following as lncRNA 1, may serve for expression or translation regulation of an inositol polyphosphate-5-phosphatase such as an inositol-1,4,5-triphosphate-5-phosphatase. Furthermore, the lncRNA-encoding nucleic acid may preferably comprise a nucleotide sequence that
(w) has a sequence of the SEQ ID No: 39, or a fragment thereof, or
(x) is complementary to a sequence from (w), or
(y) is at least 80%, 82%, 84%, 86%, or 88%—preferably, at least 90%, 91%, 92%, 93%, 94%, 95%, or 96%, or, especially preferably, at least 97%, 97.5%, 98%, 98.5%, 99%, or 99.5%—identical to a sequence from (w), or
(z) hybridizes with a sequence from (x) under stringent conditions. This lncRNA, designated in the following as lncRNA 2, may serve for expression or translation regulation of a phospholipase—especially, of the phospholipase A2 or the patatin phospholipase.

TABLE 1

Sequence index and sequence association of the nucleotide and amino acid sequences. The names of gene families/protein families correspond to the public models. Discrepant functionalities may occur in the inductors due to structural changes.

| SEQ ID No: | Gene family/protein family identifier// derived gene model | Sequence type | Source |
|---|---|---|---|
| 1 | GRMZM2G179789 SNAREv 1 (*Zea mays*) | genomic DNA | B73 |
| 2 | GRMZM2G179789 SNAREv 1 (*Zea mays*) | cDNA | B73 |

TABLE 1-continued

Sequence index and sequence association of the nucleotide and amino acid sequences. The names of gene families/protein families correspond to the public models. Discrepant functionalities may occur in the inductors due to structural changes.

| SEQ ID No: | Gene family/protein family identifier// derived gene model | Sequence type | Source |
|---|---|---|---|
| 3 | GRMZM2G179789 SNAREv 1 (*Zea mays*) | cDNA (Variant 1) | RWS |
| 4 | GRMZM2G179789 SNAREv 1 (*Zea mays*) | cDNA (Variant 2) | RWS |
| 5 | GRMZM2G179789 SNAREv 1 (*Zea mays*) | cDNA (partial sequence of nucleotide 1240 to 2321 of SEQ ID No: 3) | RWS |
| 6 | GRMZM2G412426 SNAREv 2 (*Zea mays*) | genomic DNA | B73 |
| 7 | GRMZM2G412426 SNAREv 2 (*Zea mays*) | cDNA | B73 |
| 8 | GRMZM2G471240 Patatin phospholipase (*Zea mays*) | genomic DNA, including edges | B73 |
| 9 | GRMZM2G471240 Patatin phospholipase (*Zea mays*) | genomic DNA, including edges | RWS |
| 10 | GRMZM2G471240 Patatin phospholipase (*Zea mays*) | cDNA | B73 |
| 11 | GRMZM2G471240 Patatin phospholipase (*Zea mays*) | cDNA | RWS |
| 12 | GRMZM2G347808 RNA methyl transferase (*Zea mays*) | genomic DNA, including edges | B73 |
| 13 | GRMZM2G347808 RNA methyl transferase (*Zea mays*) | genomic DNA, including edges | RWS |
| 14 | GRMZM2G347808 RNA methyl transferase (*Zea mays*) | cDNA | B73 |
| 15 | GRMZM2G347808 RNA methyl transferase (*Zea mays*) | cDNA | RWS |
| 16 | GRMZM2G179789 SNAREv 1 (*Zea mays*) | Polypeptide (Variant 1) | B73 |
| 17 | GRMZM2G179789 SNAREv 1 (*Zea mays*) | Polypeptide (Variant 2) | B73 |
| 18 | GRMZM2G179789 SNAREv 1 (*Zea mays*) | Polypeptide (Variant 1) | RWS |
| 19 | GRMZM2G179789 SNAREv 1 (*Zea mays*) | Polypeptide (Variant 2) | RWS |
| 20 | GRMZM2G412426 SNAREv 2 (*Zea mays*) | Polypeptide | B73 |
| 21 | GRMZM2G471240 Patatin phospholipase (*Zea mays*) | Polypeptide (Variant 1) | B73 |
| 22 | GRMZM2G471240 Patatin phospholipase (*Zea mays*) | Polypeptide (Variant 2) | B73 |
| 23 | GRMZM2G471240 Patatin phospholipase (*Zea mays*) | Polypeptide | RWS |
| 24 | GRMZM2G347808 RNA methyl transferase (*Zea mays*) | Polypeptide | B73 |
| 25 | GRMZM2G347808 RNA methyl transferase (*Zea mays*) | Polypeptide | RWS |
| 26 | GRMZM2G106834 Phosphoinositol phosphatase (*Zea mays*) | genomic DNA | B73 |
| 27 | GRMZM2G106834 Phosphoinositol phosphatase (*Zea mays*) | cDNA (Variant 1) | B73 |
| 28 | GRMZM2G106834 Phosphoinositol phosphatase (*Zea mays*) | cDNA (Variant 2) | B73 |
| 29 | GRMZM2G106834 Phosphoinositol phosphatase (*Zea mays*) | cDNA (Variant 3) | B73 |
| 30 | GRMZM2G062320 Phosphoglycerate mutase (*Zea mays*) | genomic DNA | B73 |
| 31 | GRMZM2G062320 Phosphoglycerate mutase (*Zea mays*) | cDNA | B73 |
| 32 | GRMZM2G106834 Phosphoinositol phosphatase (*Zea mays*) | Polypeptide (Variant 1) | B73 |
| 33 | GRMZM2G106834 Phosphoinositol phosphatase (*Zea mays*) | Polypeptide (Variant 2) | B73 |
| 34 | GRMZM2G062320 Phosphoglycerate mutase (*Zea mays*) | Polypeptide | B73 |
| 35 | lncRNA for phosphoinositol phosphatase (*Zea mays*) | cDNA (Variant 1) | B73 |
| 36 | lncRNA for phosphoinositol phosphatase (*Zea mays*) | cDNA (Variant 2) | B73 |
| 37 | lncRNA for phosphoinositol phosphatase (*Zea mays*) | cDNA (Variant 3) | B73 |
| 38 | lncRNA for phosphoinositol phosphatase (*Zea mays*) | cDNA | RWS |

TABLE 1-continued

Sequence index and sequence association of the nucleotide and amino acid sequences. The names of gene families/protein families correspond to the public models. Discrepant functionalities may occur in the inductors due to structural changes.

| SEQ ID No: | Gene family/protein family identifier// derived gene model | Sequence type | Source |
|---|---|---|---|
| 39 | lncRNA for phospholipase (*Zea mays*) | Polypeptide (Variant 1) | B73 |
| 40 | lncRNA for phosphoinositol phosphatase (*Zea mays*) | Polypeptide (Variant 2) | B73 |
| 41 | lncRNA for phosphoinositol phosphatase (*Zea mays*) | genomic DNA | B73 |
| 42 | Mitochondrial import receptor (MITO1) (*Zea mays*) | genomic DNA | RWS |
| 43 | Mitochondrial import receptor (MITO2) (*Zea mays*) | genomic DNA | RWS |
| 44 | Mitochondrial import receptor (MITO1) (*Zea mays*) | Polypeptide | RWS |
| 45 | Mitochondrial import receptor (MITO2) (*Zea mays*) | Polypeptide | RWS |
| 46 | Phospholipase (*Helianthus annuus*) | genomic DNA | |
| 47 | Phospholipase (*Helianthus annuus*) | cDNA | |
| 48 | Phospholipase (*Helianthus annuus*) | Polypeptide | |
| 49 | Patatin phospholipase D74N (*Zea mays*) | genomic DNA | TILLING |
| 50 | Patatin phospholipase D74N (*Zea mays*) | cDNA | TILLING |
| 51 | Patatin phospholipase D74N (*Zea mays*) | Polypeptide | TILLING |
| 52 | Patatin phospholipase G78R (*Zea mays*) | genomic DNA | TILLING |
| 53 | Patatin phospholipase G78R (*Zea mays*) | cDNA | TILLING |
| 54 | Patatin phospholipase G78R (*Zea mays*) | Polypeptide | TILLING |
| 55 | Snare T1 (*Zea mays*) | genomic | RWS |
| 56 | Snare T1.t1 (*Zea mays*) | cDNA | RWS |
| 57 | Snare T1.t2 (*Zea mays*) | cDNA | RWS |
| 58 | Snare T2 (*Zea mays*) | genomic | RWS |
| 59 | Snare T2 (*Zea mays*) | cDNA | RWS |
| 60 | Snare T3 (*Zea mays*) | genomic | RWS |
| 61 | Snare T3.t1 (*Zea mays*) | cDNA | RWS |
| 62 | Snare T3.t2 (*Zea mays*) | cDNA | RWS |
| 63 | Snare T1.t2 (*Zea mays*) | Polypeptide | RWS |
| 64 | Snare T2 (*Zea mays*) | Polypeptide | RWS |
| 65 | Snare T3.t1 (*Zea mays*) | Polypeptide | RWS |

In a further aspect, the present invention relates to a vector which comprises the nucleic acid according to the invention. The vector may be a plasmid, a cosmid, a phage or an expression vector, a transformation vector, shuttle vector, or cloning vector; it may be double- or single-stranded, linear or circular; or it may transform a prokaryotic or eukaryotic host, either via integration into its genome or extrachromosomally. The nucleic acid according to the invention is preferably operatively linked in a vector with one or more regulatory sequences which allow the transcription, and, optionally, the expression, in a prokaryotic or eukaryotic host cell. A regulatory sequence—preferably, DNA—may be homologous or heterologous to the nucleic acid according to the invention. For example, the nucleic acid is under the control of a suitable promoter or terminator. Suitable promoters may be promoters which are constitutively induced (example: 35S promoter from the "Cauliflower mosaic virus" (Odell et al., 1985); those promoters which are tissue-specific are especially suitable (example: Pollen-specific promoters, Chen et al. (2010), Zhao et al. (2006), or Twell et al. (1991)), or are development-specific (example: blossom-specific promoters). Suitable promoters may also be synthetic or chimeric promoters which do not occur in nature, are composed of multiple elements, and contain a minimal promoter, as well as—upstream of the minimum promoter—at least one cis-regulatory element which serves as a binding location for special transcription factors. Chimeric promoters may be designed according to the desired specifics and are induced or repressed via different factors. Examples of such promoters are found in Gurr & Rushton (2005) or Venter (2007). For example, a suitable terminator is the nos-terminator (Depicker et al., 1982).

In addition to the vectors described above, the present invention also provides a method that includes the insertion of a described vector into a host cell. For example, the vector may be introduced via conjugation, mobilization, biolistic transformation, agrobacteria-mediated transformation, transfection, transduction, vacuum infiltration, or electroporation.

Such methods, like the methods for preparation of described vectors, are commonplace to the person skilled in the art (Sambrook et al., 2001).

In a further aspect, the present invention relates to a host cell which comprises the nucleic acid according to the invention or the vector of the present invention. A host cell in the sense of the invention may be a prokaryotic (for example, bacterial) or eukaryotic cell (for example, a plant cell or a yeast cell). The host cell is preferably an agrobacterium, such as *Agrobacterium tumefaciens* or *Agrobacterium rhizogenes*, or a plant cell which comprises the nucleic acid according to the invention or the vector of the present invention. To the person skilled in the art, both numerous methods (such as conjugation or electroporation) with which he may introduce the nucleic acid according to the invention or the vector of the present invention into an agrobacterium, and methods such as diverse transformation methods (biolistic transformation, agrobacterium-mediated transformation) with which he may introduce the nucleic acid according to the invention or the vector of the present invention into a plant cell (Sambrook et al., 2001), are known.

In a further aspect, the present invention relates to a transgenic plant cell which comprises the nucleic acid according to the invention as a transgene or the vector of the present invention, and relates to a transgenic plant or a part thereof which comprises the transgenic plant cell. For example, such a plant cell or plant is a plant cell or plant which is (preferably, stably) transformed with the nucleic acid according to the invention or with the vector of the present invention. A transgenic plant of the present invention is preferably suitable for use as a haploid inductor. In a preferred embodiment of the transgenic plant, the nucleic acid is operatively linked with one or more regulatory sequences which allow the transcription and, optionally, the expression in the plant cell. A regulatory sequence, preferably DNA, may be homologous or heterologous to the nucleic acid according to the invention. The total structure made up of the nucleic acid according to the invention and the regulatory sequence(s) may then represent the transgene. A part of a plant may be a fertilized or unfertilized seed, an embryo, a pollen, a tissue, an organ, or a plant cell, wherein the fertilized or unfertilized seed, the embryo, or the pollen are generated in the transgenic plant, and the nucleic acid according to the invention is integrated into its genome as a transgene or the vector. The present invention likewise also includes a descendant of the transgenic plant in whose genome the nucleic acid according to the invention is integrated as a transgene or vector, and which is suitable for use as a haploid inductor.

In another aspect, the present invention relates to a protein or a polypeptide which is encoded by a nucleic acid according to the invention. The protein or polypeptide is preferably suitable for mediating the property of a haploid inductor in a plant, or for increasing the induction capability of a haploid inductor. The protein or polypeptide encoded by the induction-inducing nucleic acid is especially preferred. A protein or a polypeptide of the present invention preferably includes an amino acid sequence selected from SEQ ID Nos: 16, 17, 18, 19, 20, 21, 22, 23, 24, 25, 44, 45, 48, 51, 54, 63, 64, and/or 65, or from SEQ ID Nos: 32, 33, and/or 34, or from SEQ ID Nos: 40 and/or 41.

In a further aspect, the present invention describes a method for the production of a plant which is suitable for use as a haploid inductor. The method may include the following steps:

A) mutagenization of plant cells and subsequent regeneration of plants from the mutagenized plant cells or mutagenization of plants, and B) identification of a plant A) which has at least one mutation in an endogenous DNA sequence which is identical to the nucleic acid according to the invention, or in a regulatory sequence of the endogenous DNA sequence (for example, a promoter, enhancer, terminator, or intron), which mutation produces a change in the transcription or expression rate of the endogenous DNA sequence in the identified plant, in comparison to a non-mutagenized wild-type plant, or a change in the activity or stability of a protein or polypeptide encoded by the endogenous DNA sequence in the identified plant, in comparison to a non-mutagenized wild-type plant, wherein the at least one mutation causes the property of a haploid inductor to be mediated or the induction capability of a haploid inductor to be increased in the identified plant. The change in the transcription rate or expression rate, or the change in the activity or stability, preferably appears at least in a pollen of the identified plant or in a tissue of a pollen of the identified plant.

The endogenous DNA sequence from step B), or an RNA encoded from the endogenous DNA sequence, or a protein or polypeptide encoded from the DNA sequence, preferably has an influence on the pollen tube growth in a plant, on the energy metabolism of a pollen of a plant, and/or on the activity of the centromere—preferably, in a generative cell which develops into a pollen, for example.

The endogenous DNA sequence from step B) of the method for the production of a plant which is suitable for use as a haploid inductor especially preferably encodes for a SNAREv protein; an enzyme of the phospholipase class—in particular, phospholipase A2 or the patatin phospholipase; an enzyme of the inositol polyphosphate-5-phosphatase class, such as inositol-1,4,5-triphosphate-5-phosphatase; a phosphoglycerate mutase or methyl transferase—in particular, an RNA methyl transferase, wherein, in the case of the SNARE protein, the phospholipase and the methyl transferase, the transcription rate or expression rate, or the activity or stability, is preferably altered to the effect that it is increased, and wherein, in the case of the inositol polyphosphate-5-phosphatase and the phosphoglycerate mutase, the transcription rate or expression rate, or the activity or stability, is preferably altered to the effect that it is reduced.

Step B) of the method for the production of a plant is, with very particular preference, the identification of a plant from A) which a) has at least one mutation in an endogenous DNA sequence having a nucleotide sequence that is identical to the induction-inducing nucleic acid or the nucleic acid which encodes the lncRNA 1, or in a regulatory sequence of the endogenous DNA sequence (for example, a promoter, enhancer, terminator, or intron), which at least one mutation effects an increase in the transcription or expression rate of the endogenous DNA sequence or an increase in the activity or stability of a protein or polypeptide encoded by the endogenous DNA sequence; and/or b) has at least one mutation in an endogenous DNA sequence having a nucleotide sequence that is identical to the induction-inhibiting nucleic acid or the nucleic acid which encodes the lncRNA 2, or in a regulatory sequence of the endogenous DNA sequence (for example, a promoter, enhancer, terminator, or intron), which at least one mutation effects a reduction in the transcription or expression rate of the endogenous DNA sequence or a reduction in the activity or stability of a protein or polypeptide encoded by the endogenous DNA sequence, wherein the at least one mutation from a) and/or b) causes the property of a haploid inductor to be mediated or the induction capability of a haploid inductor to be increased in the identified plant. The change in the transcription rate or expression rate, or the change in the activity or stability, preferably appears at least in a pollen of the identified plant or in a tissue of a pollen of the identified plant.

A mutation means a modification at the DNA level, and thus a change in the genetics and/or epigenetics. For example, an alteration in the genetics may be the exchange of at least one nucleobase in the endogenous DNA sequence or in a regulatory sequence of the endogenous DNA sequence. If such a nucleobase exchange takes place in a promoter, for example, this may lead to an altered activity of the promoter, since, for example, cis-regulator elements are modified such that the affinity of a transcription factor to the mutated cis-regulatory elements is altered in comparison to the wild-type promoter, so that the activity of the promoter with the mutated cis-regulatory elements is increased or reduced, depending upon whether the transcription factor is a repressor or inductor, or whether the affinity of the transcription factor to the mutated cis-regulatory elements is intensified or weakened. If such a nucleobase exchange occurs, e.g., in an encoding region of the endogenous DNA sequence, this may lead to an amino acid exchange in the encoded protein, which may produce an alteration in the activity or stability of the protein, in comparison to the wild-type protein. An additional example of an alteration in the genetics is the deletion of nucleotides in the regulatory sequence and/or of the endogenous DNA sequence, as well as the addition of nucleotides in the regulatory sequence and/or the endogenous DNA sequence. Das & Martienssen (1995) shows an example of the regulation of genes via insertion of nucleotides by transposon mutagenesis in maize. An alteration in the epigenetics may take place via an altered methylation pattern of the DNA.

It is known to the person skilled in the art how a mutation in the sense of the invention may be achieved via the process of a mutagenization in step A) of the method for production of a plant which is suitable for use as a haploid inductor. The mutagenization in this connection includes both conventional mutagenesis and location-specific mutagenesis or "genome editing." In conventional mutagenesis, modification at the DNA level is not produced in a targeted manner. The plant cell or the plant is exposed to mutagenic conditions, such as TILLING, via UV light exposure or the use of chemical substances (Till et al., 2004). An additional method of random mutagenesis is mutagenesis with the aid of a transposon. The UniformMU project makes a comprehensive collection of mutants freely available. The collection and the method are described in McCarty et al. (2005). Location-specific mutagenesis enables the introduction of modification at the DNA level in a target-oriented manner at predefined locations in the DNA. For example, TALENS (WO 2010/079430, WO 2011/072246), meganucleases (Silva et al., 2011), homing endonucleases (Chevalier 2002), zinc finger nucleases (Lloyd et al., 2005), or a CRISPR/Cas System (Gaj et al., 2013) may be used for this.

The identification of a plant in step B) may take place with the aid of molecular markers or probes, for example. For example, DNA probes are primers or primer pairs which may be used in a PCR reaction. For example, Tilling mutants may be verified or identified by sequencing the target gene in a Tilling population, or via additional methods that verify the mispairings in the DNA, e.g., melting point analyses or use of mispairing-specific nucleases. For this, the present invention likewise incorporates primers/primer pairs that are usable for this, e.g., primers for phospholipase, phosphoglycerate mutase, methyl transferase and lncRNA for phospholipase. Mutants generated by means of transposons may also be verified by use of transposon-specific primers and target gene-specific primers in PCR, across the entire population and subsequent sequencing of PCR products. Such primers are also encompassed by the present invention. For example, a change in the expression rate in pollen may be determined with RT-PCR; the change in the stability may be determined by examining ubiquitin binding locations and prediction of changes to the tertiary structure, for example. Furthermore, recombinant expression of the wild-type proteins, and the corresponding mutant proteins and subsequent biochemical activity tests, are also suitable. Additional means and methods which may be used to identify a plant in step B) are known to the person skilled in the art from the prior art.

The present invention also relates to molecular markers, which demonstrate the presence or absence of a mutation in the endogenous DNA sequence, or in a regulatory sequence of the endogenous DNA sequence. For example, such markers are based upon an SNP and are specific to the mutation (examples: KASPar or TaqMan markers).

The present invention further also relates to a plant which can be or is produced with the preceding method, or a part of this plant, wherein a part of the plant may be a fertilized or unfertilized seed, an embryo, a pollen, a tissue, an organ, or a plant cell, wherein the fertilized or unfertilized seed, the embryo, or the pollen are generated at the transgenic plant, and the at least one mutation is present in its genome. The present invention likewise also includes a descendant of the plant which has the at least one mutation and is suitable for use as a haploid inductor. Two examples of plants which have been produced with the preceding method are plants—preferably, *Zea mays* or *Helianthus annuus*—that, in an endogenous DNA sequence, with the nucleic acid, comprehensively (i) has a sequence selected from SEQ ID Nos: 8, 9, and/or 46 or a functional fragment thereof; or (ii) is complementary to a sequence from (i); or (iii) is at least 80% identical to a sequence from (i); or (iv) encodes for a protein having the amino acid sequence selected from SEQ ID Nos: 21, 22, 23, and/or 48, or a functional part of the protein; or (v) encodes for a homolog, analog, or ortholog of the protein according to (iv), or a functional part thereof; or (vi) is identical to a sequence hybridized under stringent conditions from (ii), or has at least one mutation in a regulatory sequence of the endogenous DNA sequence, which produces a change in the transcription or expression rate of the endogenous DNA sequence in the identified plant, in comparison to a non-mutagenized wild-type plant, or a change in the activity or stability of a protein or polypeptide encoded by the endogenous DNA sequence in the identified plant, in comparison to a non-mutagenized wild-type plant, wherein the at least one mutation causes the property of a haploid inductor to be mediated or the induction capability of a haploid inductor to be increased in the identified plant. The mutation is preferably an alteration in the encoding sequence of SEQ ID No: 8 or 9 (for example, a point mutation) which causes an amino acid exchange between the amino acid positions 74 and 78 of SEQ ID No: 21, 22, or 23, or the mutation causes a [sic] modifications in the encoding sequence of SEQ ID No. 46 which causes an amino acid exchange in [the] corresponding encoding sequence of SEQ ID No: 48. This may here involve mutations according to SEQ ID Nos: 49 through 54. The mutation caused by TILLING in SEQ ID No: 49 causes an amino acid exchange in the encoded amino acid at position 74, wherein the aspartate is replaced by asparagine (D74N); the mutation in SEQ ID No: 52 causes an amino acid exchange in the encoded amino acid at position 78, wherein the glycine is replaced by arginine (G78R).

Furthermore, the present invention also concerns a method for isolation of a nucleic acid that mediates the property of a haploid inductor or increases the induction capability of a haploid inductor in a plant, including the following steps:

A) production of a plant according to the method described in the preceding, or provision of a plant which can be or is produced with the method described in the preceding; and B) isolation, from the genome of the plant from A), of a nucleic acid which comprises the endogenous DNA sequence having the at least one mutation. The isolation of the nucleic acid in step B) may take place via CTAB extraction or via DNA-binding columns; the verification of the mutation may take place via sequencing or molecular markers such as SNP-based KASPar or TaqMan markers, or, for insertion or deletion mutants, via length polymorphism-based markers.

The present invention also includes a nucleic acid which was obtained or can be obtained via the method for isolation as described in the preceding, as well as a vector which comprises the isolated nucleic acid.

In another aspect, the present invention also relates to a method for the production of a transgenic plant which is suitable for use as a haploid inductor. The method may include the following steps:

A) provision of the nucleic acid described above which, after transcription or expression in a plant, is suitable for mediating the property of a haploid inductor or for increasing the induction capability of a haploid inductor; or provision of the isolated nucleic acid described above, which nucleic acid comprises the endogenous DNA sequence having the at least one mutation; or provision of one of the vectors described above, B) transformation—preferably, stable transformation—of plant cells via introduction of the nucleic acid or of the vector from A), C) regeneration of transgenic plants from the transformed plant cells from B), and D) identification of a transgenic plant from C) in which, via a modified expression pattern—preferably, in pollen of the identified plant or in a tissue of a pollen of the identified plant—the property of a haploid inductor is mediated, or the induction capability of a haploid inductor is increased. The method for production of a transgenic plant which is suitable for use as a haploid inductor also includes the provision of two or more of the nucleic acids described above—alternatively, also different embodiments of the nucleic acid according to the invention and, optionally, in one or more vectors—and the transformation of plant cells via the introduction of two or more nucleic acids. Alternatively or additionally, one or more additional nucleic acids which are known to be usable for the generation of a haploid inductor (for example, manipulated cenh3 gene (Ravi & Chan, 2010)) may also be provided and transformed, in addition to the nucleic acid according to the invention.

The expression pattern is preferably altered to the effect that (I) the transcription or expression rate of the introduced induction-promoting nucleic acid or introduced nucleic acid which encodes the lncRNA 1 is increased in the identified plant in comparison to a wild-type plant which, for example, was regenerated from an isogenic, untransformed plant cell, and/or (II) the transcription or expression rate of the introduced induction-inhibiting nucleic acid or introduced nucleic acid which encodes the lncRNA 2 is reduced in the identified plant in comparison to a wild-type plant which, for example, was regenerated from an isogenic, untransformed plant cell, and/or (III) due to post-transcriptional gene silencing, the expression rate of an endogenous DNA sequence having a nucleotide sequence that is identical to the induction-inhibiting nucleic acid is reduced—via a double-stranded RNA which is encoded by the introduced nucleic acid which is described above in connection with post-transcriptional gene silencing—in the identified plant in comparison to a wild-type plant which, for example, was regenerated from an isogenic, untransformed plant cell, and/or (IV) due to transcriptional gene silencing, the transcription or expression rate of an endogenous DNA sequence having a nucleotide sequence that is identical to the induction-inducing nucleic acid or introduced nucleic acid which encodes the lncRNA 1 is increased, by a double-stranded RNA which is encoded by the introduced nucleic acid which is described above in detail in connection with transcriptional gene silencing, in comparison to a wild-type plant which, for example, was regenerated from an isogenic, untransformed plant cell; and/or the transcription or expression rate of an endogenous DNA sequence having a nucleotide sequence that is identical to the induction-inhibiting nucleic acid or introduced nucleic acid which encodes for lncRNA 2 is reduced, by a double-stranded RNA which is encoded by the introduced nucleic acid which is described above in detail in connection with transcriptional gene silencing, in comparison to a wild-type plant which, for example, was regenerated from an isogenic, untransformed plant cell. A verification of the transcription rate may take place via qRT-PCR, for example. An altered protein stability may be determined via Western blot, for example.

The present invention further also relates to a transgenic plant which can be or is produced with this method, or a part of this plant, wherein a part of the plant may be a fertilized or unfertilized seed, an embryo, a pollen, a tissue, an organ, or a plant cell, wherein the fertilized or unfertilized seed, the embryo, or the pollen are generated at the transgenic plant, and the nucleic acid according to the invention is integrated into its genome as a transgene or the vector. The present invention likewise also includes a descendant of the transgenic plant which has the introduced nucleic acid as a transgene and is suitable for use as a haploid inductor.

In another aspect, the present invention relates to a method for the production of a haploid plant, which method includes the following steps:

A) crossing a non-transgenic or transgenic plant of the present invention which is suitable for use as a haploid inductor with a plant of the same genus—preferably, of the same species, B) selecting a fertilized haploid seed or embryo, and C) generating a haploid plant from the seed or embryo from B).

The plant which is suitable for use as a haploid inductor is preferably used as a pollen parent and is crossed with a seed elder of the same genus—preferably, of the same species. The plant which is suitable for use as a haploid inductor may also be used as a seed parent and be crossed with a pollen elder of the same genus—preferably, of the same species. Both cross partners in step A)—thus, seed parent and pollen parent—may also be the same individual. The crossing step then represents a selfing.

The selection of the haploid fertilized seed or embryo may include a step of the verification of the haploidy, and the separation of the haploid fertilized seed or embryo of polyploid fertilized seed or embryo. The verification of the haploidy of a fertilized seed or embryo may take place phenotypically or genotypically, in that, for example, the inductor is provided with an embryo-specific dominant marker that is visible in all diploid descendants, but not in the induced haploid descendants. Furthermore, the ploidy status may be determined via flow cytometry. Moreover, a complete, homozygotic pattern of molecular markers provides an indication of haploid plants. For example, the separation may take place automatically on the basis of data of the verification of the haploidy.

The present invention further also relates to a haploid, fertilized seed, or embryo which is created upon crossing in step A) of the method for production of a haploid plant, as well as a haploid plant which can be or is produced with this method, or a part of this plant, wherein a part of a plant may be a seed, an embryo, a tissue, an organ, or a plant cell. The present invention likewise also includes a descendant of the plant. Furthermore, the present invention also includes a double-haploid (diploid) plant or a part thereof, wherein the double-haploid (diploid) plant or a part thereof was generated by chromosome duplication of the haploid plant or of the part thereof.

In a further aspect, the present invention relates to the use of the nucleic acid according to the invention, or of the vector according to the invention, in a plant to mediate the property of a haploid inductor or to increase the induction capability of a haploid inductor, or the use of the nucleic acid according to the invention or of the vector according to the invention to produce a plant or a transgenic plant which is suitable for use as a haploid inductor. Furthermore, the present invention also includes the use of a plant according to the invention as described above, which is suitable for use as a haploid inductor, to produce a haploid, fertilized seed or embryo, or a haploid plant. Preceding explanations regarding subject matters and methods of the present invention are also applicable to the cited uses.

In another aspect, the present invention also relates to a means for external application to plants. This means is provided for external application to plants and is suitable for mediating the property of a haploid inductor in the plant or for increasing the induction capability of a haploid inductor plant. The application preferably occurs at the point in time of the anther formation, pollen formation, or fertilization. The means comprises RNA that has a double-stranded portion, wherein at least one strand of the double-stranded portion has a nucleotide sequence which is homologous or identical to at least 14, 15, 16, 17, 18, 19, 20, 21, 22, 23, 24, or 25—preferably, to at least 30, 35, 40, 45, 50, 60, 70, 80, 90, 100, 120, or 140, and, especially preferably, to at least 160, 180, 200, 250, 300, 350, 400, 450, 500, 600, 700, 800, 900, or 1000—successive nucleotides of a coding sequence of a nucleic acid that (i) has a sequence selected from SEQ ID Nos: 26, 27, 28, 29, 30, and/or 31, or a fragment thereof in a sense or anti-sense orientation, or (ii) is complementary to a sequence from (i), or (iii) is at least 80%, 82%, 84%, 86%, or 88%—preferably, at least 90%, 91%, 92%, 93%, 94%, 95%, or 96%, or, especially preferably, at least 97%, 97.5%, 98%, 98.5%, 99%, or 99.5%—identical to a sequence from (i), or (iv) encodes for a protein with the amino acid sequence selected from SEQ ID Nos: 32, 33, and/or 34, or a part of the protein, or (v) encodes for a homolog, analog, or ortholog of the protein according to (iv), or a part thereof, or (vi) hybridizes with a sequence from (ii) under stringent conditions.

Double-stranded RNA for the production of the means according to the invention may be produced in vitro by means of the methods known to the person skilled in the art. For example, the synthesis of the double-stranded RNA may take place synthetically, wherein the RNA is formed directly in vitro. Starting from a double-stranded DNA, the double-stranded RNA may also be synthesized via the formation of an mRNA transcript, which then forms a hairpin structure, for example. The means may be used as a trigger for a haploid induction in a plant. For example, the means may be used by being sprayed in the form of a spray, or via additional ways of external application that are commonplace to the person skilled in the art, onto the plant tissue, or by spraying or mixing with additional additives before or after the flowering of the plant. For example, additives may be wetting agents, carrier substances, or RNA stabilizers, e.g., liposomes.

Surprisingly, the inventors have established that it is precisely genes or gene products which have an influence on the pollen tube growth, on the energy metabolism of a pollen and/or on the activity of the centromere—preferably, in a generative cell which develops into a pollen, for example—are especially suited for converting a non-haploid inductor into a haploid inductor. For this, multiple gene families/protein families which are of significant importance could be identified. Their use for generation of haploid inductors has neither been described nor suggested before in the prior art. Because the creation of pollen, and also the fertilization process (including the growth of the pollen tube), follow generally valid principles in mono- and dicotyledon plants, with the technical teaching of the present invention, the person skilled in the art receives the possibility of developing haploid inductors even for cultivated plants for which neither an efficient system of in vivo haploid induction nor other cell culture-based methods for the creation of double-haploid plants had previously existed. For this, using the genetic information which he obtains via the present invention, he may discover homologs, orthologs, or analogs of the described gene products via routine activity, and manipulate them as described here. The technical teaching of the present invention is, however, also suitable for further improving the already existing inductors with regard to their efficiency (i.e., haploid induction rate), and thus for making them economically applicable for the first time. Furthermore, a person skilled in the art may also combine this technical teaching with additional known mechanisms of haploid induction, such as a manipulation of the CENH3 protein (Ravi & Chan, 2010), and thus further increase the efficiency Some of the terms used in this application are explained in detail in the following:

"B73" is a maize breeding line that is used as a model genotype in maize genetics and was used to create the first maize reference sequence.

"Mediate the property of a haploid inductor" or the "mediation of the property of a haploid inductor" or a comparable phrase means that, via the use of a nucleic acid according to the invention, a plant is placed in the position for producing fertilized seeds or embryos which have a single (haploid) chromosome set from a crossing with a plant of the same genus—preferably, of the same species—which does not have the property of a haploid inductor. The property of a haploid inductor, specified as an absolute haploid induction rate, means that at least 0.1%, 0.2%, 0.3%, 0.4%, 0.5%, 0.6%, 0.7%, 0.8%, 0.9%, or 1%—preferably, at least 1.5%, 2%, 2.5%, 3%, 3.5%, 4%, 4.5%, or 5%, or, especially preferably, 6%, 7%, 8%, 9%, 10%, 11%, 12%, 13%, 14%, or 15%, or, with very particular preference, at least 20%, 25%, 30%, 35%, 40%, 45%, or 50%—of the fertilized seeds or embryos have a haploid chromosome set.

"Increase in the expression rate" or "increased expression rate" or "activation of the expression" or a comparable expression means an increase in the expression rate of a nucleotide sequence by more than 10%, 15%, 20%, 25%, or 30%—preferably, by more than 40%, 50%, 60%, 70%, 80%, 90%, or 100%, or, especially preferably, by more than 150%, 200%, 250%, 300%, 500%, or 1000%—in comparison to the specified reference. The increase in the expression rate preferably leads to a change of the phenotype of a plant in which the expression rate is increased. An altered phenotype may be the mediation of the property of a haploid inductor, or the increase in the induction capability of a haploid inductor.

"Increase in the transcription rate" or "increased transcription rate" or a comparable expression means an increase in the transcription rate of a nucleotide sequence by more than 10%, 15%, 20%, 25%, or 30%—preferably, by more than 40%, 50%, 60%, 70%, 80%, 90%, or 100%, or, especially preferably, by more than 150%, 200%, 250%, 300%, 500%, or 1000%—in comparison to the specified reference. The increase in the transcription rate preferably leads to a change of the phenotype of a plant in which the transcription rate is increased. An altered phenotype may be the mediation of the property of a haploid inductor, or the increase in the induction capability of a haploid inductor.

A "functional fragment" of a nucleotide sequence means a segment of a nucleotide sequence which has the functionality identical or comparable to the complete nucleotide sequence from which the functional fragment originates. As such, the functional fragment may possess a nucleotide sequence which is identical or homologous to the complete nucleotide sequence over a length of at least 50%, 55%, 60%, 65%, 70%, 75%, 80%, 85%, 90%, 92%, 94% 96%, 97%, 98%, or 99%. Furthermore, a "functional fragment" of a nucleotide sequence may also mean a segment of a nucleotide sequence which alters the functionality of the total nucleotide sequence, e.g., in the course of post-transcriptional or transcriptional gene silencing. As such, the functional fragment of a nucleotide sequence may include at least 14, 15, 16, 17, 18, 19, 20, 21, 22, 23, 24, or 25—preferably, at least 30, 35, 40, 45, 50, 60, 70, 80, 90, 100, 120, or 140, or, especially preferably, at least 160, 180, 200, 250, 300, 350, 400, 450, 500, 600, 700, 800, 900, or 1000—successive nucleotides of the complete nucleotide sequence.

A "functional part" of a protein means a segment of a protein, or a section of the amino acid sequence, that encodes for the protein, wherein the segment may exert functionality identical or comparable to the entire protein in a plant cell. A functional part of a protein has, over a length of at least 50%, 55%, 60%, 65%, 70%, 75%, 80%, 85%, 90%, 92%, 94%, 96%, 97%, 98%, or 99%, an identical or—under conservative and semi-conservative amino acid exchanges—similar amino acid sequence to that of the protein from which the functional part originates.

"Haploid inductor" also means an in vivo haploid inductor.

The term "heterolog" means that the introduced polynucleotide originates from, for example, a cell or an organism having a different genetic background of the same species or another species, or is homologous to the prokaryotic or eukaryotic host cell, but then is localized in a different genetic environment and thus differs from a possible, naturally present, corresponding polynucleotide. A heterologous polynucleotide may be present in addition to a corresponding endogenous gene.

In the sense of the invention, what is understood by a "homolog" is a protein of the same phylogenetic origin, what is understood by an "analog" is a protein which exerts the same function, but has a different phylogenetic origin, and what is understood by an "ortholog" is a protein from a different species that exerts the same function.

What is understood by "hybridizing" or "hybridization" is a process in which a single-stranded nucleic acid molecule is added to a nucleic acid strand that is complementary to the greatest possible extent, i.e., enters into base pairing. Standard methods for hybridization are described in Sambrook et al. 2001, for example. What is preferably understood by this is that at least 60%—more preferably, at least 65%, 70%, 75%, 80%, or 85%, or, especially preferably, 90%, 91%, 92%, 93%, 94%, 95%, 96%, 97%, 98%, or 99%—of the bases of the nucleic acid molecule enter into a base pairing with the nucleic acid strand that is complementary to the greatest possible extent. The possibility of such an addition depends upon the stringency of the hybridization conditions. The term "stringency" relates to the hybridization conditions. High stringency is present when a base pairing is made more difficult; low stringency is present if a base pairing is made easier. For example, the stringency of the hybridization conditions depends upon the salt concentration, or ion strength, and the temperature. In general, the stringency may be increased by increasing the temperature and/or decreasing the salt content. What are to be understood by "stringent hybridization conditions" are those conditions given which a hybridization predominantly occurs only between homologous nucleic acid molecules. The term "hybridization conditions" thereby relates not only to the conditions prevailing in the actual addition of the nucleic acids, but also to the conditions prevailing in the following washing steps. Stringent hybridization conditions are, for example, conditions under which, predominantly, only those nucleic acid molecules are hybridized that have at least 70%—preferably, at least 75%, at least 80%, at least 85%, at least 90%, or at least 95%—sequence identity. Stringent hybridization conditions are, for example, hybridization in 4×SSC at 65° C., and subsequent repeated washing in 0.1×SSC at 65° C. for approximately 1 hour in total. The term "stringent hybridization conditions" that is used here may also mean hybridization at 68° C. in 0.25 M sodium phosphate, pH 7.2, 7% SDS, 1 mM EDTA and 1% BSA for 16 hours, and subsequent washing twice with 2×SSC and 0.1% SDS at 68° C. A hybridization preferably occurs under stringent conditions.

"Increase the induction capability of a haploid inductor" or "the increase in the induction capability of a haploid inductor" means that the haploid induction rate of a plant which has the property of a haploid inductor is increased. The number of fertilized seeds which have a haploid chromosome set and have arisen from a crossing of the haploid inductor with a plant of the same genus (preferably, of the same species) which does not have the property of a haploid inductor may thus be higher by at least 0.1%, 0.2%, 0.3%, 0.4%, 0.5%, 0.6%, 0.7%, 0.8%, 0.9%, or 1%—preferably, at least 1.5%, 2%, 2.5%, 3%, 3.5%, 4%, 4.5%, or 5%, and, especially preferably, at least 6%, 7%, 8%, 9%, 10%, 15%, 20%, 30%, or 50%—than the number of haploid fertilized seeds which is achieved without the use of the nucleic acid in the sense of the present invention, i.e., the haploid induction rate may be increased by at least 0.1%, 0.2%, 0.3%, 0.4%, 0.5%, 0.6%, 0.7%, 0.8%, 0.9%, or 1%—preferably, at least 1.5%, 2%, 2.5%, 3%, 3.5%, 4%, 4.5%, or 5%, and, especially preferably, at least 6%, 7%, 8%, 9%, 10%, 15%, 20%, 30%, or 50%—relative to the previously achieved haploid induction rate.

"Operatively linked" means connected in a common nucleic acid molecule in such a manner that the connected elements are positioned and oriented relative to one another such that a transcription of the nucleic acid molecule may occur. A DNA which is operatively linked with a promoter is under the transcriptional control of this promoter.

Plant "organs" mean, for example, leaves, shoots, stem, roots, vegetative buds, meristems, embryos, anthers, ovules, or fruits. Plant "parts" means a combination of multiple organs, e.g., a bloom or a seed, or a part of an organ, e.g., a cross-section from the shoot. Plant "tissues" are, for example, callus tissue, storage tissue, meristematic tissue, leaf tissue, stem tissue, root tissue, plant tumor tissue, or reproductive tissue. For example, what are to be understood by plant "cells" are, for example, isolated cells having a cell wall or aggregates thereof, or protoplasts.

In the sense of the invention, insofar as not otherwise indicated, a "plant" may be of any species from the dicotyledon, monocotyledon, and gymnosperm plants. Numbering among these are, for example, *Hordeum vulgare, Sorghum bicolor, Secale cereale*, Triticale, *Saccharum officinarium, Zea mays, Setaria italic, Oryza sativa, Oryza minuta, Oryza australiensis, Oryza alta, Triticum aestivum, Triticum durum, Hordeum bulbosum, Brachypodiurn distachyon, Hordeum marinum, Aegilops tauschii, Beta vulgaris, Helianthus annuus, Daucus glochidiatus, Daucus pusillus, Daucus muricatus, Daucus carota, Eucalyptus grandis, Erythranthe guttata, Genlisea aurea, Gossypium* sp., *Musa* sp., *Avena* sp., *Nicotiana sylvestris, Nicotiana tabacum, Nicotiana tomentosiformis, Solanum lycopersicum, Solanum tuberosum, Coffea canephora, Vitis vinifera, Cucumis sativus, Morus notabilis, Arabidopsis thaliana, Arabidopsis lyrata, Arabidopsis arenosa, Crucihimalaya himalaica, Crucihimalaya wallichii, Cardamine flexuosa, Lepidiurn virginicum, Capsella bursa-pastoris, Olmarabidopsis pumila, Arabis hirsuta, Brassica napus, Brassica oleracea, Brassica rapa, Brassica juncacea, Brassica nigra, Raphanus sativus, Eruca vesicaria sativa, Citrus sinensis, Jatropha curcas, Glycine max*, and *Populus trichocarpa*. A plant according to the invention is preferably a plant of the genus *Zea*—especially of the species *Zea mays*—or sorghum.

"Reducing the expression rate" or "reduction in the expression rate" or "suppression of the expression," "reduced expression rate," or a comparable phrase means a reduction in the expression rate of a nucleotide sequence by more than 10%, 15%, 20%, 25%, or 30%—preferably, by more than 40%, 45%, 50%, 55%, 60%, or 65%, and, especially preferably, by more than 70%, 75%, 80%, 85%, 90%, 92%, 94%, 96%, or 98%—in comparison to the specified reference. However, it may also mean that the expression rate of a nucleotide sequence is reduced by 100%. The reduction in the expression rate preferably leads to a change of the phenotype of a plant in which the expression rate is reduced. An altered phenotype may be the mediation of the property of a haploid inductor, or the increase in the induction capability of a haploid inductor.

"Reduction in the transcription rate" or "reduced transcription rate" or a comparable expression means a reduction in the transcription rate of a nucleotide sequence by more than 10%, 15%, 20%, 25%, or 30%—preferably by more than 40%, 45%, 50%, 55%, 60%, or 65%, and, especially preferably, by more than 70%, 75%, 80%, 85%, 90%, 92%, 94%, 96%, or 98%—in comparison to the specified reference. However, it may also mean that the expression rate of a nucleotide sequence is reduced by 100%. The reduction in the transcription rate preferably leads to a change of the phenotype of a plant in which the transcription rate is reduced. An altered phenotype may be the mediation of the property of a haploid inductor, or the increase in the induction capability of a haploid inductor.

In connection with the present invention, the term "regulatory sequence" relates to a nucleotide sequence which affects the specificity and/or the expression strength, e.g., in that the regulatory sequence mediates a defined tissue specificity. Such a regulatory sequence may be located upstream of the transcription initiation point of a minimal promoter, but also downstream of it, e.g., as in a transcribed, but untranslated, leader sequence or within an intron.

"Suitable for use as a haploid inductor" means that a plant is in the position to produce fertilized seeds which have a single (haploid) chromosome set from a cross with a plant of the same genus—preferably, of the same species—which does not have the property of a haploid inductor. The use a haploid inductor, specified as an absolute haploid induction rate, means that at least 0.1%, 0.2%, 0.3%, 0.4%, 0.5%, 0.6%, 0.7%, 0.8%, 0.9%, or 1% —preferably, at least 1.5%, 2%, 2.5%, 3%, 3.5%, 4%, 4.5%, or 5%, or, especially preferably, 6%, 7%, 8%, 9%, 10%, 11%, 12%, 13%, 14%, or 15%, or, with very particular preference, at least 20%, 25%, 30%, 35%, 40%, 45%, or 50%—of the fertilized seeds have a haploid chromosome set.

BRIEF DESCRIPTION OF THE DRAWINGS

Designs and embodiments of the present invention are described, by way of example, with regard to the attached figures and sequences.

SNAREv 1 (GRMZM2G179789): increased expression in RWS pollen;

SNAREv 2 (GRMZM2G412426): increased expression in RWS pollen;

ITP (Inositol-1,4,5-triphosphate-5-phosphatase) (GRMZM2G106834): reduced expression in RWS pollen;

PL (Patatin phospholipase) (GRMZM2G471240): polymorphisms in encoding sequence;

MITO1 (Mitochondrial import receptor): present only in RWS;

MITO2: Homolog to MITO1, but shortened. Present only in RWS;

PGM (Phosphoglycerate mutase) (GRMZM2G062320): deleted in RWS;

lncRNA: Homolog of PL: deleted in RWS;

AC213048: anchor gene for comparison of the sequences;

MT (RNA methyl transferase) (GRMZM2G347808): polymorphisms in the regulatory region.

The GRMZM names relate to the annotation in AGPv02.

Figure 2:
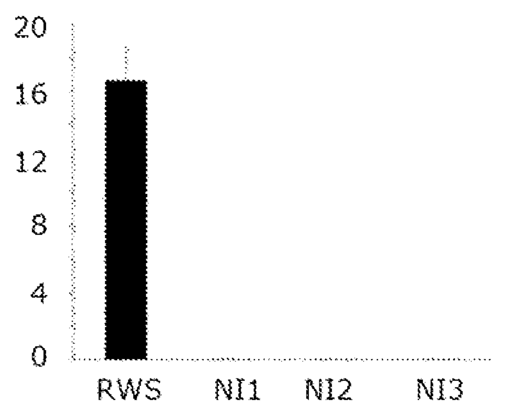
Figure 2:
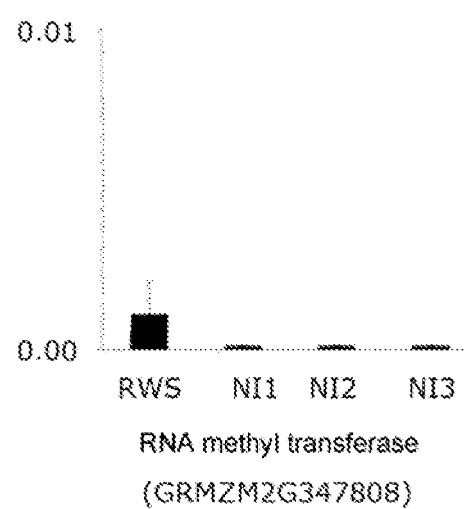
Figure 2:
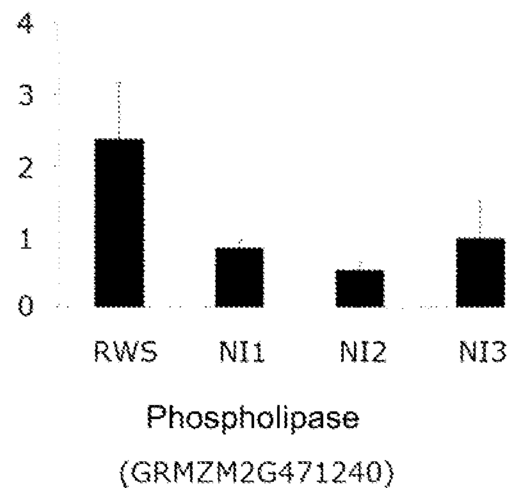

FIG. 2: RT-PCR of ripe pollen in inductor RWS and three non-inductor controls (NI1, NI2, NI3) across the genes SNAREv 1, RNA methyl transferase, and patatin phospholipase.

Figure 3:
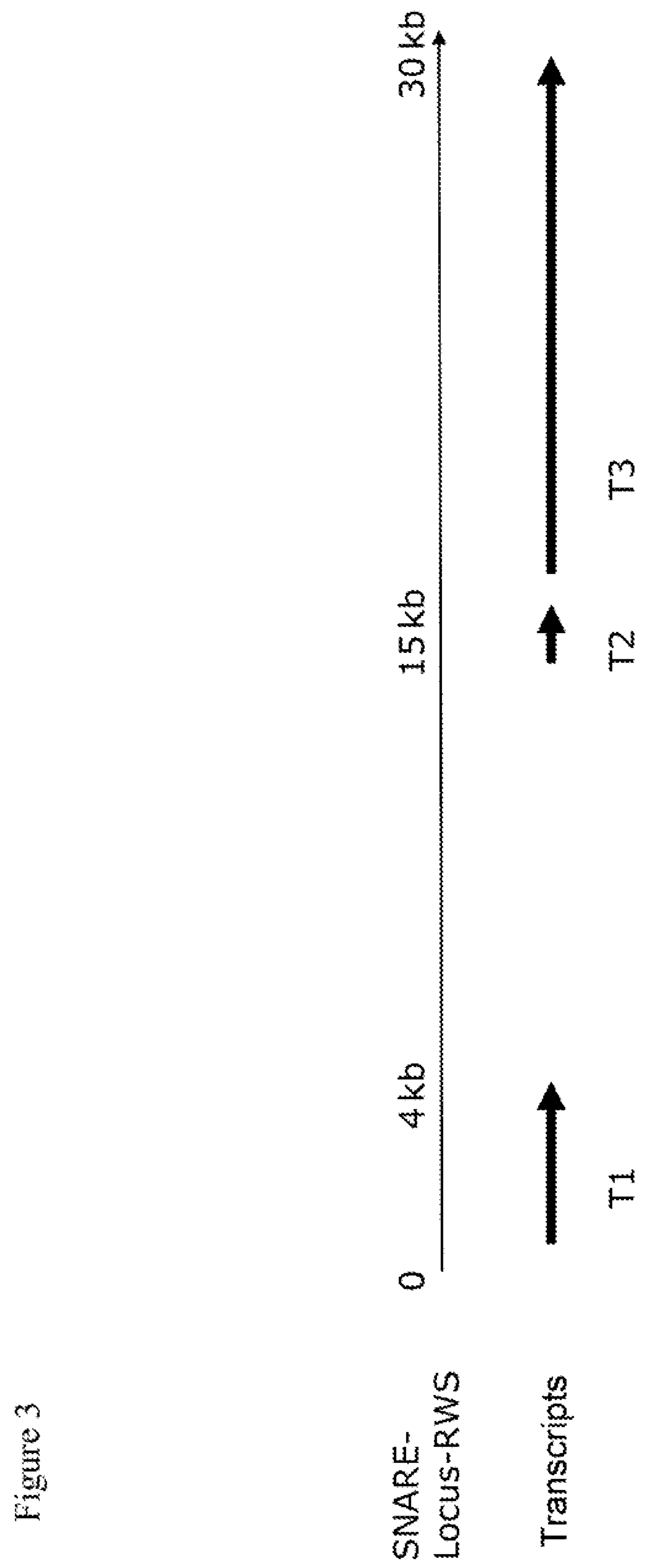

FIG. 3: RNASeq data of RWS pollen, projected onto artificial reference from AGPv02 with regions for SNARE and phospholipase loci substituted by RWS BAC's. (T1: Transcript 1. Homolog to SNARE2, but with altered exon-intron structure; T2: Homolog to SNARE1. Encoding for a protein of 131AA; T3: Homolog to SNARE1/2. RT-PCR fragment from FIG. 2).

QTL ANALYSIS AND IDENTIFICATION OF CANDIDATE GENES

In the maize haploid inductor RWS, which is to be ascribed to the inductor Stock6 (Coe, 1959), a main-QTL on chromosome 1 (bin 1.04) was identified and finely mapped. Based upon these works, the QTL in RWS should be verified and molecularly analyzed, in order to identify and functionally validate the underlying genes. A QTL mapping population from RWS×Control1 (maternal inductor×non-inductor) was tested for induction capability. It could thereby be shown that the known QTL is probably also present in the inductor RWS. However, it was further also achieved that a strong allele shift to the benefit of the non-RWS (Control 1) allele was discovered.

Figure 1:
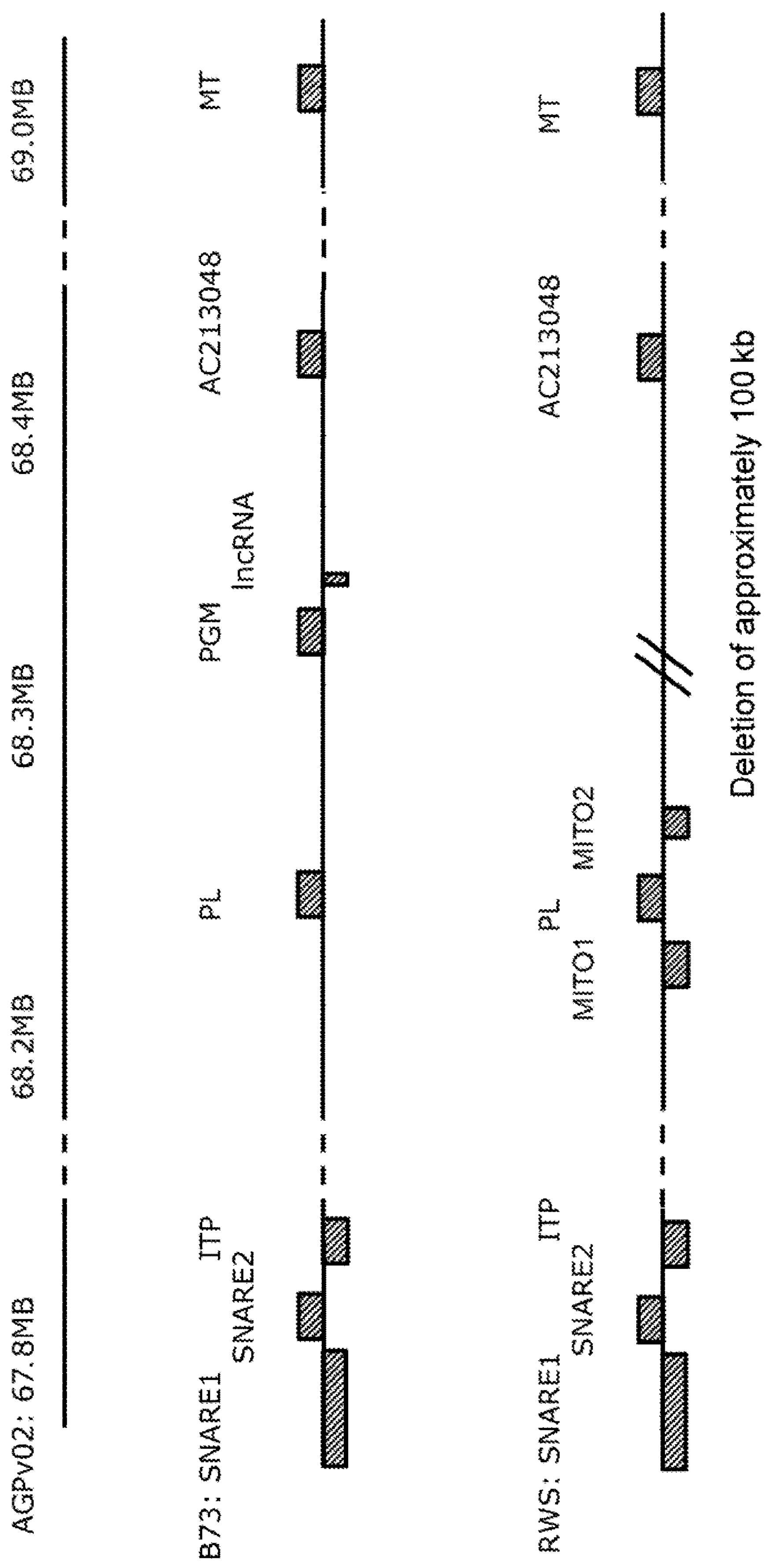
FIG. 1: Genomic arrangement of the identified genes in comparison to B73 (AGPv02)

In order to molecularly describe the locus, various sequencing approaches to DNA and at the RNA level were selected. Due to structural differences between inductors and reference genome B73, only a small proportion of classical, reference-based sequencing approaches lead to success. Expanded and complicated bioinformatic analyses had the result that structural differences would then need to be reviewed via other technologies (FIG. 1).

Within the scope of a sequence capture approach, approximately three megabases around the identified QTL in three Stock6-derived inductors, as well as RWS and five non-inductor controls, were sequenced, and were analyzed on inductor-specific polymorphisms such as presence-absence variations, SNP's, and InDel's. Initially, 16 candidate genes were thereby identified, of which three genes were confirmed via post-sequencing and analysis of expression data: one gene that encodes for an anther-specific patatin phospholipase A2 which has an RWS inductor-specific haplotype; a phosphoglycerate mutase gene which is not present in the inductor RWS; and an RNA methyl transferase gene which has a mutation in a regulatory sequence (FIG. 2).

BAC banks were also developed for RWS, EMK (an additional inductor derived from Stock6), and Control 1 and screened with probes distributed over the identified QTL. For a target range of approximately 150 kB, which was mentioned by Dong et al. 2013 in inductor UH400 as possibly being inductor-relevant, BAC's of RWS, Control 1, and EMK were extracted and sequenced. The BAC sequences were annotated and compared with comprehensive transcriptome data which were created for RWS, Control 1, EMK, and B73.

As a result, the deletion in the inductor could here be confirmed. Accordingly, the examined maternal inductors lack a region of 100 kB between 68.26 and 68.36 MB (AGP Version 2 of the B73 reference sequence) on chromosome 1. Furthermore, an inversion in a gene-similar region and a large, repetitive sequence segment that is not comparable to the reference genome of B73 and to Control 1 appears outside of the target region in the inductors.

In spite of the deletion, the already identified phospholipase is still present in the inductors, but shows the aforementioned haplotype strongly deviating from the controls, and marked genetic variations in the promoter region. As a result of the deletion, the phosphoglycerate mutase that was already identified above is no longer present.

Furthermore, it is also achieved that a non-coding RNA (lncRNA) is identified in the 100 kb deletion. Like the phospholipase, it is pollen-specifically expressed and, moreover, shows a homology of 82% with the identified phospholipase. The sequence is inherently complementary, i.e., the lncRNA forms a hairpin structure. The very high expression rate, the significant homology with the phospholipase, and the low SNP density that was determined via Sanger sequencing indicate a regulatory function of this lncRNA for the phospholipase. Theoretically, an 88 amino acid-long, truncated version of the phospholipase protein could also be translated from this transcript.

In order to also be able to measure differences in the expression level of the identified gene from the region, in addition to measuring polymorphisms at the DNA level, RT-PCR and RNASeq experiments were implemented. In addition to RWP (a subline of RWS) as an inductor, three, genetically very different, control lines were used. From these plants, pollen was harvested, anthers without pollen, and embryos from 6-7 days after pollination by selfings or crossings [sic]. The phospholipase here showed a slightly increased expression in pollen from RWP. The methyl transferase shows a weak expression in the pollen of RWP and no expression in the pollen of the control. lncRNA is expressed and absent pollen-specifically, as also expected in RWP.

RNASeq was additionally applied to pollen of the same material in order to further verify the preceding results.

The transcriptome data (RNA-Seq at Pollen RNA of RWS) was projected on an artificial reference, in which the region of the QTL in B73 was replaced with RWS-BAC's. This analysis shows an expression of the phospholipase in pollen. The exon-intron structure of the gene corresponds to that of B73, but a deletion exists at the 5' end, which leads to a stop codon and therefore to a shortened protein. Furthermore, three additional RWS-specific transcripts were detected above and below the phospholipase. A region having two transcripts is located approximately 60 kb above the phospholipase. The first transcript is non-coding; the second encodes for a 192 amino acid-long protein that shows homologies with the mitochondrial import receptor (MITO1). In B73, this is situated only 15 megabases upstream of the QTL (GRMZM2G174696). Approximately 90 kilobases (kb) below the phospholipase is an additional transcript that in turn shows high homologies with the 192 amino acid-long transcript.

In order to also receive inductor-specific expression outside of the QTL, the RNASeq data were evaluated genome-wide. Unexpectedly, new candidate genes were identified outside of, but near, the finely-mapped region cited above, which probably could not previously be found due to the technical limitations of the SeqCapture approach. Approximately 400 kb upstream of the identified phospholipase from the finely-mapped region is a gene complex which, in pollen of RWP, is expressed distinctly differently (by at least a factor of 2) in comparison to the controls. This gene complex contains three genes: two genes annotated as SNAREv genes which have a high homology to one another and are over-expressed in RWP, and one gene that is annotated as inositol-1,4,5-trisphosphate-5-phosphatase and whose expression in RWP is reduced. Cloned transcripts of these genes distinctly deviate in part from the public annotation, such that they may also encode for proteins with deviating functions, or also may function as lncRNA's. A BAC made up of RWS could be isolated from this locus, and sequenced. This sequence was integrated into the artificial reference for re-analysis of the RNASeq data in AGPv02 (FIG. 3). In addition to a transposase, two RNA's (T1 (SEQ ID Nos: 55, 56, 57, and 63) and T3 (SEQ ID Nos: 60, 61, 62, and 65)) and an RNA with an ORF of 131 amino acids are expressed in this locus (T2 (SEQ ID Nos: 58, 59, and 64)). Except for the transposase, all transcripts are situated within or between the two SNAREv genes. Although they presumably have no SNARE function themselves, they could be involved in the regulation of homologous genes. The sequence capture data of this region show that there are distinct structural deviations between inductors, controls, and reference genome. The BAC sequencing confirms the absence of both inositol-1,4,5-trisphosphate-5-phosphatase gene at the genomic level in the inductor and the absence of an lncRNA from B73 that shares the transcription start with the inositol-1,4,5-trisphosphate-5-phosphatase, but is read from the counter-strand. The isolation of a cDNA from one of the SNARE genes (GRMZM2G179789) also indicates complex structural changes in the inductors, since one part of the cDNA corresponds to the plus strand and one part corresponds to the minus strand of the reference.

Gene Functionalities

Overall, seven genes could thus be identified which could be important for the in vivo haploid induction or the in vivo haploid induction capability in maize.

Among these four genes, which are of particular importance to pollen tube growth:

the two SNAREv genes encoding for proteins which are known to be involved in vesicle transport (literature). In the model plant *Arabidopsis thaliana*, SNAREv proteins have already been demonstrated at the tip of the pollen tube, where they are involved in the transport of phospholipids and pectins (literature). The over-expression of the SNAREv proteins that was observed in the examined maize inductors would lead to increased pollen tube growth.

That the phospholipase A2 also distinctly influences the pollen tube growth could be shown in the model plant *Nicotiana tabacum*. The inhibition of phospholipase A2 accordingly leads to a suppression of the pollen tube growth (Kim et al., 2011). In the examined maize inductors, the absence of the identified lncRNA having significant homology with the phospholipase may lead to a reduction in the expression or translation rate of the phospholipase gene, which would accelerate the growth speed of the pollen tube.

In a knockout mutant of inositol-polyphosphate-5-phosphatase in *Arabidopsis thaliana*, it appeared that the pollen tube grows uninhibitedly. In the examined maize inductors, the reduced expression level of the inositol-1,4,5-trisphosphate-5-phosphatase thus may likewise lead to an accelerated pollen tube growth. The identified lncRNA associated with inositol-1,4,5-trisphosphate-5-phosphatase could here have a regulatory effect on the expression rate.

The examined maize inductors thus show a modified regulation/expression rate of the four genes, in comparison to non-inductors. This disruption should lead to a markedly faster pollen tube growth, which is also promoted by a possibly increased energy metabolism, due to the expression of a mitochondrial transporter or its regulation. This could have the result of a decoupling of the transport of the generative cells in the pollen tube with its growth. As a result, an incomplete or incorrect pollination with subsequent chromosome elimination may occur.

It is known that active centromeres play a key role in chromosome distribution and are characterized and modified via chromatin modifications at the DNA or histone level—moreover, by transcription, RNA interactions, and RNA binding. A change in the regulation of the methyl transferase gene may influence the activity of the inductor centromere during the early embryogenesis, which ultimately leads to the elimination of the inductor genome in the early seed development stage.

In the examined inductors, it could be shown that the phosphoglycerate mutase gene is no longer present. The absence of the gene may negatively affect the energy metabolism of the pollen, and therefore have effects on the pollination. Moreover, the energy metabolism may be influenced by the mitochondrial membrane protein.

Any gene individually, or any combination of the genes, may be responsible for the effect of the haploid induction.

Creation of New In Vivo Haploid Inductors

In order to develop a new inductor in other crop types or maize non-inductor genotypes, or to increase the induction capability of an inductor genotype, the following is to be performed:

Identification of the Corresponding Genes in Other Crop Types or Maize Non-Inductor Genotypes:

In single-cotyledon plants such as maize, rice, wheat, rye, or barley, the pollen-specific patatin phospholipases are strongly conserved, and, therefore, homologs of these are easy to identify. In contrast to this, regulatory lncRNA's are absent in most single-cotyledon plants. However, in the event that they are present, they may likewise be discovered using significant homologies, just as they also occurred in the examined maize inductors. In double-cotyledon plants, other phospholipase types take on the corresponding tasks in the pollen tube growth. In order to identify these, RNA banks of pollen or pollen tubes are to be created and screened for the specific phospholipase of the present invention. A patatin phospholipase that is strongly expressed in pollen could already be identified via RNASeq of sunflower pollen (SEQ ID Nos: 46-48).

The SNAREv genes and the methyl transferase gene do not need to be pollen-specific. For example, one of the identified SNAREv genes (SNAREv 1) in maize is also not expressed in a pollen-specific manner. SNAREv 1 is not expressed at all in wild-type pollen. In annotated genomes, homologous genes may be identified via BLASTP and the functional region of a SNAREv protein. In unannotated genomes, RNASeq data would need to be annotated and selected for SNARE genes.

Homologous inositol-1,4,5-trisphosphate-5-phosphatases and phosphoglycerate mutases must be expressed in pollen, in order to be used as candidate genes. The identification may take place as above, via BLASTP and subsequent RT-PCR in pollen or via annotation of RNASeq data of pollen.

Manipulation of the Candidate Gene:

Possible inductors or an increased induction capability may be achieved via transgenic expression of the phospholipases and/or SNARE's and/or methyl transferase and/or phosphoglycerate mutases and/or lncRNA's and/or of the mitochondrial import receptor described above. For this, the corresponding genes—including their promoters—are to be cloned from the inductor line RWS. These genes may be cloned in a suitable transformation vector and be transformed in the desired plant.

The pollen-expressed inositol-1,4,5-trisphosphate-5-phosphatase may be additionally or exclusively reduced in their activity via RNAi, for example. For example, for this, hairpin constructs are to be produced, which then [sic] including a suitable promoter and terminator which allow a transcription of the hairpin construct before or at the point in time of the pollen formation. These hairpin constructs would be cloned in a suitable transformation vector and be transformed in the desired plant.

Alternatively or additionally, plants having mutations (for example, in the identified genes) that stabilize the phospholipase and/or SNARE's and/or methyl transferase, amplify the expression, or increase the activity may be generated via TILLING, transposon mutagenesis or other mutagenesis methods, or "genome editing." Structural analyses of secondary and tertiary structure of the mutated proteins may be helpful for this, which mutated proteins indicate denser structures, for example, and therefore fewer attack points for proteases. Moreover, the regions of the proteins that play a role in ubiquitin interactions may be considered. Mutants in the active center of the gene may be directly tested for their activity. For verification of the functionality of the phospholipase, various Tilling mutants have already been checked for induction capability.

The exchange D74N (exchange of aspartate at Position 74 for asparagine) or G78R (exchange of glycine at Position 78 for arginine) lead to a maternal induction rate of 0.2-0.4%. In order to alternatively or additionally manipulate the inositol-1,4,5-triphosphate-5-phosphatase or the phosphoglycerate mutase, one must search for knockout mutants or for additional mutants that reduce the activity of the gene.

A Stock6-derived inductor may also be improved. This is possible via the above-described transgenic approach and via the introduction of mutations in the identified candidate genes. Insofar as they are expressed in pollen, it would additionally be possible to manipulate additional copies of the genes in the genome via transgenic or non-transgenic approaches.

Test of the induction capability: There are, for example, the following possibilities for testing the induction capability of a potential inductor:

1. Pollination of a line having a visual recessive marker (for example, glossy (Bordes et al., 1997) or liguleless (Sylvester et al., 1990), for maize). Descendants that express this feature are tested for haploidy via flow cytometry.
2. Pollination of a line that differs genetically from the inductor—optimally, via multiple markers. Use of these markers in order to identify homozygotic plants. These plants are tested for haploidy via flow cytometry.

Both possibilities were applied to test the induction capability.

REFERENCES

Barret, P., Brinkmann, M., & Beckert, M. (2008). A major locus expressed in the male gametophyte with incomplete penetrance is responsible for in situ gynogenesis in maize. *Theoretical and Applied Genetics,* 117(4), 581-594.

Bordes, J., de Vaulx, R. D., Lapierre, A., & Pollacsek, M. (1997). Haplodiploidization of maize (*Zea mays* L) through induced gynogenesis assisted by glossy markers and its use in breeding. *Agronomie,* 17(5), 291-297.

Chen, L., Tu, Z., Hussain, J., Cong, L., Yan, Y., Jin, L., . . . & He, G. (2010). Isolation and heterologous transformation analysis of a pollen-specific promoter from wheat (*Triticum aestivum* L.). *Molecular Biology Reports,* 37(2), 737-744.

Chevalier, B. S., Kortemme, T., Chadsey, M. S., Baker, D., Monnat Jr, R. J., & Stoddard, B. L. (2002). Design, activity, and structure of a highly specific artificial endonuclease. *Molecular Cell,* 10(4), 895-905.

Coe, E. H. (1959). A line of maize with high haploid frequency. *American Naturalist,* 381-382.

Das, L., & Martienssen, R. (1995). Site-selected transposon mutagenesis at the hcf106 locus in maize. *The Plant Cell Online,* 7(3), 287-294.

Deimling, S., Rober, F. K, Geiger, H. H. (1997). Methodik and Genetik der in-vivo-Haploideninduktion bei Mais. [Methods and genetics of in vivo haploid induction in maize] Presentation Pflanzenzüchtung, 38: 203-224.

Depicker, A., Stachel, S., Dhaese, P., Zambryski, P., & Goodman, H. M. (1981). Nopaline synthase: transcript mapping and DNA sequence. *Journal of Molecular and Applied Genetics,* 1(6), 561-573.

Dong, X., Xu, X., Li, L., Liu, C., Tian, X., Li, W., & Chen, S. (2014). Marker-assisted selection and evaluation of high oil in vivo haploid inducers in maize. *Molecular Breeding,* 1-12.

Dong, X., Xu, X., Miao, J., Li, L., Zhang, D., Mi, X., . . . & Chen, S. (2013). Fine mapping of qhir1 influencing in vivo haploid induction in maize. *Theoretical and Applied Genetics,* 126(7), 1713-1720.

Fire, A., Xu, S., Montgomery, M. K., Kostas, S. A., Driver, S. E., & Mello, C. C. (1998). Potent and specific genetic interference by double-stranded RNA in *Caenorhabditis elegans. Nature,* 391(6669), 806-811.

Gaj, T., Gersbach, C. A., & Barbas III, C. F. (2013). ZFN, TALEN, and CRISPR/Cas-based methods for genome engineering. *Trends in Biotechnology,* 31(7), 397-405.

Gurr, S. J., & Rushton, P. J. (2005). Engineering plants with increased disease resistance: what are we going to express? *Trends in Biotechnology,* 23(6), 275-282.

Kato, N., He, H., & Steger, A. P. (2010). A systems model of vesicle trafficking in *Arabidopsis* pollen tubes. *Plant Physiology,* 152(2), 590-601.

Kim, H. J., Ok, S. H., Bahn, S. C., Jang, J., Oh, S. A., Park, S. K., . . . & Shin, J. S. (2011). Endoplasmic reticulum- and golgi-localized phospholipase A2 plays critical roles in *Arabidopsis* pollen development and germination. *The Plant Cell Online,* 23(1), 94-110.

Lloyd, A., Plaisier, C. L., Carroll, D., & Drews, G. N. (2005). Targeted mutagenesis using zinc-finger nucleases in *Arabidopsis. Proceedings of the National Academy of Sciences of the United States of America,* 102(6), 2232-2237.

McCarty, D. R., Mark Settles, A., Suzuki, M., Tan, B. C., Latshaw, S., Porch, T., . . . & Curtis Hannah, L. (2005). Steady-state transposon mutagenesis in inbred maize. *The Plant Journal,* 44(1), 52-61.

Odell, J. T., Nagy, F., & Chua, N. H. (1985). Identification of DNA sequences required for activity of the cauliflower mosaic virus 35S promoter.

Prigge, V., Xu, X., Li, L., Babu, R., Chen, S., Atlin, G. N., & Melchinger, A. E. (2012). New insights into the genetics of in vivo induction of maternal haploids, the backbone of doubled haploid technology in maize. *Genetics,* 190(2), 781-793.

Ravi, M., & Chan, S. W. (2010). Haploid plants produced by centromere-mediated genome elimination. *Nature,* 464 (7288), 615-618.

Röber, F. K., Gordillo, G. A., & Geiger, H. H. (2005). In vivo haploid induction in maize-performance of new inducers and significance of doubled haploid lines in hybrid breeding. *Maydica,* 50(3/4), 275.

Sambrook, J., Russell, D. W., & Russell, D. W. (2001). *Molecular Cloning: A Laboratory Manual* (3-volume set) (Vol. 999). Cold Spring Harbor, N.Y.: Cold Spring Harbor Laboratory Press.

Shibuya, K., Fukushima, S., & Takatsuji, H. (2009). RNA-directed DNA methylation induces transcriptional activation in plants. *Proceedings of the National Academy of Sciences,* 106(5), 1660-1665.

Silva, G., Poirot, L., Galetto, R., Smith, J., Montoya, G., & Duchateau, P. (2011). Meganucleases and other tools for targeted genome engineering: perspectives and challenges for gene therapy. *Current Gene Therapy,* 11(1), 11.

Sylvester, A. W., Cande, W. Z., & Freeling, M. (1990). Division and differentiation during normal and liguleless-1 maize leaf development. *Development,* 110(3), 985-1000.

Till, B. J., Reynolds, S. H., Weil, C., Springer, N., Burtner, C., Young, K., . . . & Henikoff, S. (2004). Discovery of induced point mutations in maize genes by TILLING. *BMC Plant Biology,* 4(1), 12.

Twell, D., Yamaguchi, J., Wing, R. A., Ushiba, J., & McCormick, S. (1991). Promoter analysis of genes that are coordinately expressed during pollen development reveals pollen-specific enhancer sequences and shared regulatory elements. *Genes & Development,* 5(3), 496-507.

Venter, M. (2007). Synthetic promoters: genetic control through <i> cis</i> engineering. *Trends in Plant Science,* 12(3), 118-124.

Wang, Y., Chu, Y. J., & Xue, H. W. (2012). Inositol polyphosphate 5-phosphatase-controlled Ins (1, 4, 5) P3/Ca2+ is crucial for maintaining pollen dormancy and regulating early germination of pollen. *Development,* 139(12), 2221-2233.

Zhao, Y., Zhao, Q., Ao, G., & Yu, J. (2006). Characterization and functional analysis of a pollen-specific gene st901 in *Solanum tuberosum. Planta,* 224(2), 405-412.

WO/2010/079430 (Bonas et al.) Modular DNA-binding domains and methods of use.

WO/2011/072246 (Regents of the University of Minnesota) TAL effector-mediated DNA modification.

WO 2012/030893 (Monsanto Technology LLC) Molecular markers associated with haploid induction in *Zea mays.*

The invention claimed is:

1. A method for identification of a *Zea mays* plant which has at least one mutation in an endogenous DNA sequence encoding for a pollen-specific phospholipase, which endogenous pollen-specific phospholipase-encoding DNA sequence (i) has the genomic sequence of SEQ ID NO: 8 and/or leads to a cDNA comprising the sequence of SEQ ID NO: 10, or (ii) is complementary to the full length of a sequence from (i), or (iii) is at least 90% identical to the full length of a sequence from (i), or (iv) encodes for a protein with the amino acid sequence selected from the group consisting of SEQ ID NOs: 21 and 22;

comprising the step of:

(a) detecting in a pollen or a tissue of a pollen of the identified plant a change in the expression rate of the endogenous DNA sequence, in comparison to a non-mutagenized wild-type plant, or (b) verifying the at least one mutation via sequencing, molecular markers for SNPs or length polymorphism-based markers for insertion or deletion mutants, wherein the at least one mutation i) leads to the sequence of SEQ ID NO: 9 or a cDNA comprising the sequence of SEQ ID NO: 11; and/or;

ii) leads to a protein comprising the amino acid sequence of SEQ ID NO: 23; and/or iii) is an alteration in the encoding sequence of SEQ ID NO: 8 which causes an amino acid exchange between the amino acid positions 74 and 78 of SEQ ID NO: 21 or 22, and/or iv) causes an amino acid exchange in the encoded amino acid at position 74 of SEQ ID NO: 21 or 22, wherein the aspartate is replaced by asparagine (D74N) as set forth in SEQ ID NO: 51, and/or v) causes an amino acid exchange in the encoded amino acid at position 78 of SEQ ID NO: 21 or 22, wherein the glycine is replaced by arginine (G78R) as set forth in SEQ ID NO: 54, and causes the property of a haploid inductor to be mediated or the induction capability of a haploid inductor to be increased in the identified plant.

2. The method of claim 1, wherein the at least one mutation produces an alteration in the activity or stability of the pollen-specific phospholipase, in comparison to the wild-type pollen-specific phospholipase.

3. The method of claim 1, wherein the molecular marker is a DNA primer or a pair of DNA primers.

4. The method of claim 3, wherein a sample from the plant is contacted with the DNA primer or the pair of DNA primers in a polymerase chain reaction (PCR).

5. The method of claim 4, wherein the PCR is reverse transcription PCR (RT-PCR).

6. The method of claim 1, wherein the molecular markers demonstrate the presence or absence of the at least one mutation.

7. The method of claim 6, wherein the molecular markers are KASPar or TaqMan markers.

8. The method of claim 4, wherein the sample is a pollen sample.

9. The method of claim 3, wherein the DNA primer or the pair of DNA primers comprises a sequence for detection of the at least one mutation in a gene encoding for the pollen-specific phospholipase.

10. The method of claim 3, wherein the DNA primer or the pair of DNA primers are specific for a target gene.

11. The method of claim 1, wherein the at least one mutation in the endogenous DNA sequence is a point mutation.

12. The method of claim 1, further comprising developing a haploid inducer with the identified plants.

13. The method of claim 1, further comprising using the identified plant as a pollen parent in a cross with a seed parent of the same species.

14. The method of claim 1, further comprising isolating pollen from the identified *Zea mays* plant, and pollinating another plant with the isolated pollen.

15. The method of claim 1, wherein the endogenous pollen-specific phospholipase-encoding DNA sequence has the genomic sequence of SEQ ID NO: 8 or leads to a cDNA comprising the sequence of SEQ ID NO: 10, wherein the at least one mutation causes an amino acid exchange in the encoded amino acid at position 74 of SEQ ID NO: 21 or 22, and wherein the aspartate is replaced by asparagine (D74N) as set forth in SEQ ID NO: 51.

16. The method of claim 1, wherein the endogenous pollen-specific phospholipase-encoding DNA sequence has the genomic sequence of SEQ ID NO: 8 or leads to a cDNA comprising the sequence of SEQ ID NO: 10, wherein the at least one mutation causes an amino acid exchange in the encoded amino acid at position 78 of SEQ ID NO: 21 or 22, and wherein the glycine is replaced by arginine (G78R) as set forth in SEQ ID NO: 54.

* * * * *